United States Patent
Dorfman et al.

(10) Patent No.: US 9,387,225 B2
(45) Date of Patent: *Jul. 12, 2016

(54) GOLD-PLATINUM BASED BI-METALLIC NANOCRYSTAL SUSPENSIONS, ELECTROCHEMICAL MANUFACTURING PROCESSES THEREFOR AND USES FOR THE SAME

(75) Inventors: Adam R. Dorfman, Baltimore, MD (US); David A. Bryce, Elkton, MD (US); Maxwell A. Grace, Baltimore, MD (US); D. Kyle Pierce, Elkton, MD (US); Mikhail Merzliakov, Parkville, MD (US); Mark G. Mortenson, North East, MD (US)

(73) Assignee: GR INTELLECTUAL RESERVE, LLC, a Nevada LLC ( * ) Notice: Subject to any disclaimer, the term of this patent is extended or adjusted under 35 U.S.C. 154(b) by 0 days.

This patent is subject to a terminal disclaimer.

(21) Appl. No.: 14/008,931

(22) PCT Filed: Mar. 30, 2012

(86) PCT No.: PCT/US2012/031654
§ 371 (c)(1),
(2), (4) Date: Dec. 16, 2013

(87) PCT Pub. No.: WO2012/135743
PCT Pub. Date: Oct. 4, 2012

(65) Prior Publication Data
US 2014/0294963 A1    Oct. 2, 2014

Related U.S. Application Data

(60) Provisional application No. 61/469,525, filed on Mar. 30, 2011.

(51) Int. Cl.
| | |
|---|---|
| *A61K 33/24* | (2006.01) |
| *A61K 9/14* | (2006.01) |
| *C22C 1/04* | (2006.01) |
| *C22C 5/02* | (2006.01) |
| *C22C 5/04* | (2006.01) |
| *C22C 30/00* | (2006.01) |
| *A61K 9/10* | (2006.01) |

(52) U.S. Cl.
CPC . *A61K 33/24* (2013.01); *A61K 9/10* (2013.01); *A61K 9/14* (2013.01); *C22C 1/0466* (2013.01); *C22C 5/02* (2013.01); *C22C 5/04* (2013.01); *C22C 30/00* (2013.01)

(58) Field of Classification Search
CPC .......... A61K 33/24; A61K 9/10; A61K 9/14; C22C 1/0466; C22C 5/02; C22C 5/04; C22C 30/00; B01J 19/088; B01J 19/0809; B01J 2219/0828; B01J 2219/083; B01J 2219/0841; B01J 2219/0894; C02F 1/4608; H05H 1/48; H05H 2245/1225; H05H 2001/481
See application file for complete search history.

(56) References Cited

U.S. PATENT DOCUMENTS

| | | |
|---|---|---|
| 7,087,249 B2 | 8/2006 | Burrell et al. |
| 8,617,360 B2 | 12/2013 | Pierce et al. |
| 9,067,263 B2 | 6/2015 | Pierce et al. |
| 2005/0136128 A1 | 6/2005 | Gillis et al. |
| 2008/0190770 A1* | 8/2008 | Daigle et al. .......... 204/554 |
| 2008/0193373 A1 | 8/2008 | Stritzker et al. |
| 2008/0277272 A1* | 11/2008 | Pierce et al. .......... 204/164 |

OTHER PUBLICATIONS

Philipse et al. (Stable hydrosols of metallic and bimetallic nanoparticles immobilized on imogolite fibers, J. Phys. Chem., 1995, vol. 99, pp. 15120-15128.*
Toriyabe et al "Controlled formation of metallic nanoballs during plasma electrolysis", Applied Physics Letters 91, 04150, 2007, p. 1-3.*
Bruggeman et al "Non-thermal plasmas in and in contact with liquids", J. Phys. D: Appl. Phys., 42(2009)053001 (28 pp).*
Sungeun Yang, et al, A distinct platinum growth mode on shaped gold nanocrystals. ChemComm, 2012, 48, 257-259, Nov. 7, 2011.
A. S. Ghosh-Mazumdar, et al, A Pulse Radlolysis Study of Bivalent and Zerovalent Gold in Aqueous Solutions. American Chemical Society, 1968.
Yu-Chuan Liu,et al, Active catalysts of electrochemically prepared gold nanoparticles for the decomposition of aldehyde in alcohol solutions. Elsevier, May 24, 2006.
Andreas Wunder, et al., Albumin-Based Drug Delivery as Novel Therapeutic Approach for Rheumatoid Arthritis. J Immunol 2003;170;4793-4801.

(Continued)

*Primary Examiner* — Xiuyu Tai
(74) *Attorney, Agent, or Firm* — Mark G. Mortenson

(57) ABSTRACT

The present invention relates to novel gold-platinum based bi-metallic nanocrystal suspensions that have nanocrystal surfaces that are substantially free from organic or other impurities or films associated with typical chemical reductants/stabilizers and/or raw materials used in nanoparticle formation processes. Specifically, the surfaces are "clean" relative to the surfaces of metal-based nanoparticles made using chemical reduction (and other) processes that require organic (or other) reductants and/or surfactants to grow (and/or suspend) metal nanoparticles from metal ions in a solution. The invention includes novel electrochemical manufacturing apparatuses and techniques for making the bi-metallic nanocrystal suspensions. The techniques do not require the use or presence of chlorine ions/atoms and/or chlorides or chlorine-based materials for the manufacturing process/final suspension. The invention further includes pharmaceutical compositions thereof and the use of the bi-metallic nanocrystals or suspensions or colloids thereof for the treatment or prevention of diseases or conditions for which metal-based therapy is already known, including, for example, for cancerous diseases or conditions.

29 Claims, 79 Drawing Sheets

(56) References Cited

OTHER PUBLICATIONS

Shenghu Zhou, etal. AuPt Alloy Nanoparticles for CO-Tolerant Hydrogen Activation: Architectural EffectsInAu—PtBImetalliacNanocrystals. Advanced Functional Materials, Sep. 5, 2007.

Katrin Hartl, et al. AuPt core—shell nanocatalysts with bulk Pt activity. Elsevier, Electrochemistry Communications 12(2010)1487-1489.

Fabio Terzi, et al. Au/Pt nanoparticle systems in methanol and carbon monoxide electroxidation. Elsevier,ElectrochimicaActa56(2011)3673-3678.

Dingsheng Wang, et al. Bimetallic Nanocrystals: Liquid-Phase Synthesis and Catalytic Applications. Advanced Materials 2011, 23, 1044-1060.

M. Nakanishi, et al. Characterization of binary gold/platinum nanoparticles by sonochemistry technique. Elsevier,Applied Surface Science 241(2005)209-212.

H. Takatani, et al. Characterization of Noble Metal Alloy Nanoparticles Prepared byUltrasound Irradlation. Rev.Adv.Mater. Sci 5 (2003)232-238.

Suresh K. Balasubramanian, et al. Characterization, purification, and stability of gold nanoparticles. Elsevier,Biomaterials 31 (2010)9023-9030.

R.K. Roy, et al. Deposition of continuous platinum shells on gold nanoparticles by chemical preciptation. Elsevier,Journal of Colloid and Interface Science 369 (2012)91-95.

Qing Ma, et al. Elucidating Chemical and Morphological Changes in Tetrachiloroauric Solutions Induced by X-ray Photochemical Reaction. J. Phys. Chem A 2008, 4568-4572.

Takahiro Nakamura, et al. Fabrication of Gold Platinum Nanoalloy by High-Intensity Laser Irradiation of Solution. The Minerals,Metals &Materials Society, 2011 vol.2.

Takahihro Nakamura, et al. Fabrication of gold-platnium nanoparticles by intense femtosecond laser irradiation of aqueous solution. Optical Society of America 2010.

Takahiro Nakamura, et al. Fabrication of gold-platinum nanoparticles by intense, femtosecond laser irradiation of aqueous solution. Optical Society of American 2009.

Joseph Lik Hang Chau, et al. Femtosecond laser synthesis of bimetallic Pt—Au nanoparticles. Elsevier Materials Ltters 65 (2011)804-807.

Yuliati Herbani, et al. Femtosecond Laser-Induced Formation of Gold-Rich Nanoalloys from the Aqueous Mixture of Gold-Silver Ions, Journal of Nanomaterials Oct. 2010.

Bridgid Nekesa Wanjala, et al. Gold—platinum nanoparticles: alloying and phase segregation. Journal of Materials Chemistry. J. Materials Chemistry, 2011, 21, 4012-4020.

P. Hernandez-Fernandez, et al. InfluenceOfThePrep.RouteOfBimetallicPt—AuNanoparticleElectrocatalystsFor TheOxygenReductionReaction. J.Phys.Chem. C 2007, 111,2913-2923.

Yu-Chuan Liu, et al. NewPathwayForSonoelectrochemicalSynthesisOfGold-silverAlloyNanoparticlesFromTheirBulkSubstrates. Elesevier,Chem. PhysicsLetters 400(2004)436-440.

Keng-Liang Ou, et al. New strategy to prepare enriched and small gold nanoparticles by sonoelectrochernical pulse methods. Eisevier,ElectrochimicaActa 58(2011)497-502.

Cheng-Liang Wang, et al. One-pot synthesis of AuPt alloyed nanoparticles by intense x-ray Irradiation. Nanotechnology 22(2011)065605(6pp).

Gerd Stehle, et al. Pharmacokinetics of methotrexate-albumin conjugates in tumor-bearing rats. Anti-Cancer Drugs 1997, vol. 8, pp. 835-844.

Dam Zhao, et al. Platinum covering of gold nanoparticles for utilization enhancement of Pt in electrocatalysts. Physical Chemistry Chemical Physics. 2006, vol. 8, 5106-5114.

J. Monzo, et al. Removing Polyvinylpyrrolidone from Catalytic Pt Nanoparticles without Modification of Superficial Order, ChemPhysChem 2012,13,709-715.

Yu-Chuan Liu, et al. Size-Controlled Synthesis of Gold Nanoparticies from Bulk Gold Substrates by Sonoelectrochamical Methods. J. Phys. Chem. B 2004, 108,19237-19240.

Yosio Nagata, et al. Sonochemical Formation of Gold Particles in Aqueous Solution. Radiation Research, vol. 146, No. 3 (Sep. 1996) pp. 333-338.

Veronica Saez, et al. Sonoelectrochemical Synthesis of Nanoparticles. Molecules 2009, 14, 4284-4299; doi:10.3390/molecules 14104284.

Fujimoto, Taku, et al. Sonolytical Preparation of Various Types of Metal Nanoparticles in Aqueous Solution. Pergamon. Scripta meter. 44(2001)2183-2186.

Fu-Der Mai, et al. Strategy of fabricating enriched gold nanoparticles based on electrochemical methods. Elsevier. Materials Letters 65 (2001)1788-1790.

Chang-Hai Wang, et al. Structural properties of 'naked' gold nanoparticles formed by synchrotron X-ray irradiation. Journal of Synchrotron Radiation ISSN 0909-0945 Sep. 13, 2007.

Gui-Rong Zhang, et al. Surprisingly Strong Effect of Stabilizer on Properties OfAuNanoparticlesAndPtAuNanostructuresInElectrocatalysis. Nanoscale Jul. 21, 2010: DOI: 10.1039/c0nr00295j. This journal is (c) The Royal Society of Chemistry 2010. Engineering Dept. Chemistry,Tsinghua Univ.Bejiing, CN.

Yung-Chin Yang, et al. Synchrotron X-ray synthesis of colloidal gold particles for drug delivery. Elsevier. Materials Chemistry & Physics 100 (2006) 72-76.

Hamed Ataee-Esfahani, etal. SynthesisOf Bimetallic Au@Pt Nanoparticies with Au Core and NanostructuredPtShellTowardHighlyActiveElectrocatalysts. Chem. Mater.2010, 22,6310-6318.

Peter No. Njoki, et al. Synthesis of Bimetallic AuPt Nanoparticles in Aqueous Solution and Electrocatalytic Activity. Mater.Res.Soc. Symp.Proc.vol. 900E 2006 Mater.ResearchSoc.

Qingming Shen, et al. Synthesis of stabilizer-free gold nanoparticles by pulse sonoelectrochemical method. Elsevier. Ultrasonics Sonochemistry 18(2011)231-237.

Gerd Stehle, et al. The loading rate determines tumor targeting properties of methotrexate-albumin conjugates in rats. Anti-Cancer Drugs 1997,8,pp. 677-685.

Iseult Lynch, et al. The nanoparticle-protein complex as a biological entity; a compled fluids and surface science challenge for the 21st centruy. Elsevier. Advances in Colloid and Interface Science 134-135 (2007) 167-174.

Suresh K. Balasubramanian, et al. Characterization, purification, and stability of gold nanoparticles. Elsevier,Biomaterials 31 (2010) 9023-9030.

J. Kimling, et al. Turkevich Method for Gold Nanoparticles Synthesis Revisited J. Phys. Chem B 2006, 110, 1500-15707.

Silvia H. De Paoli Lacerda, et al. Interaction of Gold Nanoparticles with Common Human Blood Proteins. American Chemical Society, vol. 4, No. 1, 365-379-2010.

Nagender Reddy Panyala, et al. Gold and nano-gold in medicine: overview, toxicology and persepectives. Journal of Applied Biomedicine, 7: 75-91, 2009, ISSN 1214-0287.

Yang Qiu, et al. Surface chemistry and aspect ratio mediated cellular uptake of Au nanorodes. Elsevier. Biomaterials 31 (2010) 7606-7619.

Toshio Sakai, et al. Surfactant- and reducer-free synthesis of gold nanoparticle in aqueous solutions. Elsevier-Colloids&Surfaces A: Physicochem.Eng.Aspects 347 (2009)18-26.

Ralph A. Sperling, et al. Biological applications of gold nanoparticles. RSC Publishing, Chemical Society Reviews, vol. 37 No. 9; Sep. 2008: pp. 1745-2140

Scott F. Sweeney, et al. Rapid Purification and Size Separation of Gold Nanoparticled via Diafiltration. J.Am.Chem.Soc. vol. 128, No. 10, 2006.

Bridgid Nekesa Wanjala, et al. Gold-platinum nanoparticles: alloying and phase segregation. Journal of Materials Chemistry, 2011, 21, 4012-4020 /4019.

Robin Whyman. Gold Nanoparticles—A Renaissance in Gold Chemistry. Department of Chemistry, University of Liverpool, UK: Gold Bulletin 1996,29(1).

(56) References Cited

OTHER PUBLICATIONS

Simona E. Hunyadi Murph, et al. Tuning of size and shape of Au—Pt nanocatalysts for direct methanol fuel cells. J Nanopart Res (2011) 13:6347-6364.

Derrick Mott, et al. Nanocrystal and surface alloy properties of bimetallic Gold-Platinum nanoparticles. Nanoscale Res Lett (2007) 2:12-16 Nano Express.

* cited by examiner

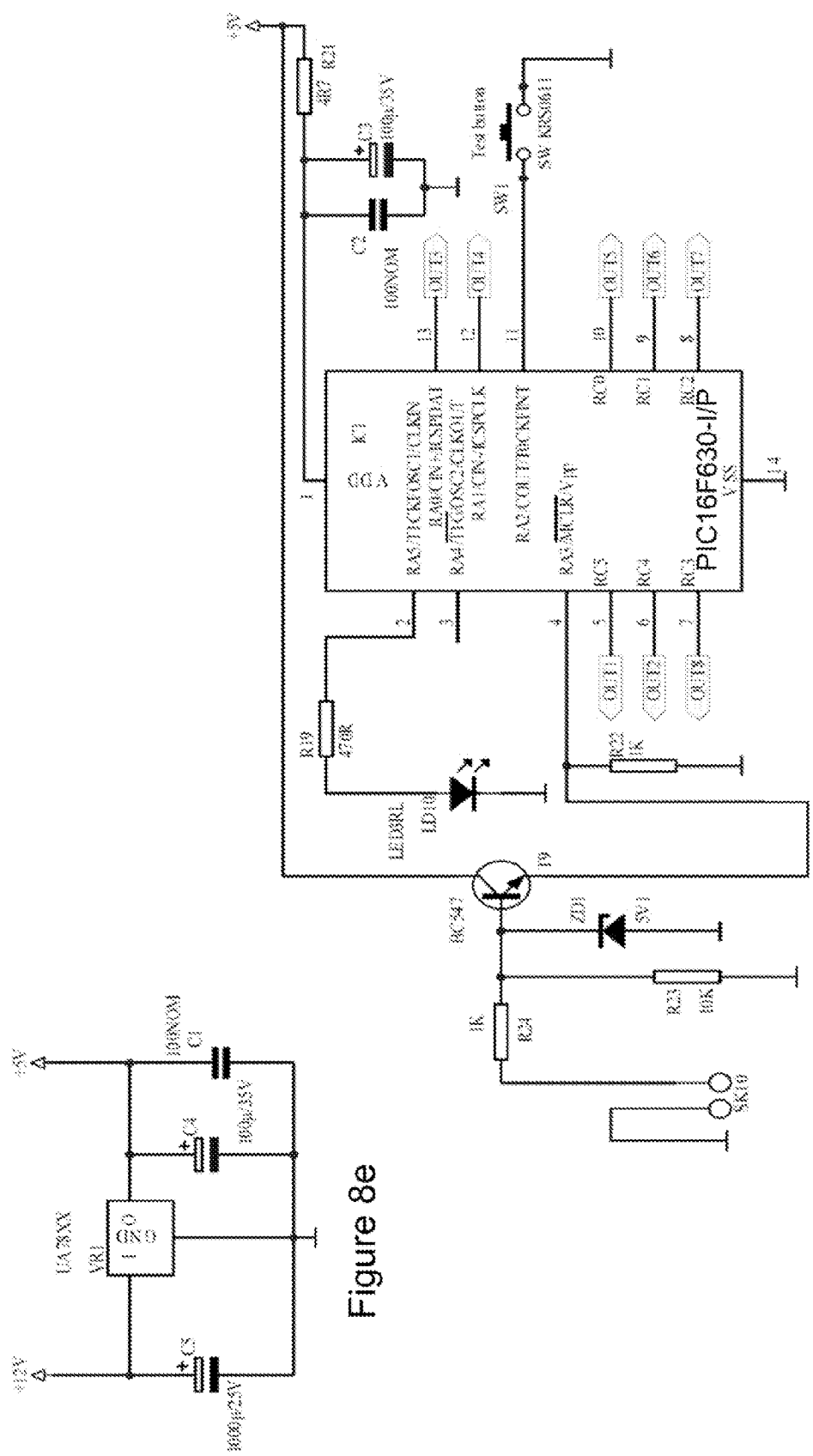

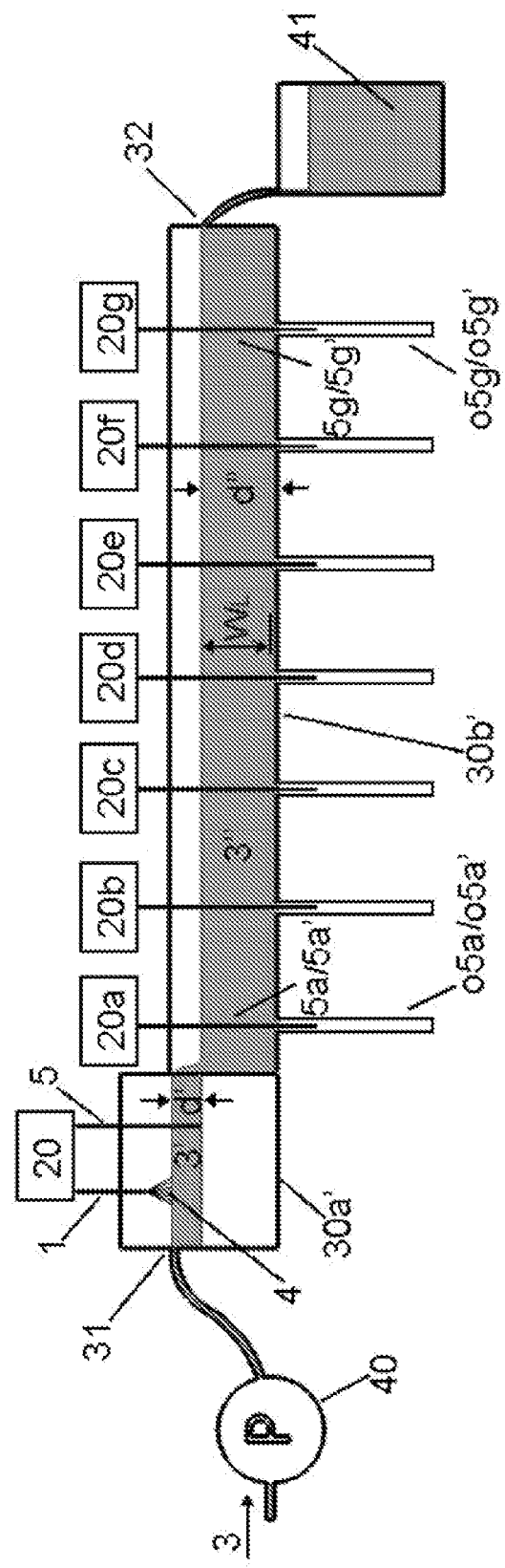

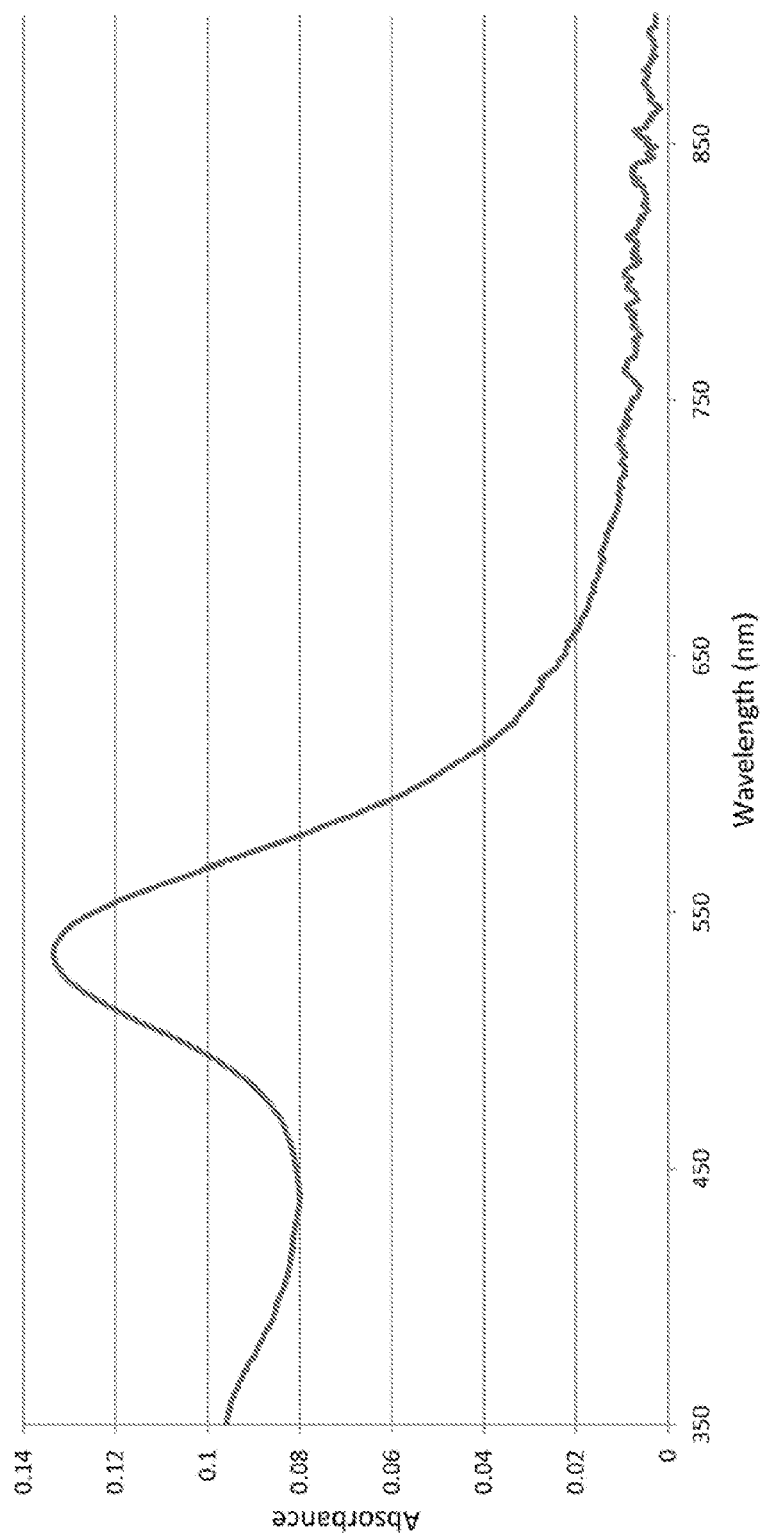

PB-013

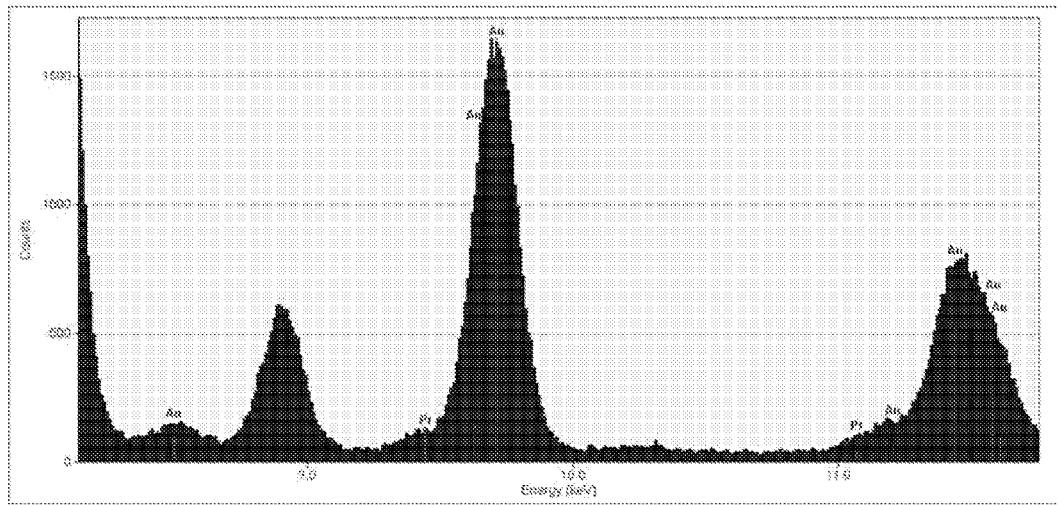
Figure 22a: EDS1
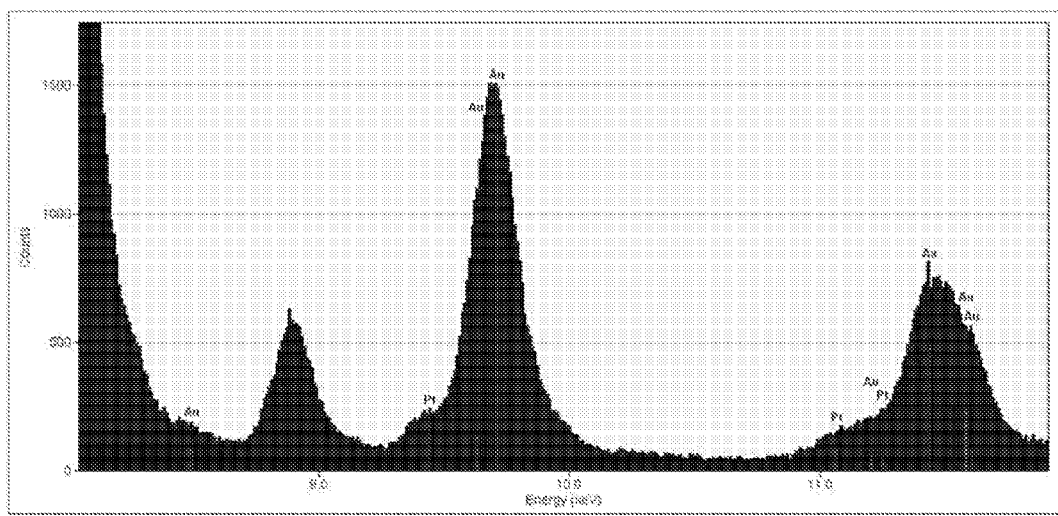
Figure 22b: EDS2

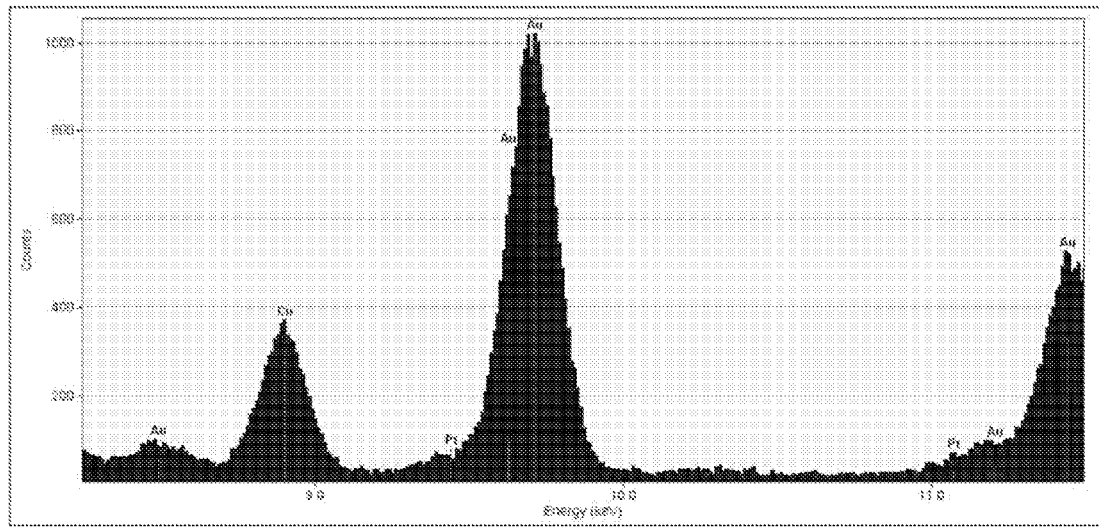
Figure 24a: EDS1
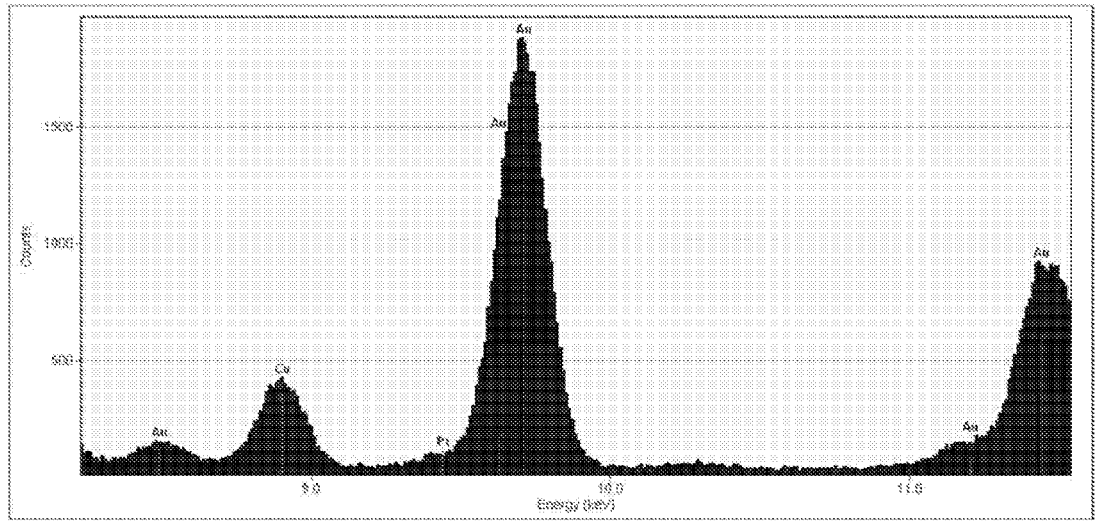
Figure 24b: EDS2

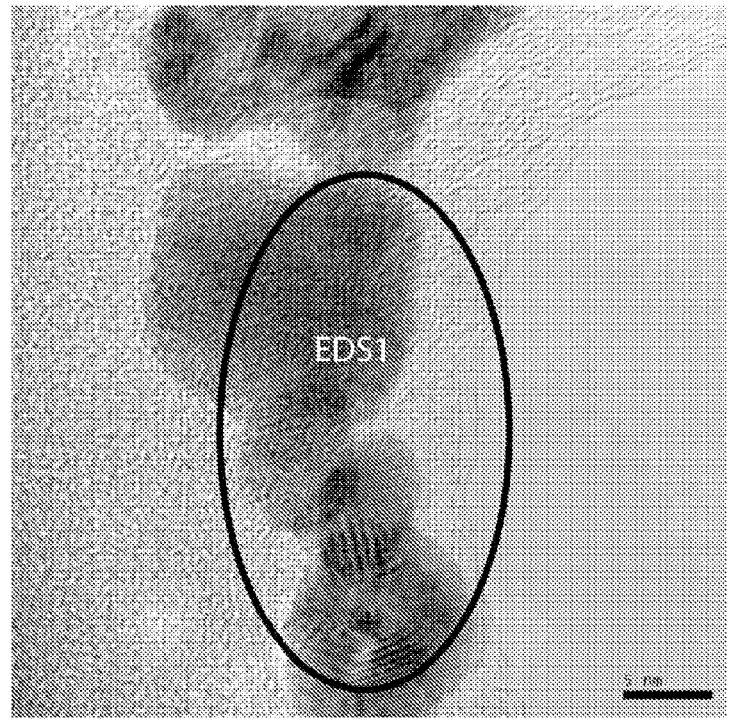
Figure 25a
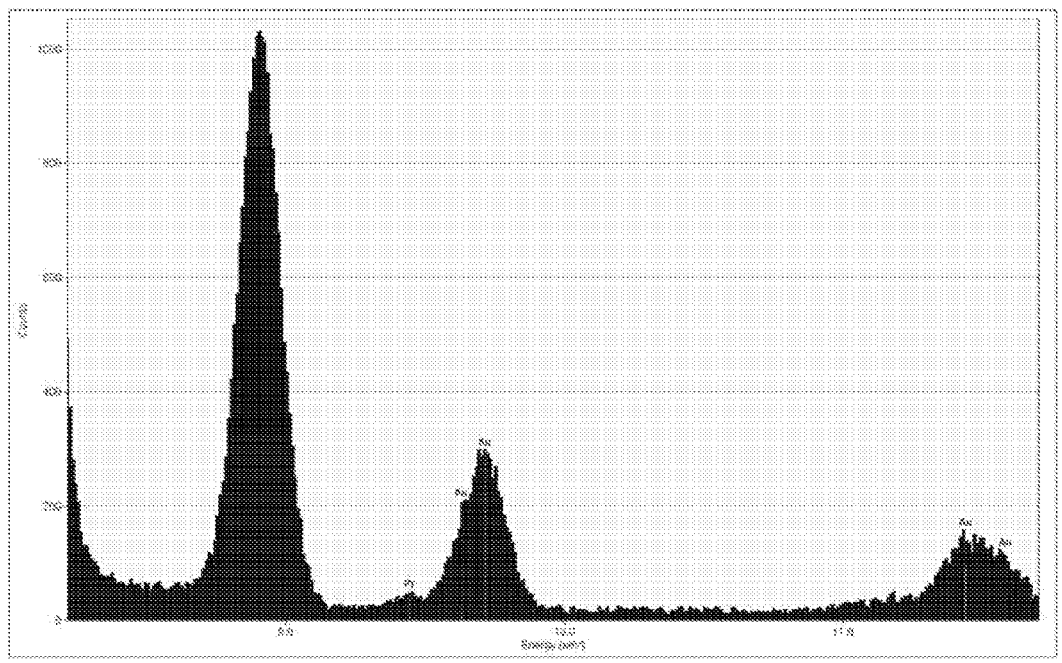
Figure 25b: EDS1

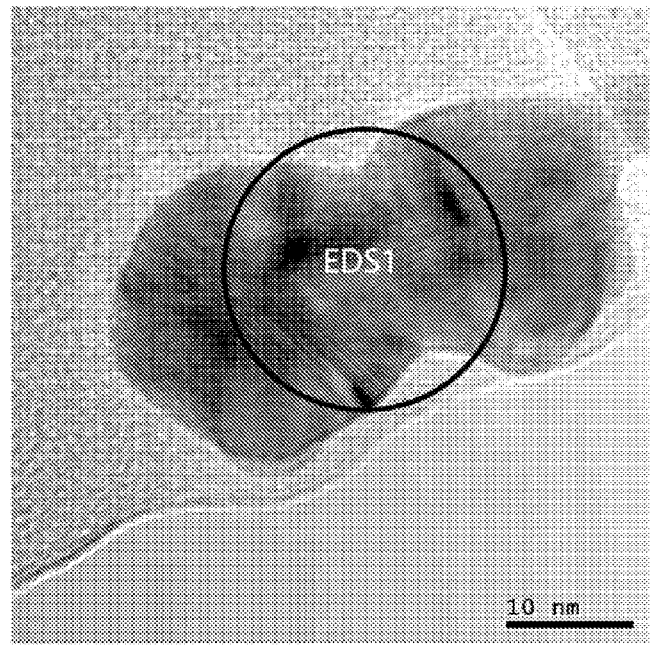
Figure 26a
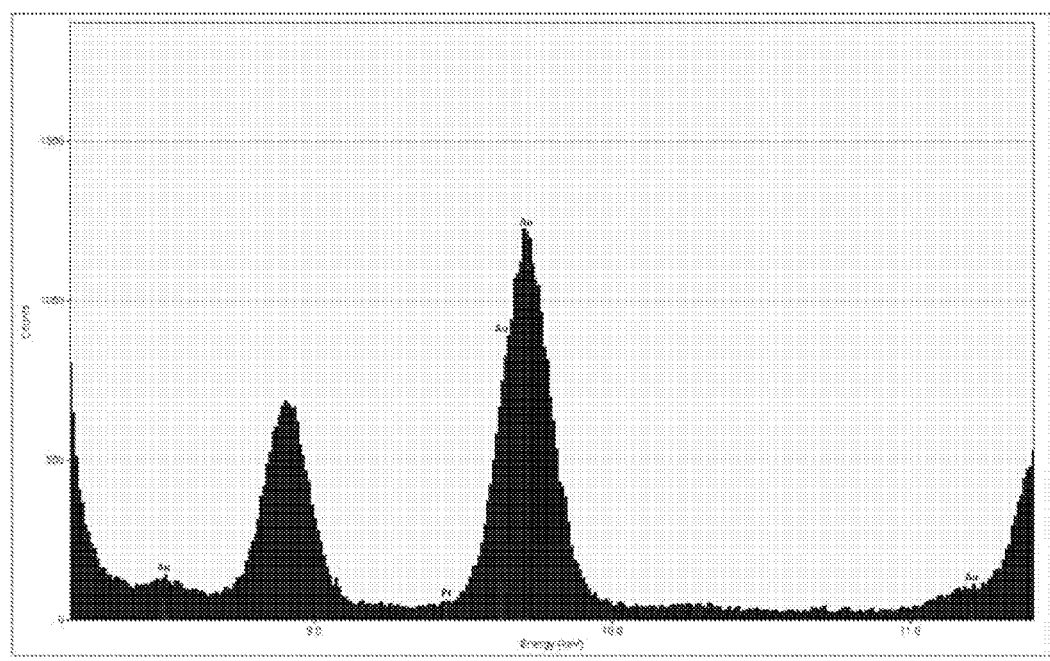
Figure 26b: EDS1

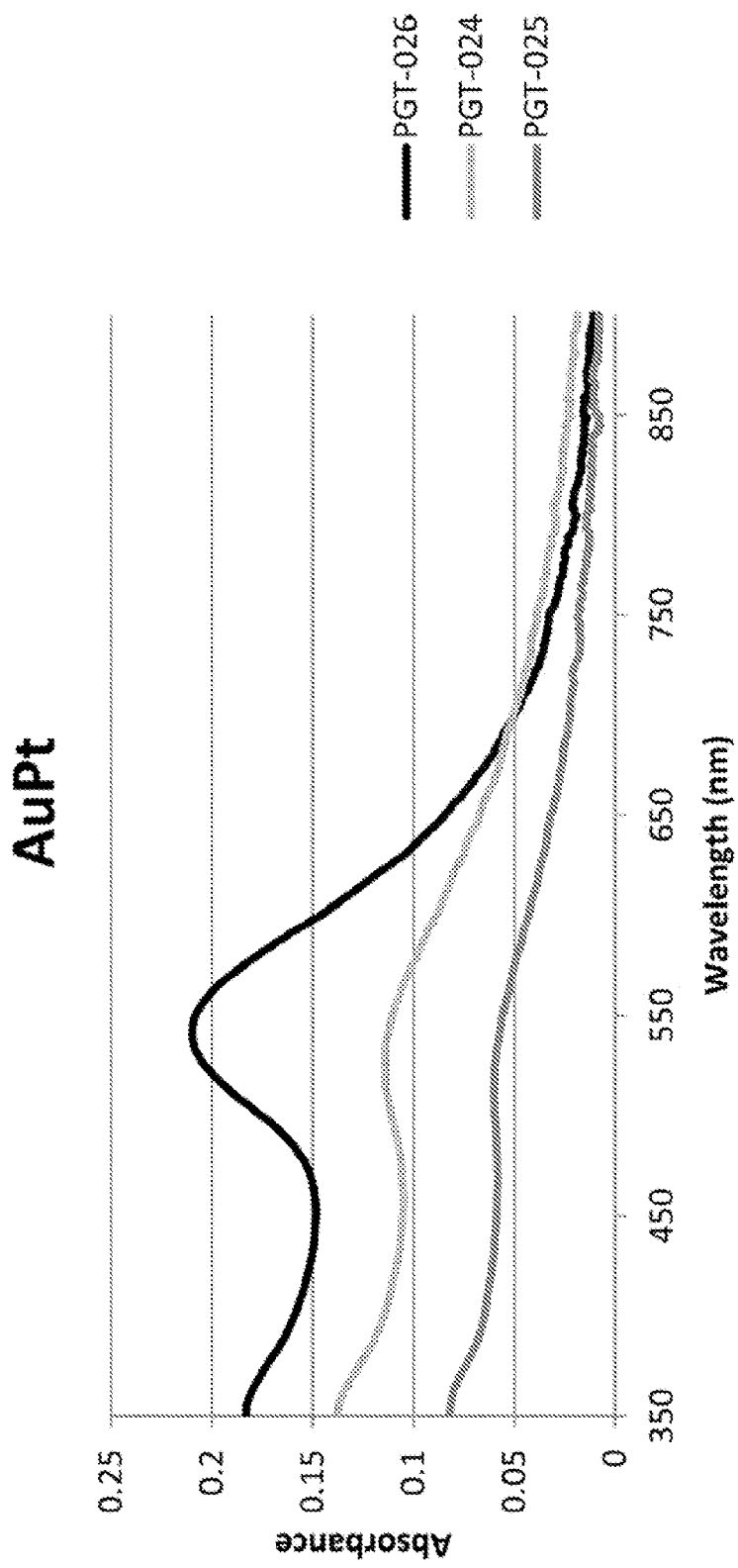

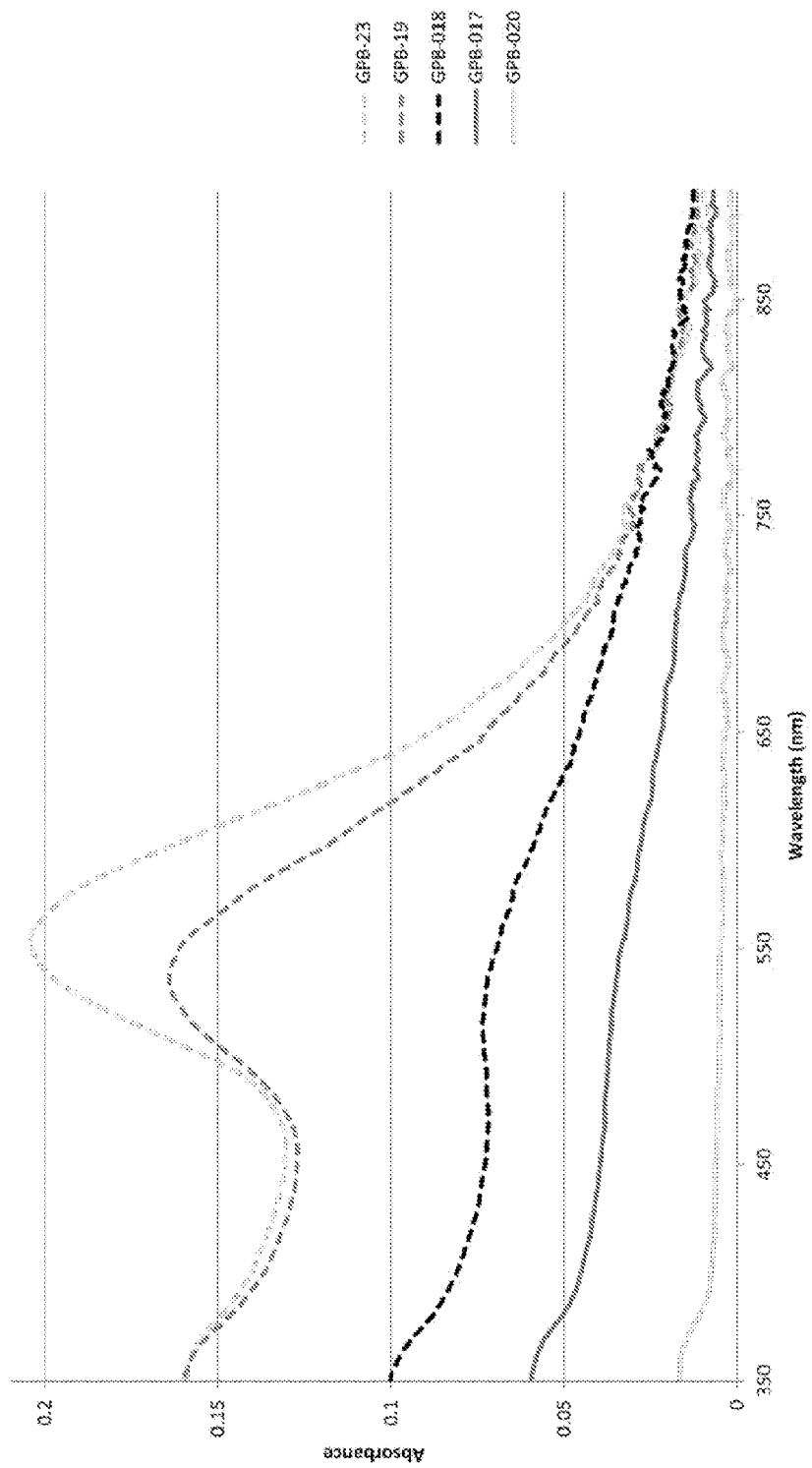

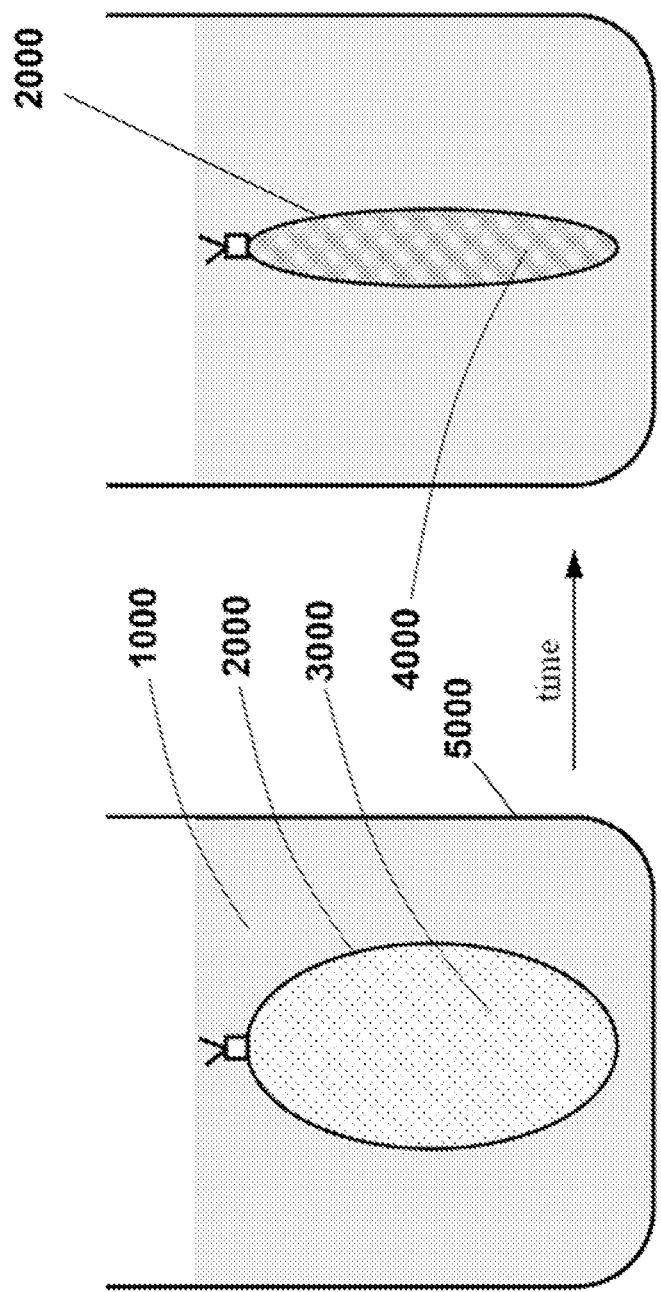

GOLD-PLATINUM BASED BI-METALLIC NANOCRYSTAL SUSPENSIONS, ELECTROCHEMICAL MANUFACTURING PROCESSES THEREFOR AND USES FOR THE SAME

The present application claims priority to U.S. Ser. No. 61/469,525 filed on Mar. 30, 2011.

FIELD OF THE INVENTION

The present invention relates to novel gold-platinum based bi-metallic nanocrystal suspensions that have nanocrystal surfaces that are substantially free from organic or other impurities or films associated with typical chemical reductants/stabilizers and/or raw materials used in nanoparticle formation processes. Specifically, the surfaces are "clean" relative to the surfaces of metal-based nanoparticles made using chemical reduction (and other) processes that require organic (or other) reductants and/or surfactants to grow (and/or suspend) metal nanoparticles from metal ions in a solution.

The invention includes novel electrochemical manufacturing apparatuses and techniques for making the bi-metallic nanocrystal suspensions. The techniques do not require the use or presence of chlorine ions/atoms and/or chlorides or chlorine-based materials for the manufacturing process/final suspension. The invention further includes pharmaceutical compositions thereof and the use of the bi-metallic nanocrystals or suspensions or colloids thereof for the treatment or prevention of diseases or conditions for which metal-based therapy is already known, including, for example, for cancerous diseases or conditions.

BACKGROUND OF THE INVENTION

One motivation for making metallic-based nanoparticles is the novel performance achieved at the nano-scale relative to bulk materials. Materials of nanoscopic dimensions offer a variety of different properties than those observed on the macroscale, thus potentially enabling a variety of unique applications. In particular, nanometals exhibit a variety of electronic, optical, magnetic and/or chemical properties which are typically not achievable when metallic materials are in their bulk form. For example, metals that are relatively inert at the macroscale, such as platinum and gold, are excellent catalysts at the nanoscale. Further, combinations of two different metals (bi-metallic) at the nanoscale offer further intriguing performance issues. The different metals may result in mixtures of metals, alloys or heterogeneous structures, each of which my exhibit different physical properties and/or performance characteristics. Applications for bi-metallic nanoparticulate metals include electronics and computing devices, bionanotechnology, medical treatment and diagnosis and energy generation and storage. The use of these bi-metallic nanometals for a variety of applications requires efficient and safe approaches for manufacturing such materials.

In general, two fundamentally different approaches have been used to manufacture bi-metallic nanomaterials and they are referred to as "top-down" and "bottom-up" approaches. In the top-down approach, bi-metallic nanomaterials are manufactured from larger entities typically, without atomic-level control. Typical top-down approaches include such techniques as photolithography and electron-beam lithography which start with large materials and use either machining or etching techniques to make small materials. Laser ablation is also a known top-down approach.

In contrast, in the "bottom-up" approach, bi-metallic nanomaterials are manufactured from two or more molecular components which are caused to be assembled into bi-metallic nanoparticulate materials. In this regard, building blocks are first formed and then the building blocks are assembled into a final nano-material. In the bottom-up approach, there are a variety of general synthetic approaches that have been utilized. For example, several bi-metallic approaches include templating, chemical synthesis, sonochemical approaches, electrochemical approaches, sonoelectrochemical approaches, thermal and photochemical reduction methods including γ-ray, x-ray, laser and microwave, each of which has certain negative process and/or product limitations associated therewith.

Whichever approach is utilized, results of bi-metallic particle size control, particle size distribution, shape control, configuration or structure control, ability to scale up, and compatibility of the formed bi-metallic nanomaterial in the ultimate application, are all issues to be considered.

In the case where two metals are formed into bi-metallic nanoparticles, further considerations such as whether the bi-metallic nanoparticles are alloys, partial alloys or partially phase segregated or completely phase segregated are also important because the specific configuration of the nanoparticles can result in different performance (e.g., biologic or catalytic). A variety of techniques exist for forming two different metals into a variety of bi-metallic nanoparticles, some of which are discussed below.

A. Chemical Reduction Techniques

Michael Faraday is credited with making the first colloidal gold suspension by chemical reduction methods around the 1850's (Faraday, 1857). Faraday used reduction chemistry techniques to reduce chemically an aqueous gold salt, chloroaurate (i.e., a gold (III) salt), utilizing either phosphorous dispersed into ether (e.g., $CH_3—CH_2—O—CH_2—CH_3$), or carbon disulfide (i.e, $CS_2$), as the reductant.

Today, most colloidal gold preparations are made by a reduction of chloric acid (hydrogen tetrachloroaurate) with a reductant like sodium citrate to result in "Tyndall's purple." There are now a variety of "typical" reduction chemistry methods used to form colloidal gold. Specifically, several classes of synthesis routes exist, each of which displays different characteristics in the final products (e.g., colloidal gold nanoparticles) produced thereby. It has been noted that in addition to the strength, amount and type of the reductant utilized, the action of a stabilizer (i.e., the chemical utilized in the solution phase synthesis process) is critical (Kimling, 2006).

While Faraday introduced colloidal gold solutions, the homogenous crystallization methods of Turkevich and Frens (and variations thereof) are most commonly used today and typically result in mostly spherical-shaped particles over a range of particle sizes (Kimling, 2006). Specifically, most current methods start with a gold (III) complex such as hydrogen tetrachloroaurate (or chloric acid) and reduce the gold in the gold complex to gold metal (i.e., gold (0) or metallic gold) by using added chemical species reductants, such as Na thiocyanate, White P, $Na_3$ citrate & tannic acid, $NaBH_4$, Citric Acid, Ethanol, Na ascorbate, $Na_3$ citrate, Hexadecylaniline and others (Brown, 2008).

Metal nanoparticle synthesis in solution(s) commonly requires the use of surface-active agents (surfactants) and/or amphiphilic polymers as stabilizing agents and/or capping agents. It is well known that surfactants and/or amphiphilic polymers serve critical roles for controlling the size, shape and stability of dispersed particles (Sakai, 2008).

Bi-metallic nanocrystals have been formed by a number of different techniques including forming nanoparticles from the solid, gaseous and solution states. The solid state typically requires high temperature heating and annealing. The typical gaseous state approaches usually utilize molecular beam techniques, namely, the vaporization of mixed metallic powder by lasers, pulsed-arc beams, etc. However, the solution state is the much more heavily utilized bi-metallic nanoparticle formation technique. In a typical solution-based procedure, the proper chemical reactants (e.g., metal-based salts and reductants and/or stabilizers), proper control of certain intermediate reactions (which can or do occur), and control of corresponding crystallization reactions are required to achieve desired metallic nanoparticles (Wang, 2011). Further, different types of bi-metallic nanocrystals can be achieved such as a core/shell (also known as a hetero-aggregate), a hetero-structure or hetero-aggregate, an intermetallic, a mixture or alloy, as well as various core shell arrangements (Wanjala, 2011). All of these different types of bi-metallic nanocrystals can have quite different physical performance capabilities.

In addition, it is known that making gold-platinum alloys can be quite difficult because such alloys are meta-stable and difficult to prepare (Zhou, 2007). Typical manufacturing difficulties arise from a variety of processing issues including the different oxidation-reduction potentials that exist for different metals/metal ions. Further, it is known that when platinum and gold are alloyed, the bi-metallic Pt—Au nanoparticles display unique physiochemical properties different from those of mono-metallic and non-alloyed solids (Hernandez-Fernandez, 2007).

A variety of different approaches exist for the formation of Pt—Au bi-metallic core-shell nanostructures, but typically gold is located at the core and platinum is located on the surface of the formed bi-metallic nanocrystals. It is relatively easy to make such core-shell structures due to the different reduction potentials of typical Au ions and Pt ions in a solution (Ataee-Esfahani, 2010).

Further, awareness is now growing that the reductant and/or stabilizers and/or other raw material components used during the formation of nanoparticles in general, including bi-metallic Pt—Au nanoparticles, may have a very large effect on the resultant performance of the nanoparticles. In particular, for example, while many have historically observed and reported on differential performance of nanoparticles due to size and shape of the nanoparticle effects (i.e., it is believed that size and shape dictate performance), only recently have attempts been made to quantify the effects of materials present at the surface of the nanoparticle. The presence of impurities such as those coming from a variety of stabilizers and/or reductants and/or the raw materials used during the manufacturing of nanoparticles, may alter performance more dramatically than size and shape alone (e.g., size and shape may be secondary, in some cases, to surface chemistry). In this regard, some are now "sounding an alert" that the stabilizer effect (e.g., impurities on the surface of nanoparticles) on properties of nanoparticles induces changes in their catalytic properties. Thus, consideration of how the nanoparticles were formed and their particular surface chemistry is paramount in understanding their performance characteristics (Zhang, 2010).

Further, it has been noted that the considerable amount of surfactants and dispersants used are also a concern because such additives complicate the assessment of the true catalytic activity of a platinum surface (e.g., the performance of the nanoparticle) (Roy, 2012).

Since the importance of nanoparticle surface chemistry is now beginning to be focused on as a key for understanding and controlling nanoparticle performance issues, attempts are now being made to remove constituents associated with manufacturing processes that are located on the surface of the formed nanoparticle (e.g., the outer layer or the presence of constituents formed as a result of reducing agent and/or surface capping agent and/or other raw materials used) including going so far as utilizing an oxygen plasma combined with electrochemical stripping (Yang, 2011). However, such surface modification approaches result in their own changes to the nanoparticle surface.

Some have measured certain properties associated with the surface morphology (i.e., constituents located on the nanoparticle surface as a function of the formation process) and concluded that the final surface morphology of nanoparticles affects their underlying catalytic activity, perhaps even more than size and shape effects (Liang, 2007).

B. Cleaning Colloidal Gold Nanoparticles Made by Chemical Reduction Techniques In some cases, the reductant surface coating or film is permitted to remain as an impurity on the surface of the nanoparticles, but in other cases, it is attempted to be removed by a variety of somewhat complex and costly techniques. When removed, the coating typically is replaced by an alternative composition or coating to permit the nanoparticles to stay in suspension when hydrated. The influence of surface purity on the chemistry and properties of nanoparticles is often overlooked; however, results now indicate that the extent of purification can have a significant impact (Sweeney, 2006). These researchers noted that sufficient purification of nanoparticles can be more challenging that the preparation itself, usually involving tedious, time-consuming and wasteful procedures such as extensive solvent washes and fractional crystallization. Absent such purification, the variables of surface chemistry-related contaminants on the surface of chemically reduced nanoparticles affects the ability to understand/control basic structure-function relationships (Sweeney, 2006).

Subsequent processing techniques may also require a set of washing steps, certain concentrating or centrifuging steps, and/or subsequent chemical reaction coating steps, all of which are required to achieve desirable results and certain performance characteristics (e.g., stabilization due to ligand exchange, efficacy, etc.) for the nanoparticles and nanoparticle suspensions (Sperling, 2008). In other cases, harsh stripping methods are used to ensure very clean nanoparticle surfaces (Panyala, 2009).

Thus, others have concluded that the development of nanoparticles in the management, treatment and/or prevention of diseases is hampered by the fact that current manufacturing methods for nanoparticles are by-and-large based on chemical reduction processes. Specifically, Robyn Whyman, in 1996, recognized that one of the main hindrances in the progress of colloidal golds manufactured by a variety of reduction chemistry techniques was the lack of any "relatively simple, reproducible and generally applicable synthetic procedures" (Whyman 1996).

Others have begun to recognize the inability to extricate completely adverse physical/biological performance of the formed nanoparticles from the chemical formation (i.e., chemical reduction) processes used to make them. In this regard, even though somewhat complex, expensive and non-environmentally friendly, washing or cleaning processes can be utilized to attempt to alter or to clean the surface of nanoparticles produced by reduction chemistry, elements of the chemical process may remain and affect the surface of nanoparticles (and thus their functioning, including biological efficacy and/or toxicity).

Others have developed methods for removal of PVP by a facile and novel chemical method combined with minimization of chemical changes during removal (Monzo, 2012) in order to attempt to achieve clean nanoparticle surfaces. However, removal of such materials through traditional washing approaches remain elusive.

In each of the colloidal compositions produced by reduction chemistry approaches, it is apparent that a surface coating comprising one or more elements of the reductant and/or the surfactant or capping agent will be present on (or in) at least a portion of the suspended nanoparticles. The use of a reductant (i.e., a reducing agent) may assist in suspending the nanoparticles in the liquid (e.g., water). However, the reducing agent coating or surface impurity is sometimes added to or even replaced by surfactant coatings or capping agents. Such reductant/surfactant coatings or films can be viewed as impurities located on and/or in the metal-based nanoparticles and may result in such colloids or sols actually possessing more of the properties of the protective coating or film than the nanoparticle per se (Weiser, p. 42, 1933).

For example, surfactants and amphiphilic polymers become heavily involved not only in the formation of nanoparticles (thus affecting size and shape), but also in the nanoparticles per se. Surface properties of the nanoparticles are modified by reductant coatings and/or surfactant molecule coatings (Sperling, 2008).

C. Nanoparticle Fabrication Techniques that do not Rely on Added Chemical Reductants 1. Sonoelectrochemistry A variety of sonoelectrochemical techniques exist for producing both single metallic nanoparticles and bi-metallic nanoparticles. Sonoelectrical processes typically direct electric and acoustic energy toward metal-based raw material salts (e.g., $HAuCl_4.4H_2O$ ($AuCl_4^-$), $NaAuCl_4.2H_2O$, $H_2PtCl_6.6H_2O$, $HAuCl_3.3H_2O$, etc.) and metal ions in those salts are caused to be reduced by one or more reductant species created by the sonoelectrochemial method. In this regard, often a single electrode induces the growth of nanoparticles thereon by an electrochemical step, followed by an acoustic step which, more or less, attempts to eject the nanoparticles off from the electrode and also creates additional reductant material by, for example, lysis of water molecules. In this regard, a single electrode typically performs a dual duty of both electrochemistry (e.g., nanoparticle formation) and acoustic chemistry (e.g., reductant formation) (Nagata, 1996).

Most of the sonoelectrochemical techniques utilize one or more reductants and/or capping agents in addition to any of those which may be formed in situ by the process. In this regard, a variety of different polymers have been utilized as capping agents for single metallic nanoparticles (Saez, 2009). However, work by others (Liu, 2004; Ou, 2011; Mai, 2011; and Liu, 2006) all disclose similar sonoelectrochemical techniques for making gold nanoparticles with sonoelectrochemical pulse methods using, allegedly, no added reductants. For example, utilization of an acid solution in combination with electrochemical cycling to strip gold ions from a gold electrode and form $AuCl_4^-$ compounds in an aqueous solution has been disclosed (Liu, 2004). Subsequently, the gold ions are reduced by created reductant species (e.g., lysis products of $H_2O$) produced in their sonoelectrochemical process. Apparently, however, the concentrations of gold nanoparticles produced are quite limited by this technique (e.g., 3 ppm) without the addition of other materials (e.g., stabilizers) (Ou, 2011).

Alternative sonoelectrochemical methods have been used to make gold nanoparticles. Specifically, starting materials of $HAuCl_4.4H_2O$ and $KNO_3$ were pH-adjusted by adding NaOH to obtain different pH's, with a pH of about 10 being noted as optimal. Nanoparticles having diameters of approximately 20 nm were produced. The surface potential of the gold nanoparticles around the pH of 10 was $-54.65$ mV. It was concluded that the $OH^-$ groups adsorbed on gold nanoparticles and caused electrostatic repulsion therebetween. Thus, no added reductants were necessary (Shen, 2010).

A variety of sonoelectrochemical techniques have also been set forth for making bi-metallic nanoparticles. For example, platinum-gold nanoparticles stabilized by PEG-MS (polyetholeneglycolmonostearate) have been manufactured (Fujimoto, 2001). Further, binary gold/platinum nanoparticles made by sonoelectrochemistry utilizing surfactants (anionic surfactants; sodium dodechal sulfate (SDS) or nonionic surfactant polyetholeneglycolmonostearate PEG-MS) have also been made (Nakanishi, 2005). In this method, the addition of some surfactants is reported as being indispensable (Nakanishi, 2005). Likewise, in some related work, the use of SDS or PEG-MS in combination with various sonoelectrochemical techniques has been reported (Takatani, 2003). These bi-metallic nanocrystals made by sonoelectrochemical techniques all require the use of surfactants.

2. Gamma-Ray Radiation

Radiolytic techniques for making nanoparticles have been directed primarily to single-metals (i.e., not bi-metals). Another older and more complex technique for minimizing or eliminating the need for reducing agents and/or minimizing undesirable oxidation products of the reductant utilizes γ-irradiation from a $^{60}Co$ source at a dose rate of $1.8\times10^4$ rad/h. In this instance, $Au(CN)_2$ was reduced by first creating hydrated electrons from the radiolysis of water and utilizing the hydrated electrons to reduce the gold ions, namely:

$$e_{aq}^- + Au(CN)_2^- \rightarrow Au^0 + 2CN^- \qquad \text{(Henglein, 1998).}$$

Further, the creation of hydrated electrons and OH radicals by pulse activation from a linear accelerator has also occurred (Ghosh-Mazumdar, 1968). Such created species assist in the reduction of various metals from aqueous metallic-based salts.

3. X-Ray Radiation

Most work using x-rays for the manufacture of metal-based nanoparticles has been focused on single metal composition metallic-based nanoparticles, however, some recent work on intense x-ray radiation has also occurred to make alloys (with surfactants).

The use of synchrotron x-ray synthesis of $HAuCl_4$, with added $NaCO_3$, has been used to make colloidal gold nanoparticles without adding additional reducing agent (Yang, 2006). In this technique, a gold salt was dissolved to make a solution and an appropriate amount of $NaHCO_3$ was added thereto. The reported result was particle sizes of 10-15 nm, as measured, a pH of about 7 and the gold suspensions were relatively stable due to the coordination of $OH^-$ groups around the gold nanoparticles (Yang, 2006).

Single metal gold nanosols stabilized by electrostatic protection due to x-ray irradiation has also occurred (Wang, 2007; Wang, 2007). The x-rays generated reductant electrons in the precursor solutions. It was noted that this approach required very intense x-ray beams (thus requiring synchrotron sources) (Wang, 2007; Wang, 2007). Additionally, the nanoparticle suspensions were formed with a pH of 9 and had a surface potential of −57.8+/−mV, as measured by a zeta meter. The formed nanoparticles were about 10 nm in size. Additionally, modification of the pH to values between 6-9 occurred by adding NaOH to the solution (Wang, 2007). Further, the x-rays used are well above the threshold energy for water radiolysis and additional x-ray energy may be causing intermediate reactions that they do not recognize (e.g., kinetic effects) (Wang, 2007).

Further, x-ray photochemical reactions have been used to make gold nanoparticle suspensions (Ma, 2008). It was noted that knowledge of the details of the intermediate reactions prior to nanoparticle formation is critical to controlling size, shape and properties (Ma, 2008).

A one-pot synthesis of Au—Pt alloys by intense x-ray irradiation has also been disclosed (Wang, 2011). The incident x-rays irradiate a gold/platinum salt solution (i.e., $HAuCl_4.3H_2O$ and $H_2PtCl_6.6H_2O$) containing PEG (a common surfactant molecule known to prevent nanoparticle aggregation). However, it was noted that PEG could negatively impact applications that are sensitive to surface conditions, such as catalysis (Wang, 2011).

4. Laser Irradiation

Bi-metallic Pt—Au nanoparticles have been made by femtosecond laser synthesis (Chau, 2011). Specifically, gold and platinum salt solutions (i.e., $HAuCl_4.4H_2O$, $H_2PtCl_6.6H_2O$) were combined with PVP (a known dispersing/stabilizing agent) and the solution was laser irradiated. In related work, high intensity laser radiation of a similar solution of gold and platinum salts occurred. However, in this solution no PEG was added and the resultant nanoparticles were found not to be stable (Nakamura, 2011; Nakamura, 2010; Nakamura, 2009).

5. Laser Ablation

A top-down laser ablation approach to make gold nanoparticles has also been attempted. However, laser ablation typically results in some sort of oxide on the surface of the metal target (Sylvestre, 2004).

6. Electron Accelerators

Bi-metallic gold-platinum nanoparticles have also been made by electron beam irradiation (Mirdamadi-Esfahani, 2010). Specifically, in this approach, the electron beam irradiation creates hydrated electrons and reducing radicals due to the radiolysis of water. Metal salts of gold and platinum (i.e., $KAuCl_4$ and $H_2PtCl_6$) are mixed with polyacrylic acid (i.e., a dispersant/stabilizing agent) and accelerated electrons are directed thereto.

D. Biological Performance

Different surface chemistries or surface films (e.g., the presence of reductant by-product compositions and/or thicknesses (e.g., films) of reductants or reductant by-products) can result in different interactions of the nanoparticles with, for example, a variety of proteins in an organism. Biophysical binding forces (e.g., electrostatic, hydrophobic, hydrogen binding, van der Waals) of nanoparticles to proteins are a function not only of the size, shape and composition of the nanoparticles, but also the type of and/or thickness of the surface impurities or coating(s) on the nanoparticles (Lacerda, 2010).

A better understanding of the biological effects of nanoparticles requires an understanding of the binding properties of the in-vivo proteins that associate themselves with the nanoparticles. Protein absorption (or a protein corona) on nanoparticles can change as a function of nanoparticle size and surface layer composition and thickness. Protein layers that "dress" the nanoparticle control the propensity of the nanoparticles to aggregate and strongly influence their interaction with biological materials (Lacerda, 2010).

Additionally, both the shape and the surface chemistry of nanoparticles influenced cytotoxicity and cellular uptake in model biological systems (Qiu, 2010). However, it was concluded that only the surface chemistry contributes to undesirable cytotoxicity. In particular, it was shown that CTAB-coated (i.e., cetyltrimethlammonium bromide) gold nanoparticles release portions of their coatings at different points in a biological process and/or different location(s) within an organism, which results in toxicity (Qui, 2010).

Further, in an important article published in 2010, the authors state that since 1981, more than 230 published studies utilize gold nanoparticles generated from the citrate reduction method with scarce data on non-gold components in the reaction system (Balassubramanian, 2010). The authors conclude it is clear that much of the testing of biological performance has been skewed by the lack of understanding of components present in/on the nanoparticles (e.g., the surface chemistry) other than nanoparticles per se (Balassubramanian, 2010).

The protein corona which forms on a nanoparticle is important because it is the protein corona that gives the biological identity to the nanoparticle (Lynch, 2007). The surface of the nanoparticle assists in the formation of the protein corona as well as its size and its shape (Lynch, 2007).

Further, albumin-based drug delivery has been recognized as a novel therapeutic approach (Wunder, 2003; Stehle, 1997; Stehle, 1997). Specifically, the albumin-binding assists in delivery of the therapeutic to desirable targeted locations resulting in higher efficacy/lower toxicity.

REFERENCES

The references cited throughout the "Background of the Invention" are listed below in detail.

Ataee-Esfahani, H., Wang, L., Nemoto, Y. & Yamauchi, Y. (2010). Synthesis of Bimetallic Au@Pt Nanoparticles with Au Core and Nanostructured Pt Shell toward Highly Active Electrocatalysts. *Chem. Mater.*, 22, 6310-6318.

Balasubramanian, S. K., Yang, L., Yung, L.-Y. L., Ong, C.-N., Ong, W.-Y. & Yu, L. E. (2010). Characterization, purification, and stability of gold nanoparticles. *Biomaterials*, 31, 9023-9030.

Brown, C. L., Whitehouse, M. W., Tiekink, E. R. T., & Bushell G. R. (2008). Colloidal metallic gold is not bio-inert. *Inflammopharmacology*, 16, 133-137.

Chau, J. L. H., Chen, C.-Y., Yang, M.-C., Lin, K.-L., Sato, S., Nakamura, T., Yang, C.-C. & Cheng, C.-W. (2011). Femtosecond laser synthesis of bimetallic Pt—Au nanoparticles. *Materials Letters*, 65, 804-807.

Faraday, M. (1857). The Bakerian lecture: Experimental relations of gold (and other metals) to light. *Philosoph. Trans. R. Soc. London*, 147, 145-181.

Fujimoto, T., Mizukoshi, Y., Nagata, Y., Maeda, Y. & Oshima, R. (2001). Sonolytical Preparation of Various Types of Metal Nanoparticles in Aqueous Solution. *Scipta mater.*, 44, 2183-2186.

Ghosh-Mazumdar, A. S. (1968). A Pulse Radiolysis Study of Bivalent and Zerovalent Gold in Aqueous Solutions. *Radiation Chemistry*, 193-209.

Henglein, A. & Meisel, D. (1998). Radiolytic Control of the Size of Colloidal Gold Nanoparticles. *Langmuir*, 14, 7392-7396.

Hernandez-Fernandez, P., Rojas, S., Ocon, P., Gomez de la Fuente, J. L., San Fabian, J., Sanza, J., Pena, M. A., Garcia-Garcia, F. J., Terreros, P. & Fierro, J. L. G. (2007) Influence of the Preparation Route of Bimetallic Pt—Au Nanoparticle Electrocatalysts for the Oxygen Reduction Reaction. *J. Phys. Chem. C,* 111, 2913-2923.

Kimling, J., Maier, M., Okenve, B., Kotaidis, V., Ballot, H. & Plech, A. (2006). Turkevich Method for Gold Nanoparticle Synthesis Revisited. *J. Phys. Chem. B,* 110, 15700-15707.

Lacerda, S. H. D. P., et al. (2010). Interaction of Gold Nanoparticles with Common Human Blood Proteins. *American Chemical Society,* 4 (1), 365-379.

Liu, Y.-C., Lin, L.-H. & Chiu, W.-H. (2004) Size-Controlled Synthesis of Gold Nanoparticles from Bulk Gold Substrates by Sonoelectrochemical Methods. *J. Phys. Chem. B,* 108, 19237-19240.

Liu, Y.-C., Yu, C.-C, & Yang, K.-H. (2006). Active catalysts of electrochemically prepared gold nanoparticles for the decomposition of aldehyde in alcohol solutions. *Electrochemistry Communications,* 8, 1163-1167.

Liu, Y.-C., Lee, H.-T. & Peng, H.-H. (2004). New pathway for sonoelectrochemical synthesis of gold-silver alloy nanoparticles from their bulk substrates. *Chemical Physics Letters,* 400, 436-440.

Lynch, I., Cedervall, T., Lundqvist, M., Cabaleiro-Lago, C., Linse, S. & Dawson, K. A. (2007). The nanoparticle-protein complex as a biological entity; a complex fluids and surface science challenge for the 21$^{st}$ century. *Advances in Colloid and Interface Science,* 134-135.

Ma, Q., Divan, R., Mancini, D. C. & Keane, D. T. (2008). Elucidating Chemical and Morphological Changes in Tetrachloroauric Solutions Induced by X-ray Photochemical Reaction. *J. Phys. Chem. A.,* 112, 4568-4572.

Mai, F.-D., Hsu, T.-C., Liu, Y.-C. & Yang, K.-H. (2011). Strategy of fabricating enriched gold nanoparticles based on electrochemical methods. *Materials Letters,* 65, 1788-1790.

Mirdamadi-Esfahani, M., Mostafavi, M., Keita, B., Nadjo, L., Kooyman, P. & Remita, H. (2010). Bimetallic Au—Pt nanoparticles synthesized by radiolysis: Application in electro-catalysis. *Gold Bulletin,* 43, (1).

Monzo, J., Koper, M. T. M. & Rodriguez, P. (2012). Removing Polyvinylpyrrolidone from Catalytic Pt Nanoparticles without Modification of Superficial Order. *Chem Phys Chem,* 13, 709-715.

Nagata, Y., Mizukoshi, Y. Okitsu, K. & Maeda, Y. (1996). Sonochemical Formation of Gold Particles in Aqueous Solution. *Radiation Research,* 146, 333-338.

Nakamura, T., Herbani, Y. & Sato, S. (2011). Fabrication of Gold-Platinum Nanoalloy by High-Intensity Laser Irradiation of Solution. *Supplemental Proceedings,* 2, 3-8.

Nakamura, T., Herbani, Y. & Sato, S. (2010). Fabrication of gold-platinum nanoparticles by intense, femtosecond laser irradiation of aqueous solution. *Optical Society of America.*

Nakamura, T., Magara, H., Herbani, Y., Ito, A. & Sato, S. (2009). Fabrication of gold-platinum nanoparticles by intense, femtosecond laser irradiation of aqueous solution. *Optical Society of America.*

Nakanishi, M., Takatani, H., Kobayashi, Y., Hori, F., Taniguchi, R., Iwase, A. & Oshima, R. (2005). Characterization of binary gold/platinum nanoparticles prepared by sonochemistry technique. *Applied Surface Science,* 241, 209-212.

Ou, K.-L., Yang, K.-H., Liu, Y.-C., Hsu, T.-C. & Chen, Q.-Y. (2011). New strategy to prepare enriched and small gold nanoparticles by sonoelectrochemical pulse methods. *Electrochimica Acta,* 58, 497-502.

Panyala, N. G., Pena-Mendez, E. M., & Havel, J. (2009). Gold and nano-gold in medicine: overview, toxicology and perspectives. *Journal of Applied Biomedicine,* 7, 75-91.

Qiu, Y., et al. (2010). Surface chemistry and aspect ratio mediated cellular uptake of Au nanorods. *Biomaterials,* 31, 7606-7619.

Roy, R. K., Njagi, J. I., Farrell, B., Halaciuga, I., Lopez, M. & Goia, D. V. (2012). Deposition of continuous platinum shells on gold nanoparticles by chemical precipitation. *Journal of Colloid and Interface Science,* 369, 91-95.

Saez, V. & Mason, T. J. (2009). Sonoelectrochemical Synthesis of Nanoparticles. *Molecules,* 14, 4284-4299.

Sakai, T., Enomoto, H., Torigoe, K., Kakai, H. & Abe, M. (2008). Surfactant- and reducer-free synthesis of gold nanoparticles in aqueous solutions. *Colloids and Surface A: Physiocochemical and Engineering Aspects,* 18-26.

Shen, Q., Min, Q., Shi, J., Jiang, L., Hou, W. & Zhu, J.-J. (2011). Synthesis of stabilizer-free gold nanoparticles by puls sonoelectrochemical method. *Ultrasonics Sonochemistry,* 18, 231-237.

Sperling, R. A., Gil, P. R., Zhang, F., Zanella, M., & Parak, W. J. (2008). Biological applications of gold nanoparticles. *Chem. Soc. Rev,* 37, 1896-1908.

Stehle, G., Sinn, H., Wunder, A., Schrenk, H. H., Schutt, S., Maier-Borst, W. & Heene, L. (1997). The loading rate determines tumor targeting properties of methotrexate-albumin conjugates in rats. *Anti-Cancer Drugs,* 8, 677-685.

Stehle, G., Wunder, A., Sinn, H., Schrenk, H. H., Schutt, S., Frei, E., Hartung, G., Maier-Borst, W. & Heene, D. L. (1997). Pharmacokinetics of methotrexate-albumin conjugates in tumor-bearing rats. *Anti-Cancer Drugs,* 8, 835-844.

Sweeney, S. F., Woehrle, G. H. & Hutchison, J. E. (2006). Rapid Purification and Size Separation of Gold Nanoparticles via Diafiltration. *J. Am. Chem. Soc.,* 128, 3190-3197.

Sylvestre, J.-P., Poulin, S., Kabashin, A. V., Sacher, E., Meunier, M. & Luong, J. H. T. (2004). Surface Chemistry of Gold Nanoparticles Produced by Laser Ablation in Aqueous Media. *J. Phys. Chem. B.,* 16864-16869.

Takatani, H., Kago, H., Nakanishi, M., Kobayashi, Y., Hori, F. & Oshima, R. (2003). Characterization of Noble Metal Alloy Nanoparticles Prepared by Ultrasound Irradiation. *Rev. Adv. Mater. Sci.,* 5, 232-238.

Wang, C. H., et al. (2007). Aqueous gold nanosols stabilized by electrostatic protection generated by X-ray irradiation assisted radical reduction. *Materials Chemistry and Physics,* 106, 323-329.

Wang, D. & Li, Y. (2011). Bimetallic Nanocrystals: Liquid-Phase Synthesis and Catalytic Applications. *Adv. Mater,* 23, 1044-1060.

Wang, C.-H., Hua, T.-E., Chien, C.-C., Yu, Y.-L., Yang, T.-Y., Liu, C.-J., Leng, W.-H., Hwu, Y., Yang, Y.-C., Kim, C.-C., Je, J.-H., Chen, C.-H., Lin, H.-M. & Margaritondo, G. (2007). Aqueous gold nanosols stabilized by electrostatic protection generated by X-ray irradiation assisted radical reduction. *Materials Chemistry and Physics,* 106, 323-329.

Wang, C.-H., Chien, C.-C., Yu, Y.-Lu., Liu, C.-J., Lee, C.-F., Chen, C.-H., Hwu, Y., Yang, C.-S., Je, J.-H. & Margaritondo, G. (2007). Structural properties of 'naked' gold nanoparticles formed by synchrotron X-ray irradiation. *J. Synchrotron Rad.,* 14, 477-482.

Wang, C.-L., Hsao, B.-J., Lai, S.-F., Chen, W.-C., Chen, H.-H., Chen, Y.-Y., Chien, C.-Ch. Cai, X., Kempson, I. M., Hwu, Y. & Margaritondo, G. (2011). One-pot synthesis of AuPt alloyed nanoparticles by intense x-ray irradiation. *Nanotechnology*, 22, 065605-065611.

Wanjala, B. N., Luo, J., Fang, B., Mott, D. & Zhong, C-J. (2011). Gold-platinum nanoparticles: alloying and phase segregation. *J. Mater. Chem*, 21, 4012-4020.

Weiser, H. B. *Inorganic Colloid Chemistry—Volume I: The Colloidal Elements*. New York: John Wiley & Sons, Inc., 1933.

Whyman, R. (1996). Gold Nanoparticles A Renaissance in Gold Chemistry. *Gold Bulletin*, 29(1), 11-15.

Wunder, A. Muller-Ladner, U., Stelzer, E. H. K., Funk, J., Neumann, E., Stehle, G., Pap, T., Sinn, H., Gay, S. & Fiehn, C. (2003). Albumin-Based Drug Delivery as Novel Therapeutic Approach for Rheumatoid Arthritis. *The Journal of Immunology*, 170, 4793-4801.

Yang, S., Park, N.-Y., Han, J. W., Kim, C., Lee, S.-C. & Lee, H. (2012). A distinct platinum growth mode on shaped gold nanocrystals. *Chem. Commun*, 48, 257-259.

Yang, Y.-C., Wang, C.-H., Hwu, Y.-K. & Je, J.-H. (2006). Synchrotron X-ray synthesis of colloidal gold particles for drug delivery. *Materials Chemistry and Physics*, 100, 72-76.

Zhang, G.-R. & Xu, B.-Q. (2010). Surprisingly strong effect of stabilizer on the properties of Au nanoparticles and Pt^Au nanostructures in electrocatalysts. *Nanoscale*, 2, 2798-2804.

Zhou, S., Jackson, G. S. & Eichhorn, B. (2007). AuPt Alloy Nanoparticles for CO-Tolerant Hydrogen Activation: Architectural Effects in Au—Pt Bimetallic Nanocrystals. *Adv. Funct. Mater.*, 17, 3099-3104.

SUMMARY OF THE INVENTION

New bi-metallic nanocrystal suspensions are provided that have nanocrystalline surfaces that can be substantially free (as defined herein) from organic or other impurities or films, or in certain cases may contain some desirable film or partial coating. Specifically, the surfaces are "clean" relative to those made using chemical reduction processes that require chemical reductants and/or surfactants to grow gold nanoparticles from metal ions in solution. Resulting bi-metallic nanocrystalline suspensions or colloids have desirable pH ranges such as 4.0-12.0, but more typically 5.0-11.0, and even more typically 8.0-11.0, and in many embodiment, 10.0-11.0 and zeta potential values of at least –20 mV, and more typically at least –40 mV, and even more typically at least –50 mV for the pH ranges of interest.

The shapes and shape distributions of these bi-metallic nanocrystals prepared according to the manufacturing process described below include, but are not limited to, spheres, pentagons, hexagons (e.g., hexagonal bipyramids, icosahedrons, octahedrons), and "others".

Any desired average size of bi-metallic nanocrystals below 100 nm can be provided. The most desirable crystalline size ranges include those having an average crystal size (as measured and determined by specific techniques disclosed in detail herein) that is predominantly less than 100 nm, and more typically less than 50 nm, even more typically less than 30 nm, and in many of the preferred embodiments disclosed herein, the average crystal size for the nanocrystal size distribution is less than 20 nm and with an even more preferable range of 8-18 nm. However, for certain applications, the electrochemical techniques disclosed herein can be utilized to result in larger nanocrystals, if desired.

A variety of concentrations of bi-metallic nanocrystals can be provided according to the invention. For example, total atomic metal concentrations of bi-metallic nanocrystals produced initially can be a few parts per million (i.e., µg/ml or mg/l) up to a few hundred ppm, but are typically in the range of 2-200 ppm (i.e., 2 µg/ml-200 µg/ml) and more often in the range of 2-50 ppm (i.e., 2 µg/ml-50 µg/ml) and even more typically 5-20 ppm (i.e., 5 µg/ml-20 µg/ml). However, novel concentration techniques are disclosed herein which allow concentrated "initial" product to be formed with ppm's between 200-5,000 ppm and more preferably, 200-3,000 ppm and more preferably, 200-1,000 ppm.

The bi-metallic nanocrystals in suspension can be made as alloys, partial alloys, phase-segregated or heteroaggregates or mixtures. In preferred embodiments herein, the bi-metallic nanocrystals are alloys and/or heteroaggregates. Gold is typically the major constituent (i.e., more by weight and more by volume) and platinum is typically the minor constituent (i.e., less by weight and less by volume). Typical ratios range from 2/1 to 10/1, with preferred ranges being 3/1 to 8/1, and even more preferred 3/1 to 6/1.

A novel set of processes are provided to produce these unique bi-metallic nanocrystals. Each process involves the creation of the bi-metallic nanocrystals in water. In a preferred embodiment, the water contains an added "process enhancer" which does not significantly bind to the formed nanocrystals, but rather facilitates nucleation/crystal growth during the electrochemical-stimulated growth process. The process enhancer serves important roles in the process including, for example, providing charged ions in the electrochemical solution to permit the crystals to be grown.

In a preferred embodiment, a first step includes forming a platinum metal-based species with at least one process enhancer and the formed aqueous suspension/solution is then used as a raw material solution/suspension in a second step where a gold metal-based species is reduced and/or co-reduced to grow the bi-metallic nanocrystals in water. Specifically, the processes involve first forming electrochemically at least one platinum species in water and at least one lysis product of water, thereby creating a platinum species and water material; and using the created platinum/water material in a second electrochemical reaction to form a suspension of bi-metallic gold-platinum nanocrystals in water.

By following the inventive electrochemical manufacturing processes of the invention, these bi-metallic nanocrystals can form alloys or metal "coatings" (or portions of coatings, e.g., islands) on core metals or alternatively, form heteroaggregates. Alternatively, a mixture of nanocrystals can be made. Also, a range of alloys or mixtures or heteroaggregates may result within a single colloid or suspension, if desired. In some cases, desirable residual metal ions may be in solution in the suspension.

These novel electrochemical processes can occur in either a batch, semi-continuous or continuous process. These processes result in controlled bi-metallic nanocrystalline concentrations, controlled nanocrystal sizes and controlled nanocrystal size ranges. Novel manufacturing assemblies are provided to produce these bi-metallic nanocrystals.

Since these bi-metallic nanocrystals have substantially cleaner surfaces than the prior available metallic-based (or bi-metallic-based) nanoparticles, and can desirably contain spatially extended low index crystallographic planes forming novel crystal shapes and/or crystal shape distributions, the bi-metallic nanocrystals appear to be more active (e.g., more biologically active and may be less toxic) relative to those containing surface contaminants such as chemical reductants and/or surfactants or residual raw materials that result from traditional chemical reduction (or other) processes. Therefore, uses for nanoparticles, such as, catalysis processes, medical treatments, biologic processes, medical diagnostics, etc., may be affected at lower concentrations of metallic-based nanocrystals made according to the techniques herein.

Further, because the raw material metal ions used to grow the bi-metallic nanocrystals are provided by sacrificial metal electrodes used during the various electrochemical processes, there are no requirements for gold-based salts (or the equivalent) or platinum-based salts (or the equivalent) to be provided as raw materials for the formation of Au—Pt bi-metallic nanocrystal suspensions. Accordingly, components such as Cl⁻, chlorides or chlorine-based materials are not required to be part of the novel process or part of the novel bi-metallic nanocrystal suspensions produced. Additionally, no chlorine-based acids are required to produce the Au—Pt bi-metallic suspensions.

Still further, the aforementioned metal-based bi-metallic nanocrystal suspensions or colloids of the present invention can be mixed or combined with other metallic-based solutions or colloids to form novel solution or colloid mixtures (e.g., in this instance, distinct metal species can still be discerned, either as composites or distinct species in a suspension).

BRIEF DESCRIPTION OF THE FIGURES

FIGS. 8d, 8e, 8f and 8g show wiring diagrams used to monitor and/or control the devices 20.

FIGS. 10a-10d show an alternative design of the trough member 30b' wherein the trough member portions 30a' and 30b' are contiguous.

FIG. 11e shows the UV-Vis spectral patterns of each of the gold suspension made according to Example 1.

FIGS. 22a and 22b are representative EDS spectra corresponding to FIGS. 21a and 21b, respectively.

FIGS. 24a and 24b are representative EDS spectra corresponding to FIGS. 23a and 23b, respectively.

FIG. 25a shows a representative TEM photomicrograph of dried constituents made according to Example 10; and FIG. 25b is a representative EDS spectra corresponding to FIG. 25a.

FIG. 26a shows a representative TEM photomicrograph of dried constituents made according to Example 11; and FIG. 26b is a representative EDS spectra corresponding to FIG. 26a.

FIG. 28a shows three UV-Vis spectrographs of three Au—Pt bi-metallic suspensions.

FIG. 28b shows UV-Vis spectrographs for five different GPB bi-metallic suspensions.

FIG. 29b is a representative EDS spectra corresponding to FIG. 29a.

FIGS. 31a and 31b are schematic representations of the dialysis procedure used in Example 18.

FIGS. 33a and 33b show the results of the cancer xenograft tests set forth in Example 20a.

DETAILED DESCRIPTION OF THE PREFERRED EMBODIMENTS

I. Novel Metallic-Based Nanocrystals

Figure 1:
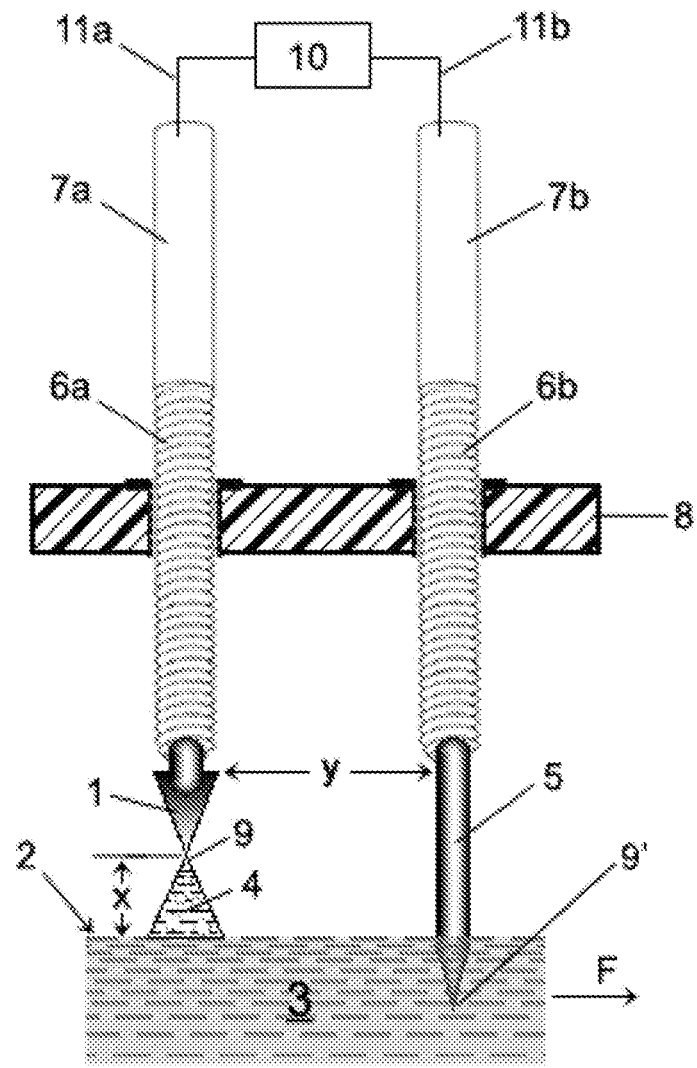
FIG. 1 shows a schematic cross-sectional view of a manual electrode assembly according to the present invention.

New aqueous-based bi-metallic nanocrystal suspensions are manufactured from a combination of gold and platinum donor electrode materials, such bi-metallic nanocrystals including nanocrystalline surfaces that can be substantially free from organic or other impurities or films. Specifically, the surfaces of the bi-metallic nanocrystals are "clean" relative to those surfaces of similar chemical composition nanoparticles made using: (1) chemical reduction processes that require chemical reductants and/or surfactants and/or various salt compounds as parts of the raw materials used to form bi-metallic-based nanoparticles from transition metal ions contained in raw material solution; and (2) other processes (including, sonoelectrochemistry, gamma-ray radiation, x-ray radiation, laser irradiation, electron accelerators, etc.) which use, for example, a variety of reductants or chlorine-based (or salt-based) raw materials (e.g., metal salts).

The new bi-metallic nanocrystals of gold and platinum are produced via novel electrochemical manufacturing procedures, described in detail herein. The new electrochemical manufacturing procedures do not require the addition of chemical reductants and/or surfactants (e.g., organic compounds) or other agents, to be added to reduce metal ions and/or stabilize the formed bi-metallic nanocrystals. Further, the processes do not require the addition of raw materials which contain both metal ions (which are reduced to form metal nanoparticles) and associated ions or species which counterbalance the electrical charge of the positively charged metal ion(s). Such added reductants, stabilizers and non-metal ion portions of raw materials are undesirable when they are typically carried along in, or on, the particles, or are undesirably adhered to at least a portion of the surface of the chemically reduced particles and/or remain as ions in the suspension. It is now understood that certain nanocrystal performance requirements can not be met with such impurities located on or bonded to the surface and such impurities need to be subsequently stripped or removed using various undesirable processes, which process themselves can affect the surface of the nanoparticles (e.g., plasma etching).

In a preferred embodiment, a first set of electrochemical steps of the process involves the in situ creation of platinum species (e.g., raw materials) from a platinum metal source. The platinum species is created in water which contains a "process enhancer" or "processing enhancer" (typically an inorganic material or carbonate or such) which does not significantly bind to the formed nanocrystals in suspension, but rather facilitates removal of metal ions from a donor platinum metal electrode source, and/or assists in nucleation/growth during electrochemical-stimulated nanocrystal growth processes. More specifically, the process enhancer serves important roles in the process including providing charged ions in the electrochemical solution to permit metal ions to be in solution and/or to cause the nanocrystals to be grown. The process enhancer is critically a compound(s) which remains in solution, and/or does not form a coating (e.g., an organic coating), and/or does not adversely affect the performance of the formed nanocrystals or the formed suspension(s) (e.g., is inert), and/or can be destroyed, evaporated, removed or otherwise lost during one or more steps of the electrochemical process. A preferred process enhancer is sodium bicarbonate. Examples of other process enhancers are sodium carbonate, sodium hydroxide, potassium bicarbonate, potassium carbonate, potassium hydroxide, trisodium phosphate, disodium phosphate, monosodium phosphate, potassium phosphates or the like and combinations thereof. Another particularly preferred processing enhancer is a mixture of sodium bicarbonate and potassium hydroxide.

Desirable concentration ranges for the processing enhancer in the first step of the process include typically 0.01-20 grams/gallon (0.0026-2.1730 mg/ml), more typically, 0.1-7.5 grams/gallon (0.0264-1.9813 mg/ml) and most typically, 0.5-2.0 grams/gallon (0.13210-0.5283 mg/ml).

Further, desirable concentrations of the platinum species made in the first electrochemical steps of the process range from about 0.5 ppm to about 20 ppm and most typically about 1-8 ppm, and even more typically about 0.5-4 ppm. The result of the first set of electrochemical steps is a platform species in water. The platinum species can be predominantly nanocrystals or a mixture of nanocrystals and platinum ions. In a preferred embodiment, the platinum species is predominantly ions and the platinum ions-water material is used in a second set of electrochemical steps to form bi-metallic Au—Pt nanocrystals in suspension.

Specifically, in a preferred embodiment, a second set of steps of the electrochemical process involves the nucleation and growth of bi-metallic nanocrystals, such growth including: (1) mixtures of two metals, (2) alloys of two metals and/or (3) heteroaggregates (e.g., composites) of two metals. For example, the platinum species and water output from the first steps of the preferred embodiment (note that electrochemical processing enhancer used during the first electrochemical processing is also present) act as raw material input into the second electrochemical processing steps of a preferred embodiment. Depending on the particular concentrations and type of formed platinum species, processing enhancer(s) components, raw material and run conditions of the electrochemical processes (including devices used), one or more of the aforementioned bi-metallic nanocrystalline components can be produced as stable nanocrystals in the aqueous suspension during the second set of electrochemical processing steps.

Because the grown bi-metallic nanocrystals have "bare" or "clean" surfaces of gold and/or platinum metal (e.g., in the zero oxidation state) bi-metallic nanocrystal surfaces are highly catalytic or are highly biocatalytic (as well as highly bioavailable). The bi-metallic nanocrystals are essentially surrounded by a water-based jacket comprising, for example, water species which are made available due to, for example, lysing of the water which occurs in one or more steps of a preferred embodiment. The lysed species may include hydrated electrons, OH$^-$, H*, H$_3$O, H$_2$O$_2$, etc. However, without wishing to be bound by any particular theory or explanation, OH$^-$ groups (e.g., from either lysed water or processing enhancer) may locate themselves around the formed bi-metallic crystals and create an electrostatic interaction therewith. These clean surface features provide novel and enhanced performance in a variety of industrial and medical applications and/or can result in decreased general undesirable toxicity in medical applications because no undesirable toxins or poisons are present on the surfaces due to the manufacturing process.

In a preferred embodiment, the nanocrystals are not dried before use but instead are directly used in the liquid they were formed in (i.e., forming a suspension). Alternatively, the formed suspensions can be formed into a concentrate or a reconstituted concentrate thereof. It appears that completely removing these crystals from their suspension liquid (e.g., completely drying) may, in certain cases, adversely affect the surface properties of the crystals, (e.g., partial oxidation may occur, the stabilizing groups may be irreparably damaged, etc.) and/or may adversely affect the ability to rehydrate the crystals. For example, if the initially formed water jacket includes OH$^-$ which assist in electrostatic interactions, then changing the OH$^-$ coordination may upset the stability of the suspension.

However, it has been discovered that a certain concentration process utilizing a dialysis procedure can be used. The dialysis procedure involves placement of the formed bi-metallic nanocrystal suspension inside of a dialysis bag. A polyethylene solution is located on the outside of the dialysis bag (e.g., the dialysis bag can be placed with a suitable container housing polyethylene glycol (PEG)) permits water to be removed from the formed bi-metallic nanocrystal suspension by osmotic pressure without comprising the stability of the nanocrystals in suspension. Further, if certain ionic constituents remain in the liquid which suspends the nanocrystals, some or all of such ionic constituents can be removed from such liquid, if desired, so long as such removal does not adversely affect the stability and/or performance of the bi-metallic nanocrystals or nanocrystal suspension.

Further, for some medical-based products, it may be optimal to use sterile pharmaceutical grade water (e.g., USP) or the like in addition to the aforementioned process enhancers used in the manufacturing processes. In some cases, the water could be even more pure than USP by using reverse osmosis and/or ionic filtration means.

Alternatively, in another embodiment, the bi-metallic nanocrystals may be dried in situ into/onto, for example, an electrode or substrate which takes part in another reaction such as another electrochemical, chemical or catalytic process. For example, the bi-metallic nanocrystals made according to this invention can also be used for industrial applications where metal reactivity is important (e.g., catalytic and/or electrochemical processes) but where pharmaceutical grade products/ingredients are not required. When prepared for non-pharmaceutical uses, the bi-metallic nanocrystals can be made in a wider variety of solvents and with a wider variety of process enhancers, as discussed herein, depending on the specific application. However, the clean aspects of the bi-metallic nanocrystal surfaces should be preserved to achieve superior performance.

In another preferred embodiment of the invention, the electrochemical process steps of the invention can be controlled so as to result in more than one type of bi-metallic nanocrystal being present in the resultant suspension. For example, mixtures of platinum and gold nanocrystals may exist in suspension, alloys of platinum and gold nanocrystals may exist in suspension and/or nanocrystal heteroaggregates of platinum and gold may also exist in suspension.

According to the processes herein, the bi-metallic nanocrystals can be grown in a manner that provides unique and identifiable surface characteristics such as spatially extended low index, crystal planes {111}, {110} and/or {100} and groups of such planes (and their equivalents). Such crystal planes can show different and desirable catalytic performances. A variety of crystalline shapes can be found in bi-metallic nanoparticle suspensions made according to embodiments disclosed herein. Further, the surfaces of bi-metallic nanocrystals grown should be highly active due to their crystalline condition (e.g., surface defects) as well as being clean.

Any desired average size of bi-metallic nanocrystals below 100 nm can be achieved. The most desirable nanocrystalline size ranges include those having an average crystal size (as measured and determined by specific techniques disclosed in detail herein) that is predominantly less than 100 nm, and more typically less than 50 nm, even more typically less than 30 nm, and in many of the preferred embodiments disclosed herein, the mode for the nanocrystal size distribution is less than 20 nm and within an even more preferable range of 8-18 nm. However, for some applications, the techniques of the invention can be used to manufacture much larger particles.

Resulting bi-metallic nanocrystalline suspensions or colloids can be provided that have or are adjusted to have target pH ranges. When prepared with, for example, a sodium bicarbonate or other "basic" (e.g., one where the OH$^-$ concentration is caused to be relatively high) process enhancer, in the amounts disclosed in detail herein, the pH range is typically 8-11, which can be adjusted as desired. Still further, the use of certain processing enhancers can result in even higher pH ranges, such as a pH of about 9-12 or even 10.3-12.0.

The nature and/or amount of the surface charge (i.e., positive or negative) on formed bi-metallic nanocrystals can have a large influence on the behavior and/or effects of the nanocrystal/suspension or colloid (or the concentrated nanocrystals). For example, for biomedical applications, protein coronas such as albumin coronas and/or transferrin coronas formed in vivo can be influenced by surface charge or surface characteristics (e.g., including impurities or residual components present from processing techniques) of a nanoparticle.

Such coronas dictate the biological identity of the nanoparticle and thus direct biologic availability.

Such surface charges are commonly referred to as "zeta potential". It is known that the larger the zeta potential (either positive or negative), the greater the stability of the nanoparticles in the solution (i.e., the suspension is more stable). By controlling the nature and/or amount of the surface charges of formed nanoparticles or nanocrystals, the performance of such nanoparticle suspensions can be controlled in biological and non-biological applications.

Zeta potential is known as a measure of the electo-kinetic potential in colloidal systems and is also referred to as surface charge on particles. Zeta potential is the potential difference that exists between the stationary layer of fluid and the fluid within which the particle is dispersed. A zeta potential is often measured in millivolts (i.e., mV). The zeta potential value of approximately 20-25 mV is an arbitrary value that has been chosen to determine whether or not a dispersed particle is stable in a dispersion medium. Thus, when reference is made herein to "zeta potential", it should be understood that the zeta potential referred to is a description or quantification of the magnitude of the electrical charge present at the double layer.

The zeta potential is calculated from the electrophoretic mobility by the Henry equation:

$$U_E = \frac{2\varepsilon z f(ka)}{3\eta}$$

where z is the zeta potential, $U_E$ is the electrophoretic mobility, $\in$ is a dielectric constant, $\eta$ is a viscosity, $f(ka)$ is Henry's function. For Smoluchowski approximation $f(ka)=1.5$.

Zeta potentials ("ZP") for the bi-metallic nanocrystals prepared according the methods herein typically have a ZP of at least −20 mV, more typically at least about −30 mV, even more typically, at least about −40 mV and even more typically at least about −50 mV.

Further, another important aspect of the preferred embodiments is that the raw material metal ions are produced by the donor electrode metals of Pt and Au (e.g., sacrificial or donor electrodes) due to the processing conditions of the preferred embodiments. This "top-down" first set of electrochemical steps means that materials typically used to make metal-based nanoparticles in other techniques, such as metal salts (e.g., Pt salts, Au salts, etc.) are not required to be used in the embodiments disclosed herein. Thus, other constituents (which can be undesirable) of the metal salts, such as Cl⁻ or various chlorine-based materials, do not occur, or are not a required part of a product made according to the preferred embodiments herein. In other words, for example, the other constituents that comprise various metal-based raw material salts do not need to be present in the bi-metallic nanocrystal suspensions discussed herein (e.g., bi-metallic suspensions can be chlorine or chloride-free). Of course, it should be noted that the presence of chlorine-based materials dissolved in the suspension, and were not required or essential to the nanoparticle production process, are contemplated as being within the metes and bounds of this disclosure.

II. Method of Manufacturing Bi-Metallic Nanocrystals

A set of novel process steps is provided to produce these unique bi-metallic nanocrystals. The process steps involve the creation of the bi-metallic nanocrystals in water. In a preferred embodiment, the water contains an added "process enhancer" which does not significantly bind to the formed nanocrystals, but rather facilitates nucleation/crystal growth during the electrochemical-stimulated growth process. The process enhancer serves important roles in the process including providing charged ions in the electrochemical solution to permit the crystals to be grown. These novel electrochemical processes can occur in either a batch, semi-continuous or continuous process. These processes result in controlled bi-metallic nanocrystalline concentrations of gold and platinum, controlled bi-metallic nanocrystal sizes and controlled bi-metallic nanocrystal size ranges. Novel manufacturing assemblies are provided to produce these bi-metallic nanocrystals. In another embodiment, metallic-based constituents, such as desirable metallic ions, can be included separately or combined with bi-metallic nanocrystal suspensions.

In one preferred embodiment, the bi-metallic nanocrystal suspensions or colloids are made or grown by electrochemical techniques in either a batch, semi-continuous or continuous process, wherein the amount, average particle size, crystal plane(s) and/or particle shape(s) and/or particle shape distributions are controlled and/or optimized to achieve high biological activity and low cellular/biologic toxicity (e.g., a high therapeutic index). Desirable average crystal sizes include a variety of different ranges, but the most desirable ranges include average crystal sizes that are predominantly less than 100 nm and more typically, for many uses, less than 50 nm and even more typically for a variety of, for example, oral uses, less than 30 nm, and in many of the preferred embodiments disclosed herein, the mode for the nanocrystal size distribution is less than 20 nm and within an even more preferable range of 2-18 nm, as measured by a zetasizer (as described in more detail herein). Further, the particles desirably contain crystal planes, such desirable (and often highly reactive) crystal planes, include crystals having {111}, and/or {100} facets, as well as defects, which can result in superior interactions such as catalytic.

Further, by following the inventive electrochemical manufacturing processes of the invention, these bi-metallic nanocrystals can be alloys, or can be combined with other metals in liquids such that metal "coatings" may occur on other metals to form composites or heteroaggregates or alternatively, mixtures of metal-based nanocrystals can be made.

Still further, bi-metallic nanocrystal suspensions or colloids of the present invention can be mixed or combined with other metallic-based solutions or colloids to form novel solutions or colloid mixtures (e.g., in this instance, distinct metal species can still be discerned).

Methods for making novel metallic-based nanocrystal suspensions or colloids according to the invention relate generally to novel methods and novel devices for the continuous, semi-continuous and batch manufacture of a variety of constituents in a liquid including micron-sized particles, nanocrystals, ionic species and aqueous-based compositions of the same, including, nanocrystal/liquid(s), solution(s), colloid(s) or suspension(s). The constituents and bi-metallic nanocrystals produced can comprise a variety of possible compositions, concentrations, sizes, crystal planes (e.g., spatially extended low index crystal planes) and/or shapes, which together can cause the inventive compositions to exhibit a variety of novel and interesting physical, catalytic, biocatalytic and/or biophysical properties. The liquid(s) used and created/modified during the process can play an important role in the manufacturing of, and/or the functioning of the constituents (e.g., nanocrystals) independently or synergistically with the liquids which contain them. The particles (e.g., nanocrystals) are caused to be present (e.g., created and/or the liquid is predisposed to their presence (e.g., conditioned)) in at least one liquid (e.g., water) by, for example, typically utilizing at least one adjustable plasma (e.g., created by at least one AC and/or DC power source), which adjustable plasma communicates with at least a portion of a surface of the liquid. However, effective constituent (e.g., nanocrystals) suspensions or colloids can be achieved without the use of such plasmas as well.

Gold and platinum-based electrodes of various composition(s) and/or unique configurations or arrangements are preferred for use in the formation of the adjustable plasma(s). Utilization of at least one subsequent and/or substantially simultaneous adjustable electrochemical processing technique is also preferred. Gold and platinum-based electrodes are preferred for use in the electrochemical processing technique(s). Electric fields, magnetic fields, electromagnetic fields, electrochemistry, pH, zeta potential, chemical/crystal constituents present, etc., are just some of the variables that can be positively affected by the adjustable plasma(s) and/or adjustable electrochemical processing technique(s) of the invention. Multiple adjustable plasmas and/or adjustable electrochemical techniques are preferred in many embodiments of the invention to achieve many of the processing advantages of the present invention, as well as many of the novel bi-metallic nanocrystals and bi-metallic nanocrystal compositions which result from practicing the teachings of the preferred embodiments to make an almost limitless set of inventive aqueous solutions, suspensions and/or colloids.

In the continuous process preferred embodiments of the invention, at least one liquid, for example water, flows into, through and out of at least one first trough member and such liquid is processed, conditioned, modified and/or effected by said at least one adjustable plasma and/or said at least one adjustable electrochemical technique. The results of the continuous processing in the first trough member include new constituents in the liquid, such as ionic constituents, nanocrystals (e.g., platinum-based nanocrystals) of novel and/or controllable size, hydrodynamic radius, concentration, crystal sizes and crystal size ranges, zeta potential, pH and/or properties, such platinum nanocrystal/ion/liquid mixture being produced in an efficient and economical manner.

Further, in a preferred embodiment, a first set of steps of the process involves the in situ creation of platinum species (e.g., raw materials) from a platinum metal source. The platinum species is created in water which contains a "process enhancer" or "processing enhancer" (typically an inorganic material or carbonate or such) which does not significantly bind to the formed nanocrystals in suspension, but rather facilitates removal of metal ions from a donor metal source, and/or assists in nucleation/growth during electrochemical-stimulated nanocrystal growth processes. More specifically, the process enhancer serves important roles in the process including providing charged ions in the electrochemical solution to permit the nanocrystals to be grown. The process enhancer is critically a compound(s) which remains in solution, and/or does not form a coating (e.g., an organic coating), and/or does not adversely affect the performance of the formed nanocrystals or the formed suspension(s) (e.g., is inert), and/or can be destroyed, evaporated, removed or otherwise lost during one or more steps of the electrochemical process. A preferred process enhancer is sodium bicarbonate. Examples of other process enhancers are sodium carbonate, potassium bicarbonate, potassium carbonate, trisodium phosphate, disodium phosphate, monosodium phosphate, potassium phosphates or the like and combinations thereof. Another particularly preferred processing enhancer is a mixture of sodium bicarbonate and potassium hydroxide.

Desirable concentration ranges for the processing enhancer include typically 0.01-20 grams/gallon (0.0026-2.1730 mg/ml), more typically, 0.1-7.5 grams/gallon (0.0264-1.9813 mg/ml) and most typically, 0.5-2.0 grams/gallon (0.13210-0.5283 mg/ml).

In a preferred embodiment, a second set of steps of the process involves the nucleation and growth of bi-metallic-based nanocrystals, such growth being: (1) mixtures of two metals, (2) alloys of two metals and/or (3) heteroaggregates of two metals. For example, the aqueous output from the first steps of the preferred embodiment containing water, platinum species resulting from the first steps of the process, and processing enhancer used during the first set of steps, acts as raw material input into the second electrochemical steps of a preferred embodiment. Depending on the particular concentrations of platinum species, processing enhancer(s) constituent(s) and run conditions of the electrochemical processes (including devices used), one or more of the aforementioned bi-metallic nanocrystalline components can be produced as stable bi-metallic nanocrystals in the aqueous suspension during the second set of steps.

Certain processing enhancers may dissociate into positive ions (cations) and negative ions (anions). The anions and/or cations, depending on a variety of factors including liquid composition, concentration of ions, change state of ions, applied fields, frequency of applied fields, waveform of the applied filed, temperature, pH, zeta potential, etc., will navigate or move toward oppositely charged electrodes. When said ions are located at or near such electrodes, the ions may take part in one or more reactions with the electrode(s) and/or other constituent(s) located or created at or near such electrode(s). Sometimes ions may react with one or more materials in the electrode. Such reactions may be desirable in some cases or undesirable in others. Further, sometimes ions present in a solution between electrodes may not react to form a product, but rather may influence material in the electrode (or near the electrode) to form metallic nano-crystals that are "grown" from material provided by the donor electrode. For example, certain metal ions may enter the liquid 3 from the electrode 5 and be caused to come together (e.g., nucleate) to form constituents (e.g., ions, nanocrystals, etc.) within the liquid 3.

Further, it is important to select a process enhancer that will not negatively impact performance such as, for example, impart negative performance or, for example, toxicity to the bi-metallic nanocrystal, or to the liquid that the crystal is suspended in, to maximize acceptability for various commercial uses (e.g., pharmaceutical, catalytic, medical diagnostic, etc). For example, for certain applications, chlorine ions or chlorides or chlorine-based materials may be undesired if such species create, for example, gold chloride salts, which may be undesirable for several reasons (e.g., may affect toxicity, stability, etc.).

Additionally, certain processing enhancers that involve hydroxyl groups $OH^-$ (e.g., which are part of the processing enhancer or result from addition of processing enhancers to the liquid 3) can also be desirable. In this regard, desirable processing enhancers of NaOH, KOH and $NaHCO_3$ (and mixtures of the same) are specifically disclosed as being desirable in some preferred embodiments herein.

Further, depending upon the specific formed products, drying, concentrating and/or freeze drying can also be utilized to remove at least a portion of, or substantially all of, the suspending liquid, resulting in, for example, partially or substantially completely dehydrated bi-metallic nanocrystals. If such nanocrystals are ultimately located on a substrate (e.g., a catalysis substrate or an electrode) complete drying may be required. If solutions, suspensions or colloids are completely dehydrated, the metal-based species, in some cases, should be capable of being rehydrated by the addition of liquid (e.g., of similar or different composition than that which was removed). However, not all compositions/colloids of the present invention can be completely dehydrated without adversely affecting performance of the composition/colloid. For example, many nanocrystals formed in a liquid tend to clump or stick together (or adhere to surfaces) when dried. If such clumping is not reversible during a subsequent rehydration step, dehydration should be avoided. However, for a variety of applications such clumping may be acceptable. Further, when drying on a substrate, such clumping may be avoided.

In general, it is possible to concentrate, several fold, certain solutions, suspensions or colloids of bi-metallic nanocrystals made according to the invention, without destabilizing the composition. For example, without wishing to be bound, if the initially formed water jacket includes OH⁻ which assist in electrostatic interactions, then changing the OH⁻ coordination in any way may upset the stability of the suspension.

However, it has been discovered that a certain concentration process utilizing a dialysis procedure can be used. The dialysis procedure involves placement of the formed bi-metallic nanocrystal suspension inside of a dialysis bag. A polyethylene solution is located on the outside of the dialysis bag (e.g., the dialysis bag can be placed with a suitable container holding polyethylene glycol (PEG)) and water can be removed from the formed bi-metallic nanocrystal suspension by osmotic pressure without comprising the stability of the nanocrystals in suspension. Further, if certain ionic constituents remain in the liquid which suspends the nanocrystals, some or all of such ionic constituents can be removed from such liquid, so long as such removal does not adversely affect the stability and/or performance of the bi-metallic nanocrystals or nanocrystal suspension.

While the following discussion is believed to be complete, the reader is also directed to a related application, International Publication No. WO/2011/006007 published on 13 Jan. 2011, the subject matter of which is expressly incorporated herein by reference.

One important aspect of the invention involves the creation of at least one adjustable plasma, which adjustable plasma is located between at least one electrode positioned adjacent to (e.g., above) at least a portion of the surface of a liquid (e.g., water) and at least a portion of the surface of the liquid itself. The liquid is placed into electrical communication with at least one second electrode (or a plurality of second electrodes) causing the surface of the liquid to function as an electrode, thus taking part in the formation of the adjustable plasma. This configuration has certain characteristics similar to a dielectric barrier discharge configuration, except that the surface of the liquid is an active electrode participant in this configuration.

Each adjustable plasma utilized can be located between the at least one electrode located above a surface of the liquid and a surface of the liquid due to at least one electrically conductive electrode being located somewhere within (e.g., at least partially within) the liquid. At least one power source (in a preferred embodiment, at least one source of volts and amps such as a transformer or power source) is connected electrically between the at least one electrode located above the surface of the liquid and the at least one electrode contacting the surface of the liquid (e.g., located at least partially, or substantially completely, within the liquid). The electrode(s) may be of any suitable composition (however, platinum and gold are preferred) and suitable physical configuration (e.g., size and shape) which results in the creation of a desirable plasma between the electrode(s) located above the surface of the liquid and at least a portion of the surface of the liquid itself.

The applied power (e.g., voltage and amperage) between the electrode(s) (e.g., including the surface of the liquid functioning as at least one electrode for forming the plasma) can be generated by any suitable source (e.g., voltage from a transformer) including both AC and DC sources and variants and combinations thereof. Generally, the electrode or electrode combination located within (e.g., at least partially below the surface of the liquid) takes part in the creation of a plasma by providing voltage and current to the liquid or solution. However, the adjustable plasma is actually located between at least a portion of the electrode(s) located above the surface of the liquid (e.g., at a tip or point thereof) and one or more portions or areas of the liquid surface itself. In this regard, the adjustable plasma can be created between the aforementioned electrodes (i.e., those located above at least a portion of the surface of the liquid and a portion of the liquid surface itself) when a breakdown voltage of the gas or vapor around and/or between the electrode(s) and the surface of the liquid is achieved or maintained.

In one embodiment of the invention, the liquid comprises water (or water containing certain processing enhancer(s)), and the gas between the surface of the water and the electrode(s) above the surface of the water (i.e., that gas or atmosphere that takes part in the formation of the adjustable plasma) comprises air. The air can be controlled to contain various different water content(s) or a desired humidity which can result in different compositions, concentrations, crystal size distributions and/or crystal shape distributions of constituents (e.g., nanocrystals) being produced according to the present invention (e.g., different amounts of certain constituents in the adjustable plasma and/or in the solution or suspension can be a function of the water content in the air located above the surface of the liquid) as well as different processing times required to obtain certain concentrations of various constituents in the liquid, etc.

The breakdown electric field at standard pressures and temperatures for dry air is about 3 MV/m or about 30 kV/cm. Thus, when the local electric field around, for example, a metallic point exceeds about 30 kV/cm, a plasma can be generated in dry air. Equation (1) gives the empirical relationship between the breakdown electric field "$E_c$" and the distance "d" (in meters) between two electrodes:

$$E_c = 3000 + \frac{1.35}{d} \text{kV/m} \qquad \text{Equation 1}$$

Of course, the breakdown electric field "$E_c$" will vary as a function of the properties and composition of the gas or vapor located between electrodes. In this regard, in one preferred embodiment where water (or water containing a processing enhancer) is the liquid, significant amounts of water vapor can be inherently present in the air between the "electrodes" (i.e., between the at least one electrode located above the surface of the water and the water surface itself which is functioning as one electrode for plasma formation) and such water vapor should have an effect on at least the breakdown electric field required to create a plasma therebetween. Further, a higher concentration of water vapor can be caused to be present locally in and around the created plasma due to the interaction of the adjustable plasma with the surface of the water. The amount of "humidity" present in and around the created plasma can be controlled or adjusted by a variety of techniques discussed in greater detail later herein. Likewise, certain components present in any liquid can form at least a portion of the constituents forming the adjustable plasma located between the surface of the liquid and the electrode(s) located adjacent (e.g., along) the surface of the liquid. The constituents in the adjustable plasma, as well as the physical properties of the plasma per se, can have a dramatic influence on the liquid, as well as on certain of the processing techniques (discussed in greater detail later herein).

The electric field strengths created at and near the electrodes are typically at a maximum at a surface of an electrode and typically decrease with increasing distance therefrom. In cases involving the creation of an adjustable plasma between a surface of the liquid and the at least one electrode(s) located adjacent to (e.g., above) the liquid, a portion of the volume of gas between the electrode(s) located above a surface of a liquid and at least a portion of the liquid surface itself can contain a sufficient breakdown electric field to create the adjustable plasma. These created electric fields can influence, for example, behavior of the adjustable plasma, behavior of the liquid (e.g., influence the crystal state of the liquid) behavior of constituents in the liquid, etc.

In this regard, FIG. 1 shows one embodiment of a point source electrode 1 having a triangular cross-sectional shape located a distance "x" above the surface 2 of a liquid 3 flowing, for example, in the direction "F". An adjustable plasma 4 can be generated between the tip or point 9 of the electrode 1 and the surface 2 of the liquid 3 when an appropriate power source 10 is connected between the point source electrode 1 and the electrode 5, which electrode 5 communicates with the liquid 3 (e.g., is at least partially below the surface 2 of the liquid 3).

The adjustable plasma region 4, created in the embodiment shown in FIG. 1 can typically have a shape corresponding to a cone-like structure or an ellipsoid-like structure, for at least a portion of the process, and in some embodiments of the invention, can maintain such shape (e.g., cone-like shape) for substantially all of the process. The volume, intensity, constituents (e.g., composition), activity, precise locations, etc., of the adjustable plasma(s) 4 will vary depending on a number of factors including, but not limited to, the distance "x", the physical and/or chemical composition of the electrode 1, the shape of the electrode 1, the power source 10 (e.g., DC, AC, rectified AC, the applied polarity of DC and/or rectified AC, AC or DC waveform, RF, etc.), the power applied by the power source (e.g., the volts applied, which is typically 1000-5000 Volts, and more typically 1000-1500 Volts, the amps applied, electron velocity, etc.) the frequency and/or magnitude of the electric and/or magnetic fields created by the power source applied or ambient, electric, magnetic or electromagnetic fields, acoustic fields, the composition of the naturally occurring or supplied gas or atmosphere (e.g., air, nitrogen, helium, oxygen, ozone, reducing atmospheres, etc.) between and/or around the electrode 1 and the surface 2 of the liquid 3, temperature, pressure, volume, flow rate of the liquid 3 in the direction "F", spectral characteristics, composition of the liquid 3, conductivity of the liquid 3, cross-sectional area (e.g., volume) of the liquid near and around the electrodes 1 and 5, (e.g., the amount of time (i.e., dwell time) the liquid 3 is permitted to interact with the adjustable plasma 4 and the intensity of such interactions), the presence of atmosphere flow (e.g., air flow) at or near the surface 2 of the liquid 3 (e.g., fan(s) or atmospheric movement means provided) etc., (discussed in more detail later herein).

The composition of the electrode(s) 1 involved in the creation of the adjustable plasma(s) 4 of FIG. 1, in one preferred embodiment of the invention, are metal-based compositions (e.g., metals such as gold, platinum and/or alloys or mixtures thereof, etc.), but the electrodes 1 and 5 may be made out of any suitable material compatible with the various aspects (e.g., processing parameters) of the inventions disclosed herein. In this regard, while the creation of a plasma 4 in, for example, air above the surface 2 of a liquid 3 (e.g., water) will, typically, produce at least some ozone, as well as amounts of nitrogen oxide and other components. These produced components can be controlled and may be helpful or harmful to the formation and/or performance of the resultant constituents in the liquid (e.g., nanocrystals) and/or, nanocrystal suspensions or colloids produced and may need to be controlled by a variety of different techniques. As shown in FIG. 1, the adjustable plasma 4 actually contacts the surface 2 of the liquid 3. In this embodiment of the invention, material (e.g., metal) from the electrode 1 may comprise a portion of the adjustable plasma 4 (e.g., and thus be part of the emission spectrum of the plasma) and may be caused, for example, to be "sputtered" onto and/or into the liquid 3 (e.g., water). Accordingly, when metal(s) are used as the electrode(s) 1, a variety of constituents can be formed in the electrical plasma, resulting in certain constituents becoming part of the processing liquid 3 (e.g., water), including, but not limited to, elementary metal(s), metal ions, Lewis acids, Bronsted-Lowry acids, metal oxides, metal nitrides, metal hydrides, metal hydrates and/or metal carbides, etc., can be found in the liquid 3 (e.g., for at least a portion of the process and may be capable of being involved in simultaneous/subsequent reactions), depending upon the particular set of operating conditions associated with the adjustable plasma 4 and/or subsequent electrochemical processing operations. Such constituents may be transiently present in the processing liquid 3 or may be semi-permanent or permanent. If such constituents are transient or semi-permanent, then the timing of subsequent reactions (e.g., electrochemical reactions) with such formed constituents can influence final products produced. If such constituents are permanent, they should not adversely affect the desired performance of the active ingredient nanocrystals.

Further, depending on, for example, electric, magnetic and/or electromagnetic field strength in and around the liquid 3 and the volume of liquid 3 exposed to such fields, the physical and chemical construction of the electrode(s) 1 and 5, atmosphere (naturally occurring or supplied), liquid composition, greater or lesser amounts of electrode(s) materials(s) (e.g., metal(s) or derivatives of metals) may be found in the liquid 3. In certain situations, the material(s) (e.g., metal(s) or metal(s) composite(s)) or constituents (e.g., Lewis acids, Bronsted-Lowry acids, etc.) found in the liquid 3 (permanently or transiently), or in the plasma 4, may have very desirable effects, in which case relatively large amounts of such materials will be desirable; whereas in other cases, certain materials found in the liquid 3 (e.g., by-products) may have undesirable effects, and thus minimal amounts of such materials may be desired in the liquid-based final product. Accordingly, electrode composition can play an important role in the materials that are formed according to the embodiments disclosed herein. The interplay between these components of the invention are discussed in greater detail later herein.

Still further, the electrode(s) 1 and 5 may be of similar chemical composition (e.g., have the same chemical element as their primary constituent) and/or mechanical configuration or completely different compositions (e.g., have different chemical elements as their primary constituent) in order to achieve various compositions and/or structures of liquids and/or specific effects discussed later herein.

The distance "y" between the electrode(s) 1 and 5; or 1 and 1 (shown later herein) or 5 and 5 (shown later herein) is one important aspect of the invention. In general, when working with power sources capable of generating a plasma under the operating condition, the location of the smallest distance "y" between the closest portions of the electrode(s) used in the present invention should be greater than the distance "x" in order to prevent an undesirable arc or formation of an unwanted corona or plasma occurring between the electrode (e.g., the electrode(s) 1 and the electrode(s) 5) (unless some type of electrical insulation is provided therebetween). Features of the invention relating to electrode design, electrode location and electrode interactions between a variety of electrodes are discussed in greater detail later herein.

The power applied through the power source 10 may be any suitable power which creates a desirable adjustable plasma 4 under all of the process conditions of the present invention. In one preferred mode of the invention, an alternating current from a step-up transformer is utilized. Preferred transformer(s) 60 (see e.g., FIGS. 7*a*-7*b*) for use in various embodiments disclosed herein, have deliberately poor output voltage regulation made possible by the use of magnetic shunts in the transformer 60. These transformers 60 are known as neon sign transformers. This configuration limits current flow into the electrode(s) 1/5. With a large change in output load voltage, the transformer 60 maintains output load current within a relatively narrow range.

The transformer 60 is rated for its secondary open circuit voltage and secondary short circuit current. Open circuit voltage (OCV) appears at the output terminals of the transformer 60 only when no electrical connection is present. Likewise, short circuit current is only drawn from the output terminals if a short is placed across those terminals (in which case the output voltage equals zero). However, when a load is connected across these same terminals, the output voltage of the transformer 60 should fall somewhere between zero and the rated OCV. In fact, if the transformer 60 is loaded properly, that voltage will be about half the rated OCV.

The transformer 60 is known as a Balanced Mid-Point Referenced Design (e.g., also formerly known as balanced midpoint grounded). This is most commonly found in mid to higher voltage rated transformers and most 60 mA transformers. This is the only type transformer acceptable in a "midpoint return wired" system. The "balanced" transformer 60 has one primary coil 601 with two secondary coils 603, one on each side of the primary coil 601 (as shown generally in the schematic view in FIG. 7*b*). This transformer 60 can in many ways perform like two transformers. Just as the unbalanced midpoint referenced core and coil, one end of each secondary coil 603 is attached to the core 602 and subsequently to the transformer enclosure and the other end of the each secondary coil 603 is attached to an output lead or terminal. Thus, with no connector present, an unloaded 15,000 volt transformer of this type, will measure about 7,500 volts from each secondary terminal to the transformer enclosure but will measure about 15,000 volts between the two output terminals. These exemplary transformers 60 were utilized to form the plasmas 4 disclosed in the Examples herein. However, other suitable transformers (or power sources) should also be understood as falling within the metes and bounds of the invention. However, a different power supply 501AC (discussed elsewhere herein) is utilized for the electrodes 5/5' in most of the other examples disclosed herein.

In further reference to the configurations shown in FIG. 1, electrode holders 6*a* and 6*b* are capable of being lowered and raised by any suitable means (and thus the electrodes are capable of being lowered and raised). For example, the electrode holders 6*a* and 6*b* are capable of being lowered and raised in and through an insulating member 8 (shown in cross-section). The mechanical embodiment shown here includes male/female screw threads. The portions 6*a* and 6*b* can be covered by, for example, additional electrical insulating portions 7*a* and 7*b*. The electrical insulating portions 7*a* and 7*b* can be any suitable material (e.g., plastic, polycarbonate, poly (methyl methacrylate), polystyrene, acrylics, polyvinylchloride (PVC), nylon, rubber, fibrous materials, etc.) which prevent undesirable currents, voltage, arcing, etc., that could occur when an individual interfaces with the electrode holders 6*a* and 6*b* (e.g., attempts to adjust the height of the electrodes). Likewise, the insulating member 8 can be made of any suitable material which prevents undesirable electrical events (e.g., arcing, melting, etc.) from occurring, as well as any material which is structurally and environmentally suitable for practicing the present invention. Typical materials include structural plastics such as polycarbonates, plexiglass (poly (methyl methacrylate), polystyrene, acrylics, and the like. Additional suitable materials for use with the present invention are discussed in greater detail elsewhere herein.

Preferred techniques for automatically raising and/or lowering the electrodes 1, 5 are discussed later herein. The power source 10 can be connected in any convenient electrical manner to the electrodes 1 and 5. For example, wires 11*a* and 11*b* can be located within at least a portion of the electrode holders 6*a*, 6*b* (and/or electrical insulating portions 7*a*, 7*b*) with a primary goal being achieving electrical connections between the portions 11*a*, 11*b* and thus the electrodes 1, 5.

Figure 2:
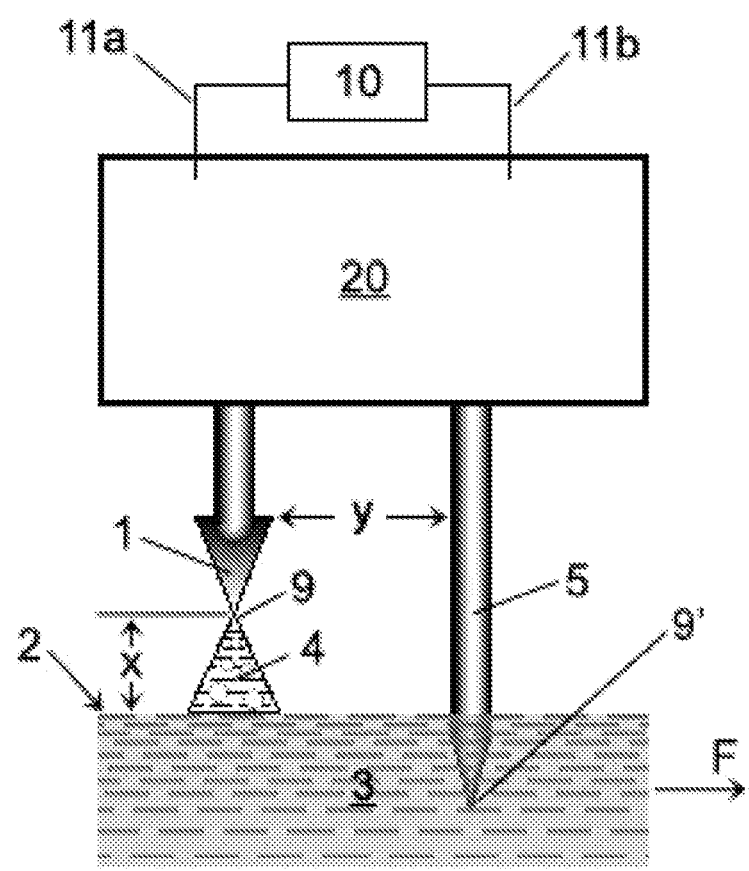
FIG. 2 shows a schematic cross-sectional view of an automatic electrode control assembly according to the present invention.
Figure 3A:
FIGS. 3a-3e show five different representative embodiments of configurations for the electrode 1.
Figure 3B:
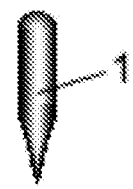
Figure 3C:
Figure 3D:
Figure 3E:
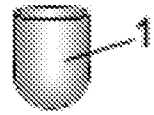

FIG. 2 shows another schematic of a preferred embodiment of the invention, wherein a control device 20 is connected to the electrodes 1 and 5, such that the control device 20 remotely (e.g., upon command from another device or component) raises and/or lowers the electrodes 1, 5 relative to the surface 2 of the liquid 3. The control device 20 is discussed in more detail later herein. In this one preferred aspect of the invention, the electrodes 1 and 5 can be, for example, remotely lowered and controlled, and can also be monitored and controlled by a suitable controller or computer (not shown in FIG. 2) containing an appropriate software control program. Accordingly, the embodiment shown in FIG. 1 should be considered to be a manually controlled apparatus for use with the techniques of the present invention, whereas the embodiment shown in FIG. 2 should be considered to include an automatic apparatus or assembly 20 which can remotely raise and lower the electrodes 1 and 5 in response to appropriate commands. Further, the FIG. 2 preferred embodiments of the invention can also employ computer monitoring and computer control of the distance "x" of the tips 9 of the electrodes 1 (and tips 9' of the electrodes 5) away from the surface 2; or computer monitoring and/or controlling the rate(s) which the electrode 5 is advanced into/through the liquid 3. Thus, the appropriate commands for raising and/or lowering the electrodes 1 and 5 can come from an individual operator and/or a suitable control device such as a controller or a computer (not shown in FIG. 2).

FIGS. 3*a*-3*e* show perspective views of various desirable electrode configurations for the electrode 1 shown in FIGS. 1-2 (as well as in other Figures and embodiments discussed later herein). The electrode configurations shown in FIGS. 3*a*-3*e* are representative of a number of different configurations that are useful in various embodiments of the present invention. Criteria for appropriate electrode selection for the electrode 1 include, but are not limited to the following conditions: the need for a very well defined tip or point 9, composition, mechanical limitations, the ability to make shapes from the material comprising the electrode 1, conditioning (e.g., heat treating or annealing) of the material comprising the electrode 1, convenience, the constituents introduced into the plasma 4, the influence upon the liquid 3, etc. In this regard, a small mass of material comprising the electrodes 1 shown in, for example, FIGS. 1-2 may, upon creation of the adjustable plasmas 4 according to the present invention (discussed in greater detail later herein), rise to operating temperatures where the size and or shape of the electrode(s) 1 can be adversely affected. In this regard, for example, if the electrode 1 was of relatively small mass (e.g., if the electrode(s) 1 was made of gold and weighed about 0.5 gram or less) and included a very fine point as the tip 9, then it is possible that under certain sets of conditions used in various embodiments herein that a fine point (e.g., a thin wire having a diameter of only a few millimeters and exposed to a few hundred to a few thousand volts; or a triangular-shaped piece of metal) would be incapable of functioning as the electrode 1 (e.g., the electrode 1 could deform undesirably or melt), absent some type of additional interactions (e.g., internal cooling means or external cooling means such as a fan, etc.). Accordingly, the composition of (e.g., the material comprising) the electrode(s) 1 may affect possible suitable electrode physical shape due to, for example, melting points, pressure sensitivities, environmental reactions (e.g., the local environment of the adjustable plasma 4 could cause undesirable chemical, mechanical and/or electrochemical erosion of the electrode(s)), etc.

Figure 4:
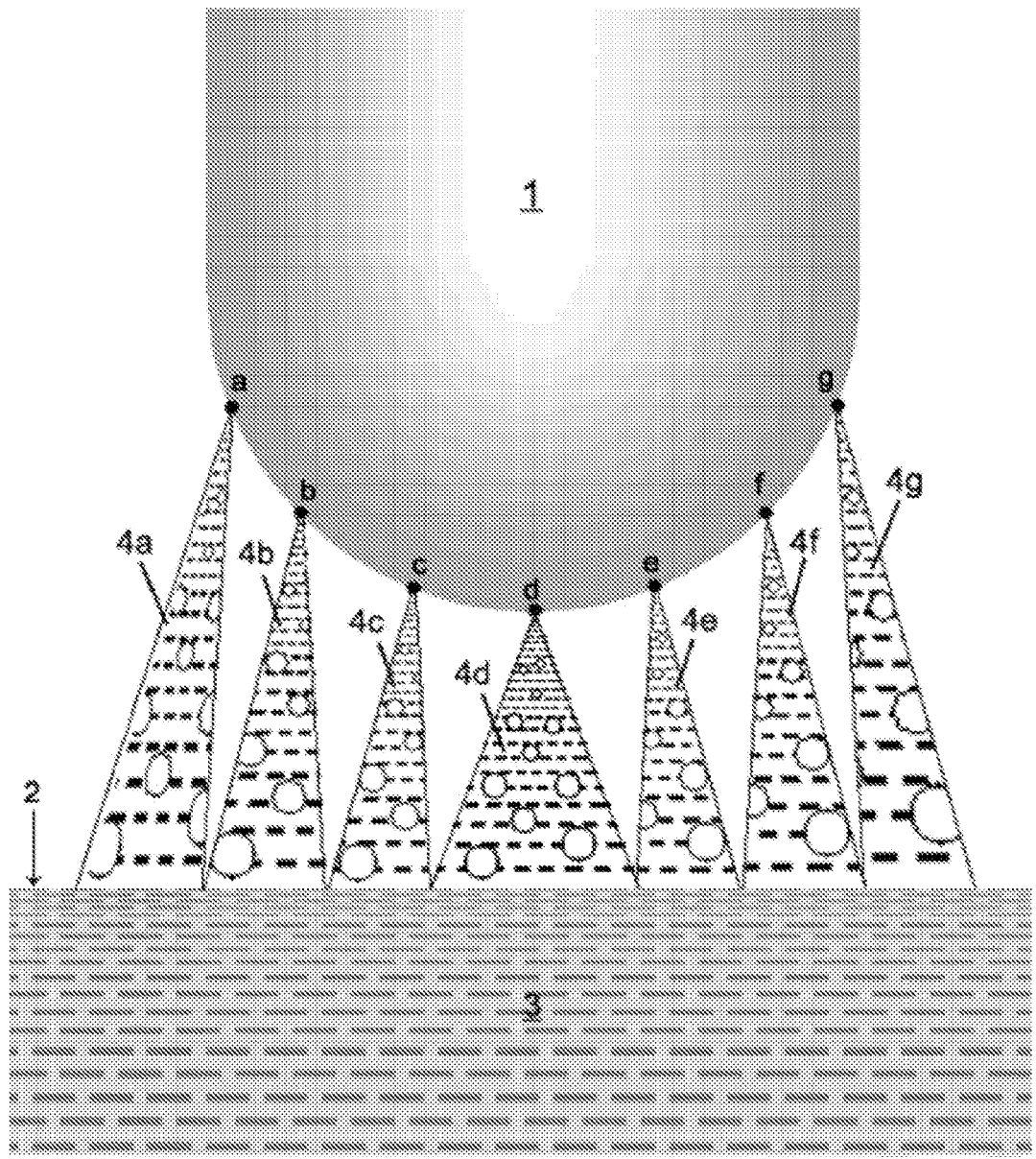
FIG. 4 shows a cross-sectional schematic view of plasmas produced utilizing one specific configuration of the electrode 1 corresponding to FIG. 3e.

Moreover, it should be understood that in alternative preferred embodiments of the invention, well defined sharp points are not always required for the tip 9. In this regard, the electrode 1 shown in FIG. 3e comprises a rounded tip 9. It should be noted that partially rounded or arc-shaped electrodes can also function as the electrode 1 because the adjustable plasma 4, which is created in the inventive embodiments shown herein (see, for example, FIGS. 1-2), can be created from rounded electrodes or electrodes with sharper or more pointed features. During the practice of the inventive techniques of the present invention, such adjustable plasmas can be positioned or can be located along various points of the electrode 1 shown in FIG. 3e. In this regard, FIG. 4 shows a variety of points "a-g" which correspond to initiating points 9 for the plasmas 4a-4g which occur between the electrode 1 and the surface 2 of the liquid 3. Accordingly, it should be understood that a variety of sizes and shapes corresponding to electrode 1 can be utilized in accordance with the teachings of the present invention. Still further, it should be noted that the tips 9, 9' of the electrodes 1 and 5, respectively, shown in various Figures herein, may be shown as a relatively sharp point or a relatively blunt end. Unless specific aspects of these electrode tips 9, 9' are discussed in greater contextual detail, the actual shape of the electrode tip(s) 9, 9' shown in the Figures should not be given great significance.

The electrode configurations shown generally in FIGS. 1 and 2 can create different results (e.g., different conditioning effects for the fluid 3, different pH's in the fluid 3, different nanocrystals sizes and size distribution, different nanocrystal shapes and nanocrystal shape distributions, and/or amounts of constituents (e.g., nanocrystal matter and/or metal ions from the donor electrode(s)) found in the fluid 3, different functioning of the fluid/nanocrystal combinations (e.g., different biologic/biocatalytic effects), different zeta potentials, etc.) as a function of a variety of features including the electrode orientation and position relative to the fluid flow direction "F", cross-sectional shape and size of the trough member 30 (or 30a' and/or 30b'), and/or amount of the liquid 3 within the trough member 30 and/or rate of flow of the liquid 3 within the trough member 30 and in/around the electrodes 5a/5b, the thickness of the electrodes, the number of electrode pairs provided and their positioning in the trough member 30 relative to each other as well as their depth into the liquid 3 (i.e., amount of contact with the liquid 3), the rate of movement of the electrodes into/through the liquid 3 (which maintains or adjusts the surface profile or shape if the electrodes), the power applied to the electrode pairs, etc. Further, the electrode compositions, size, specific shape(s), number of different types of electrodes provided, voltage applied, amperage applied and/or achieved within the liquid 3, AC source (and AC source frequency and AC waveform shape, duty cycle, etc.), DC source, RF source (and RF source frequency, duty cycle, etc.), electrode polarity, etc., can all influence the properties of the liquid 3 (and/or the nanocrystals formed or contained in the liquid 3) as the liquid 3 contacts, interacts with and/or flows past these electrodes 1, 5 and hence resultant properties of the materials (e.g., the nanocrystals produced, metal ions, and/or the suspension or colloid) produced therefrom.

FIGS. 5a-5e show cross-sectional views of the liquid containing trough member 30 used in preferred embodiments herein. The distance "S" and "S'" for the preferred embodiment shown in each of FIGS. 5a-5e measures, for example, between about 0.25" and about 6" (about 0.6 cm-15 cm). The distance "M" ranges from about 0.25" to about 6" (about 0.6 cm-15 cm). The distance "R" ranges from about ½" to about 7" (about 1.2 cm to about 17.8 cm). All of these embodiments (as well as additional configurations that represent alternative embodiments are within the metes and bounds of this inventive disclosure) can be utilized in combination with the other inventive aspects of the invention. It should be noted that the amount of liquid 3 contained within each of the liquid containing trough members 30 (or 30a' and/or 30b') is a function not only of the depth "d", but also a function of the actual cross-section. Briefly, the amount of liquid 3 present in and around the electrode(s) 1 and 5 can influence one or more effects of the adjustable plasma 4 upon the liquid 3 as well as the electrochemical interaction(s) of the electrode 5 with the liquid 3. Further, the flow rate of the liquid 3 in and around the electrode(s) 1 and 5 can also influence many of properties of the nanocrystals formed in the resulting colloids or suspensions. These effects include not only adjustable plasma 4 conditioning effects (e.g., interactions of the plasma electric and magnetic fields, interactions of the electromagnetic radiation of the plasma, creation of various chemical species (e.g., Lewis acids, Bronsted-Lowry acids) within the liquid, pH changes, temperature variations of the liquid (e.g., slower liquid flow can result in higher liquid temperatures and/or longer contact or dwell time with or around the electrodes 1/5 which can also desirably influence final products produced, such as size/shape of the formed nanocrystals, etc.) upon the liquid 3, but also the concentration or interaction of the adjustable plasma 4 with the liquid 3. Similarly, the influence of many aspects of the electrode 5 on the liquid 3 (e.g., electrochemical interactions, temperature, etc.) is also, at least partially, a function of the amount of liquid juxtaposed to the electrode(s) 5. All of these factors can influence a balance which exists between nucleation and growth of the nanocrystals grown in the liquid 3, resulting in, for example, particle size and size range control and/or particle shape and shape range control.

Also, the initial temperature of the liquid 3 input into the trough member 30 (or 30a' and/or 30b') can also affect a variety of properties of products produced according to the disclosure herein. For example, different temperatures of the liquid 3 can affect nanocrystal size(s) and nanocrystal shape(s), concentration or amounts of various formed constituents (e.g., transient, semi-permanent or permanent constituents), ionic control of the liquid, pH, zeta potential, etc. Likewise, temperature controls along at least a portion of, or substantially all of, the trough member 30 (or 30a' and/or 30b') can have desirable effects. For example, by providing localized cooling, resultant properties of products formed (e.g., nanocrystal size(s) and/or nanocrystal shape(s)) can be controlled. Preferable liquid 3 temperatures during the processing thereof are between freezing and boiling points, more typically, between room temperature and boiling points, and even more typically, between about 40-98 degrees C., and more typically, between about 50-98 degrees C. Such temperature can be controlled by, for example, conventional means for cooling located at or near various portions of the processing apparatus.

Further, certain processing enhancers may also be added to or mixed with the liquid(s) 3. The processing enhancers include both solids and liquids (and gases in some cases). The processing enhancer(s) may provide certain processing advantages and/or desirable final product characteristics. Some portion of the processing enhancer(s) may function, influence as or become part of, for example, desirable seed crystals (or promote desirable seed crystals, or be involved in the creation of a nucleation site) and/or crystal plane growth promoters/preventers in the electrochemical growth processes of the invention; or may simply function as a current or power regulator in the electrochemical processes of the invention. Such processing enhancers may also desirably affect current and/or voltage conditions between electrodes 1/5 and/or 5/5.

A preferred processing enhancer is sodium bicarbonate. Examples of other process enhancers are sodium carbonate, potassium bicarbonate, potassium carbonate, trisodium phosphate, disodium phosphate, monosodium phosphate, potassium hydroxide, potassium phosphates or the like and combinations thereof. Another particularly preferred processing enhancer is a mixture of sodium bicarbonate and potassium hydroxide. Still other process enhancers to make bi-metallic nanocrystals for medical applications under certain conditions may be any material that assists in the electrochemical growth processes described herein; and any material is not substantially incorporated into or onto the surface of the gold nanocrystal; and does not impart toxicity to the nanocrystals or to the suspension containing the nanocrystals. Processing enhancers may assist in one or more of the electrochemical reactions disclosed herein; and/or may assist in achieving one or more desirable properties in products formed according to the teachings herein. Preferably, such processing enhancers do not contain $Cl^-$ or chlorides or chlorine-based materials which are required by other processing techniques.

For example, certain processing enhancers may dissociate into positive ions (cations) and negative ions (anions). The anions and/or cations, depending on a variety of factors including liquid composition, concentration of ions, applied fields, frequency of applied fields, waveform of the applied filed, temperature, pH, zeta potential, etc., will navigate or move toward oppositely charged electrodes. When said ions are located at or near such electrodes, the ions may take part in one or more intermediate reactions with the electrode(s) and/or other constituent(s) located at or near such electrode(s). Sometimes ions may react with one or more materials in the electrode and cause metallic ions to be produced in the liquid. Specifically, sometimes ions present in a solution between electrodes may influence material in the electrode (or near the electrode) to form metallic nano-crystals that are "grown" from material provided by the electrode. For example, certain metal ions may enter the liquid 3 from the electrode 5 and be caused to come together (e.g., nucleate) to form constituents (e.g., ions, nanocrystals, etc.) within the liquid 3. Such ions can then be used as a raw material for the growth of bi-metallic nanocrystals.

The presence of certain nanocrystalline shapes (or shape distributions) containing specific spatially extended low index crystal planes can cause different reactions (e.g., different catalytic, electrochemical, biocatalytic and/or biophysical reactions and/or cause different biological signaling pathways to be active/inactive relative to the absence of such shaped nanoparticles) and/or different reactions selectively to occur under substantially identical conditions. Such differences in performance may be due to differing surface plasmon resonances and/or intensity of such resonances. Thus, by controlling amount (e.g., concentration), nanocrystal sizes, the presence or absence of certain extended growth crystal planes, and/or nanocrystalline shapes or shape distribution(s), certain reactions (e.g., catalytic, electrochemical, biological reactions and/or biological signaling pathways) can be desirably influenced and/or controlled. Such control can result in the prevention and/or treatment of a variety of different diseases or indications that are a function of certain biologic reactions and/or signaling pathways, as well as control of a number of non-biological reaction pathways.

Further, certain processing enhancers may also include materials that may function as charge carriers, but may themselves not be ions. Specifically, metallic-based particles, either introduced or formed in situ (e.g., heterogeneous or homogenous nucleation/growth) by the electrochemical processing techniques disclosed herein, can also function as charge carriers, crystal nucleators and/or growth promoters, which may result in the formation of a variety of different crystalline shapes (e.g., hexagonal plates, octahedrons, techahedrons, pentagonal bipyramids (decahedrons), etc.). Once again, the presence of particular particle crystal sizes, extended crystal planes and/or shapes or shape distributions of such crystals, can desirably influence certain reactions (e.g., binding to a particular protein or protein homologue and/or affecting a particular biological signaling pathway such as an inflammatory pathway or a proteasomal pathway) to occur.

For example, in reference to FIGS. 9 and 10a-10d, platinum species that are formed in a first trough member 30a'/30b' are caused to flow into a second trough member 30a'/30b' and take part in the formation of bi-metallic nanocrystals therein. More specifically, a first set of electrochemical reactions occur in a water containing a suitable processing enhancer to create a modified water-processing enhancer solution/suspension, which then serves as a raw material supply for a second set of electrochemical reactions that occur in a second trough member 30a'/30b'. In some cases, the two separate trough members are kept as separate members and the output of the first trough member is allowed to cool before being input into the second trough member. However, in another embodiment, the two trough members can be an integral unit, with or without cooling means located between the two identifiable portions 30a'/30b'.

Further, since the processing enhancers of the present invention do not contemplate those traditional organic-based molecules used in traditional reduction chemistry techniques, the lack of such chemical reductant (or added surfactant) means that the surfaces of the grown nanocrystals on the invention are very "clean" relative to nanoparticles that are formed by traditional reduction chemistry approaches. It should be understood that when the term "clean" is used with regard to nanocrystal surfaces or when the phrase "substantially free from organic impurities or films" (or a similar phrase) is used, what is meant is that the formed nanocrystals do not have chemical constituents adhered or attached to their surfaces which (1) alter the functioning of the nanocrystal and/or (2) form a layer, surface or film which covers a significant portion (e.g., at least 25% of the crystal, or more typically, at least 50% of the crystal). In preferred embodiments, the nanocrystal surfaces are completely free of any organic contaminants or reactants which materially change their functionality. It should be further understood that incidental components that are caused to adhere to nanocrystals of the invention and do not adversely or materially affect the functioning of the inventive nanocrystals, should still be considered to be within the metes and bounds of the invention.

The lack of added chemicals (e.g., organics or chlorine-based materials) permits the growth of the metal atoms and also does not adversely affect the performance of the nanocrystals (e.g., in catalysis reactions or in biological reactions, in vivo it affects the protein corona formed around the nanoparticles/nanocrystals in, for example, serum and/or reduces toxic compounds introduced into cells or an organism). For example, but without wishing to be bound by any particular theory or explanation, in biological reactions, protein corona formation can control location of a nanoparticle/nanocrystal in vivo, as well as control protein folding of proteins at or near the nanoparticle/nanocrystal surfaces. Such differences in performance may be due to such factors including, but not limited to, surface charge, surface plasmon resonance, epitaxial effects, surface double layers, zones of influence, toxic surface contaminants and others. Such novel shapes also affect, for example, catalysis.

Still further, once a seed crystal occurs in the process and/or a set of extended crystal planes begins to grow (e.g., homogenous nucleation) or a seed crystal is separately provided (e.g., heterogenous nucleation) the amount of time that a formed particle (e.g., a metal atom) is permitted to dwell at or near one or more electrodes in an electrochemical process can result in the size of bi-metallic nanocrystals increasing as a function of time (e.g., metal atoms can assemble into metal nanocrystals and, if unimpeded by certain organic constituents in the liquid, they can grow into a variety of shapes and sizes). The amount of time that crystal nucleation/growth conditions are present can control the shape(s) and sizes(s) of grown bi-metallic nanocrystals. Accordingly, dwell time at/around electrodes, liquid flow rate(s), trough cross-sectional shape(s), etc, all contribute to nanocrystal growth conditions, as discussed elsewhere herein.

In many of the preferred embodiments herein, one or more AC sources are utilized (e.g., transformer(s) 60 and power supply 501AC). The rate of change from "+" polarity on one electrode to "−" polarity on the same electrode is known as Hertz, Hz, frequency, or cycles per second. In the United States, the standard output frequency is 60 Hz, while in Europe it is predominantly 50 Hz. As shown in the Examples herein, the frequency can also influence size and/or shape and/or presence of nanocrystals and/or ions formed according to the electrochemical techniques disclosed herein. Preferable frequencies are 5-1000 Hz, more typically, 20-500 Hz, even more typically, 40-200 Hz, and even more typically, 50-100 Hz. For example, and without wishing to be bound by any particular theory or explanation, nucleated or growing crystals can first have attractive forces exerted on them (or on crystal growth constituents, such as ions or atoms, taking part in forming the crystal(s)) due to, for example, unlike charges attracting and then repulsive forces being exerted on such constituents (e.g., due to like charges repelling). These factors also clearly play a large role in nucleation and/or crystal growth of the novel nanocrystals formed by affecting particle size and/or shapes; as well as permitting the crystals to be formed without the need for reductants or surfactants (i.e., that needed to be added to take part in the prior art reduction chemistry techniques) causing the nanocrystal surfaces to be free of such added chemical species. The lack of organic-based coatings on the surface of grown nanocrystals alters (and in some cases controls) their biological function. Further, when water is used as the liquid, hydrolysis can occur at the electrodes, resulting in gas production and the production of other lysis products of water including hydrated electrons, $OH^-$, $H^*$, $H_3O$, $H_2O_2$, etc. Such lysis products also may assist in the crystal growth processes disclosed herein and/or assist in the stabilization of the bi-metallic nanocrystals in the suspension.

Moreover, the particular waveform that is used for a specific frequency also affects nanocrystal growth conditions, and thus effects nanocrystal size(s) and/or shape(s). While the U.S. uses a standard AC frequency of 60 Hz, it also uses a standard waveform of a "sine" wave. As shown in the Examples herein, changing the waveform from a sine wave to a square wave or a triangular wave also affects nanocrystal crystallization conditions and thus affects resultant nanocrystal size(s) and shape(s). Preferred waveforms include sine waves, square waves and triangular waves, however hybrid waveforms should be considered to be within the metes and bounds of the invention.

Still further, the voltage applied in the novel electrochemical techniques disclosed herein can also affect nanocrystalline size(s) and shape(s). A preferred voltage range is 20-2000 Volts, a more preferred voltage range is 50-1000 Volts and an even more preferred voltage range is 100-300 Volts. In addition to voltage, the amperages used with these voltages typically are 0.1-10 Amps, a more preferred amperage range is 0.1-5 Amps and an even more preferred amperage range is 0.4-1 Amps per electrode set under the processing parameters disclosed herein.

Still further, the "duty cycle" used for each waveform applied in the novel electrochemical techniques disclosed herein can also affect nanocrystalline size(s) and shape(s). In this regard, without wishing to be bound by any particular theory or explanation, the amount of time that an electrode is positively biased can result in a first set of reactions, while a different set of reactions can occur when the electrode is negatively biased. By adjusting the amount of time that the electrodes are positively or negatively biased, size(s) and/or shape(s) of grown nanocrystals can be controlled. Further, the rate at which an electrode converts to + or − is also a function of waveform shape and also influences nanocrystal size(s) and/or shape(s).

Temperature can also play an important role. In some of the preferred embodiments disclosed herein, the boiling point temperature of the water is approached in at least a portion of the processing vessel where nanocrystals are nucleated and grown. For example, output water temperature in the continuous processing Examples herein ranges from about 60° C.-99° C. However, as discussed elsewhere herein, different temperature ranges are also desirable. Temperature can influence resultant product (e.g., size and/or shape of nanocrystals) as well as the amount of resultant product (i.e., ppm level of nanocrystals in the suspension or colloid). For example, while it is possible to cool the liquid 3 in the trough member 30 by a variety of known techniques (as disclosed in some of the Examples herein), many of the Examples herein do not cool the liquid 3, resulting in evaporation of a portion of the liquid 3 during processing thereof.

It should be understood that a variety of different shapes and/or cross-sections can exist for the trough member 30 (or 30a' and/or 30b'), any one of which can produce desirable results as a function of a variety of design and production considerations. For example, one or more constituents produced in the portion(s) 30a', or 30b' could be transient (e.g., a seed crystal or nucleation point) and/or semi permanent (e.g., grown nanocrystals present in a colloid). If such constituent(s) produced, for example, in portion 30a' is to be desirably and controllably reacted with one or more constituents produced in, for example, portion 30b', then a final product (e.g., properties of a final product) which results from such mixing could be a function of when constituents formed in the portions 30a' and 30b' are mixed together. Further, transient constituents formed in a first trough member 30a'/30b' can also affect subsequent bi-metallic nanocrystal formation in a second trough member 30a'/30b'. Thus, the amount of time that lapses between the production of a first aqueous product in a first trough member and wherein such first product becomes a raw material in a second trough member can also influence the bi-metallic nanocrystal suspension formed. Thus, the temperature of liquids entering and exiting can be monitored/controlled to maximize certain desirable processing conditions and/or desirable properties of final products and/or minimize certain undesirable products. Still further, processing enhancers may be selectively utilized in one or more of the portions of the different trough members.

Figure 6:
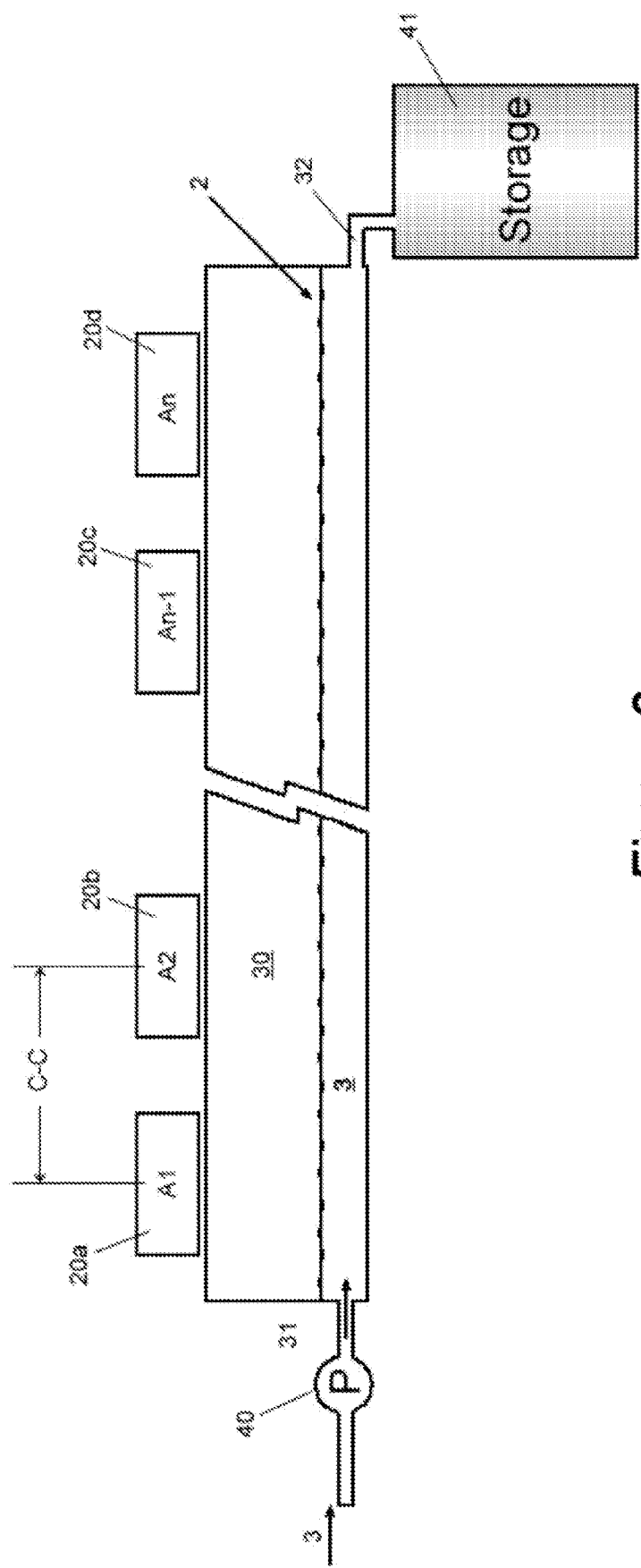
FIG. 6 shows a schematic cross-sectional view of a set of control devices 20 located on a trough member 30 with a liquid 3 flowing therethrough and into a storage container 41.

FIG. 6 shows a schematic view of the general apparatus utilized in accordance with the teachings of some of the preferred embodiments of the present invention. In particular, this FIG. 6 shows a side schematic view of the trough member 30 containing a liquid 3 therein. On the top of the trough member 30 rests a plurality of control devices 20a-20d which are, in this embodiment, removably attached thereto. The control devices 20a-20d may of course be permanently fixed in position when practicing various embodiments of the invention. The precise number of control devices 20 (and corresponding electrode(s) 1 and/or 5 as well as the configuration(s) of such electrodes) and the positioning or location of the control devices 20 (and corresponding electrodes 1 and/or 5) are a function of various preferred embodiments of the invention discussed in greater detail elsewhere herein. However, in general, an input liquid 3 (for example water or purified water containing a process enhancer) is provided to a liquid transport means 40 (e.g., a liquid pump, gravity or liquid pumping means for pumping the liquid 3) such as a peristaltic pump 40 for pumping the liquid 3 into the trough member 30 at a first-end 31 thereof. The liquid transport means 40 may include any means for moving liquids 3 including, but not limited to a gravity-fed or hydrostatic means, a pumping means, a regulating or valve means, etc. However, the liquid transport means 40 should be capable of reliably and/or controllably introducing known amounts of the liquid 3 into the trough member 30. The amount of time that the liquid 3 is contained within the trough member 30 (e.g., at or around one or more electrode(s) 1/5) also influences the products produced (e.g., the sizes(s) and/or shapes(s) of the grown nanocrystals).

Once the liquid 3 is provided into the trough member 30, means for continually moving the liquid 3 within the trough member 30 may or may not be required. However, a simple means for continually moving the liquid 3 includes the trough member 30 being situated on a slight angle θ (e.g., less than a degree to a few degrees for a low viscosity fluid 3 such as water) relative to the support surface upon which the trough member 30 is located. For example, a difference in vertical height of less than one inch between an inlet portion 31 and an outlet portion 32, spaced apart by about 6 feet (about 1.8 meters) relative to the support surface may be all that is required, so long as the viscosity of the liquid 3 is not too high (e.g., any viscosity around the viscosity of water can be controlled by gravity flow once such fluids are contained or located within the trough member 30). The need for a greater angle θ could be a result of processing a liquid 3 having a viscosity higher than water; the need for the liquid 3 to transit the trough 30 at a faster rate, etc. Further, when viscosities of the liquid 3 increase such that gravity alone is insufficient, other phenomena such as specific uses of hydrostatic head pressure or hydrostatic pressure can also be utilized to achieve desirable fluid flow. Further, additional means for moving the liquid 3 along the trough member 30 could also be provided inside the trough member 30. Such means for moving the fluid include mechanical means such as paddles, fans, propellers, augers, etc., acoustic means such as transducers, thermal means such as heaters and/or chillers (which may have additional processing benefits), etc., are also desirable for use with the present invention.

FIG. 6 also shows a storage tank or storage vessel 41 at the end 32 of the trough member 30. Such storage vessel 41 can be any acceptable vessel and/or pumping means made of one or more materials which, for example, do not negatively interact with the liquid 3 (or constituents contained therein) produced within the trough member 30. Acceptable materials include, but are not limited to plastics such as high density polyethylene (HDPE), glass, metal(s) (such a certain grades of stainless steel), etc. Moreover, while a storage tank 41 is shown in this embodiment, the tank 41 should be understood as including a means for distributing or directly bottling or packaging the fluid 3 processed in the trough member 30.

Figure 8A:
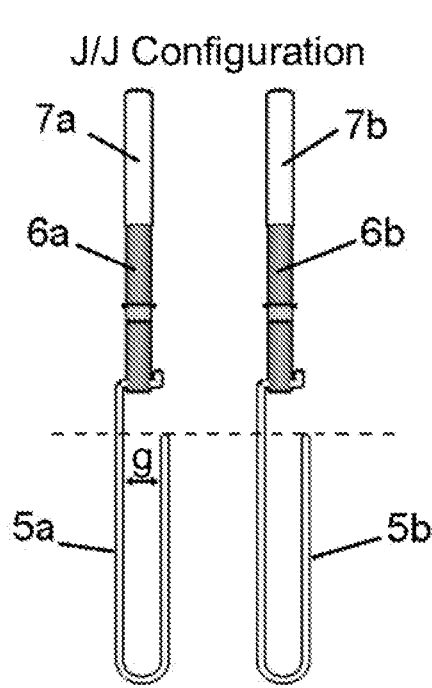
FIG. 8a shows a view of gold wires 5a and 5b used in some examples herein.
Figure 8B:
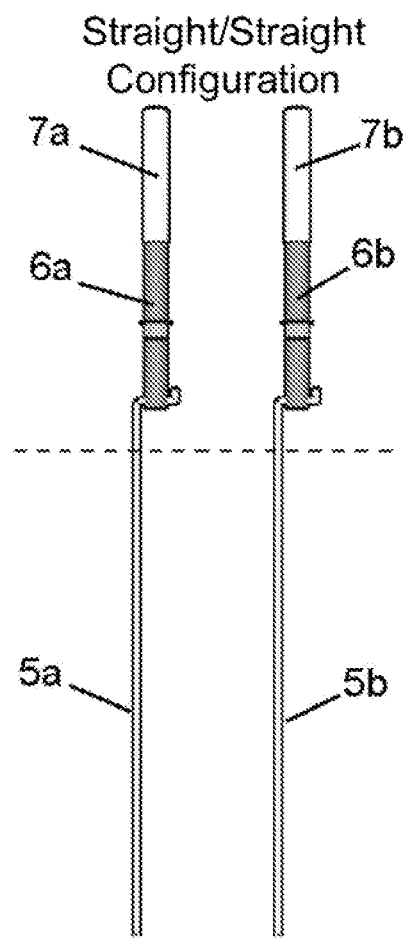
FIG. 8b shows a view of the gold wires 5a and 5b used in some examples herein.
Figure 8C:
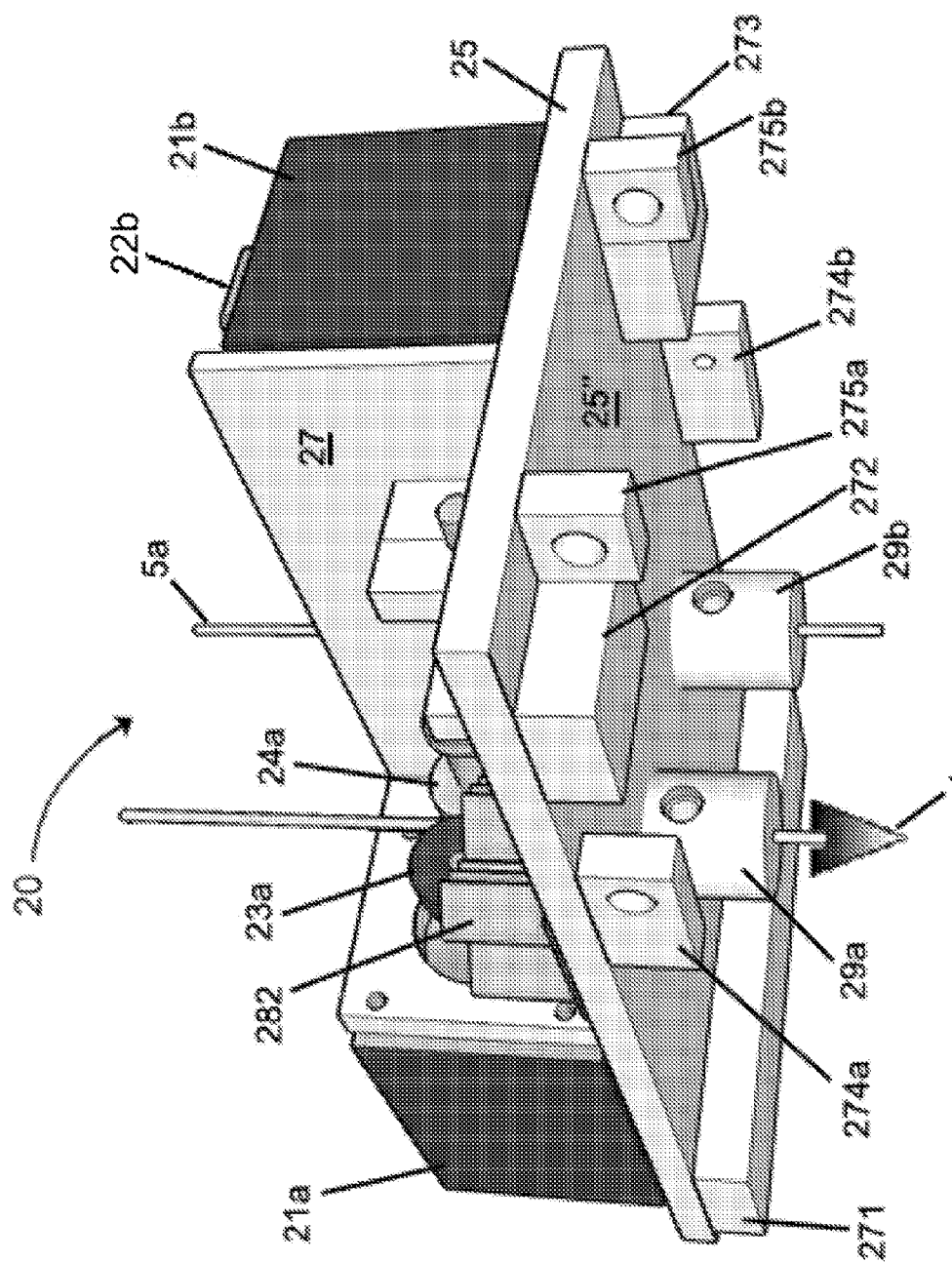
FIG. 8c shows the device 20 used in all trough Examples herein that utilize a plasma.
Figure 8D:
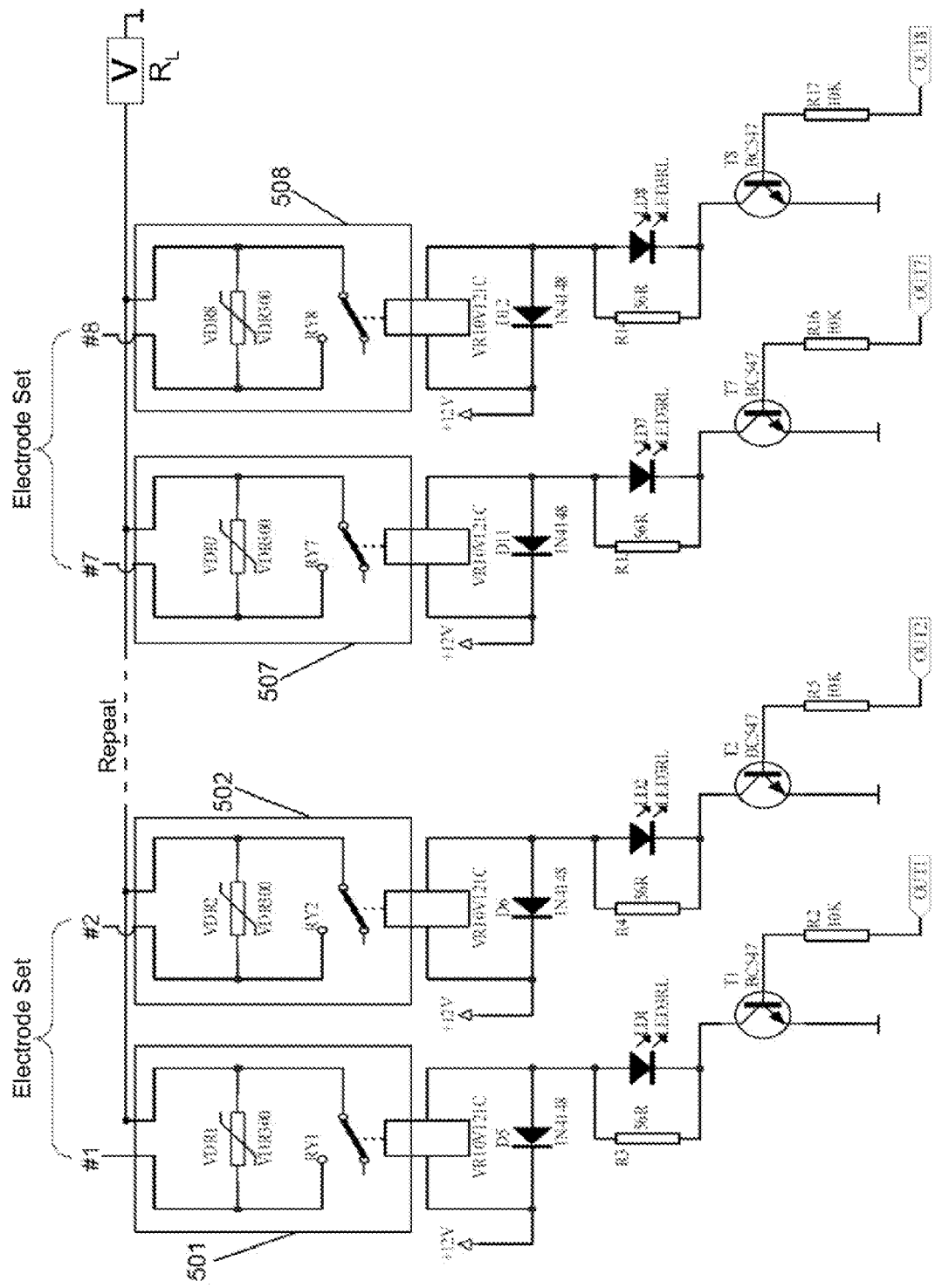

The electrode control devices shown generally in, for example, FIGS. 2 and 6 are shown in greater detail in FIG. 8c. In particular, FIG. 8c shows a perspective view of the control device 20. FIG. 8c shows a base portion 25 is provided, said base portion having a top portion 25' and a bottom portion 25". The base portion 25 is made of a suitable rigid plastic material including, but not limited to, materials made from structural plastics, resins, polyurethane, polypropylene, nylon, teflon, polyvinyl, etc. A dividing wall 27 is provided between two electrode adjustment assemblies. The dividing wall 27 can be made of similar or different material from that material comprising the base portion 25. Two servo-step motors 21a and 21b are fixed to the surface 25' of the base portion 25. The step motors 21a, 21b could be any step motor capable of slightly moving (e.g., on a 360 degree basis, slightly less than or slightly more than 1 degree) such that a circumferential movement of the step motors 21a/21b results in a vertical raising or lowering of an electrode 1 or 5 communicating therewith. In this regard, a first wheel-shaped component 23a is the drivewheel connected to the output shaft 231a of the drive motor 21a such that when the drive shaft 231a rotates, circumferential movement of the wheel 23a is created. Further, a slave wheel 24a is caused to press against and toward the drivewheel 23a such that frictional contact exists therebetween. The drivewheel 23a and/or slavewheel 24a may include a notch or groove on an outer portion thereof to assist in accommodating the electrodes 1,5. The slavewheel 24a is caused to be pressed toward the drivewheel 23a by a spring 285 located between the portions 241a and 261a attached to the slave wheel 24a. In particular, a coiled spring 285 can be located around the portion of the axis 262a that extends out from the block 261a. Springs should be of sufficient tension so as to result in a reasonable frictional force between the drivewheel 24a and the slavewheel 24a such that when the shaft 231a rotates a determined amount, the electrode assemblies 5a, 5b, 1a, 1b, etc., will move in a vertical direction relative to the base portion 25. Such rotational or circumferential movement of the drivewheel 23a results in a direct transfer of vertical directional changes in the electrodes 1,5 shown herein. At least a portion of the drivewheel 23a should be made from an electrically insulating material; whereas the slavewheel 24a can be made from an electrically conductive material or an electrically insulating material, but typically, an electrically insulating material.

The drive motors 21a/21b can be any suitable drive motor which is capable of small rotations (e.g., slightly below 1°/360° or slightly above 1°/360°) such that small rotational changes in the drive shaft 231a are translated into small vertical changes in the electrode assemblies. A preferred drive motor includes a drive motor manufactured by RMS Technologies model 1MC17-504 step motor, which is a DC-powered step motor. This step motors 21a/21b include an RS-232 connection 22a/22b, respectively, which permits the step motors to be driven by a remote control apparatus such as a computer or a controller.

The portions 271, 272 and 273 are primarily height adjustments which adjust the height of the base portion 25 relative to the trough member 30. The portions 271, 272 and 273 can be made of same, similar or different materials from the base portion 25. The portions 274a/274b and 275a/275b can also be made of the same, similar or different material from the base portion 25. However, these portions should be electrically insulating in that they house various wire components associated with delivering voltage and current to the electrode assemblies 1a/1b, 5a/5b, etc.

With regard to the size of the control device 20 shown in FIG. 8c, length and width can be any dimension which accommodates the size of the step motors 21a/21b, and the width of the trough member 30. In this regard, length should be at least as long as the trough member 30 is wide, and typically slightly longer (e.g., 10-30%). The width needs to be wide enough to house the step motors 21a/21b and not be so wide as to unnecessarily underutilize longitudinal space along the length of the trough member 30. In one preferred embodiment of the invention, the length is about 7 inches (about 19 millimeters) and the width is about 4 inches (about 10.5 millimeters). The thickness of the base member 25 is any thickness sufficient which provides structural, electrical and mechanical rigidity for the base member 25 and should be of the order of about ¼"-¾" (about 6 mm-19 mm). While these dimensions are not critical, the dimensions give an understanding of size generally of certain components of one preferred embodiment of the invention.

Further, the base member 25 (and the components mounted thereto), can be covered by a suitable cover (not shown) to insulate electrically, as well as creating a local protective environment for all of the components attached to the base member 25. Such cover can be made of any suitable material which provides appropriate safety and operational flexibility. Exemplary materials include plastics similar to that used for other portions of the trough member 30 and/or the control device 20 and are typically transparent. This cover member can also be made of the same type of materials used to make the base portion 25. The cover can include through-holes which can be aligned with excess portions of, for example, electrodes 5, which can be connected to, for example, a spool of electrode wire (not shown in these drawings).

Figure 8G:
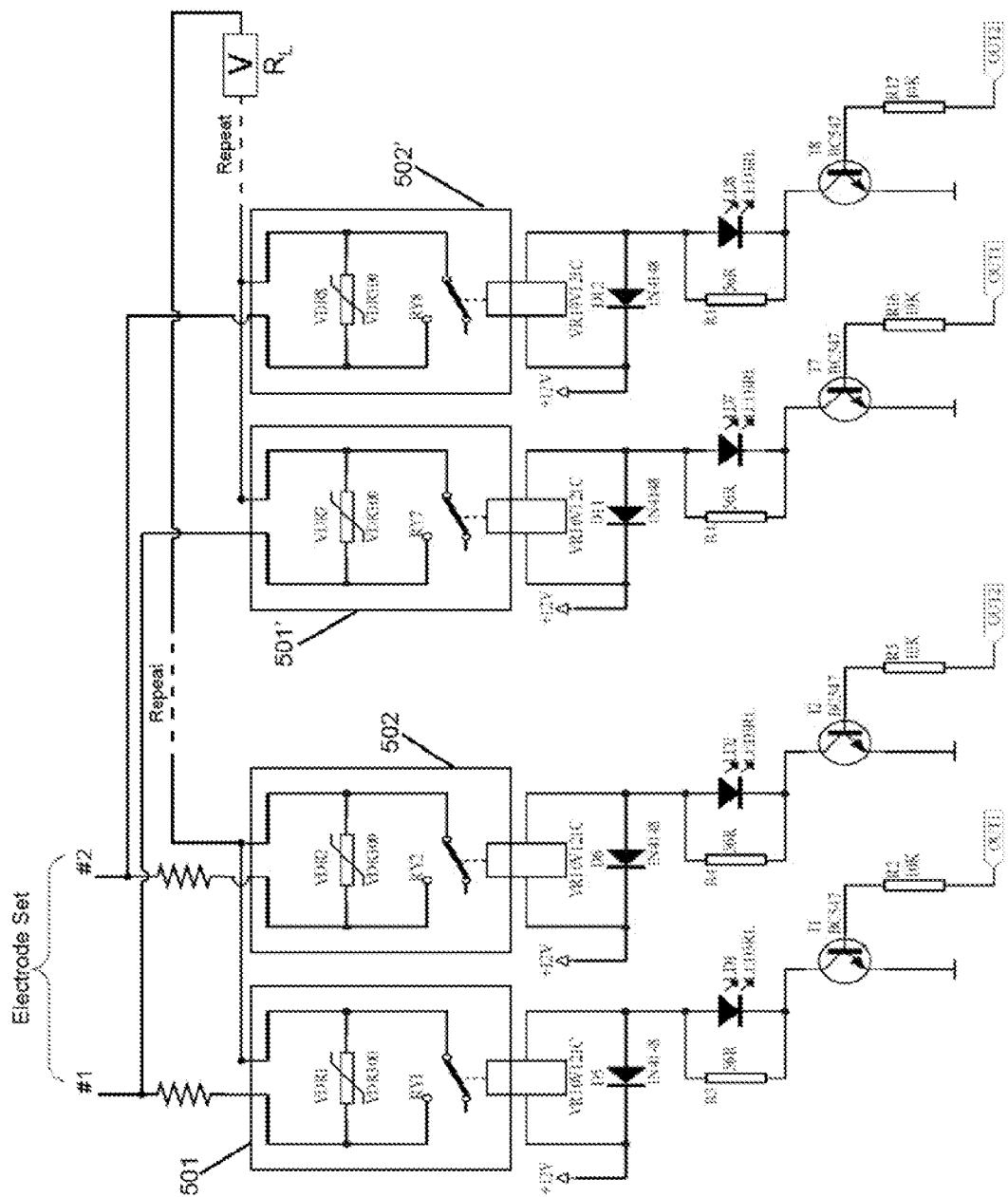
Figure 8H:
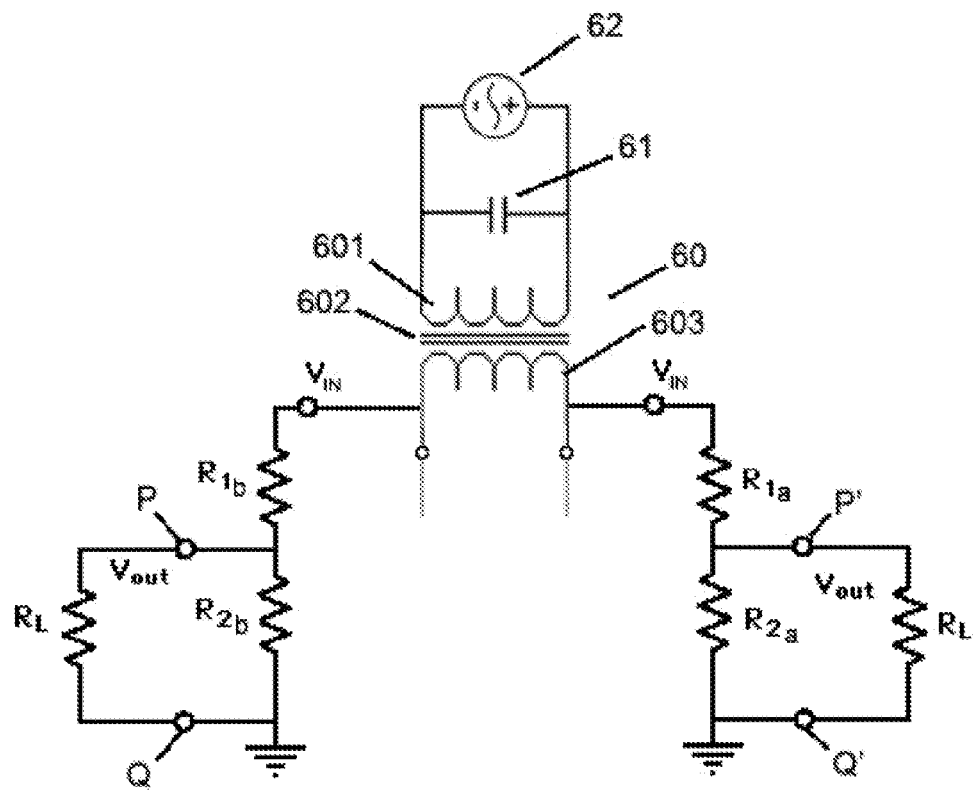
FIGS. 8h and 8i show wiring diagrams used to power devices 20.
Figure 8I:
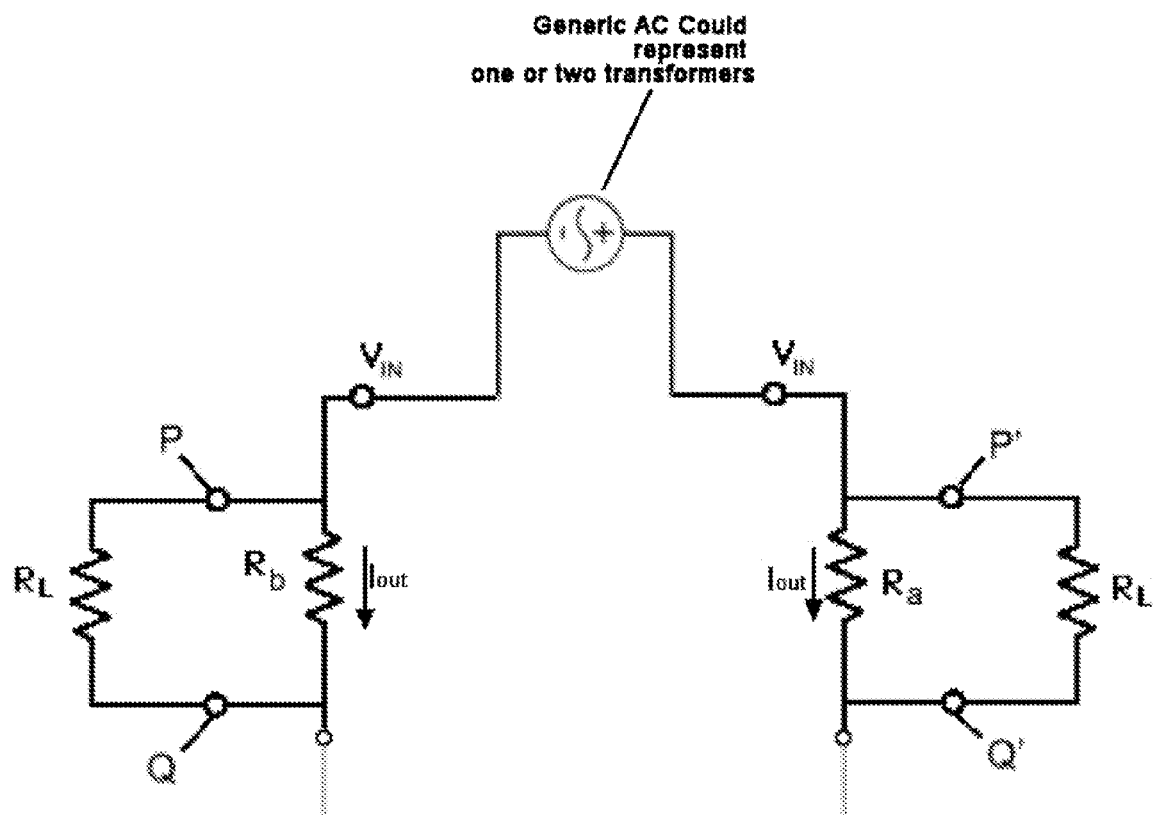
Figure 8J:
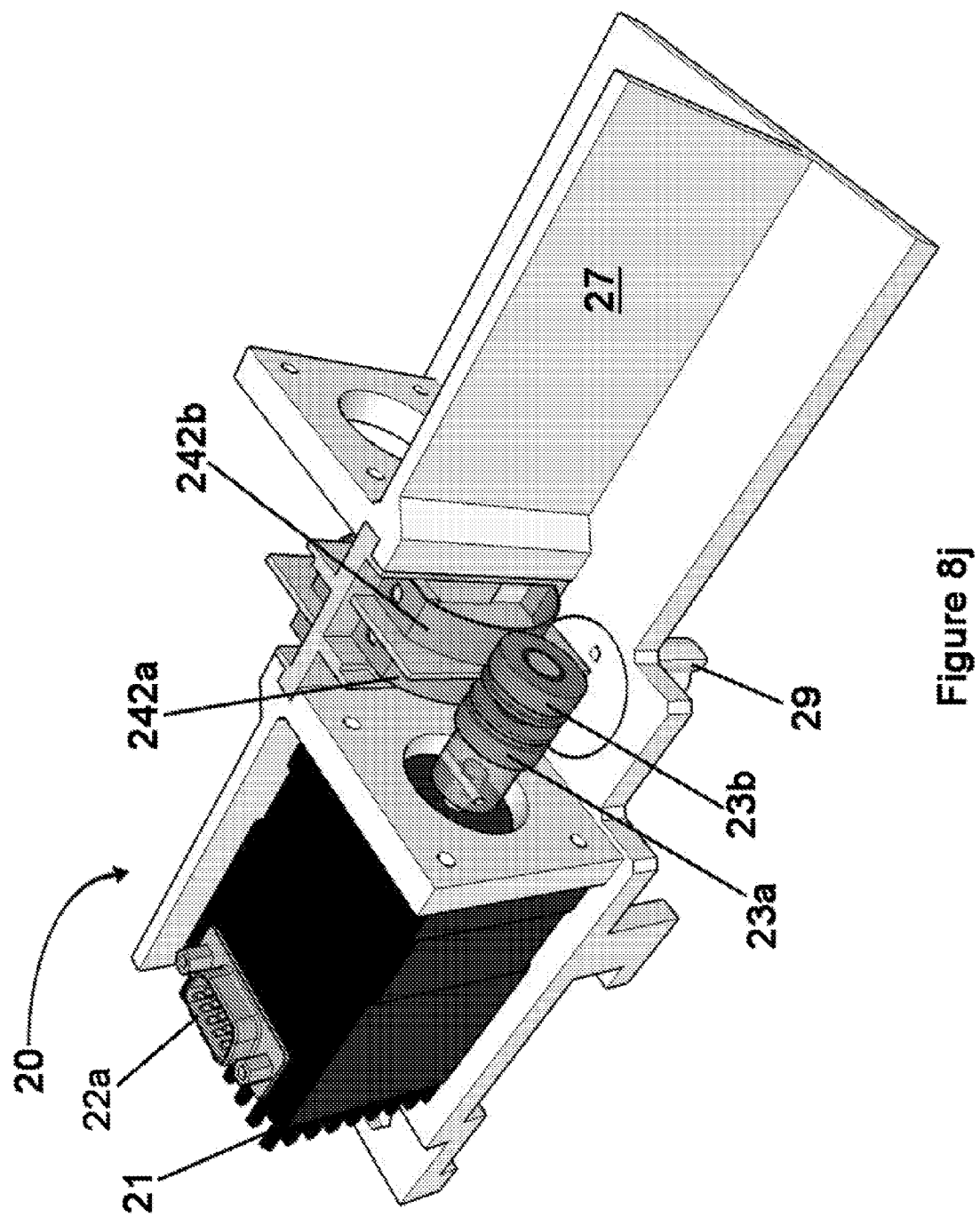
FIG. 8j shows a design for powering wires 5/5 in the devices 20.

As shown in FIG. 8j, the portions 242, 242a and 242b provide resilient tension for the wire 5a or 5b to be provided therebetween. Additionally, this control device design causes there to be an electrical connection between the power sources 60 or 501AC and the electrodes 1/5. The servo-motor 21a functions as discussed above, but two electrodes are driven by a single servo drive motor 21a. Accordingly, a single drive motor 21a can replace two drive motors in the case of the embodiment shown in FIG. 8j. Further, by providing the electrical contact between the wires 1/5 and the power sources 60/501AC, all electrical connections are provided on a top surface of (i.e., the surface further away from the liquid 3) resulting in certain design and production advantages.

FIG. 8c shows a refractory material component 29a, 29b. The component 29 is made of, for example, suitable refractory component, including, for example, aluminum oxide or the like. The refractory component 29 may have a transverse through-hole therein which provides for electrical connections to the electrode(s) 1 and/or 5. Further a longitudinal through-hole is present along the length of the refractory component 29 such that electrode assemblies 1/5 can extend therethrough.

FIG. 8c specifically shows one electrode(s) 1a as extending through a first refractory portion 29a and one electrode(s) 5a is shown as extending through a second refractory portion 29b. Accordingly, each of the electrode assemblies expressly disclosed herein, as well as those referred to herein, can be utilized in combination with the preferred embodiments of the control device shown herein.

In order for the control devices 20 to be actuated, two general processes need to occur. A first process involves electrically activating the electrode(s) 1 and/or 5 (e.g., applying power thereto from a preferred power source 10), and the second general process occurrence involves determining, for example, how much power (e.g., voltage and/or current) is applied to the electrode(s) and appropriately adjusting electrode 1/5 height in response to such determinations (e.g., manually and/or automatically adjusting the height of the electrodes 1/5); or adjusting the electrode height or simply moving the electrode into (e.g., progressively advancing the electrode(s) 5 through the liquid 3) or out of contact with the liquid 3, as a function of time. In the case of utilizing a control device 20, suitable instructions are communicated to the step motor 21 through the RS-232 ports 22a and 22b. Important embodiments of components of the control device 20, as well as the electrode activation process, are discussed herein.

A preferred embodiment of the invention utilizes the automatic control devices 20 shown in various figures herein. The step motors 21a and 21b shown in, for example, FIG. 8c. The electrodes 1/5 are monitored either by the electrical circuit diagrammed in each of FIGS. 8d-8h (e.g., for electrode sets 1/5 that make a plasma 4 or for electrode sets 5/5); or are monitored by the electrical circuit diagrammed in each of FIGS. 8g and 8i for electrode sets 5/5, in some embodiments herein.

In particular, in this embodiment, the electrical circuit of FIG. 8h is a voltage monitoring circuit. Specifically, voltage output from each of the output legs of the secondary coil 603 in the transformer 60 are monitored over the points "P-Q" and the points "P'-Q'". Specifically, the resistor denoted by "$R_L$" corresponds to the internal resistance of the multi-meter measuring device (not shown). The output voltages measured between the points "P-Q" and "P'-Q'" typically, for several preferred embodiments shown in the Examples later herein, range between about 200 volts and about 4,500 volts. However, higher and lower voltages can work with many of the embodiments disclosed herein. Desirable target voltages have been determined for each electrode set 1 and/or 5 at each position along a trough member 30a'. Such desirable target voltages are achieved as actual applied voltages by, utilizing, for example, the circuit control shown in FIGS. 8d, 8e and 8f. These FIGS. 8d, 8e and 8f refer to sets of relays controlled by a Velleman K8056 circuit assembly (having a micro-chip PIC16F630-I/P). Each transformer 60 is connected electrically in a manner shown in FIG. 8*h*. Each transformer 60 and associated measuring points "P-Q" and "P'-Q'" are connected to an individual relay. For example, the points "P-Q" correspond to relay number 501 in FIG. 8*d* and the points "P'-Q'" correspond to the relay 502 in FIG. 8*d*. Accordingly, two relays are required for each transformer 60. Each relay, 501, 502, etc., sequentially interrogates a first output voltage from a first leg of a secondary coil 603 and then a second output voltage from a second leg of the secondary coil 603; and such interrogation continues onto a first output voltage from a second transformer 60*b* on a first leg of its secondary coil 603, and then on to a second leg of the secondary coil 603, and so on.

The computer or logic control for the disclosed interrogation voltage adjustment techniques are achieved by any conventional program or controller, including, for example, in a preferred embodiment, standard visual basic programming steps utilized in a PC. Such programming steps include interrogating, reading, comparing, and sending an appropriate actuation symbol (e.g., raise or lower an electrode relative to the surface 2 of the liquid 3). Such techniques should be understood by an artisan of ordinary skill.

Further, in another preferred embodiment of the invention utilized in Example 1 for the electrode sets 5/5', the automatic control devices 20 are controlled by the electrical circuits of FIGS. 8*e*, 8*f*, 8*g* and 8*i*. In particular, the electrical circuit of FIG. 8*i* is a voltage monitoring circuit used to measure current. In this case, voltage and current are the same numerical value due to choice of a resistor (discussed later herein). Specifically, voltage output from each power source 501AC is monitored over the points "P-Q" and the points "P'-Q'". Specifically, the resistor denoted by "$R_L$" corresponds to the internal resistance of the multi-meter measuring device (not shown). The output voltages measured between the points "P-Q" and "P'-Q'" typically, for several preferred embodiments shown in the Examples later herein, range between about 0.05 volts and about 5 volts. However, higher and lower voltages can work with many of the embodiments disclosed herein. Desirable target voltages have been determined for each electrode set 5/5' at each position along a trough member 30*b'*. Such desirable target voltages are achieved as actual applied voltages by, utilizing, for example, the circuit control shown in FIGS. 8*e*, 8*f*, 8*g* and 8*i*. These FIG. 8 refer to sets of relays controlled by a Velleman K8056 circuit assembly (having a micro-chip PIC16F630-I/P).

In particular, the servo-motor 21 is caused to rotate at a specific predetermined time in order to maintain a desirable electrode 5 profile. The servo-motor 21 responds by rotating a predetermined amount in a clockwise direction. Specifically the servo-motor 21 rotates a sufficient amount such that about 0.009 inches (0.229 mm) of the electrode 5 is advanced toward and into the female receiver portion o5 (shown, for example in FIGS. 10*b* and 11*a*). Thus, the electrode 5 is progressively advanced through the liquid 3. In one preferred embodiment discussed herein, such electrode 5 movement occurs about every 4.3 minutes. Accordingly, the rate of vertical movement of each electrode 5 into the female receiver portion o5 is about 1 inch (about 1.9 cm) every 8 hours. Accordingly, a substantially constant electrode 5 shape or profile is maintained by its constant or progressive advance into and through the liquid 3. Further, once the advancing end of the electrode 5 reaches the longitudinal end of the female receiver portion o5, the electrode 5 can be removed from the processing apparatus. Alternatively, an electrode collecting means for collecting the "used" portion of the electrode can be provided.

Such means for collecting the electrode(s) 5 include, but are not limited to, a winding or spooling device, and extended portion o5, a wire clipping or cutting device, etc. However, in order to achieve different current/voltage profiles (and thus a variety of different nanocrystal size(s) and/or shapes(s), other rates of electrode movement are also within the metes and bounds of this invention.

Moreover, with specific reference to FIGS. 8*e*, 8*f*, 8*g* and 8*i*, it should be noted that an interrogation procedure occurs sequentially by determining the voltage of each electrode, which in the embodiments herein, are equivalent to the amps because in FIG. 8*i* the resistors Ra and Rb are approximately 1 ohm, accordingly, V=I. In other words, each power source 501AC is connected electrically in a manner shown in FIGS. 8*e*, 8*f*, 8*g* and 8*i*. Each power source 501AC and associated measuring points "P-Q" and "P'-Q'" are connected to two individual relays. For example, the points "P-Q" correspond to relay number 501 and 501' in FIG. 8*g* and the points "P'-Q'" correspond to the relay 502, 502' in FIG. 8*g*. Accordingly, relays are required for each electrode set 5/5. Each relay, 501/501' and 502/502', etc., sequentially interrogates the output voltage from the power source 501AC and then a second voltage from the same power source 501AC, and so on.

The computer or logic control for the disclosed electrode height adjustment techniques are achieved by any conventional program or controller, including, for example, in a preferred embodiment, standard visual basic programming steps utilized in a PC. Such programming steps include reading and sending an appropriate actuation symbol to lower an electrode relative to the surface 2 of the liquid 3. Such techniques should be understood by an artisan of ordinary skill.

DEFINITIONS

For purposes of the present invention, the terms and expressions below, appearing in the Specification and Claims, are intended to have the following meanings:

"Substantially clean", as used herein should be understood when used to describe nanocrystal surfaces means that the nanocrystals do not have chemical constituents adhered or attached to their surfaces in such an amount that would materially alter the functioning of the nanocrystal in at least one of its significant properties of the metallic-based nanocrystals set forth in the Examples herein. Alternatively, the metallic-based nanocrystal does not have a layer, surface or film which covers a significant portion (e.g., at least 25% of the crystal, or in another embodiment at least 50% of the crystal). It also can mean that the nanocrystal surfaces are completely free of any organic contaminants which materially change their functionality over bare gold crystal surfaces. It should be understood that incidental components that are caused to adhere to nanocrystals of the invention and do not adversely or materially affect the functioning of the inventive nanocrystals, should still be considered to be within the metes and bounds of the invention. The term should also be understood to be a relative term referencing the lack of traditional organic-based molecules (i.e., those used in traditional reduction chemistry techniques) on the surfaces of the grown nanocrystals of the invention.

As used herein, the term "processing-enhancer" or "processing-enhanced" or "process enhancer" means at least one material (e.g., solid, liquid and/or gas) and typically means an inorganic material, which material does not significantly bind to the formed nanocrystals, but rather facilitates nucleation/ growth during an electrochemical-stimulated growth process. The material serves important roles in the process including providing charged ions in the electrochemical solution to permit the crystals to be grown. The process enhancer is critically a compound(s) which remains in solution, and/or does not form a coating (in one embodiment an organic coating), and/or does not adversely affect the formed nanocrystals or the formed suspension(s), and/or is destroyed, evaporated, or is otherwise lost during the electrochemical crystal growth process.

The phrase "trough member" as used herein should be understood as meaning a large variety of fluid handling devices including, pipes, half pipes, channels or grooves existing in materials or objects, conduits, ducts, tubes, chutes, hoses and/or spouts, so long as such are compatible with the electrochemical processes disclosed herein.

The following Examples serve to illustrate certain embodiments of the invention but should not to be construed as limiting the scope of the disclosure as defined in the appended claims.

Example 1

Manufacturing Gold Based Nanocrystals/Nanocrystal Suspensions NE10214

Figure 9:
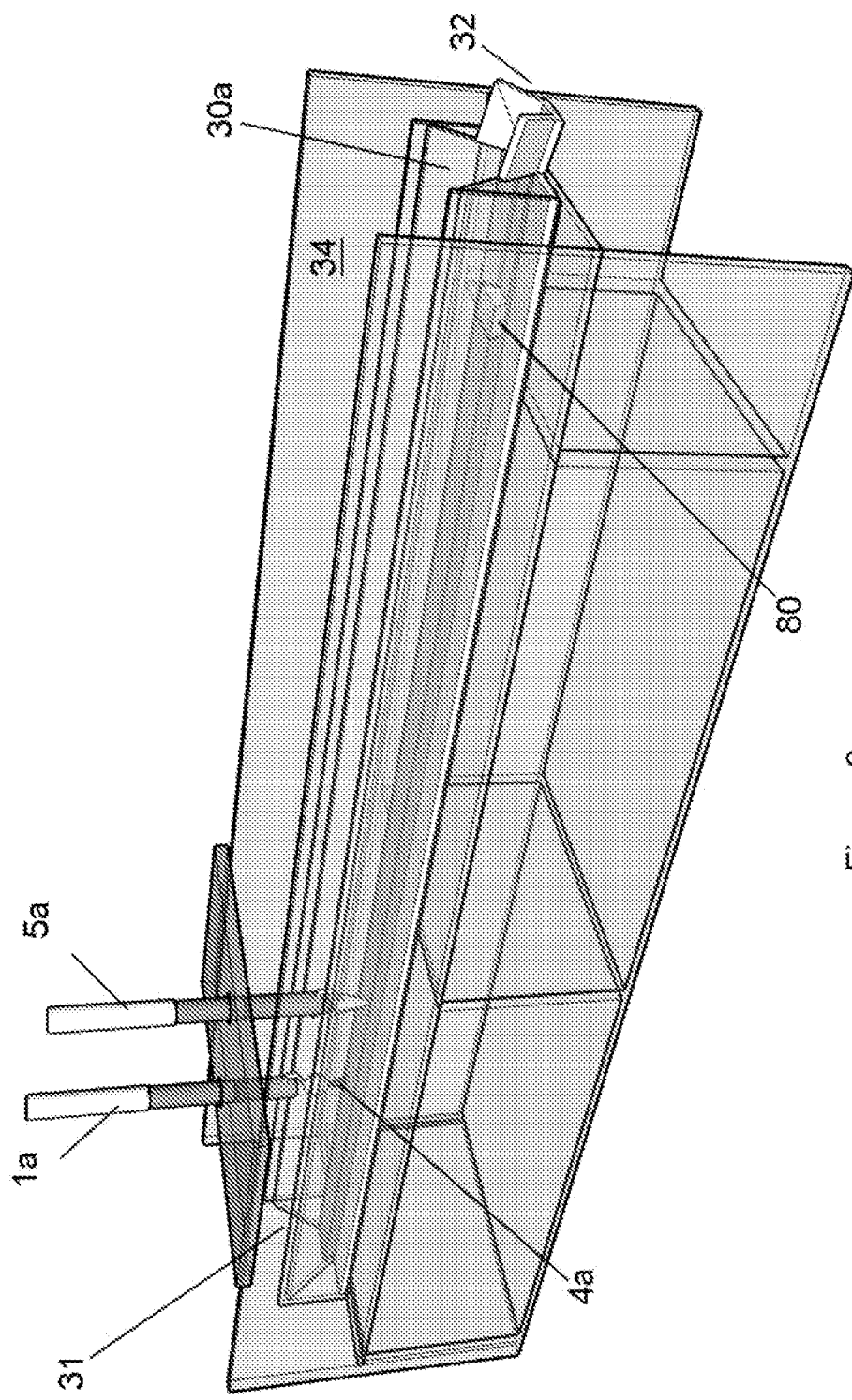
FIG. 9 shows a first trough member 30a' wherein one plasma 4a is created. The output of this first trough member 30a' flows into a second trough member 30b'.
Figure 10A:
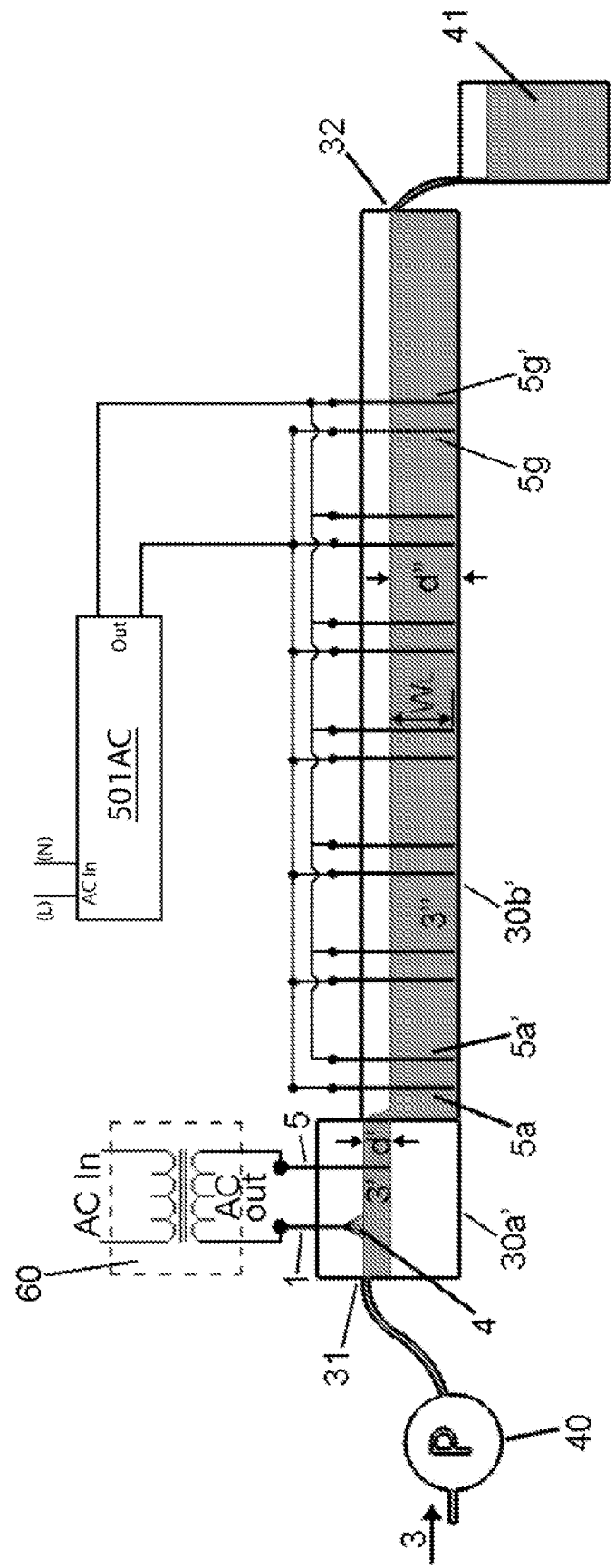
Figure 11A:
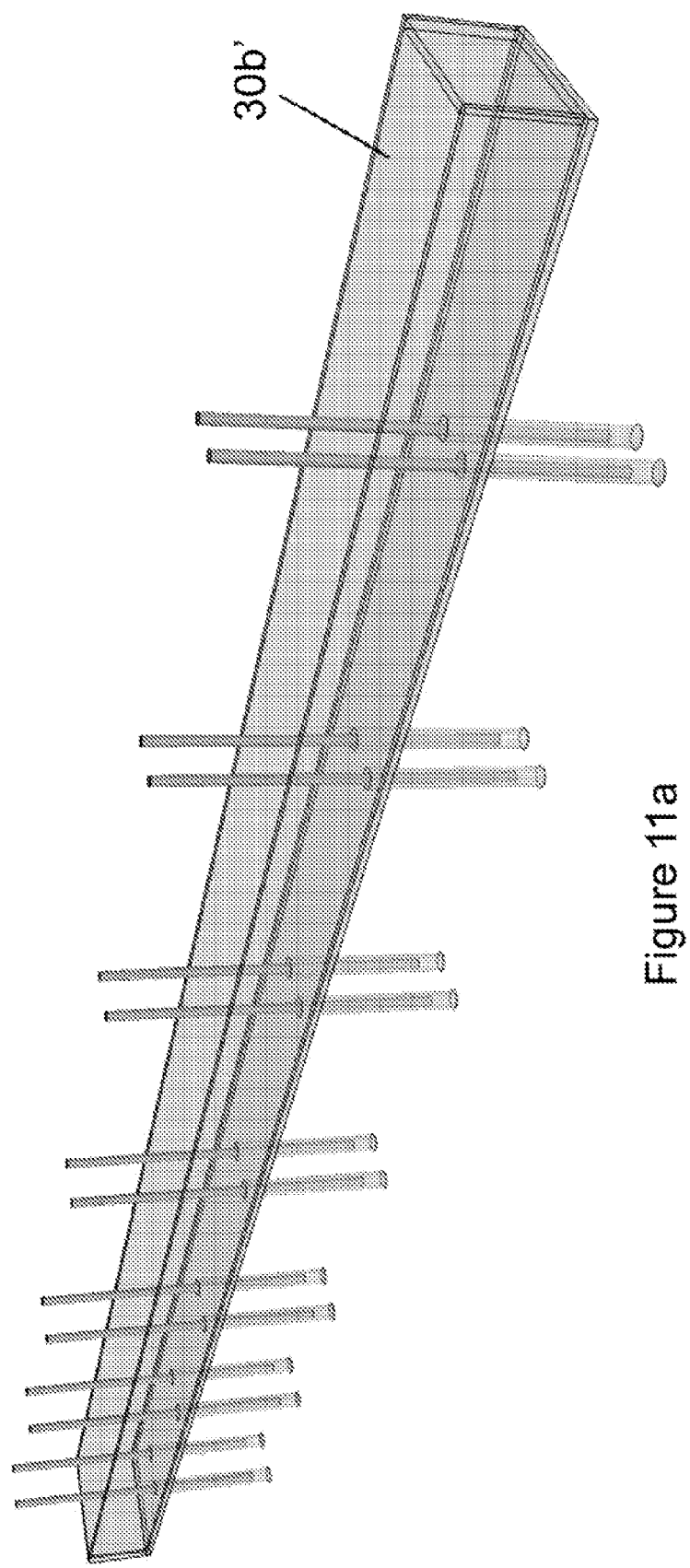
FIGS. 11a-11b show two trough members 30b' used in connection with FIGS. 10a-10d and various Examples herein.

In general, this Example utilizes certain embodiments of the invention associated with the apparatuses generally shown in FIGS. 9, 10c, and 11a. All trough members 30a' and 30b' in the aforementioned Figures were made from ⅛" (about 3 mm) thick plexiglass, and ¼" (about 6 mm) thick polycarbonate, respectively. The support structure 34 (not shown in many of the Figures but shown in FIG. 9) was also made from plexiglass which was about ¼" thick (about 6-7 mm thick). Each trough member 30a' was integral with trough member 30b'. The cross-sectional shape of the trough member 30a' used in this Example corresponded to that shape shown in FIG. 5b (i.e., was a trapezoidal-shaped cross-section). Relevant dimensions for 30a' were "S,S'" which measured about 1.5" (about 3.81 cm), "M" which measured about 2.5" (about 6.35 cm), "R" measured about ¾" (about 1.9 cm) and "d'" which measured about ½" (about 1.3 cm).

Figure 5A:
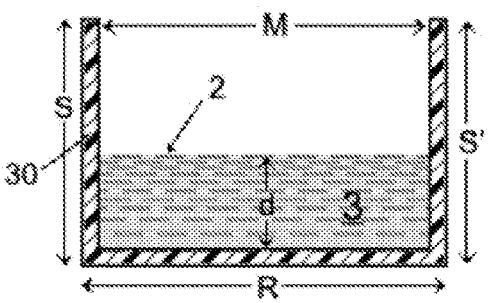
FIGS. 5a-5e show a variety of cross-sectional views of various trough members 30.
Figure 5B:
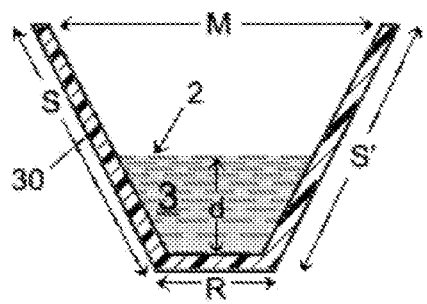
Figure 5C:
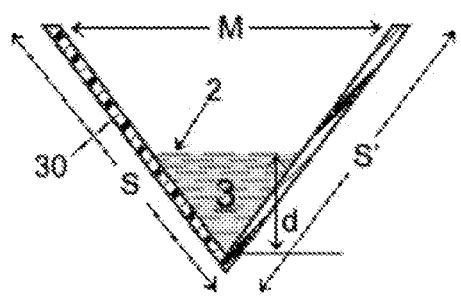
Figure 5D:
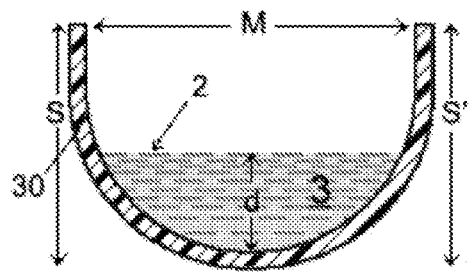
Figure 5E:
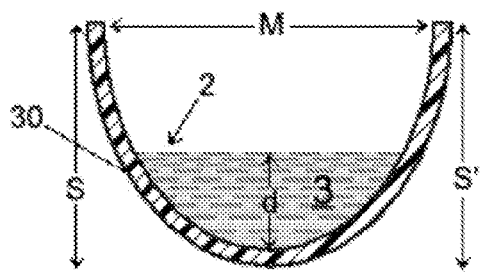

Each trough member portion 30b' had a cross-sectional shape corresponding to FIG. 5a. The relevant dimensions for trough member portion 30b' are reported in Table 1 as "M" (i.e., inside width of the trough at the entrance and exact portion of the trough member 30b'), "$L_T$" (i.e., transverse length or flow length of the trough member 30b'), "S" (i.e., the height of the trough member 30b'), and "d''" (i.e., depth of the liquid 3' within the trough member 30b'). The thickness of each sidewall portion of trough 30b' also measured about ¼" (about 6 mm) thick.

The water 3 used in Example 1 as an input into the trough member 30a' (and used in Examples 1-17 in combination with a processing enhancer) was produced by a Reverse Osmosis process and deionization process (referred to herein as de-ionized water). In essence, Reverse Osmosis (RO) is a pressure driven membrane separation process that separates species that are dissolved and/or suspended substances from the ground water. It is called "reverse" osmosis because pressure is applied to reverse the natural flow of osmosis (which seeks to balance the concentration of materials on both sides of the membrane). The applied pressure forces the water through the membrane leaving the contaminants on one side of the membrane and the purified water on the other. The reverse osmosis membrane utilized several thin layers or sheets of film that are bonded together and rolled in a spiral configuration around a plastic tube. (This is also known as a thin film composite or TFC membrane.) In addition to the removal of dissolved species, the RO membrane also separates out suspended materials including microorganisms that may be present in the water. After RO processing a mixed bed deionization filter was used. The total dissolved solvents ("TDS") after both treatments was about 0.2 ppm, as measured by an Accumet® AR20 pH/conductivity meter.

TABLE 1

| | | Run ID: NE10214 |
|---|---|---|
| Flow Rate: | In (ml/min) | 230 |
| | Out (ml/min) | 220 |
| Volts: | Set # 1 | 750 |
| | Set #'s 2-8 | 220 |
| | Set #'s 2-8 frequency, Hz | 60 |
| PE/Concentration (mg/mL) | | 0.528 |
| Wire Diameter (mm) | | 1.0 |
| Contact "$W_L$" (in/mm) | | 1/25.4 |
| Electrode Separation "y" (in/mm) | | .25/6.4 |
| Electrode Config. Figure | | 8b, 11a |
| Produced Au PPM | | 6.6 |
| Output Temp ° C. at 32 | | 72 |
| Dimensions | Plasma 4 Figs. | 9 |
| | Process Figures | 10c |
| | M (in/mm) | 1.5/38 |
| | $L_T$ (in/mm) | 36/914 |
| | d" (in/mm) | 1/25 |
| | S (in/mm) | 1.5/38 |
| Electrode Curr. (A) | | 0.71 |
| Total Curr. Draw (A) | | 5 |
| Hydrodynamic r (nm) | | 19.43 |
| TEM Avg. Dia. (nm) | | 12.38 |
| | "c-c" (mm) | 76 |
| Set 1 | electrode # | 1a |
| | "x" (in/mm) | 0.25/6.4 |
| | electrode # | 5a |
| | "c-c" (mm) | 102 |
| Set 2 | electrode # | 5b |
| | "x" (in/mm) | n/a |
| | electrode # | 5b' |
| | "c-c" (mm) | 76 |
| Set 3 | electrode # | 5c |
| | electrode # | 5c' |
| | "c-c" (mm) | 76 |
| Set 4 | electrode # | 5d |
| | electrode # | 5d' |
| | "c-c" (mm) | 127 |
| Set 5 | electrode # | 5e |
| | electrode # | 5e' |
| | "c-c" (mm) | 127 |
| Set 6 | electrode # | 5f |
| | electrode # | 5f' |
| | "c-c" (mm) | 152 |
| Set 7 | electrode # | 5g |
| | electrode # | 5g' |
| | "c-c" (mm) | 178 |
| Set 8 | electrode # | 5h |
| | electrode # | 5h' |
| | "c-c" (mm) | 76 |

Table 1 shows that the amount of processing enhancer (PE) ($NaHCO_3$) that was added to purified water was about 0.53 mg/ml. It should be understood that other amounts of this processing enhancer also function within the metes and bounds of the invention. The purified water/$NaHCO_3$ mixture was used as the liquid 3 input into trough member 30a'. The depth "d'" of the liquid 3' in the trough member 30a' (i.e., where the plasma(s) 4 is formed) was about 7/16" to about ½" (about 11 mm to about 13 mm) at various points along the trough member 30a'. The depth "d'" was partially controlled through use of the dam 80 (shown in FIG. 9). Specifically, the dam 80 was provided near the output end 32 of the trough member 30a' and assisted in creating the depth "d"' (shown in FIG. 5b as "d") to be about ⅞"-½" (about 11-13 mm) in depth. The height of the dam 80 measured about ¼" (about 6 mm) and the longitudinal length measured about ½" (about 13 mm). The width was completely across the bottom dimension "R" of the trough member 30a'. Accordingly, the total volume of liquid 3' in the trough member 30a' during operation thereof was about 2.14 in³ (about 35 ml) to about 0.89 in³ (about 14.58 ml).

The rate of flow of the liquid 3' into the trough member 30a' as well as into trough member 30b', was about 230 ml/minute and the rate of flow out of the trough member 30b' at the point 32 was about 220 ml/minute (i.e., due to evaporation). Other acceptable flow rates should be considered to be within the metes and bounds of the invention.

Such flow of liquid 3' was obtained by utilizing a Masterflex® L/S pump drive 40 rated at 0.1 horsepower, 10-600 rpm. The model number of the Masterflex® pump 40 was 7523-80. The pump drive had a pump head also made by Masterflex® known as Easy-Load Model No. 77201-60. In general terms, the head for the pump 40 is known as a peristaltic head. The precise settings on the pump was 230 milliliters per minute. Tygon® tubing having a diameter of ¼" (i.e., size 06419-25) was placed into the peristaltic head. The tubing was made by Saint Gobain for Masterflex®. One end of the tubing was delivered to a first end 31 of the trough member 30'a.

Figure 7A:
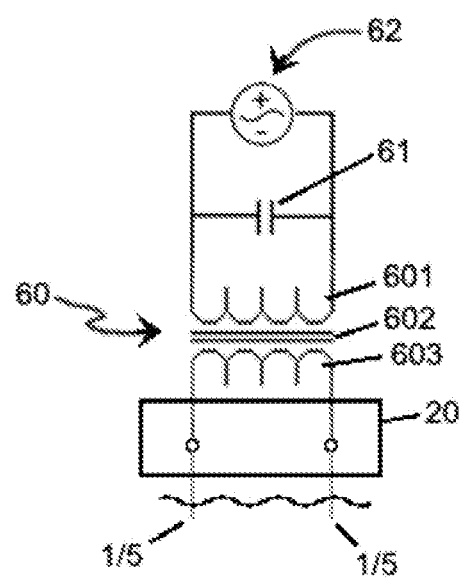
FIG. 7a shows an AC transformer electrical wiring diagram for use with different embodiments of the invention.
Figure 7B:
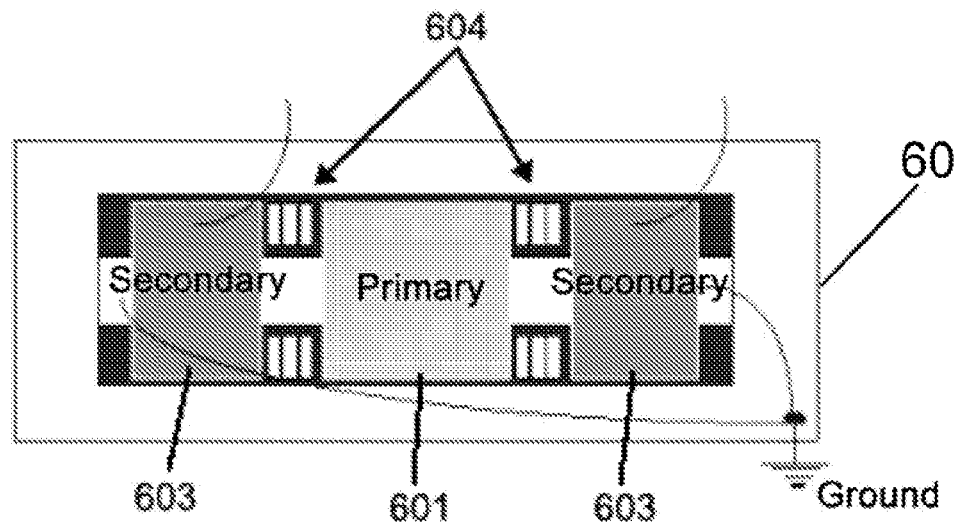
FIG. 7b shows a schematic view of a transformer 60 and FIGS. 7c and 7d show schematic representations of two sine waves in phase and out of phase, respectively.

Table 1 shows that there was a single electrode set 1a/5a. The power source for each electrode set 1/5 was an AC transformer 60. Specifically, FIG. 7a shows a source of AC power 62 connected to a transformer 60. In addition, a capacitor 61 is provided so that, for example, loss factors in the circuit can be adjusted. The output of the transformer 60 is connected to the electrode(s) 1/5 through the control device 20. A preferred transformer for use with the present invention is one that uses alternating current flowing in a primary coil 601 to establish an alternating magnetic flux in a core 602 that easily conducts the flux.

When a secondary coil 603 is positioned near the primary coil 601 and core 602, this flux will link the secondary coil 603 with the primary coil 601. This linking of the secondary coil 603 induces a voltage across the secondary terminals. The magnitude of the voltage at the secondary terminals is related directly to the ratio of the secondary coil turns to the primary coil turns. More turns on the secondary coil 603 than the primary coil 601 results in a step up in voltage, while fewer turns results in a step down in voltage.

Preferred transformer(s) 60 for use in these Examples have deliberately poor output voltage regulation made possible by the use of magnetic shunts in the transformer 60. These transformers 60 are known as neon sign transformers. This configuration limits current flow into the electrode(s) 1/5. With a large change in output load voltage, the transformer 60 maintains output load current within a relatively narrow range.

The transformer 60 is rated for its secondary open circuit voltage and secondary short circuit current. Open circuit voltage (OCV) appears at the output terminals of the transformer 60 only when no electrical connection is present. Likewise, short circuit current is only drawn from the output terminals if a short is placed across those terminals (in which case the output voltage equals zero). However, when a load is connected across these same terminals, the output voltage of the transformer 60 should fall somewhere between zero and the rated OCV. In fact, if the transformer 60 is loaded properly, that voltage will be about half the rated OCV.

The transformer 60 is known as a Balanced Mid-Point Referenced Design (e.g., also formerly known as balanced midpoint grounded). This is most commonly found in mid to higher voltage rated transformers and most 60 mA transformers. This is the only type transformer acceptable in a "midpoint return wired" system. The "balanced" transformer 60 has one primary coil 601 with two secondary coils 603, one on each side of the primary coil 601 (as shown generally in the schematic view in FIG. 7bg). This transformer 60 can in many ways perform like two transformers. Just as the unbalanced midpoint referenced core and coil, one end of each secondary coil 603 is attached to the core 602 and subsequently to the transformer enclosure and the other end of the each secondary coil 603 is attached to an output lead or terminal. Thus, with no connector present, an unloaded 15,000 volt transformer of this type, will measure about 7,500 volts from each secondary terminal to the transformer enclosure but will measure about 15,000 volts between the two output terminals.

Figure 7C:
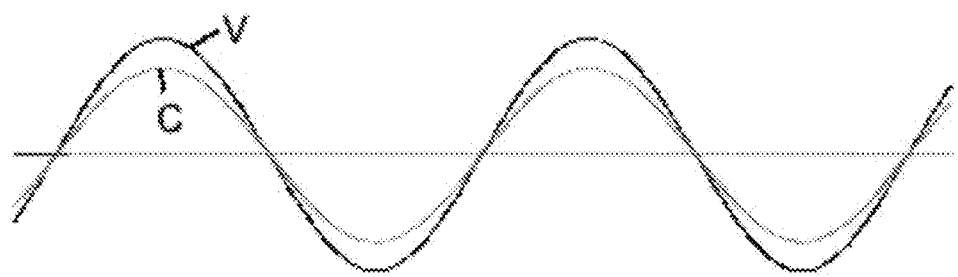
Figure 7D:
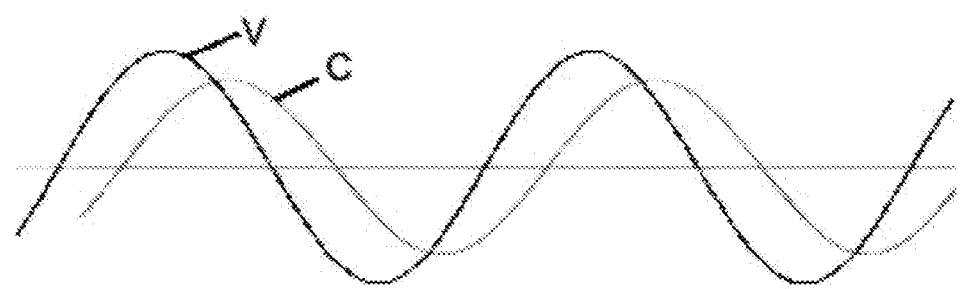

In alternating current (AC) circuits possessing a line power factor of 1 (or 100%), the voltage and current each start at zero, rise to a crest, fall to zero, go to a negative crest and back up to zero. This completes one cycle of a typical sine wave. This happens 60 times per second in a typical US application. Thus, such a voltage or current has a characteristic "frequency" of 60 cycles per second (or 60 Hertz) power. Power factor relates to the position of the voltage waveform relative to the current waveform. When both waveforms pass through zero together and their crests are together, they are in phase and the power factor is 1, or 100%. FIG. 7c shows two waveforms "V" (voltage) and "C" (current) that are in phase with each other and have a power factor of 1 or 100%; whereas FIG. 7d shows two waveforms "V" (voltage) and "C" (current) that are out of phase with each other and have a power factor of about 60%; both waveforms do not pass through zero at the same time, etc. The waveforms are out of phase and their power factor is less than 100%.

The normal power factor of most such transformers 60 is largely due to the effect of the magnetic shunts 604 and the secondary coil 603, which effectively add an inductor into the output of the transformer's 60 circuit to limit current to the electrodes 1/5. The power factor can be increased to a higher power factor by the use of capacitor(s) 61 placed across the primary coil 601 of the transformer, 60 which brings the input voltage and current waves more into phase.

The unloaded voltage of any transformer 60 to be used in the present invention is important, as well as the internal structure thereof. Desirable unloaded transformers for use in the present invention include those that are around 9,000 volts, 10,000 volts, 12,000 volts and 15,000 volts. However, these particular unloaded volt transformer measurements should not be viewed as limiting the scope acceptable power sources as additional embodiments. A specific desirable transformer for use in these Examples is made by Franceformer, Catalog No. 9060-P-E which operates at: primarily 120 volts, 60 Hz; and secondary 9,000 volts, 60 mA.

Accordingly, each transformer assembly 60a-60h (and/or 60a'-60h'; and/or 60a"-60h") can be the same transformer, or can be a combination of different transformers (as well as different polarities). The choice of transformer, power factor, capacitor(s) 61, polarity, electrode designs, electrode location, electrode composition, cross-sectional shape(s) of the trough member 30a', local or global electrode composition, atmosphere(s), local or global liquid 3 flow rate(s), liquid 3' local components, volume of liquid 3' locally subjected to various fields in the trough member 30a', neighboring (e.g., both upstream and downstream) electrode sets, local field concentrations, the use and/or position and/or composition of any membrane used in the trough member, etc., are all factors which influence processing conditions as well as composition and/or volume of constituents produced in the liquid 3', nanocrystals and nanocrystal/suspensions or colloids made according to the various embodiments disclosed herein. Accordingly, a plethora of embodiments can be practiced according to the detailed disclosure presented herein.

The wires used to attach electrode 1 to the transformer 60 were, for Examples 1-3, 99.95% (3N5) gold wire, having a diameter of about 1 mm. The plasma 4 was created with an electrode 1 similar in shape to that shown in FIG. 3e, and weighed about 9.2 grams. This electrode was 99.95% pure gold. The other electrode 5a measured about 1 mm thick gold wire (99.95%) and having about 9 mm submerged in the liquid 3'.

Figure 10B:
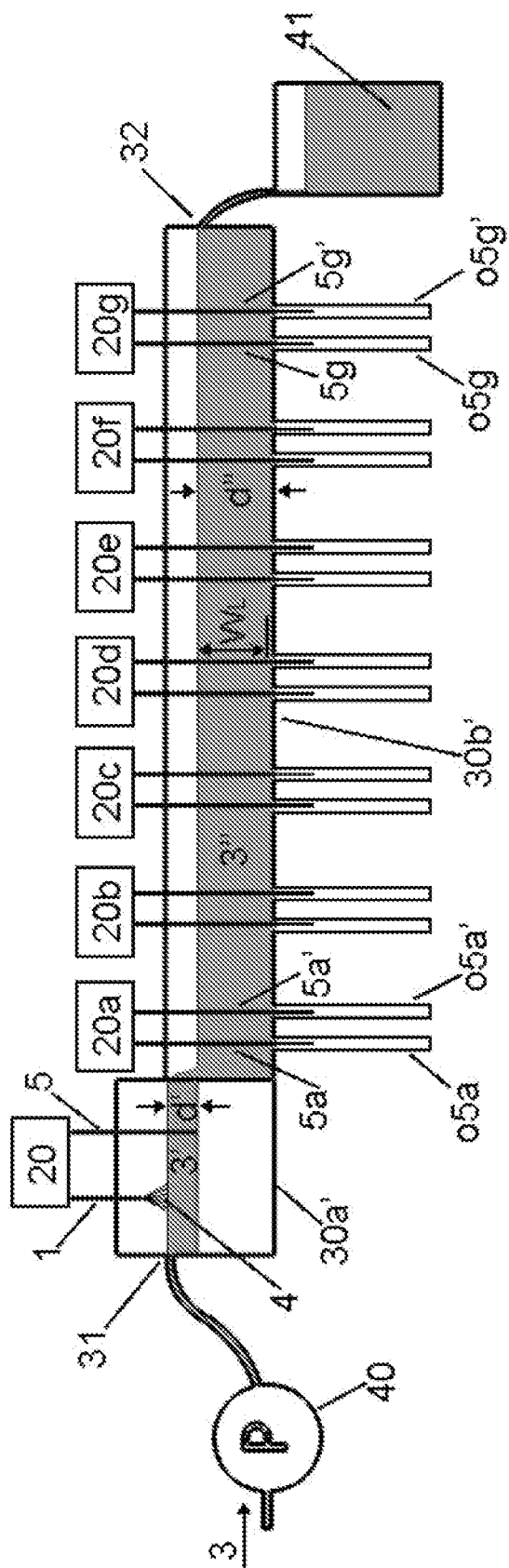

As shown in FIGS. 10b and 11a, the output from the trough member 30a' was the conditioned liquid 3' and this conditioned liquid 3' flowed directly into a second trough member 30b'. The second trough member 30b', shown in FIGS. 10b and 11a had measurements as reported in Table 1. This trough member 30b' contained about 885 ml of liquid 3". Table 1 reports the electrode configuration, as shown in FIGS. 8b and 11a, which means seven sets of electrodes 5/5' (shown in FIG. 8b) were positioned as shown in FIG. 11a (i.e., perpendicular to the flow direction of the liquid 3"). Each of the electrode sets 5/5' comprised 99.99% pure gold wire measuring about 1.0 mm in diameter, as reported in Table 1. The length of each wire electrode 5 that was in contact with the liquid 3" (reported as "$W_L$" in Table 1) measured about 1" (about 25.4 mm). Other orientations fit within the metes and bounds of this disclosure.

Figure 13:
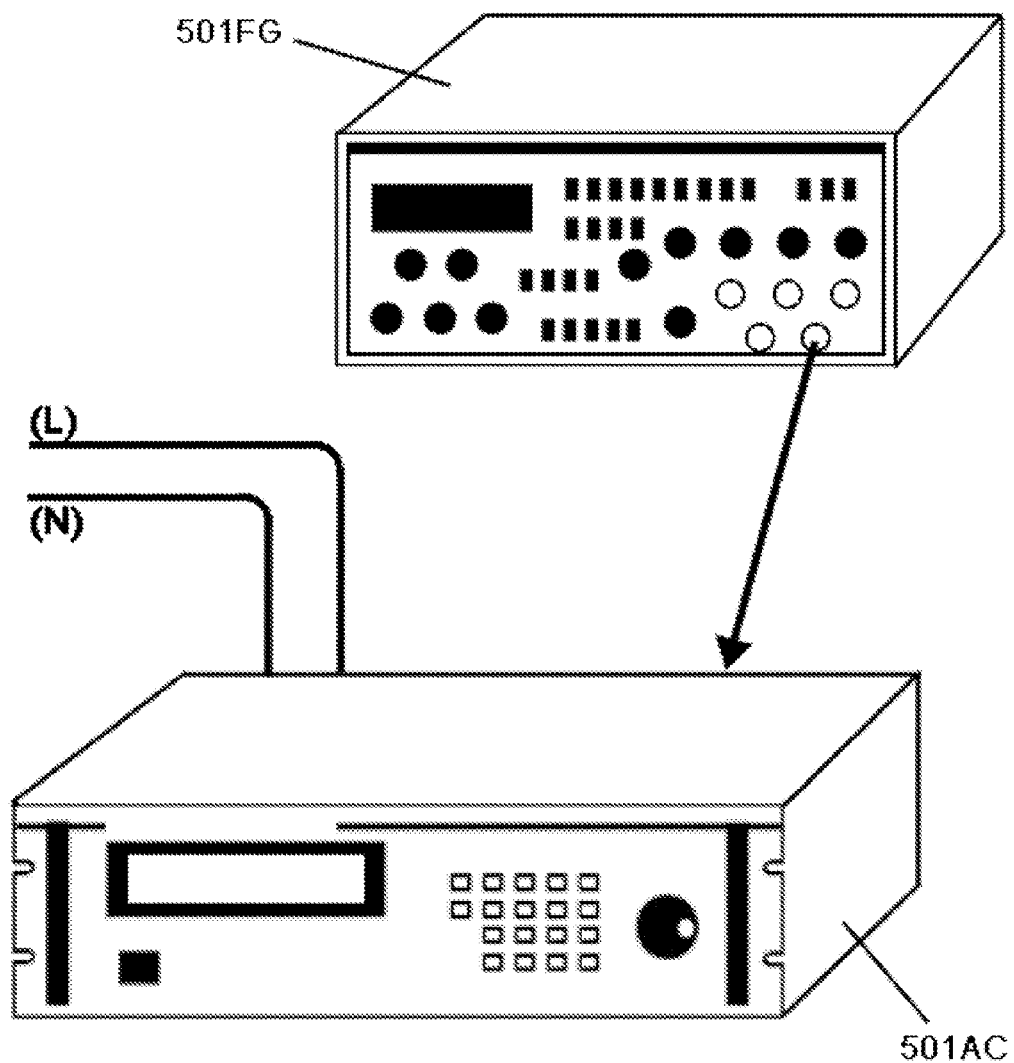
FIG. 13 is a schematic of the power supply electrical setup used to generate the nanocrystals in the many Examples herein.

The AC power source (or transformer) 501AC, illustrated in FIG. 13, was used as the power supply for examples contained herein. This transformer 501 AC was an AC power source (Chroma 61604) having an AC voltage range of 0-300V, a frequency range of 15-1000 Hz and a maximum power rating of about 2 kVA. With regard to FIGS. 10a-10d and 11a-11b, each separate electrode set 5/5' (e.g., Set 2, Set 3-Set 8 or Set 9) were electrically connected to the power supply 501AC as shown in FIG. 10a. Specifically, power supply 501AC was electrically connected to each electrode set, according to the wiring diagram show in FIG. 10a. Table 1 refers to each of the electrode sets by "Set #" (e.g., "Set 1" through "Set 8"). Each electrode of the 1/5 or 5/5 electrode sets was set to operate at a specific voltage. The voltages listed in Table 1 are the voltages used for each electrode set. The distance "c-c" (with reference to FIG. 6) from the centerline of each electrode set to the adjacent electrode set is also reported. Further, the distance "x" associated with each electrode 1 utilized is also reported. For the electrode 5, no distance "x" is reported. Other relevant parameters are also reported in Table 1. All materials for the electrodes 1/5 were obtained from Hi-Rel having an address of 23 Lewis Street, Fort Erie, Ontario, Canada, L2A 2P6. With reference to FIGS. 10b, 10c and 11a, each electrode 5/5' was first placed into contact with the liquid 3" such that it just entered the female receiver tube o5. After a certain amount of process time, gold metal was removed from each wire electrode 5 which caused the electrode 5 to thin (i.e., become smaller in diameter) which changed, for example, current density and/or the rate at which gold nanoparticles were formed. Accordingly, the electrodes 5 were moved toward the female receiver tubes o5 resulting in fresh and thicker electrodes 5 entering the liquid 3" at a top surface portion thereof. In essence, an erosion profile or tapering effect was formed on the electrodes 5 after some amount of processing time has passed (i.e., portions of the wire near the surface of the liquid 3" were typically thicker than portions near the female receiver tubes o5), and such wire electrode profile or tapering can remain essentially constant throughout a production process, if desired, resulting in essentially identical product being produced at any point in time after an initial pre-equilibrium phase during a production run allowing, for example, the process to be cGMP under current FDA guidelines and/or be ISO 9000 compliant as well.

The electrodes 5/5 were actuated or moved at a rate of about 1 inch per 8 hours. Samples were collected only from the equilibrium phase. The pre-equilibrium phase occurs because, for example, the concentration of nanocrystals produced in the liquid 3" increases as a function of time until the concentration reaches equilibrium conditions (e.g., substantially constant nucleation and growth conditions within the apparatus), which equilibrium conditions remain substantially constant through the remainder of the processing due to the control processes disclosed herein.

The eight electrode sets 1/5 and 5/5 were all connected to control devices 20 through 20g which automatically adjusted the height of, for example, each electrode 1/5 or 5/5 in each electrode set. Two female receiver tubes o5a/o5a'-o5g/o5g' were connected to a bottom portion of the trough member 30b' such that the electrodes in each electrode set 5/5 could be removably inserted into each female receiver tube o5 when, and if, desired. Each female receiver tube o5 was made of polycarbonate and had an inside diameter of about ⅛ inch (about 3.2 mm) and was fixed in place by a solvent adhesive to the bottom portion of the trough member 30b'. Holes in the bottom of the trough member 30b' permitted the outside diameter of each tube o5 to be fixed therein such that one end of the tube o5 was flush with the surface of the bottom portion of the trough 30b'. The bottom portion of the tube o5 is sealed. The inside diameters of the tubes o5 effectively prevented any significant quantities of liquid 3" from entering into the female receiver tube o5. However, some liquid may flow into the inside of one or more of the female receiver tubes o5. The length or vertical height of each female receiver tube o5 used in this Example was about 6 inches (about 15.24 cm) however, shorter or longer lengths fall within the metes and bounds of this disclosure. Further, while the female receiver tubes o5 are shown as being subsequently straight, such tubes could be curved in a J-shaped or U-shaped manner such that their openings away from the trough member 30b' could be above the top surface of the liquid 3," if desired.

The run described in this example utilize the following processing enhancer, Specifically, about 2.0 grams/gallon (i.e., about 0.528 g/liter) of sodium hydrogen carbonate ("soda"), having a chemical formula of $NaHCO_3$, was added to and mixed with the water 3. The soda was obtained from Alfa Aesar and the soda had a formula weight of 84.01 and a density of about 2.159 $g/cm^3$.

In particular, a sine wave AC frequency at 60 Hz was utilized to make nanocrystal suspensions or colloids and/or ion solutions in accordance with the teachings herein. The AC power source 501AC utilized a Chroma 61604 programmable AC source. The applied voltage was about 220 volts. The applied current was between about 4.5 amps and about 5.5 amps.

Table 1 summarizes key processing parameters used in conjunction with FIGS. 9 and 10c. Also, Table 1 discloses: 1) "Produced Au PPM" (e.g., gold nanocrystal concentrations); 2) "TEM Average Diameter" which is the mode, corresponding to the crystal diameter that occurs most frequently, determined by the TEM analysis; and 3) "Hydrodynamic radius" as measured by the Zetasizer ZS-90. These physical characterizations were performed as discussed elsewhere herein.

Transmission Electron Microscopy

Specifically, TEM samples were prepared by utilizing a Formvar coated grid stabilized with carbon having a mesh size of 200. The grids were first pretreated by a plasma treatment under vacuum. The grids were placed on a microscope slide lined with a rectangular piece of filter paper and then placed into a Denton Vacuum apparatus with the necessary plasma generator accessory installed. The vacuum was maintained at 75 mTorr and the plasma was initiated and run for about 30 seconds. Upon completion, the system was vented and the grids removed. The grids were stable up to 7-10 days depending upon humidity conditions, but in all instances were used within 12 hours.

Approximately 1 µL of each inventive nanocrystal suspension was placed onto each grid and was allowed to air dry at room temperature for 20-30 minutes, or until the droplet evaporated. Upon complete evaporation, the grids were placed onto a holder plate until TEM analysis was performed.

A Philips/FEI Tecnai 12 Transmission Electron Microscope was used to interrogate all prepared samples. The instrument was run at an accelerating voltage of 100 keV. After alignment of the beam, the samples were examined at various magnifications up to and including 630,000×. Images were collected via the attached Olympus Megaview III side-mounted camera that transmitted the images directly to a PC equipped with iTEM and Tecnai User Interface software which provided for both control over the camera and the TEM instrument, respectively.

Figure 11B:
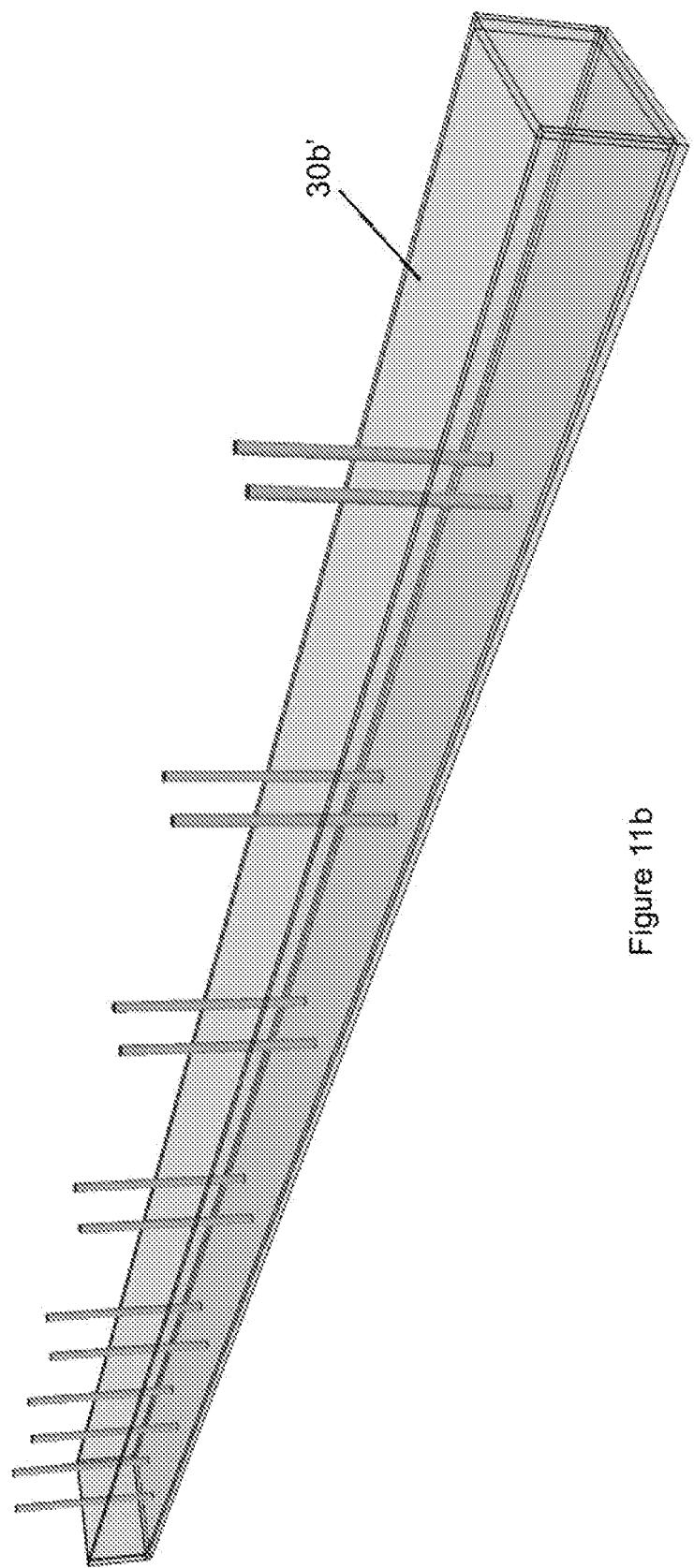
Figure 11C:
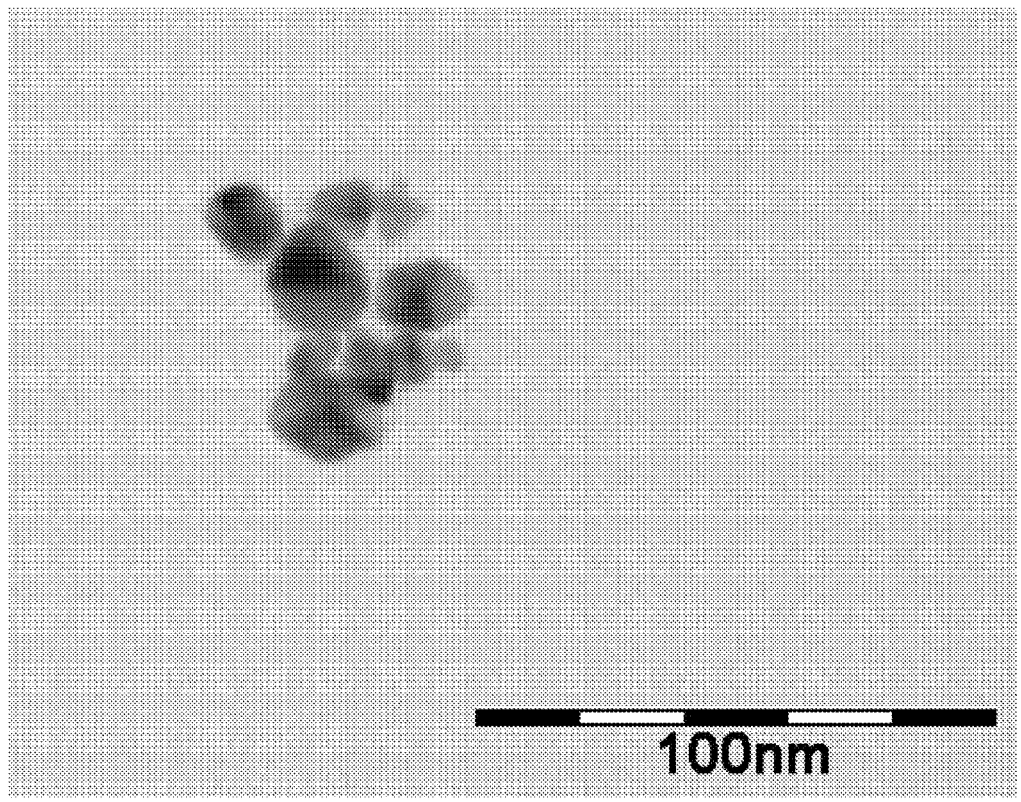
FIG. 11c shows a representative TEM photomicrograph of dried gold constituents formed in connection with Example 1.
Figure 11D:
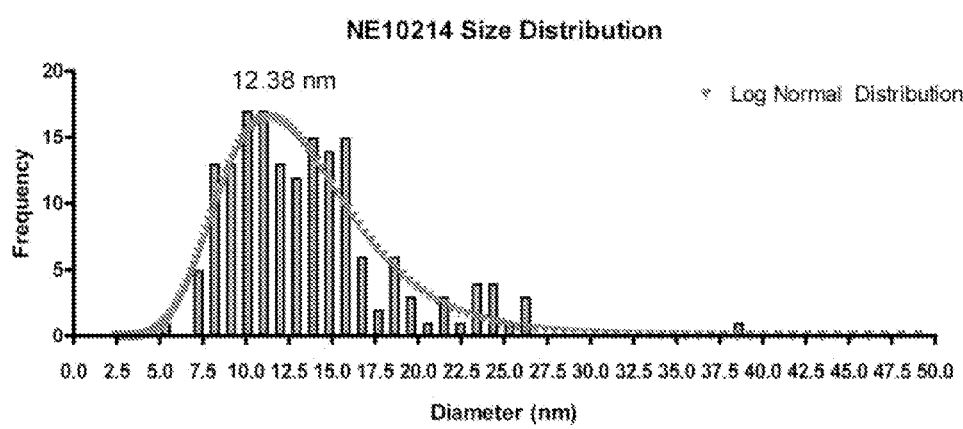
FIG. 11d shows a particle size distribution histogram from TEM measurements for the constituents formed in connection with Example 1.

FIG. 11c shows a representative TEM photomicrograph corresponding to dried solution NE10214 comprised of gold nanocrystals, dried from suspension, made according to this example. FIG. 11d corresponds to the measured TEM size distribution used to calculate the TEM average diameter and referenced in Table 1.

The pH measurements were made by using an Accumet® AR20 pH/conductivity meter wherein the pH probe was placed into a 50 mL vial containing the samples of interest and allowed to stabilize. Three separate pH measurements were then taken and averaged per sample. NE10214 had a pH of about 8.94.

Energy absorption spectra were obtained for the samples by using UV-VIS spectroscopy. This information was acquired using a Thermofisher Evolution 201 UV-VIS spectrometer equipped with a double beam Czerny-Turner monochromator system and dual silicon photodiodes. Instrumentation was provided to support measurement of low-concentration liquid samples using one of a number of fuzed-quartz sample holders or "cuvettes." Data was acquired over the wavelength range between about 300-900 nm with the following parameters: bandwidth of 1 nm, data pitch of 0.5 nm. A xenon flash lamp was the primary energy source. The optical pathway of the spectrometer was arranged to allow the energy beam to pass through the center of each sample cuvette. Sample preparation was limited to filling and capping the cuvettes and then physically placing the samples into the cuvette holder, within the fully enclosed sample compartment of the spectrometer. Optical absorption of energy of each sample was determined. Data output was measured and displayed as Absorbance Units (per Beer-Lambert's Law) versus wavelength.

FIG. 11e shows UV-Vis spectral patterns for the suspension/colloid NE10214, for the wavelength range of about 350 nm-900 nm.

Dynamic Light Scattering Zetasizer

Specifically, dynamic light scattering (DLS) measurements were performed on Zetasizer Nano ZS-90 DLS instrument. In DLS, as the laser light hits small particles and/or organized water structures around the small particles (smaller than the wavelength), the light scatters in all directions, resulting in a time-dependent fluctuation in the scattering intensity. Intensity fluctuations are due to the Brownian motion of the scattering particles/water structure combination and contain information about the crystal size distribution.

The instrument was allowed to warm up for at least 30 min prior to the experiments. The measurements were made using square glass cell with 1 cm pathlength, PCS8501. The following procedure was used:
1. First, 1 ml of DI water was added into the cell using 1 ml micropipette, then water was poured out of the cell to a waste beaker and the rest of the water was shaken off the cell measuring cavity. This step was repeated two more times to thoroughly rinse the cell.
2. 1 ml of the sample was added into the cell using 1 ml micropipette. After that all liquid was removed out of the cell with the same pipette using the same pipette tip and expelled into the waste beaker. 1 ml of the sample was added again using the same tip.
3. The cell with the sample was placed into a temperature controlled cell block of the Zetasizer instrument with engraved letter facing forward. A new experiment in Zetasizer software was opened. The measurement was started 1 min after the temperature equilibrated and the laser power attenuated to the proper value. The results were saved after all runs were over.
4. The cell was taken out of the instrument and the sample was removed out of the cell using the same pipette and the tip used if step 2.
5. Steps 2 to 4 were repeated two more times for each sample.
6. For a new sample, a new pipette tip for 1 ml pipette was taken to avoid contamination with previous sample and steps 1 through 5 were repeated.

Data collection and processing was performed with Zetasizor software, version 6.20. The following parameters were used for all the experiments: Run Duration—2o; Experiments—10; Solvent—water, 0 mmol; Viscosity—0.8872 cP; Refractive Index—1.333; block temperature—+25° C. After data for each experiment were saved, the results were viewed on "Records View" page of the software. Particle size distribution (i.e., hydrodynamic radii) was analyzed in "Intensity PSD" graph. Dynamic light scattering techniques were utilized to obtain an indication of crystal sizes (e.g., hydrodynamic radii) produced according to this example. Hydrodynamic radius is reported in Table 1 as 19.43 nm.

Atomic Absorption Spectroscopy

The AAS values were obtained from a Perkin Elmer AAnalyst 400 Spectrometer system. Atomic absorption spectroscopy is used to determine concentration of species, reported in "ppm" (parts per million).

I) Principle

The technique of flame atomic absorption spectroscopy requires a liquid sample to be aspirated, aerosolized and mixed with combustible gases, such as acetylene and air. The mixture is ignited in a flame whose temperature ranges from about 2100 to about 2400 degrees C. During combustion, atoms of the element of interest in the sample are reduced to free, unexcited ground state atoms, which absorb light at characteristic wavelengths. The characteristic wavelengths are element specific and are accurate to 0.01-0.1 nm. To provide element specific wavelengths, a light beam from a hollow cathode lamp (HCL), whose cathode is made of the element being determined, is passed through the flame. A photodetector detects the amount of reduction of the light intensity due to absorption by the analyte. A monochromator is used in front of the photodetector to reduce background ambient light and to select the specific wavelength from the HCL required for detection. In addition, a deuterium arc lamp corrects for background absorbance caused by non-atomic species in the atom cloud.

II) Sample Preparation 10 mL of sample, 0.6 mL of 36% v/v hydrochloric acid and 0.15 mL of 50% v/v nitric acid are mixed together in a glass vial and incubated for about 10 minutes in 70 degree C. water bath. If gold concentration in the suspension is expected to be above 10 ppm a sample is diluted with DI water before addition of the acids to bring final gold concentration in the range of 1 to 10 ppm. For example, for a gold concentration around 100 ppm, 0.5 mL of sample is diluted with 9.5 mL of DI water before the addition of acids. Aliquoting is performed with adjustable micropipettes and the exact amount of sample, DI water and acids is measured by an Ohaus PA313 microbalance. The weights of components are used to correct measured concentration for dilution by DI water and acids.

Each sample is prepared in triplicate and after incubation in water bath is allowed to cool down to room temperature before measurements are made.

III) Instrument Setup

The following settings are used for Perkin Elmer AAnalyst 400 Spectrometer system:
a) Burner head: 10 cm single-slot type, aligned in three axes according to the manufacture procedure to obtain maximum absorbance with a 2 ppm Cu standard.
b) Nebulizer: plastic with a spacer in front of the impact bead.
c) Gas flow: oxidant (air) flow rate about 12 L/min, fuel (acetylene) flow rate about 1.9 mL/min.
d) Lamp/monochromator: Au hollow cathode lamp, 10 mA operating current, 1.8/1.35 mm slits, 242.8 nm wavelength, background correction (deuterium lamp) is on.

IV) Analysis Procedure a) Run the Au lamp and the flame for approximately 30 minutes to warm up the system.
b) Calibrate the instrument with 1 ppm, 4 ppm and 10 ppm Au standards in a matrix of 3.7% v/v hydrochloric acid. Use 3.7% v/v hydrochloric acid as a blank.
c) Verify calibration scale by measuring 4 ppm standard as a sample. The measured concentration should be between 3.88 ppm and 4.12 ppm. Repeat step b) if outside that range.
d) Measure three replicas of a sample. If the standard deviation between replicas is higher than 5%, repeat measurement, otherwise proceed to the next sample.
e) Perform verification step c) after measuring six samples or more often. If verification fails, perform steps b) and c) and remeasure all the samples measured after the last successful verification.

V) Data Analysis

Measured concentration value for each replica is corrected for dilution by water and acid to calculate actual sample concentration. The reported Au ppm value is the average of three corrected values for individual replica.

Table 1 references the AAS concentration result as "Produced Au PPM", with a corresponding value of 6.6 ppm Example 2

Figure 12A:
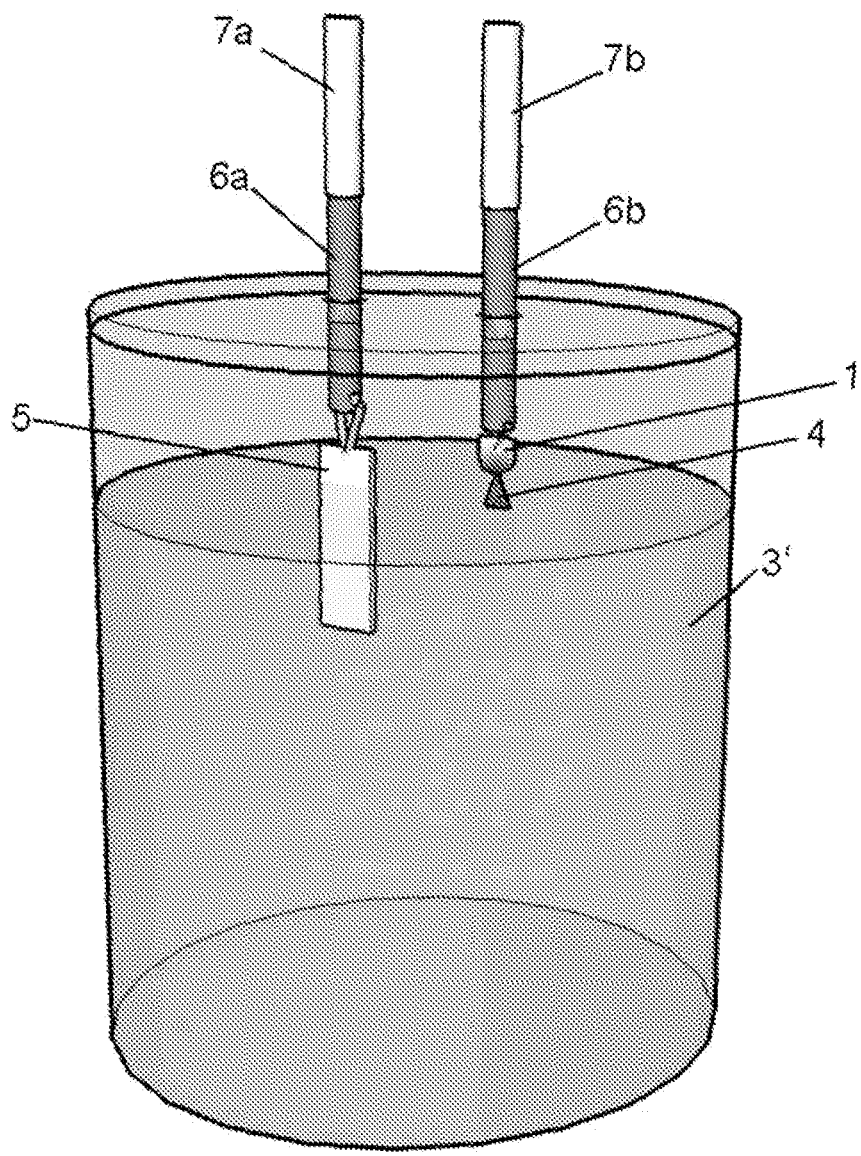
FIG. 12a shows a schematic of an apparatus used in a batch method whereby in a first step, a plasma 4 is created to condition a fluid 3'.
Figure 12B:
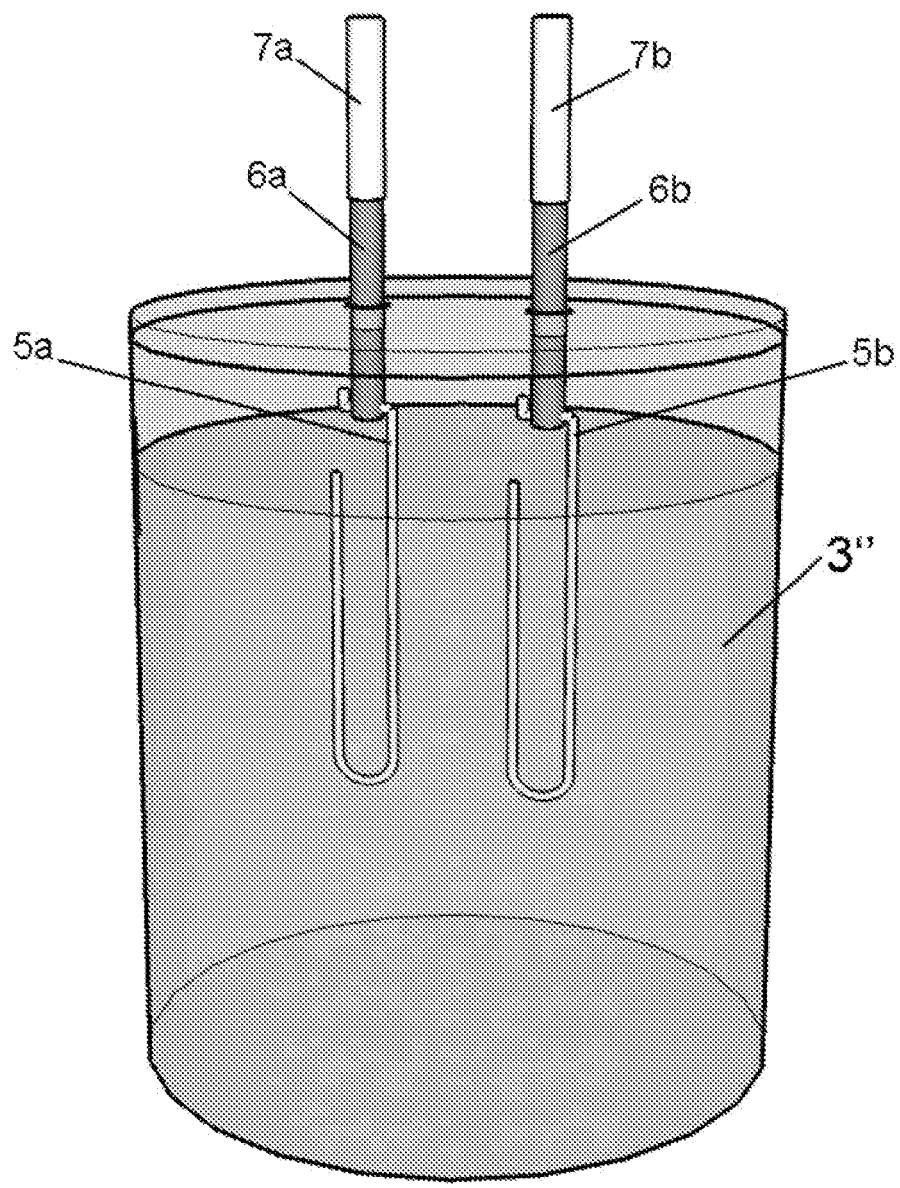
FIGS. 12b and 12c show a schematic of an apparatus used in a batch method utilizing wires 5a and 5b to form bi-metallic nanocrystals in suspension (e.g., a colloid) in association with the apparatus shown in FIG. 12a and as discussed in various Examples herein.

Manufacturing Platinum-Based Nanoparticles/Nanoparticle Solutions or Colloids by a Batch Process This Example utilized a batch process according to the present invention. FIG. 12a shows the apparatus used to condition the liquid 3. Once conditioned, the liquid 3' was processed in the apparatus shown in FIG. 12c The amount of $NaHCO_3$ processing enhancer used was about 0.375 grams/gallon (i.e., about 0.10 g/L) to about 3.0 grams/gallon (i.e., about 0.79 g/L). The amount of KOH processing enhancer used was about 0.95 grams/gallon (i.e., about 0.25 g/L). The amount of KBr processing enhancer used was about 4.6 grams/gallon (i.e., about 1.22 g/L). The amount of $Na_3PO_4$ processing enhancer used was about 3.94 grams/gallon (i.e., about 1.04 g/L). The amount of $KH_2PO_4$ processing enhancer was about 3.24 grams/gallon (i.e., about 0.86 g/L). The amount of time that the water 3 with processing enhancer was exposed to the plasma 4 was about 30 minutes, prior to subsequent processing in the apparatus shown in FIG. 12c.

The applied voltage for each plasma 4 made by electrode 1 was about 750 volts. This voltage was achieved by a transformer 60 (i.e., the Balanced Mid-Point Referenced Design) discussed elsewhere herein.

Figure 12C:
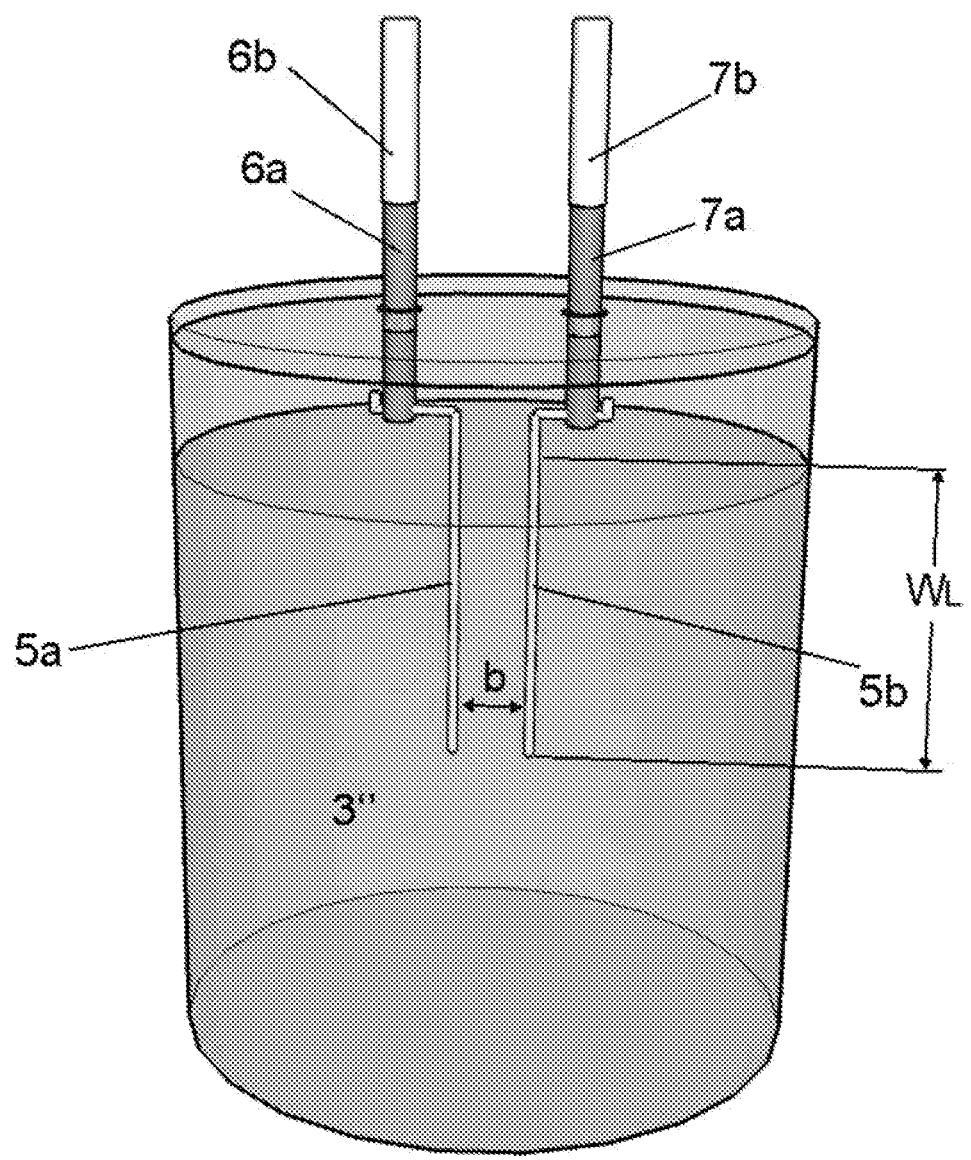

A second and different transformer was electrically connected to the electrodes 5a/5b shown in FIG. 12c. This transformer was an by AC power source having a voltage range of 0-300V, a frequency range of 47-400 Hz and a maximum power rating of 1 kVA. The applied voltage ranged between about 58 volts and about 300 volts. The diameter of the platinum wire electrodes was either about 0.5 mm or 1 mm.

Another power supply was utilized for those processes with frequency between 1 and 5 Hz, inclusive. The electrodes 5a, 5b were electrically connected to power amplifier, as shown in FIG. 12e. The power supply for the amplifier is set forth in FIG. 12f. The power amplifier was driven by an external function generator connected to the input pins in the amplifier.

The amount of platinum nanoparticles produced in the suspensions varied between about 10 ppm and about 25 ppm, as measured by the atomic absorption spectroscopy techniques discussed elsewhere herein. The sizes of the nanoparticles made according to this Example are fully discussed in Tables 2 and 3 herein.

Transmission electron microscopy (TEM) sample preparation was identical to the methods described earlier although interrogation was performed on a Philips EM 420 TEM equipped with a SIS Megaview III CCD digital camera. The TEM micrographs show that the particles have an average diameter of less than 10 nm.

Figure 14:
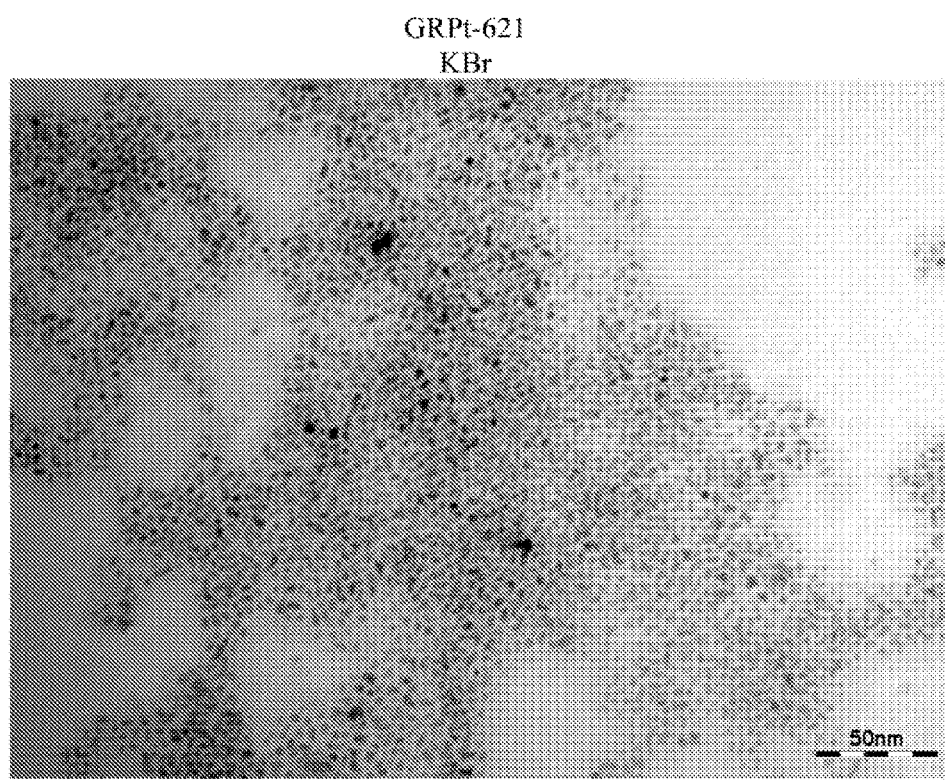
FIG. 14 shows a representative TEM photomicrograph of dried platinum constituents formed in connection with Example 2.

FIG. 14 shows a representative TEM Photomicrograph of platinum nanocrystals, dried from suspension GRPt-621, made according to this example.

TABLE 2

| GRPt | Potential, Peak to Peak (V) | Frequency (Hz) | t (min) | Container Volume (mL) | Liquid Volume (mL) | Processing Enhancer | pH, Liquid | GZA (min) | $W_L$ (cm) | Diameter, 5a & 5b (mm) | ppm | pH, Final |
|---|---|---|---|---|---|---|---|---|---|---|---|---|
| 601 | 76 | 1 | 60 | 600 | 400 | 2.0 g/gal NaHCO₃ ** | 8.6 | 30 | 2 | 0.5 | 13.3 | 9.1 |
| 602 | 100 | 1 | 94 | 600 | 400 | 2.0 g/gal NaHCO₃ ** | 8.6 | 30 | 2 | 0.5 | 16.8 | 9.3 |
| 603 | 69.6 | 1 | 182 | 600 | 450 | 2.0 g/gal NaHCO₃ ** | 8.6 | 30 | 2.9 | 0.5 | 24.5 | 9.2 |
| 605 | 128 | 1 | 11 | 600 | 400 | 2.0 g/gal NaHCO₃ ** | 8.6 | 30 | 4 | 0.5 | 11.6 | 8.7 |
| 6a | 58.4 | 1 | 14 | 10 | 5 | 0.75 g/gal NaHCO₃ | 8.6 | 30 | 2 | 0.5 | 18.7 | |
| 606 | 128 | 1 | 32 | 600 | 400 | 0.75 g/gal NaHCO₃ | 8.6 | 30 | 4 | 0.5 | 17.9 | 8.6 |
| 607 | 128 | 1 | 51 | 600 | 400 | 0.375 g/gal NaHCO₃ | 8.6 | 30 | 4 | 0.5 | 16.3 | 8.2 |
| 611 | 130 | 1 | 51 | 600 | 400 | 0.375 g/gal NaHCO₃ | 8.6 | 30 | 2 | 0.5 | 12.8 | 7.8 |
| 612 | 130 | 1 | 56 | 600 | 400 | 0.375 g/gal NaHCO₃ | 8.6 | 30 | 2 | 0.5 | 15.8 | 8.1 |
| 613 | 130 | 1 | 40 | 600 | 400 | 0.375 g/gal NaHCO₃ | 8.6 | 30 | 2 | 0.5 | 12.8 | 7.9 |
| 614a | 128 | 5 | 24 | 600 | 400 | 3 g/gal NaHCO₃ | 8.6 | 30 | 3.2 | 1 | 11.1 | 9.0 |
| 614b | 128 | 1 | 24 | 600 | 400 | 3 g/gal NaHCO₃ | 8.6 | 30 | 3.2 | 1 | 12.6 | 9.4 |
| 614c | 128 | 0.5 | 29 | 600 | 400 | 3 g/gal NaHCO₃ | 8.6 | 30 | 3.2 | 1 | 10.5 | 9.4 |
| 614di | 128 | 3 | 24 | 600 | 400 | 3 g/gal NaHCO₃ | 8.6 | 30 | 3.2 | 1 | 12.1 | 9.1 |
| 615a | 130 | 1 (square) | 23 | 600 | 400 | 3.24 g/gal KH₂PO₄ | 4.9 | n/a | 3.2 | 1 | 10.3 | 5.1 |
| 615b | 130 | 1 | 26 | 600 | 400 | 3.24 g/gal KH₂PO₄ | 4.9 | n/a | 3.2 | 1 | 10.4 | 4.9 |
| 616 | 130 | 1 (square) | 16 | 600 | 400 | 3 g/gal NaHCO₃ | 8.6 | n/a | 3.2 | 1 | 16.8 | 9.5 |
| 619 | 104 | 1 | 25 | 600 | 400 | 3.94 g/gal Na₃PO₄ ** | 11.4 | n/a | 3.2 | 1 | 12.7 | 11.5 |
| 620 | 130 | 2 | 20 | 150 | 100 | 0.95 g/gal KOH ** | 11.7 | n/a | 3.2 | 1 | 16.7 | 11.6 |
| 621 | 104 | 2 | 24 | 150 | 100 | 4.6 g/gal KBr ** | 6.3 | n/a | 3.2 | 1 | 23.7 | 9.4 |
| 622 | 90 | 2 | 41 | 150 | 100 | 1:1 4.6 g/gal KBr: 0.95 g/gal KOH ** | 11.2 | n/a | 3.2 | 1 | 24.5 | 11.2 |

TABLE 3

| Lot Number | Voltage | Frequency (Hz) | t (min) | Container Volume (mL) | Liquid Volume (mL) | Processing Enhancer | pH, Liquid | GZA (min) | $W_L$ (cm) | Diameter, 5a & 5b (mm) | ppm | pH, Final |
|---|---|---|---|---|---|---|---|---|---|---|---|---|
| CAC-002-1 | 100 | 1 | 35 | 1000 | 800 | 4 g/gal NaHCO₃ | 8.5 | 30 | 1.9 | 1 | 22.9 | n/m |
| CAC-001-2 | 100 | 1 | 35 | 1000 | 800 | 4 g/gal NaHCO₃ | 8.5 | 30 | 1.9 | 1 | 10.5 | n/m |
| CAC-003-2 | 170 | 1 | 35 | 1000 | 800 | 3 g/gal NaHCO₃ | 8.5 | 30 | 1.9 | 1 | 9.3 | n/m |
| CAC-003-3 | 230 | 1 | 35 | 1000 | 800 | 2 g/gal NaHCO₃ | 8.5 | 30 | 1.9 | 1 | 9.7 | n/m |
| CAC-003-6 | 300 | 1 | 35 | 1000 | 800 | 1 g/gal NaHCO₃ | 8.5 | 30 | 1.9 | 1 | 7.9 | n/m |
| CAC-001-3 | 100 | 7 | 35 | 1000 | 800 | 4 g/gal NaHCO₃ | 8.5 | 30 | 1.9 | 1 | 11.4 | n/m |
| CAC-002-4 | 100 | 15 | 35 | 1000 | 800 | 4 g/gal NaHCO₃ | 8.5 | 30 | 1.9 | 1 | 10.4 | n/m |
| 071210-1 | 100 | 47 | 35 | 1000 | 800 | 4 g/gal NaHCO₃ | 8.5 | 30 | 1.9 | 1 | 6.9 | n/m |
| 071210-2 | 100 | 60 | 35 | 1000 | 800 | 4 g/gal NaHCO₃ | 8.5 | 30 | 1.9 | 1 | 7.2 | n/m |
| CAC-003-1 | 170 | 60 | 35 | 1000 | 800 | 3 g/gal NaHCO₃ | 8.5 | 30 | 1.9 | 1 | 6.5 | n/m |
| CAC-003-4 | 230 | 60 | 35 | 1000 | 800 | 2 g/gal NaHCO₃ | 8.5 | 30 | 1.9 | 1 | 9.2 | n/m |
| CAC-003-5 | 300 | 60 | 35 | 1000 | 800 | 1 g/gal NaHCO₃ | 8.5 | 30 | 1.9 | 1 | 8.4 | n/m |
| 070110-3 | 100 | 100 | 35 | 1000 | 800 | 4 g/gal NaHCO₃ | 8.5 | 30 | 1.9 | 1 | 6.6 | n/m |
| 071310-4 | 100 | 200 | 35 | 1000 | 800 | 4 g/gal NaHCO₃ | 8.5 | 30 | 1.9 | 1 | 7.6 | n/m |

Example 3

Manufacturing Platinum-Based Nanoparticles/Nanoparticle Solutions or Colloids by a Batch Process This Example utilized a batch process according to the present invention. FIG. 12a shows the apparatus used to condition the liquid 3. Once conditioned, the liquid 3' was processed in the apparatus shown in FIG. 12d.

The amount of KBr processing enhancer used was about 4.6 grams/gallon (i.e., about 1.2 grams/Liter) or about 1.4 g/gal (i.e., about 0.4 g/L). The amount of Na₃PO₄ processing enhancer used was about 1.9 grams/gallon (i.e., about 0.5 g/L). The amount of time that the water 3 with each processing enhancer was exposed to the plasma 4 was about 30 minutes, prior to subsequent processing in the apparatus shown in FIG. 12d.

The applied voltage for each plasma 4 made by electrode 1 was about 750 volts. This voltage was achieved by a transformer 60 (i.e., the Balanced Mid-Point Referenced Design) discussed elsewhere herein.

A power supply (shown in FIG. 12f) was utilized to apply a sinusoidal voltage with a frequency of about 2.5 Hz to the electrodes 5a and 5b. The electrodes were electrically connected to a power amplifier, as shown in FIG. 12e. The distance between the electrodes was fixed in all suspensions at approximately 7 mm. The amplifier was driven by an external function generator connected to the input pins in the amplifier.

The amount of platinum-based nanoparticles and/or platinum based ions produced in the suspensions was measured by the atomic absorption spectroscopy techniques discussed elsewhere herein. Suspensions PRX37-01 and PRX37-02 show that for a given conductivity of water 3, and a given voltage applied at a fixed distance to electrodes 5a and 5b, the amount of platinum in the final suspension increased as the amount of KBr processing enhancer was increased.

The average hydrodynamic radii of the formed particles in water were analyzed with the dynamic light scattering technique discussed elsewhere herein. The hydrodynamic radius is not reported (NR) for formulation PRX37-02 because the transmission amount reported in the DLS device was 100%, indicating a high presence of dissolved platinum species (e.g., ions).

Figure 15A:
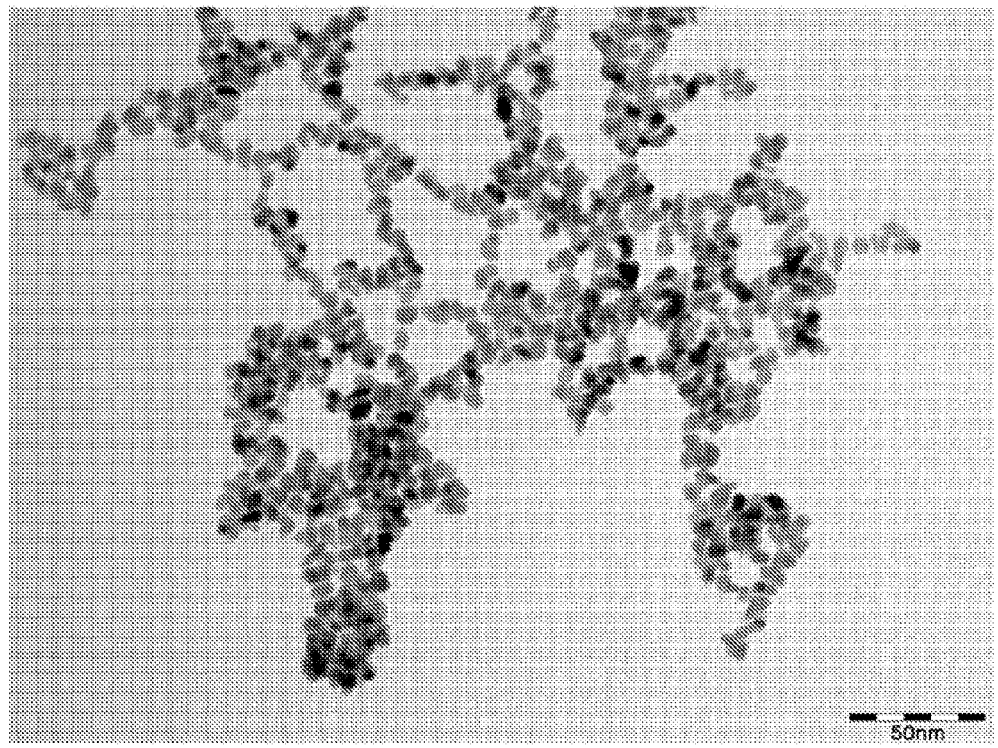
FIG. 15a shows a representative TEM photomicrograph of dried platinum constituents formed in connection with Example 3.
Figure 15B:
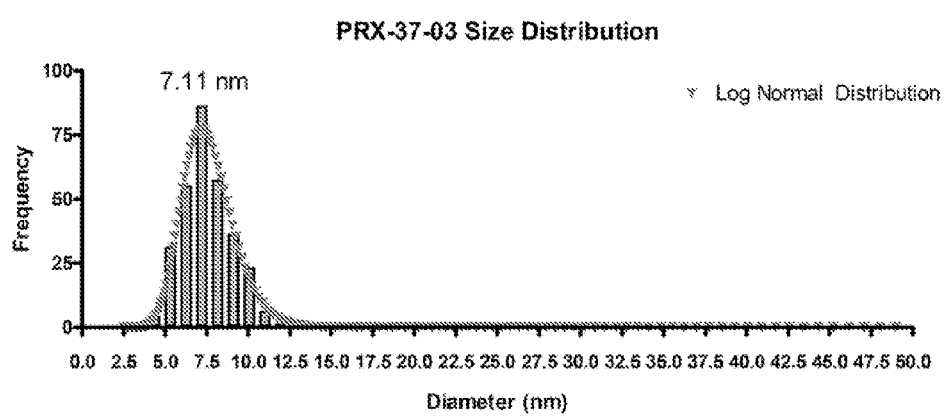
FIG. 15b shows a particle size distribution histogram from TEM measurements for the constituents formed in connection with Example 3.

Transmission electron microscopy (TEM) sample preparation was identical to the methods described earlier although interrogation was performed on a Philips EM 420 TEM equipped with a SIS Megaview III CCD digital camera. PRX37-03 was the only formulation analyzed by TEM. The TEM micrographs show that the particles in suspension in formulation PRX37-03 had an average diameter of approximately 7 nm. The distribution of particle size is shown in FIG. 15b. FIG. 15a shows a representative TEM Photomicrograph of platinum nanocrystals, dried from suspension PRX37-03, made according to this Example 3. Table 4 is included to show the relevant processing conditions used as well as certain resultant physical properties of the formulation PRX37.

TABLE 4

| | PRX37 | | |
|---|---|---|---|
| | 01 | 02 | 03 |
| Potential, Peak to Peak (V) | 50 | 50 | 75 |
| Frequency (Hz) | 2.5 | 2.5 | 2.5 |
| t (min) | 1250 | 1320 | 1370 |
| Liquid Volume (mL) | 3800 | 3800 | 3800 |
| Processing Enhancer | 4.6 g/gal KBr | 1.9 g/gal Na3PO4, 1.4 g/gal KBr | 1.4 g/gal KBr |
| GZA (min) | 30 | 30 | 30 |
| pH, Liquid | 3.8 | 11.3 | 3.8 |
| Conductivity (mS/cm) | 1.6 | 1.6 | 0.7 |
| $W_L$ (cm) | 3.8 | 3.8 | 3.8 |
| Diameter, 5a & 5b (cm) | 0.05 | 0.05 | 0.05 |
| $r_{hydro}$ (nm) (global max.) | 15 | NR | 9 |
| $r_{TEM}$ (nm) (global max.) | NM | NM | 7 |
| ppm | 40.3 | 22.5 | 22.1 |
| pH, Final | 4.3 | 11.2 | 4.0 |

Example 4

Manufacturing Platinum-Based Nanoparticles/Nanoparticle Solutions or Colloids or Ions by a Trough Process Using a Variety of Process Enhancers (PB-09, PB-10/PB-13, PB-16, PB-17, PB-18, PB-19, PB-20, PB-21, PB-23, PB-24, PB-25, PB-26, PB-27, PB-28, PB-32, PB-33, PB-34, PB-35, PB-40, PB-41, PB-42, PB-43)

Figure 10D:
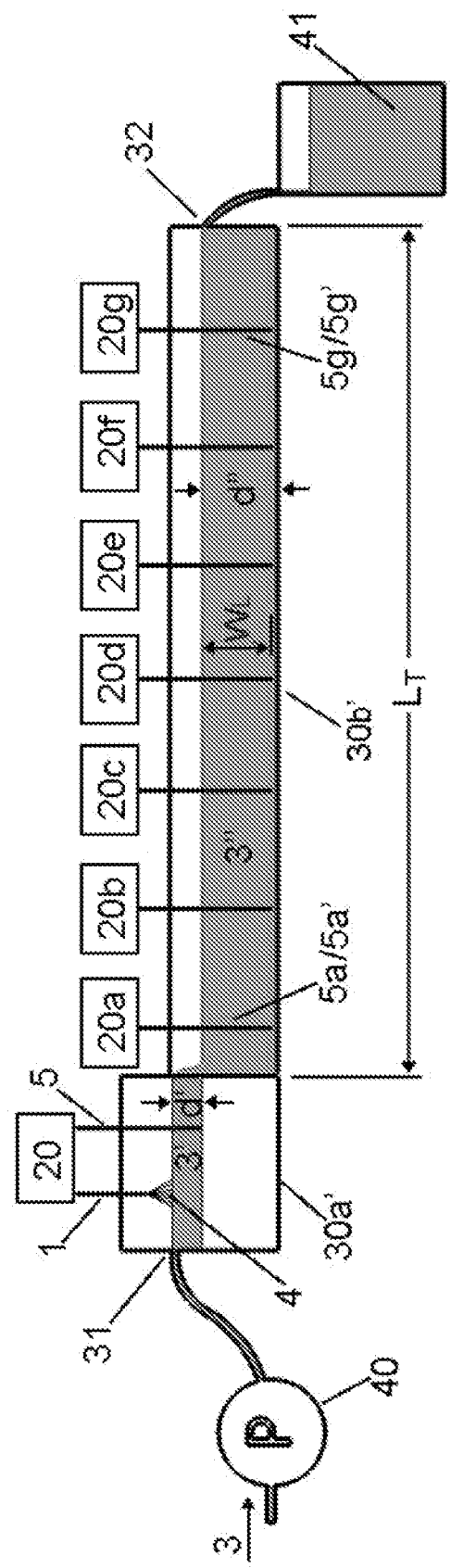

In general, this Example utilizes certain embodiments of the invention associated with the apparatuses generally shown in FIGS. 9, 10d and 11b. The AC power source (or transformer) 501AC, illustrated in FIG. 13, was used as the power supply for the examples contained herein, while the function generator 501FG was sometimes used (as disclosed herein) to drive the AC power source 501AC. This transformer 501 AC was an AC power source (Chroma 61604) having an AC voltage range of 0-300V, a frequency range of 15-1000 Hz and a maximum power rating of about 2 kVA. The precise electrical connections are discussed elsewhere herein. Control devices 20, as illustrated in FIGS. 8c and 8j, were connected to the electrodes 1/5 and 5/5, respectively. However, due to the short run times in each "Run ID," there was no need to actuate the control devices 20. Thus, the ends 9' of the electrodes 5a and 5b were juxtaposed with the bottom of the trough member 30b'.

The amount of $NaHCO_3$ (Fisher Scientific, Cat# S631-3) processing enhancer used was about 2.5 grams/gallon (i.e., about 0.67 g/L) to about 3.5 grams/gallon (i.e., about 0.93 g/L). The amount of $KHCO_3$ processing enhancer used was about 2.31 grams/gallon (i.e., about 0.61 g/L). The amount of NaOH processing enhancer used was about 0.70 grams/gallon (i.e., about 0.19 g/L). The amount of KOH processing enhancer used was about 0.72 grams/gallon (i.e., about 0.19 g/L). The amount of NaBr processing enhancer was about 2.18 grams/gallon (i.e., about 0.58 g/L). The amount of KBr processing enhancer was about 2.04 grams/gallon (i.e., about 0.54 g/L). The amount of $Na_2PO_4$ processing enhancer was about 1.08 grams/gallon (i.e., about 0.29 g/L). The amount of NaCl processing enhancer was about 1.27 grams/gallon (i.e., about 0.34 g/L). The amount of $CaCl_2$ processing enhancer was about 1.16 grams/gallon (i.e., about 0.31 g/L).

The applied voltage for each plasma 4 made by electrode 1 was about 750 volts. This voltage was achieved by a transformer 60 (i.e., the Balanced Mid-Point Referenced Design) discussed elsewhere herein.

The AC power source 501AC utilized a Chroma 61604 programmable unit. In particular, sine wave AC frequencies at 5 Hz and 80 Hz were utilized to make nanocrystal suspensions or colloids and/or ions, in accordance with the teachings herein. The applied voltage was about 175 volts. Additionally, the function generator 501FG provided sine waves at frequencies less than 15 Hz to the AC power source 501AC, which subsequently amplified the input signal to about 175 volts at different frequencies. The applied current varied between about 3.0 amps and about 6.5 amps.

Figure 16:
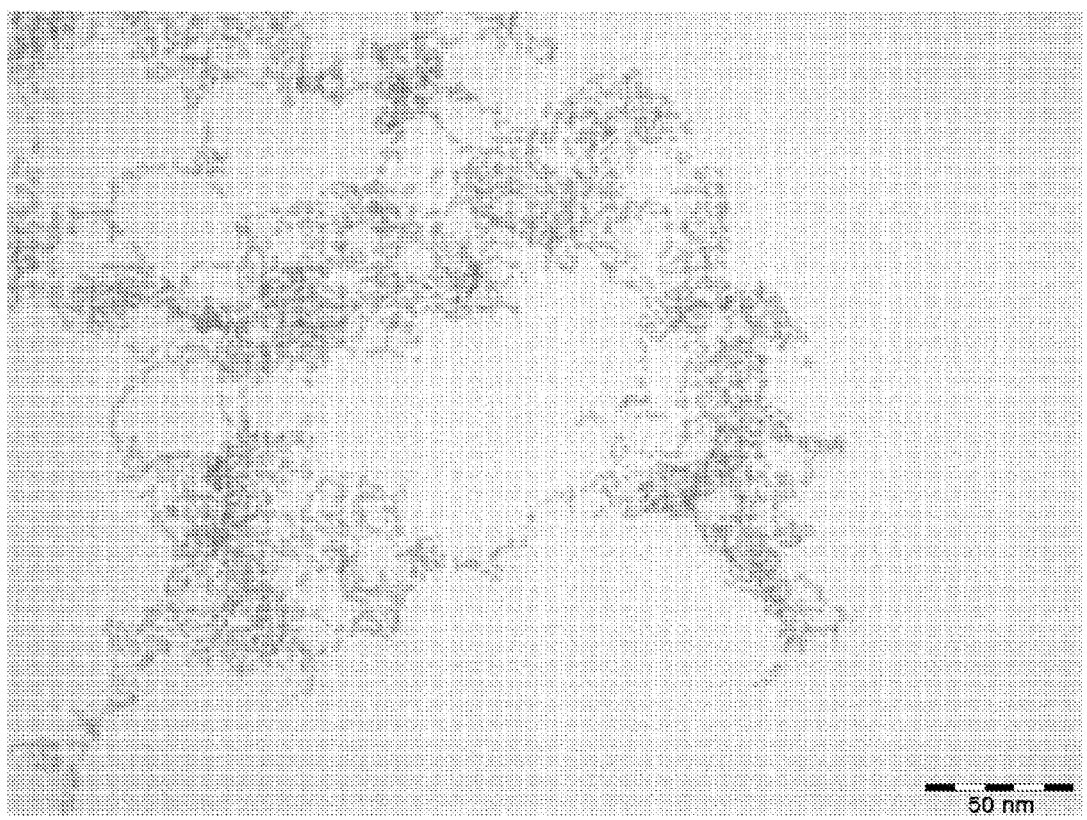
FIG. 16 shows a representative TEM photomicrograph of dried platinum constituents formed in connection with Example 4.

Transmission electron microscopy (TEM) sample preparation methods were identical to the methods described earlier herein, although the interrogations were performed on a FEI Tecnai 12 TEM equipped with a SIS Megaview III CCD digital camera. The TEM micrographs show that the formed particles have an average diameter of less than 10 nm. FIG. 16 shows a representative TEM Photomicrograph of platinum nanocrystals, dried from suspension PB-13, made according to this Example 4.

The amount of platinum nanoparticles or ions produced in the formulations varied between about 1.0 ppm and about 15 ppm, as measured by the atomic absorption spectroscopy techniques discussed elsewhere herein.

Tables 5-8 summarize key processing parameters used in conjunction with FIGS. 9a and 10d. Also, Tables 5-8 disclose: 1) resultant "ppm" (e.g., platinum nanocrystal/ion concentrations.)

Note, while two different chlorine-based processing enhancers were used to make platinum species in water, a variety of issues exist when making gold-based nanocrystal suspensions which render them less than desirable for Au—Pt nanocrystal suspensions.

TABLE 5

| | Run ID: | PB-09 | PB-10/PB-13 | PB-16 | PB-17 | PB-18 | PB-19 |
|---|---|---|---|---|---|---|---|
| Flow Rate: | In (ml/min) | 220 | 220 | 220 | 220 | 220 | 220 |
| | Out (ml/min) | 200 | 200 | 200 | 200 | 200 | 200 |
| Volts: | Set # 1 | 750 | 750 | 750 | 750 | 750 | 750 |
| | Set #'s 2-8 | 175 | 175 | 175 | 175 | 175 | 175 |
| | Set #'s 2-8 frequency, Hz | 80 | 5 | 80 | 5 | 80 | 5 |

TABLE 5-continued

| Run ID: | | PB-09 | PB-10/PB-13 | PB-16 | PB-17 | PB-18 | PB-19 |
|---|---|---|---|---|---|---|---|
| PE/Concentration(mg/ml) | | $NaHCO_3$/0.67 | $NaHCO_3$/0.67 | $KHCO_3$/0.61 | $KHCO_3$/0.61 | $K_2CO_3$/0.33 | $K_2CO_3$/0.33 |
| Wire Diameter (mm) | | 1.0 | 1.0 | 1.0 | 1.0 | 1.0 | 1.0 |
| Contact "$W_L$" (in/mm) | | 1/25 | 1/25 | 1/25 | 1/25 | 1/25 | 1/25 |
| Electrode Separation "y" (in/mm) | | .25/6.4 | .25/6.4 | .25/6.4 | .25/6.4 | .25/6.4 | .25/6.4 |
| Electrode Config. Figure | | 8b | 8b | 8b | 8b | 8b | 8b |
| Produced Pt PPM | | 8.1 | 11.8 | 2.3 | 5.9 | 2.4 | 7.0 |
| Output Temp ° C. at 32 | | 70 | 70 | 65 | 63 | 66 | 64 |
| Dimensions | Plasma 4 Figs. | 9 | 9 | 9 | 9 | 9 | 9 |
| | Process Figures | 10a, 10d | 10a, 10d | 10a, 10d | 10a, 10d | 10a, 10d | 10a, 10d |
| | M (in/mm) | 1.5/38 | 1.5/38 | 1.5/38 | 1.5/38 | 1.5/38 | 1.5/38 |
| | LT (in/mm) | 36/914 | 36/914 | 36/914 | 36/914 | 36/914 | 36/914 |
| | d (in/mm) | 1/25 | 1/25 | 1/25 | 1/25 | 1/25 | 1/25 |
| | S (in/mm) | 1.5/38 | 1.5/38 | 1.5/38 | 1.5/38 | 1.5/38 | 1.5/38 |
| Electrode Curr. (A) | | 0.72 | 0.67 | 0.67 | 0.61 | 0.67 | 0.60 |
| Total Curr. Draw (A) | | 5.00 | n/m | 4.64 | 4.78 | 4.70 | 4.79 |
| "c-c" (mm) | | 76 | 76 | 76 | 76 | 76 | 76 |
| Set 1 | electrode # | 1a | 1a | 1a | 1a | 1a | 1a |
| | "x" (in/mm) | 0.25/6.4 | 0.25/6.4 | 0.25/6.4 | 0.25/6.4 | 0.25/6.4 | 0.25/6.4 |
| | electrode # | 5a | 5a | 5a | 5a | n/a | 5a |
| "c-c" (mm) | | 102 | 102 | 102 | 102 | 102 | 102 |
| Set 2 | electrode # | 5b | 5b | 5b | 5b | 5b | 5b |
| | "x" (in/mm) | n/a | n/a | n/a | n/a | n/a | n/a |
| | electrode # | 5b' | 5b' | 5b' | 5b' | 5b' | 5b' |
| "c-c" (mm) | | 76 | 76 | 76 | 76 | 76 | 76 |
| Set 3 | electrode # | 5c | 5c | 5c | 5c | 5c | 5c |
| | electrode # | 5c' | 5c' | 5c' | 5c' | 5c' | 5c' |
| "c-c" (mm) | | 76 | 76 | 76 | 76 | 76 | 76 |
| Set 4 | electrode # | 5d | 5d | 5d | 5d | 5d | 5d |
| | electrode # | 5d' | 5d' | 5d' | 5d' | 5d' | 5d' |
| "c-c" (mm) | | 127 | 127 | 127 | 127 | 127 | 127 |
| Set 5 | electrode # | 5e | 5e | 5e | 5e | 5e | 5e |
| | electrode # | 5e' | 5e' | 5e' | 5e' | 5e' | 5e' |
| "c-c" (mm) | | 127 | 127 | 127 | 127 | 127 | 127 |
| Set 6 | electrode # | 5f | 5f | 5f | 5f | 5f | 5f |
| | electrode # | 5f' | 5f' | 5f' | 5f' | 5f' | 5f' |
| "c-c" (mm) | | 152 | 152 | 152 | 152 | 152 | 152 |
| Set 7 | electrode # | 5g | 5g | 5g | 5g | 5g | 5g |
| | electrode # | 5g' | 5g' | 5g' | 5g' | 5g' | 5g' |
| "c-c" (mm) | | 178 | 178 | 178 | 178 | 178 | 178 |
| Set 8 | electrode # | 5h | 5h | 5h | 5h | 5h | 5h |
| | electrode # | 5h' | 5h' | 5h' | 5h' | 5h' | 5h' |
| "c-c" (mm) | | 76 | 76 | 76 | 76 | 76 | 76 |

TABLE 6

| Run ID: | | PB-20 | PB-21 | PB-23 | PB-24 | PB-25 | PB-26 |
|---|---|---|---|---|---|---|---|
| Flow Rate: | In (ml/min) | 220 | 220 | 220 | 220 | 220 | 220 |
| | Out (ml/min) | 200 | 200 | 200 | 200 | 200 | 200 |
| Volts: | Set # 1 | 750 | 750 | 750 | 750 | 750 | 750 |
| | Set #'s 2-8 | 175 | 175 | 175 | 175 | 175 | 175 |
| | Set #'s 2-8 frequency, Hz | 80 | 5 | 80 | 5 | 80 | 5 |
| PE/Concentration(mg/ml) | | $Na_2CO_3$/0.30 | $Na_2CO_3$/0.30 | NaOH/0.19 | NaOH/0.19 | KOH/0.19 | KOH/0.19 |
| Wire Diameter (mm) | | 1.0 | 1.0 | 1.0 | 1.0 | 1.0 | 1.0 |
| Contact "$W_L$" (in/mm) | | 1/25 | 1/25 | 1/25 | 1/25 | 1/25 | 1/25 |
| Electrode Separation "y" (in/mm) | | .25/6.4 | .25/6.4 | .25/6.4 | .25/6.4 | .25/6.4 | .25/6.4 |
| Electrode Config. Figure | | 8b | 8b | 8b | 8b | 8b | 8b |
| Produced Pt PPM | | 2.4 | 7.0 | 1.1 | 3.6 | 1.4 | 3.9 |
| Output Temp ° C. at 32 | | 68 | 66 | 60 | 60 | 63 | 60 |
| Dimensions | Plasma 4 Figs. | 9 | 9 | 9 | 9 | 9 | 9 |
| | Process Figures | 10a, 10d | 10a, 10d | 10a, 10d | 10a, 10d | 10a, 10d | 10a, 10d |
| | M (in/mm) | 1.5/38 | 1.5/38 | 1.5/38 | 1.5/38 | 1.5/38 | 1.5/38 |
| | LT (in/mm) | 36/914 | 36/914 | 36/914 | 36/914 | 36/914 | 36/914 |
| | d (in/mm) | 1/25 | 1/25 | 1/25 | 1/25 | 1/25 | 1/25 |
| | S (in/mm) | 1.5/38 | 1.5/38 | 1.5/38 | 1.5/38 | 1.5/38 | 1.5/38 |
| Electrode Curr. (A) | | 0.73 | 0.63 | 0.55 | 0.51 | 0.53 | 0.51 |
| Total Curr. Draw (A) | | 5.09 | 4.95 | 3.83 | 3.67 | 4.11 | 3.63 |
| "c-c" (mm) | | 76 | 76 | 76 | 76 | 76 | 76 |

TABLE 6-continued

|  |  | PB-20 | PB-21 | PB-23 | PB-24 | PB-25 | PB-26 |
|---|---|---|---|---|---|---|---|
| Set 1 | electrode # | 1a | 1a | 1a | 1a | 1a | 1a |
|  | "x" (in/mm) | 0.25/6.4 | 0.25/6.4 | 0.25/6.4 | 0.25/6.4 | 0.25/6.4 | 0.25/6.4 |
|  | electrode # | 5a | 5a | 5a | 5a | n/a | 5a |
| "c-c" (mm) |  | 102 | 102 | 102 | 102 | 102 | 102 |
| Set 2 | electrode # | 5b | 5b | 5b | 5b | 5b | 5b |
|  | "x" (in/mm) | n/a | n/a | n/a | n/a | n/a | n/a |
|  | electrode # | 5b' | 5b' | 5b' | 5b' | 5b' | 5b' |
| "c-c" (mm) |  | 76 | 76 | 76 | 76 | 76 | 76 |
| Set 3 | electrode # | 5c | 5c | 5c | 5c | 5c | 5c |
|  | electrode # | 5c' | 5c' | 5c' | 5c' | 5c' | 5c' |
| "c-c" (mm) |  | 76 | 76 | 76 | 76 | 76 | 76 |
| Set 4 | electrode # | 5d | 5d | 5d | 5d | 5d | 5d |
|  | electrode # | 5d' | 5d' | 5d' | 5d' | 5d' | 5d' |
| "c-c" (mm) |  | 127 | 127 | 127 | 127 | 127 | 127 |
| Set 5 | electrode # | 5e | 5e | 5e | 5e | 5e | 5e |
|  | electrode # | 5e' | 5e' | 5e' | 5e' | 5e' | 5e' |
| "c-c" (mm) |  | 127 | 127 | 127 | 127 | 127 | 127 |
| Set 6 | electrode # | 5f | 5f | 5f | 5f | 5f | 5f |
|  | electrode # | 5f' | 5f' | 5f' | 5f' | 5f' | 5f' |
| "c-c" (mm) |  | 152 | 152 | 152 | 152 | 152 | 152 |
| Set 7 | electrode # | 5g | 5g | 5g | 5g | 5g | 5g |
|  | electrode # | 5g' | 5g' | 5g' | 5g' | 5g' | 5g' |
| "c-c" (mm) |  | 178 | 178 | 178 | 178 | 178 | 178 |
| Set 8 | electrode # | 5h | 5h | 5h | 5h | 5h | 5h |
|  | electrode # | 5h' | 5h' | 5h' | 5h' | 5h' | 5h' |
| "c-c" (mm) |  | 76 | 76 | 76 | 76 | 76 | 76 |

TABLE 7

|  |  | PB-27 | PB-28 | PB-32 | PB-33 | PB-34 | PB-35 |
|---|---|---|---|---|---|---|---|
| Flow Rate: | In (ml/min) | 220 | 220 | 220 | 220 | 220 | 220 |
|  | Out (ml/min) | 200 | 200 | 200 | 200 | 200 | 200 |
| Volts: | Set # 1 | 750 | 750 | 750 | 750 | 750 | 750 |
|  | Set #'s 2-8 | 175 | 175 | 175 | 175 | 175 | 175 |
|  | Set #'s 2-8 frequency, Hz | 80 | 5 | 80 | 5 | 80 | 5 |
| PE/Concentration(mg/ml) |  | NaBr/0.58 | NaBr/0.58 | KBr/0.54 | KBr/0.54 | Na$_2$PO$_4$/0.29 | KOH/0.29 |
| Wire Diameter (mm) |  | 1.0 | 1.0 | 1.0 | 1.0 | 1.0 | 1.0 |
| Contact "W$_L$" (in/mm) |  | 1/25 | 1/25 | 1/25 | 1/25 | 1/25 | 1/25 |
| Electrode Separation "y" (in/mm) |  | .25/6.4 | .25/6.4 | .25/6.4 | .25/6.4 | .25/6.4 | .25/6.4 |
| Electrode Config. Figure |  | 8b | 8b | 8b | 8b | 8b | 8b |
| Produced Pt PPM |  | 2.5 | 9.9 | 2.2 | 7.1 | 1.6 | 4.1 |
| Output Temp ° C. at 32 |  | 68 | 70.5 | 61.5 | 64 | 61 | 61 |
| Dimensions | Plasma 4 Figs. | 9 | 9 | 9 | 9 | 9 | 9 |
|  | Process Figures | 10a, 10d | 10a, 10d | 10a, 10d | 10a, 10d | 10a, 10d | 10a, 10d |
|  | M (in/mm) | 1.5/38 | 1.5/38 | 1.5/38 | 1.5/38 | 1.5/38 | 1.5/38 |
|  | LT (in/mm) | 36/914 | 36/914 | 36/914 | 36/914 | 36/914 | 36/914 |
|  | d (in/mm) | 1/25 | 1/25 | 1/25 | 1/25 | 1/25 | 1/25 |
|  | S (in/mm) | 1.5/38 | 1.5/38 | 1.5/38 | 1.5/38 | 1.5/38 | 1.5/38 |
| Electrode Curr. (A) |  | 0.70 | 0.73 | 0.70 | 0.68 | 0.47 | 0.55 |
| Total Curr. Draw (A) |  | 4.88 | 5.31 | 3.95 | 4.14 | 4.03 | 4.43 |
| "c-c" (mm) |  | 76 | 76 | 76 | 76 | 76 | 76 |
| Set 1 | electrode # | 1a | 1a | 1a | 1a | 1a | 1a |
|  | "x" (in/mm) | 0.25/6.4 | 0.25/6.4 | 0.25/6.4 | 0.25/6.4 | 0.25/6.4 | 0.25/6.4 |
|  | electrode # | 5a | 5a | 5a | 5a | n/a | 5a |
| "c-c" (mm) |  | 102 | 102 | 102 | 102 | 102 | 102 |
| Set 2 | electrode # | 5b | 5b | 5b | 5b | 5b | 5b |
|  | "x" (in/mm) | n/a | n/a | n/a | n/a | n/a | n/a |
|  | electrode # | 5b' | 5b' | 5b' | 5b' | 5b' | 5b' |
| "c-c" (mm) |  | 76 | 76 | 76 | 76 | 76 | 76 |
| Set 3 | electrode # | 5c | 5c | 5c | 5c | 5c | 5c |
|  | electrode # | 5c' | 5c' | 5c' | 5c' | 5c' | 5c' |
| "c-c" (mm) |  | 76 | 76 | 76 | 76 | 76 | 76 |
| Set 4 | electrode # | 5d | 5d | 5d | 5d | 5d | 5d |
|  | electrode # | 5d' | 5d' | 5d' | 5d' | 5d' | 5d' |
| "c-c" (mm) |  | 127 | 127 | 127 | 127 | 127 | 127 |
| Set 5 | electrode # | 5e | 5e | 5e | 5e | 5e | 5e |
|  | electrode # | 5e' | 5e' | 5e' | 5e' | 5e' | 5e' |
| "c-c" (mm) |  | 127 | 127 | 127 | 127 | 127 | 127 |
| Set 6 | electrode # | 5f | 5f | 5f | 5f | 5f | 5f |
|  | electrode # | 5f' | 5f' | 5f' | 5f' | 5f' | 5f' |
| "c-c" (mm) |  | 152 | 152 | 152 | 152 | 152 | 152 |

TABLE 7-continued

|   | Run ID: | PB-27 | PB-28 | PB-32 | PB-33 | PB-34 | PB-35 |
|---|---|---|---|---|---|---|---|
| Set 7 | electrode # | 5g | 5g | 5g | 5g | 5g | 5g |
|   | electrode # | 5g' | 5g' | 5g' | 5g' | 5g' | 5g' |
| "c-c" (mm) |   | 178 | 178 | 178 | 178 | 178 | 178 |
| Set 8 | electrode # | 5h | 5h | 5h | 5h | 5h | 5h |
|   | electrode # | 5h' | 5h' | 5h' | 5h' | 5h' | 5h' |
| "c-c" (mm) |   | 76 | 76 | 76 | 76 | 76 | 76 |

TABLE 8

|   |   | Run ID: | | | |
|---|---|---|---|---|---|
|   |   | PB-40 | PB-41 | PB-42 | PB-43 |
| Flow Rate: | In (ml/min) | 220 | 220 | 220 | 220 |
|   | Out (ml/min) | 200 | 200 | 200 | 200 |
| Volts: | Set # 1 | 750 | 750 | 750 | 750 |
|   | Set #'s 2-8 | 175 | 175 | 175 | 175 |
|   | Set #'s 2-8 frequency, Hz | 80 | 5 | 80 | 5 |
| PE/Concentration (mg/ml) |   | NaCl/0.34 | NaCl/0.34 | $CaCl_2$/0.31 | $CaCl_2$/0.31 |
| Wire Diameter (mm) |   | 1.0 | 1.0 | 1.0 | 1.0 |
| Contact "$W_L$" (in/mm) |   | 1/25 | 1/25 | 1/25 | 1/25 |
| Electrode Separation "y" (in/mm) |   | .25/6.4 | .25/6.4 | .25/6.4 | .25/6.4 |
| Electrode Config. Figure |   | 8b | 8b | 8b | 8b |
| Produced Pt PPM |   | 1.5 | 10.2 | 2.0 | 2.0 |
| Output Temp ° C. at 32 |   | 69 | 70.5 | 72 | 72 |
| Dimensions | Plasma 4 Figs. | 9 | 9 | 9 | 9 |
|   | Process Figures | 10a, 10d | 10a, 10d | 10a, 10d | 10a, 10d |
|   | M (in/mm) | 1.5/38 | 1.5/38 | 1.5/38 | 1.5/38 |
|   | $L_T$ (in/mm) | 36/914 | 36/914 | 36/914 | 36/914 |
|   | d (in/mm) | 1/25 | 1/25 | 1/25 | 1/25 |
|   | S (in/mm) | 1.5/38 | 1.5/38 | 1.5/38 | 1.5/38 |
| Electrode Curr. (A) |   | 0.72 | 0.72 | 0.77 | 0.73 |
| Total Curr. Draw (A) |   | 5.00 | 6.08 | 5.36 | 5.77 |
|   | "c-c" (mm) | 76 | 76 | 76 | 76 |
| Set 1 | electrode # | 1a | 1a | 1a | 1a |
|   | "x" (in/mm) | 0.25/6.4 | 0.25/6.4 | 0.25/6.4 | 0.25/6.4 |
|   | electrode # | 5a | 5a | 5a | 5a |
|   | "c-c" (mm) | 102 | 102 | 102 | 102 |
| Set 2 | electrode # | 5b | 5b | 5b | 5b |
|   | "x" (in/mm) | n/a | n/a | n/a | n/a |
|   | electrode # | 5b' | 5b' | 5b' | 5b' |
|   | "c-c" (mm) | 76 | 76 | 76 | 76 |
| Set 3 | electrode # | 5c | 5c | 5c | 5c |
|   | electrode # | 5c' | 5c' | 5c' | 5c' |
|   | "c-c" (mm) | 76 | 76 | 76 | 76 |
| Set 4 | electrode # | 5d | 5d | 5d | 5d |
|   | electrode # | 5d' | 5d' | 5d' | 5d' |
|   | "c-c" (mm) | 127 | 127 | 127 | 127 |
| Set 5 | electrode # | 5e | 5e | 5e | 5e |
|   | electrode # | 5e' | 5e' | 5e' | 5e' |
|   | "c-c" (mm) | 127 | 127 | 127 | 127 |
| Set 6 | electrode # | 5f | 5f | 5f | 5f |
|   | electrode # | 5f' | 5f' | 5f' | 5f' |
|   | "c-c" (mm) | 152 | 152 | 152 | 152 |
| Set 7 | electrode # | 5g | 5g | 5g | 5g |
|   | electrode # | 5g' | 5g' | 5g' | 5g' |
|   | "c-c" (mm) | 178 | 178 | 178 | 178 |
| Set 8 | electrode # | 5h | 5h | 5h | 5h |
|   | electrode # | 5h' | 5h' | 5h' | 5h' |
|   | "c-c" (mm) | 76 | 76 | 76 | 76 |

Example 5

Manufacturing Platinum-Based Species in Water with a Variety of Frequencies Applied to the Electrodes in a Continuous Trough Process In general, this Example utilizes certain embodiments of the invention associated with the apparatuses generally shown in FIGS. 9, 10*d* and 11*b*. The AC power source (or transformer) 501AC, illustrated in FIG. 13, was used as the power supply for the examples contained herein, while the function generator 501FG was sometimes used (as disclosed herein) to drive the AC power source 501AC. This transformer 501 AC was an AC power source (Chroma 61604) having an AC voltage range of 0-300V, a frequency range of 15-1000 Hz and a maximum power rating of about 2 kVA. The precise electrical connections are discussed elsewhere herein. Control devices 20, illustrated in FIGS. 8*c* and 8*j*, were connected to the electrodes 1/5 and 5/5, respectively. However, due to the short run times in each "Run ID," there was no need to actuate the control devices 20. Thus, the ends 9' of the electrodes 5a and 5b were juxtaposed with the bottom of the trough member 30b'. Each run in this example utilized about 2.5 g/gallon of NaHCO₃ as a processing enhancer and a liquid flow rate of about 220 ml/min.

Moreover, to show the effect of different frequencies on the process and/or products formulated, varying sine wave frequencies were utilized. In particular, sine wave AC frequencies as low as about 1 Hz and as high as about 200 Hz were utilized to make nanocrystal suspensions or colloids and/or ions, in accordance with the teachings herein. The AC power source 501AC utilized a Chroma 61604 programmable AC source. The applied voltage was about 175 volts with a corresponding sine wave at six different frequencies of about 15, 40, 60, 80, 100 and 200 Hz. Additionally, the function generator 501FG provided sine waves at frequencies less than 15 Hz to the power supply 501AC which subsequently amplified the input signal to about 175V at different frequencies, namely 1 Hz and 5 Hz. The applied current varied between about 4.5 amps and 6.0 amps.

The amount of platinum nanoparticles and/or ions produced in the formulations varied between about 7.0 ppm and about 15 ppm, as measured by the atomic absorption spectroscopy techniques discussed elsewhere herein.

Tables 9-10 summarize key processing parameters used in conjunction with FIGS. 9 and 10d. Also, Tables 9-10 disclose: 1) resultant "ppm" (i.e., platinum concentrations.)

Figure 17:
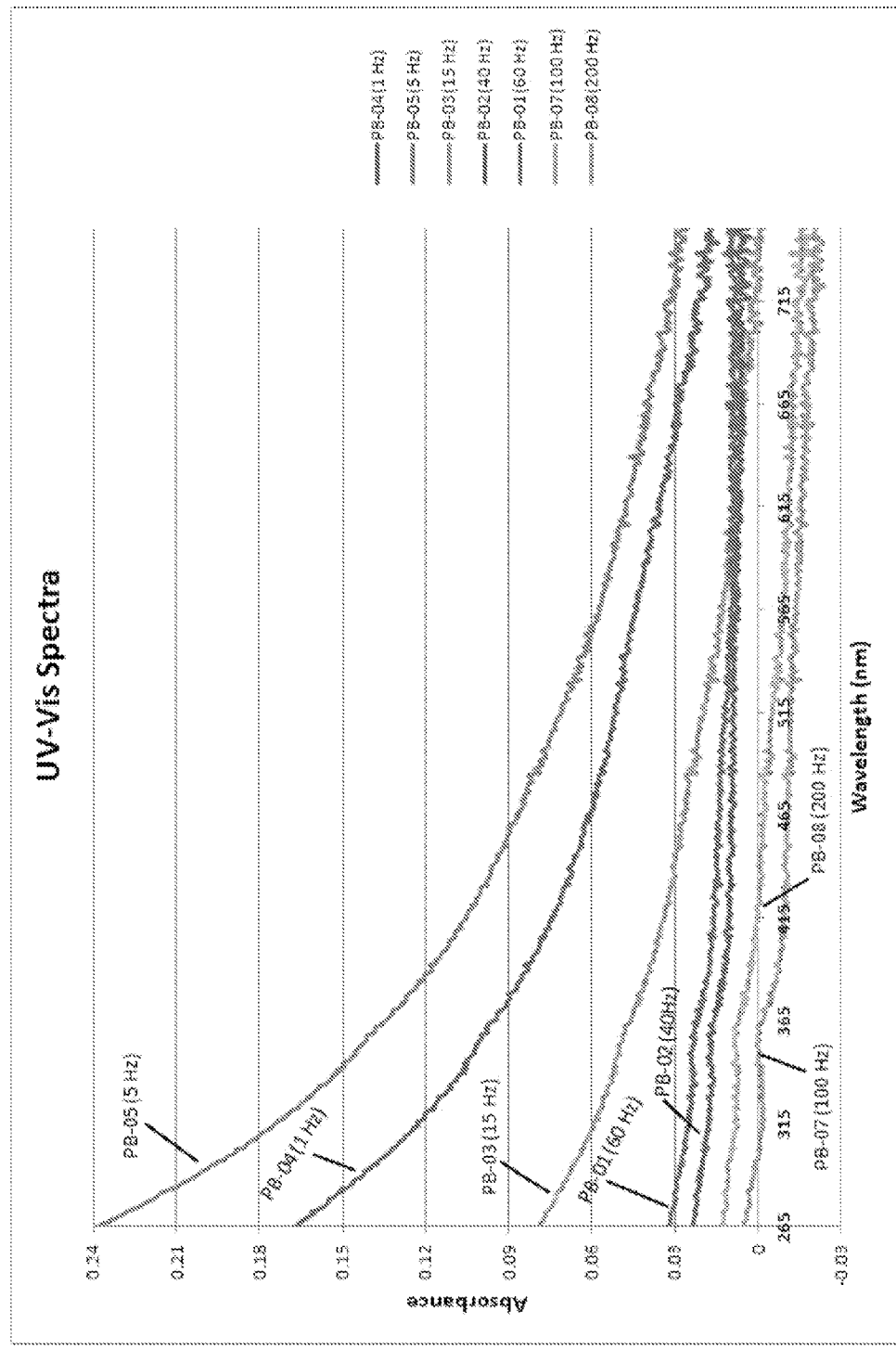
FIG. 17 shows the UV-Vis spectral patterns of each of the seven platinum solutions/suspensions made according to Example 5.

Energy absorption spectra were obtained for the samples by using UV-VIS spectroscopy methods as outlined elsewhere herein. FIG. 17 contains the UV-Vis data collected for the samples above, specifically displaying the 265 nm-750 nm range.

TABLE 9

| | Run ID: | PB-01 | PB-02 | PB-03 | PB-04 | PB-05 | PB-06 |
|---|---|---|---|---|---|---|---|
| Flow Rate: | In (ml/min) | 220 | 220 | 220 | 220 | 220 | 220 |
| | Out (ml/min) | 184 | 200 | 200 | 200 | 200 | 200 |
| Volts: | Set # 1 | 750 | 750 | 750 | 750 | 750 | 750 |
| | Set #'s 2-8 | 175 | 175 | 175 | 175 | 175 | 175 |
| | Set #'s 2-8 frequency, Hz | 60 | 40 | 15 | 1 | 5 | 80 |
| PE: NaHCO3 (mg/ml) | | 0.67 | 0.67 | 0.67 | 0.67 | 0.67 | 0.67 |
| Wire Diameter (mm) | | 1.0 | 1.0 | 1.0 | 1.0 | 1.0 | 1.0 |
| Contact "$W_L$" (in/mm) | | 1/25 | 1/25 | 1/25 | 1/25 | 1/25 | 1/25 |
| Electrode Separation "y" (in/mm) | | .25/6.4 | .25/6.4 | .25/6.4 | .25/6.4 | .25/6.4 | .25/6.4 |
| Electrode Config. Figure | | 8b | 8b | 8b | 8b | 8b | 8b |
| Produced Pt PPM | | 9.7 | 8.6 | 8.7 | 12.1 | 14.6 | 7.7 |
| Output Temp ° C. at 32 | | 72 | 72 | 72 | 71 | 72 | 71 |
| Dimensions | Plasma 4 Figs. | 9 | 9 | 9 | 9 | 9 | 9 |
| | Process Figures | 10a, 10d | 10a, 10d | 10a, 10d | 10a, 10d | 10a, 10d | 10a, 10d |
| | M (in/mm) | 1.5/38 | 1.5/38 | 1.5/38 | 1.5/38 | 1.5/38 | 1.5/38 |
| | LT (in/mm) | 36/914 | 36/914 | 36/914 | 36/914 | 36/914 | 36/914 |
| | d (in/mm) | 1/25 | 1/25 | 1/25 | 1/25 | 1/25 | 1/25 |
| | S (in/mm) | 1.5/38 | 1.5/38 | 1.5/38 | 1.5/38 | 1.5/38 | 1.5/38 |
| Electrode Curr. (A) | | 0.77 | 0.77 | 0.76 | 0.32 | 0.71 | 0.75 |
| Total Curr. Draw (A) | | 5.43 | 5.40 | 5.33 | n/m | n/m | n/m |
| "c-c" (mm) | | 76 | 76 | 76 | 76 | 76 | 76 |
| Set 1 | electrode # | 1a | 1a | 1a | 1a | 1a | 1a |
| | "x" (in/mm) | 0.25/6.4 | 0.25/6.4 | 0.25/6.4 | 0.25/6.4 | 0.25/6.4 | 0.25/6.4 |
| | electrode # | 5a | 5a | 5a | 5a | n/a | 5a |
| "c-c" (mm) | | 102 | 102 | 102 | 102 | 102 | 102 |
| Set 2 | electrode # | 5b | 5b | 5b | 5b | 5b | 5b |
| | "x" (in/mm) | n/a | n/a | n/a | n/a | n/a | n/a |
| | electrode # | 5b' | 5b' | 5b' | 5b' | 5b' | 5b' |
| "c-c" (mm) | | 76 | 76 | 76 | 76 | 76 | 76 |
| Set 3 | electrode # | 5c | 5c | 5c | 5c | 5c | 5c |
| | electrode # | 5c' | 5c' | 5c' | 5c' | 5c' | 5c' |
| "c-c" (mm) | | 76 | 76 | 76 | 76 | 76 | 76 |
| Set 4 | electrode # | 5d | 5d | 5d | 5d | 5d | 5d |
| | electrode # | 5d' | 5d' | 5d' | 5d' | 5d' | 5d' |
| "c-c" (mm) | | 127 | 127 | 127 | 127 | 127 | 127 |
| Set 5 | electrode # | 5e | 5e | 5e | 5e | 5e | 5e |
| | electrode # | 5e' | 5e' | 5e' | 5e' | 5e' | 5e' |
| "c-c" (mm) | | 127 | 127 | 127 | 127 | 127 | 127 |
| Set 6 | electrode # | 5f | 5f | 5f | 5f | 5f | 5f |
| | electrode # | 5f' | 5f' | 5f' | 5f' | 5f' | 5f' |
| "c-c" (mm) | | 152 | 152 | 152 | 152 | 152 | 152 |
| Set 7 | electrode # | 5g | 5g | 5g | 5g | 5g | 5g |
| | electrode # | 5g' | 5g' | 5g' | 5g' | 5g' | 5g' |
| "c-c" (mm) | | 178 | 178 | 178 | 178 | 178 | 178 |
| Set 8 | electrode # | 5h | 5h | 5h | 5h | 5h | 5h |
| | electrode # | 5h' | 5h' | 5h' | 5h' | 5h' | 5h' |
| "c-c" (mm) | | 76 | 76 | 76 | 76 | 76 | 76 |

TABLE 10

| | | Run ID: | |
|---|---|---|---|
| | | PB-07 | PB-08 |
| Flow Rate: | In (ml/min) | 220 | 220 |
| | Out (ml/min) | 200 | 200 |
| Volts: | Set # 1 | 750 | 750 |
| | Set #'s 2-8 | 175 | 175 |

TABLE 10-continued

| | | Run ID: | |
|---|---|---|---|
| | | PB-07 | PB-08 |
| Set #'s 2-8 frequency, Hz | | 100 | 200 |
| PE: NaHCO3 (mg/ml) | | 0.67 | 0.67 |
| Wire Diameter (mm) | | 1.0 | 1.0 |
| Contact "$W_L$" (in/mm) | | 1/25 | 1/25 |
| Electrode Separation "y" (in/mm) | | .25/6.4 | .25/6.4 |
| Electrode Config. Figure | | 8b | 8b |
| Produced Pt PPM | | 9.7 | 8.6 |
| Output Temp ° C. at 32 | | 71 | 71 |
| Dimensions | Plasma 4 Figs. | 9 | 9 |
| | Process Figures | 10a, 10d | 10a, 10d |
| | M (in/mm) | 1.5/38 | 1.5/38 |
| | $L_T$ (in/mm) | 36/914 | 36/914 |
| | d (in/mm) | 1/25 | 1/25 |
| | S (in/mm) | 1.5/38 | 1.5/38 |
| Electrode Curr. (A) | | 0.76 | 0.77 |
| Total Curr. Draw (A) | | 5.24 | 5.33 |
| | "c-c" (mm) | 76 | 76 |
| Set 1 | electrode # | 1a | 1a |
| | "x" (in/mm) | 0.25/6.4 | 0.25/6.4 |
| | electrode # | 5a | 5a |
| | "c-c" (mm) | 102 | 102 |
| Set 2 | electrode # | 5b | 5b |
| | "x" (in/mm) | n/a | n/a |
| | electrode # | 5b' | 5b' |
| | "c-c" (mm) | 76 | 76 |
| Set 3 | electrode # | 5c | 5c |
| | electrode # | 5c' | 5c' |
| | "c-c" (mm) | 76 | 76 |
| Set 4 | electrode # | 5d | 5d |
| | electrode # | 5d' | 5d' |
| | "c-c" (mm) | 127 | 127 |
| Set 5 | electrode # | 5e | 5e |
| | electrode # | 5e' | 5e' |
| | "c-c" (mm) | 127 | 127 |
| Set 6 | electrode # | 5f | 5f |
| | electrode # | 5f' | 5f' |
| | "c-c" (mm) | 152 | 152 |
| Set 7 | electrode # | 5g | 5g |
| | electrode # | 5g' | 5g' |
| | "c-c" (mm) | 178 | 178 |
| Set 8 | electrode # | 5h | 5h |
| | electrode # | 5h' | 5h' |
| | "c-c" (mm) | 76 | 76 |

Example 6

Manufacturing an Au—Pt Bi-Metallic Nanocrystal Suspension by a Batch Process Using NaHCO$_3$ as a Process Enhancer—ID#111710-9

This Example utilizes a batch process according to the present invention. FIG. 12*a* shows the apparatus used to condition the liquid 3. Once conditioned, the liquid 3' was processed in the apparatus shown in FIG. 12*c* or 12*d*, for platinum ions/particles and bi-metallic nanocrystals, respectively. The overall process of creating a bi-metallic nanocrystal suspension is described below and is summarized in Table 11.

Initially, platinum ions and/or particles were created in water by the following process. Approximately 4.0 grams/gallon (i.e., about 1.06 mg/mL) of processing enhancer baking soda (i.e., NaHCO$_3$) was added to about 1 gallon of de-ionized water. The amount of time that the water 3 with processing enhancer was exposed to the plasma 4 was about 30 minutes, prior to subsequent processing in the apparatus shown in FIG. 12*c*.

The applied voltage for each plasma 4 created at electrode 1 was about 750 volts. This voltage was achieved by a transformer 60 (i.e., the Balanced Mid-Point Referenced Design) discussed elsewhere herein. Note that in Table 11 (and elsewhere herein) the reference to "GZA" is synonymous with creation of plasma 4.

A second and different transformer was electrically connected to the electrodes 5*a*/5*b* shown in FIG. 12*c*. This transformer was a hy AC power source having a voltage range of about 0-300V, a frequency range of about 47-400 Hz and a maximum power rating of about 1 kVA. The applied voltage was about 100 volts with a frequency of about 60 hertz for approximately a 2-hour operating time. The diameter of the platinum wire electrodes was 1 mm. The length of the platinum wires was about 51 mm.

Subsequently, the platinum species and water formulation (raw material) prepared above was mixed with an equal amount of conditioned water, which conditioned water 3' was achieved with a platinum electrode 1 creating a plasma 4 for about 30 minutes, and processing enhancer NaHCO$_3$ 0.5 g/gallon (0.132 mg/mL) NaHCO$_3$) at a ratio of 1:1 to a total volume of about 800 mL. The liquid 3' was then processed via the apparatus in FIG. 12*d* with gold electrodes (99.99%, about 0.5 mm diameter and a length of about 6.25 in (15.88 cm) for about 40 minutes, with a hy AC power source having an applied voltage of about 160 volts and about 47 hertz. The hydrodynamic radius of the bi-metallic nanocrystals made was about 14.7 nm as measured by ViscoTek. The suspension contained about 16.1 ppm of Au and about 2.1 ppm of Pt as measured by the atomic absorption spectroscopy techniques discussed elsewhere herein.

Figure 18:
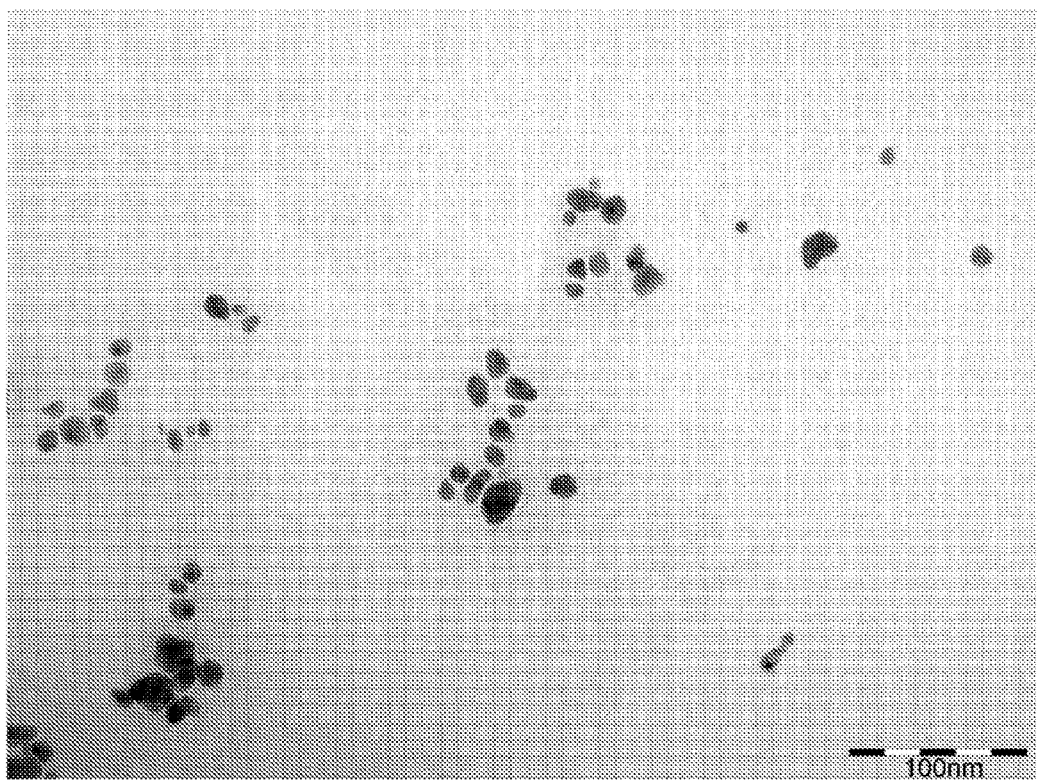
FIG. 18 shows a representative TEM photomicrograph of the dried constituents made according to Example 6.

FIG. 18 shows a representative TEM Photomicrograph of the bi-metallic nanocrystal suspension dried from formulation 110910-4, which was made by techniques equivalent to those discussed elsewhere herein.

Energy absorption spectra was obtained for this sample (111710-a) using Uv-Vis spectroscopy methods as outlined elsewhere herein. FIG. 12*g* contains the UV-Vis data collected for this sample (111710-a), specifically displaying the 350-900 nm range.

TABLE 11

| Component 1 | | | |
|---|---|---|---|
| Pretreatment - GZA | | | |
| Run ID | Volume (mL) | NaHCO$_3$ (grams) | time (hrs) |
| 110910-2 | 3785 | 4 | 0.5 |
| Pt ion treatment (Pt wires, 99.99%) | | | |
| Volume (mL) | Voltage (V) | Frequency (Hz) | Time (hrs) | Length of Wire (in/cm) | Wire Diameter (mm) |
| 3785 | 100 | 60 | 2 | 2.01/5.1 | 1 |

TABLE 11-continued

Component 2
Pretreatment - Pt GZA

| Run ID | Volume (mL) | NaHCO₃ (grams) | time (hrs) |
|---|---|---|---|
| N/A | 3785 | 0.5 | 0.5 |

Composite Mix

Mixture of Component 1 & 2

| Run ID | Comp. 1 Vol. (mL) | Comp. 2 Vol. (mL) | Volume (mL) |
|---|---|---|---|
| 111710-9 | 400 | 400 | 800 |

Gold Nanoparticle Treatment (Au wires, 99.99%)

| Voltage (V) | Frequency (Hz) | Time (hrs) | Current (A) | Length of Wire (in/cm) | Wire Diameter (mm) |
|---|---|---|---|---|---|
| 160 | 47 | 0.67 | 1.28 | 6.25/15.88 | 0.5 |

Dynamic Light Scattering

Specifically, dynamic light scattering (DLS) measurements were performed on Viscotek 802 DLS instrument. In DLS, as the laser light hits small particles and/or organized water structures around the small particles (smaller than the wavelength), the light scatters in all directions, resulting in a time-dependent fluctuation in the scattering intensity. Intensity fluctuations are due to the Brownian motion of the scattering particles/water structure combination and contain information about the crystal size distribution.

The instrument was allowed to warm up for at least 30 min prior to the experiments. The measurements were made using 12 μl quartz cell. The following procedure was used:
7. First, 1 ml of DI water was added into the cell using 1 ml micropipette, then water was poured out of the cell to a waste beaker and the rest of the water was shaken off the cell measuring cavity. This step was repeated two more times to thoroughly rinse the cell.
8. 100 μl of the sample was added into the cell using 200 μl micropipette. After that all liquid was removed out of the cell with the same pipette using the same pipette tip and expelled into the waste beaker. 100 μl of the sample was added again using the same tip.
9. The cell with the sample was placed into a temperature controlled cell block of the Viscotek instrument with frosted side of the cell facing left. A new experiment in Viscotek OmniSIZE software was opened. The measurement was started 1 min after the temperature equilibrated and the laser power attenuated to the proper value. The results were saved after all runs were over.
10. The cell was taken out of the instrument and the sample was removed out of the cell using the same pipette and the tip used if step 2.
11. Steps 2 to 4 were repeated two more times for each sample.
12. For a new sample, a new pipette tip for 200 μl pipette was taken to avoid contamination with previous sample and steps 1 through 5 were repeated.

Data collection and processing was performed with OmniSIZE software, version 3.0.0.291. The following parameters were used for all the experiments: Run Duration—3 s; Experiments—100; Solvent—water, 0 mmol; Viscosity—1 cP; Refractive Index—1.333; Spike Tolerance—20%; Baseline Drift—15%; Target Attenuation—300 kCounts; block temperature—+40° C. After data for each experiment were saved, the results were viewed on "Results" page of the software. Particle size distribution (i.e., hydrodynamic radii) was analyzed in "Intensity distribution" graph. On that graph any peaks outside of 0.1 nm-10 μm range were regarded as artifacts. Particularly, clean water (no particles) results no peaks within 0.1 nm-10 μm range and a broad peak below 0.1 nm. This peak is taken as a noise peak (noise flow) of the instrument. Samples with very low concentration or very small size of suspended nanocrystals or nanoparticles may exhibit measurable noise peak in "Intensity distribution" graph. If the peaks within 0.1 nm-10 μm range have higher intensity than the noise peak, those peaks considered being real, otherwise the peaks are questionable and may represent artifacts of data processing.

It should be noted that the dynamic light scattering particle size information is different from the TEM measured histograms because dynamic light scattering uses algorithms that assume the nanocrystals are all spheres (which they are not) as well as measures the hydrodynamic radius (e.g., the nanocrystal's influence on the water is also detected and reported in addition to the actual physical radii of the particles). Accordingly, it is not surprising that there is a difference in the reported particle sizes between those reported in the TEM histogram data and those reported in the dynamic light scattering data, just as in the other Examples included herein.

Example 7

Manufacturing an Au—Pt Bi-Metallic Nanocrystal Suspension by a Batch Process Using NaHCO₃ as a Process Enhancer—ID#110810

This Example utilizes a batch process according to the present invention. FIG. 12a shows the apparatus used to condition the liquid 3. Once conditioned, the liquid 3' was processed in the apparatus shown in FIG. 12c or 12d, for platinum ions/particles and bi-metallic nanocrystals, respectively. The overall process of creating a bi-metallic nanocrystal suspension is described below and is summarized in Table 12.

Initially, platinum ions and/or particles were created in water by the following process. Approximately 4.0 grams/gallon (i.e., about 1.06 mg/mL) of processing enhancer baking soda (i.e., NaHCO₃) was added to about 1 gallon of de-ionized water. The amount of time that the water 3 with processing enhancer was exposed to the plasma 4 was about 30 minutes, prior to subsequent processing in the apparatus shown in FIG. 12c. Note that in Table 12 (and elsewhere herein) the reference to "GZA" is synonomous with creation of plasma 4.

The applied voltage for each plasma 4 created at electrode 1 was about 750 volts. This voltage was achieved by a transformer 60 (i.e., the Balanced Mid-Point Referenced Design) discussed elsewhere herein.

A second and different transformer was electrically connected to the electrodes 5a/5b shown in FIG. 12c. This transformer was a hy AC power source having a voltage range of 0-300V, a frequency range of about 47-400 Hz and a maximum power rating of about 1 kVA. The applied voltage was about 100 volts with a frequency of about 60 hertz for approximately a 2-hour operating time. The diameter of the platinum wire electrodes was about 1 mm.

Subsequently, the platinum species and water formulation (raw material) prepared above was mixed with about 6.29 mM $NaHCO_3$ at a ratio of about 3:1 to create a total volume of about 3785 mL. This liquid 3' was then processed via the apparatus shown in FIG. 12d with gold electrodes (99.99%, 0.5 mm) for about 90 minutes, with a hy AC power source having an applied voltage of about 200 volts and about 60 hertz. The hydrodynamic radius of the bi-metallic nanocrystals made was about 15.4 nm as measured by ViscoTek. The suspension contained about 5.6 ppm of Au and about 1.6 ppm of Pt as measured by the atomic absorption spectroscopy techniques discussed elsewhere herein.

Figure 19:
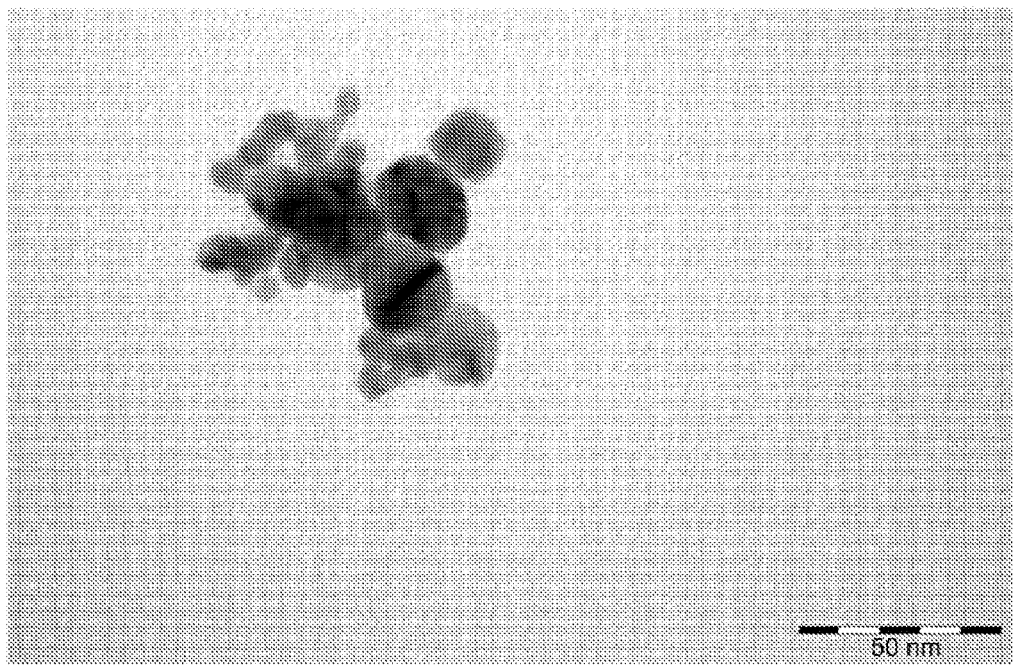
FIG. 19 shows a representative TEM photomicrograph of the dried constituents made according to Example 7.

FIG. 19 shows a representative TEM Photomicrograph of the bi-metallic nanocrystal suspension dried from formulation 101910-6, which was obtained by techniques equivalent to those disclosed elsewhere herein.

TABLE 12

| Component 1 | | | |
|---|---|---|---|
| Pretreatment - GZA | | | |
| Run ID | Volume (mL) | $NaHCO_3$ (grams) | time (hrs) |
| 102910 | 3785 | 4 | 0.5 |
| Pt ion treatment (Pt wires, 99.99%) | | | | | |
| Volume (mL) | Voltage (V) | Frequency (Hz) | Time (hrs) | Length of Wire (in/cm) | Wire Diameter (mm) |
| 3785 | 100 | 60 | 2 | 2.01/5.1 | 1 |
| Component 2 2 g $NaHCO_3$ (No GZA) | | | |
| Run ID | Volume (mL) | $NaHCO_3$ (grams) | time (hrs) |
| N/A | 3785 | 2.0 | N/A |
| Composite Mix | | | |
| Mixture of Component 1 & 2 | | | |
| Run ID | Comp. 1 Vol. (mL) | Comp. 2 Vol. (mL) | Volume (mL) |
| 110810 | 946 | 2839 | 3785 |
| Gold Nanoparticle Treatment (Au wires, 99.99%) | | | | | |
| Voltage (V) | Frequency (Hz) | Time (hrs) | Current (A) | Length of Wire (in/cm) | Wire Diameter (mm) |
| 200 | 60 | 1.5 | 1.07 | 6.25/15.88 | 0.5 |

Example 8

Manufacturing an Au—Pt Bi-Metallic Nanocrystal Suspension by a Batch Process Using KOH as a Process Enhancer—ID#122310A This Example utilizes a batch process according to the present invention. FIG. 12a shows the apparatus used to condition the liquid 3. Once conditioned, the liquid 3' was processed in the apparatus shown in FIG. 12c or 12d, for platinum ions/particles and bi-metallic nanocrystals, respectively. The overall process of creating a bi-metallic nanocrystal suspension is described below and is summarized in Table 13.

Initially, platinum ions and/or particles were created in water by the following process. Approximately 0.580 grams/gallon (i.e., about 0.153 mg/mL) of processing enhancer potassium hydroxide (i.e., KOH) was added to about 1 gallon of de-ionized water. The amount of time that the water 3 with processing enhancer was exposed to the plasma 4 was about 30 minutes, prior to subsequent processing in the apparatus shown in FIG. 12c.

The applied voltage for each plasma 4 created at electrode 1 was about 750 volts. This voltage was achieved by a transformer 60 (i.e., the Balanced Mid-Point Referenced Design) discussed elsewhere herein. Note that in Table 13 (and elsewhere herein) the reference to "GZA" is synonomous with creation of plasma 4.

A second and different transformer was electrically connected to the electrodes 5a/5b shown in FIG. 12c. This transformer was a hy AC power source having a voltage range of about 0-300V, a frequency range of about 47-400 Hz and a maximum power rating of about 1 kVA. The applied voltage was about 260 volts with a frequency of about 60 hertz for approximately a 2-hour operating time. The diameter of the platinum wire electrodes was about 1 mm. The length of the platinum wires was about 51 mm (2.01 inch/5.1 cm).

Subsequently, the platinum species and water formulation (raw material) prepared above was further processed as described below. The liquid 3' was then processed via the apparatus in FIG. 12d with gold electrodes (99.99%, about 0.5 mm diameter and about 6.25 inches (15.88 cm) total length for about 2 hours, with a hy AC power source having an applied voltage of about 180 volts and about 47 hertz. The hydrodynamic radius of the gold/platinum material made was about 12.5 nm as measured by ViscoTek. The suspension contained about 8.0 ppm of Au and about 1.8 ppm of Pt as measured by the atomic absorption spectroscopy techniques discussed elsewhere herein.

Figure 20:
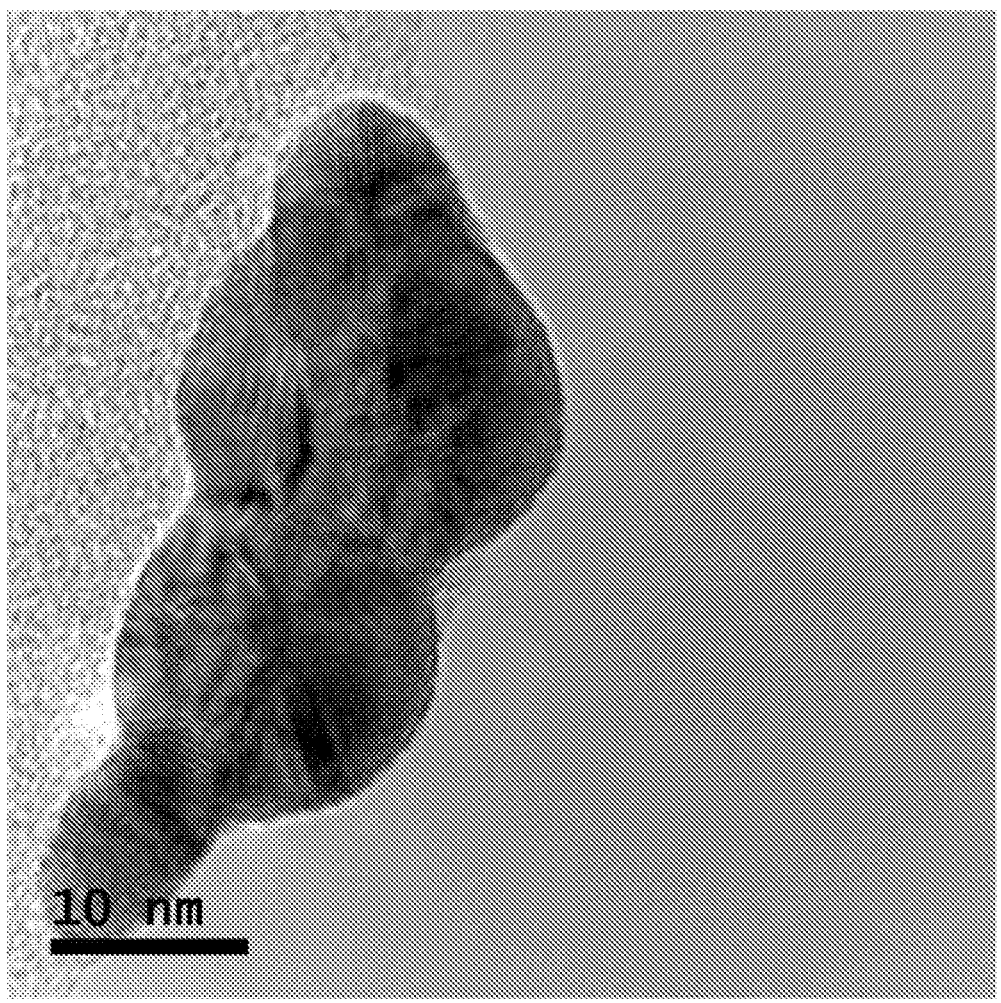
FIG. 20 shows a representative TEM photomicrograph of the dried constituents made according to Example 8.

FIG. 20 shows a representative TEM Photomicrograph of the bi-metallic nanocrystal suspension dried from formulation ID#122310A, made according to this Example 8.

TABLE 13

| Component 1 | | | |
|---|---|---|---|
| Pretreatment - GZA | | | |
| Run ID | Volume (mL) | KOH (grams) | time (hrs) |
| 122210-2 | 3785 | 0.580 | 0.5 |
| Pt ion treatment (Pt wires, 99.99%) | | | | | |
| Volume (mL) | Voltage (V) | Frequency (Hz) | Time (hrs) | Length of Wire (in/cm) | Wire Diameter (mm) |
| 3785 | 260 | 60 | 2 | 2.01/5.1 | 1 |

TABLE 13-continued

| | Component 2 N/A | | |
|---|---|---|---|
| Run ID | Volume (mL) | NaHCO$_3$ (grams) | time (hrs) |
| N/A | N/A | N/A | N/A |

| Composite Mix | | | |
|---|---|---|---|
| Mixture of Component 1 & 2 | | | |
| Run ID | Comp. 1 Vol. (mL) | Comp. 2 Vol. (mL) | Volume (mL) |
| 122310A | 3785 | 0 | 3785 |

| Gold Nanoparticle Treatment (Au wires, 99.99%) | | | | | |
|---|---|---|---|---|---|
| Voltage (V) | Frequency (Hz) | Time (hrs) | Current (A) | Length of Wire (in/cm) | Wire Diameter (mm) |
| 180 | 47 | 2.0 | 0.717 | 6.25/15.88 | 0.5 |

Example 9

Comparison of Bi-Metallic Nanocrystals Made by Two Different Techniques

This Example utilizes a batch process according to the present invention. FIG. 12a shows the apparatus used to condition the liquid 3. Once conditioned, the liquid 3' was processed in the apparatus shown in FIG. 12c or 12d, for platinum ions/nanocrystal and for gold nanocrystals, respectively. The overall process of creating the individual nanocrystal suspensions and thus mixing them together to form a bi-metallic nanoparticle suspension is described below and is summarized in Table 14.

Initially, platinum ions and/or particles were created in water by the following process. Approximately 4.0 grams/gallon (i.e., about 1.06 mg/mL) of processing enhancer baking soda (i.e., NaHCO$_3$) was added to about 1 gallon of de-ionized water. The amount of time that the water 3 with processing enhancer was exposed to the plasma 4 was about 30 minutes, prior to subsequent processing in the apparatus shown in FIG. 12c.

The applied voltage for each plasma 4 created at electrode 1 was about 750 volts. This voltage was achieved by a transformer 60 (i.e., the Balanced Mid-Point Referenced Design) discussed elsewhere herein.

A second and different transformer was electrically connected to the electrodes 5a/5b shown in FIG. 12c. This transformer was a hy AC power source having a voltage range of about 0-300V, a frequency range of about 47-400 Hz and a maximum power rating of about 1 kVA. The applied voltage was about 130 volts with a frequency of about 60 hertz for approximately a 30-minute operating time. The diameter of the platinum wire electrodes was about 1 mm. The length of the platinum wires was about 51 mm. The platinum species and water material was set aside.

A separate suspension of gold nanocrystals was prepared as follows. Approximately 1.0 gram/gallon (i.e., about 0.264 mg/mL) of processing enhancer baking soda (i.e., NaHCO$_3$) was added to about 1 gallon of de-ionized water. The amount of time that the water 3 with processing enhancer was exposed to the plasma 4 was about 30 minutes, prior to subsequent processing in the apparatus shown in FIG. 12c.

The applied voltage for each plasma 4 made by electrode 1 was about 750 volts. This voltage was achieved by a transformer 60 (i.e., the Balanced Mid-Point Referenced Design) discussed elsewhere herein.

Figure 12D:
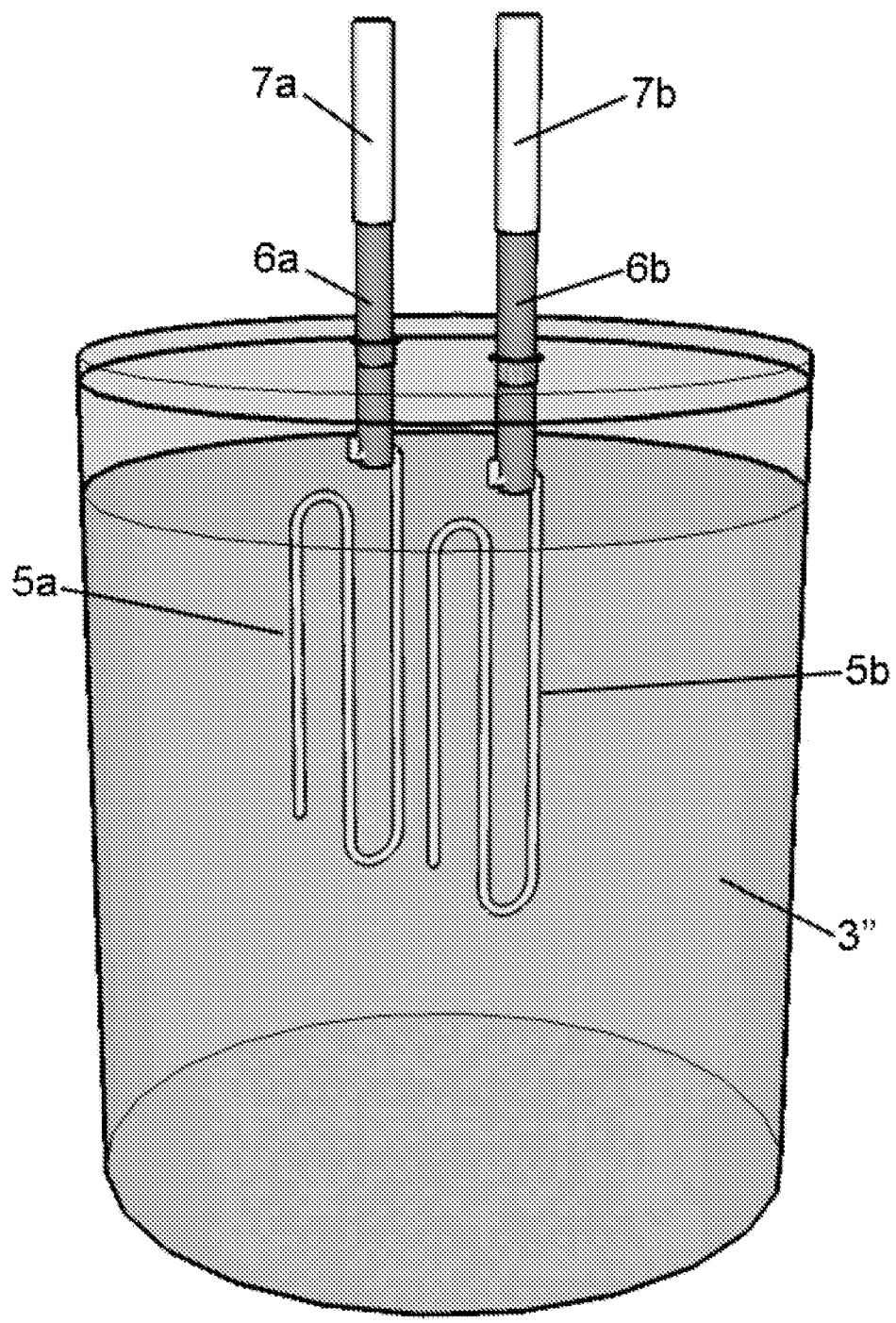
FIG. 12d shows a schematic of an apparatus used in a batch method utilizing wires 5a and 5b to form bi-metallic nanocrystals in suspension (e.g., colloid) in association with the apparatus shown in FIG. 12a, and as discussed in various examples herein.
Figure 12E:
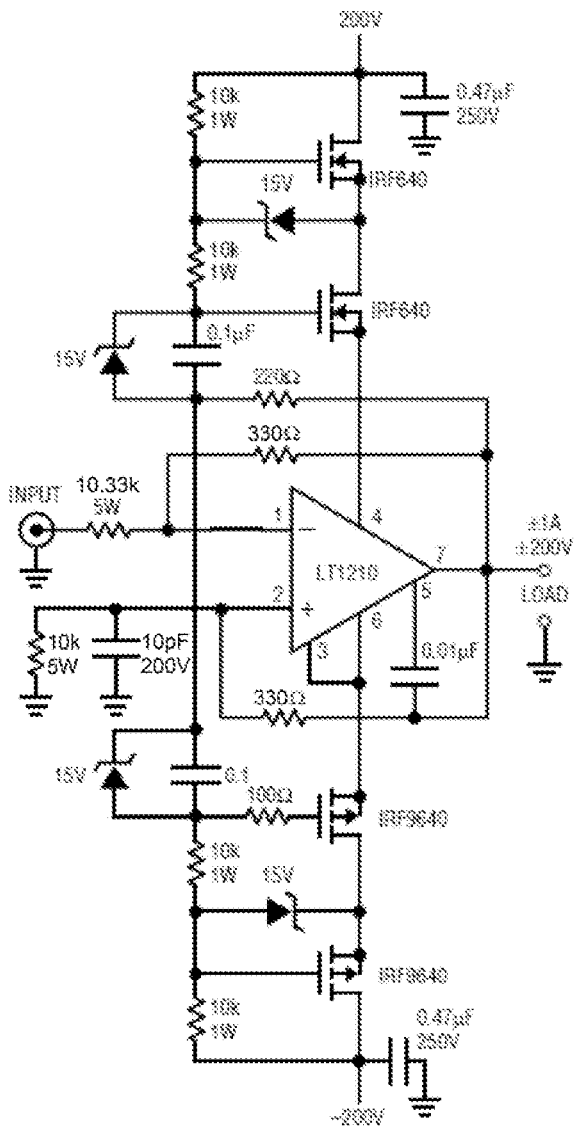
FIG. 12e shows a schematic view of the amplifier used in Examples 2 and 3.
Figure 12F:
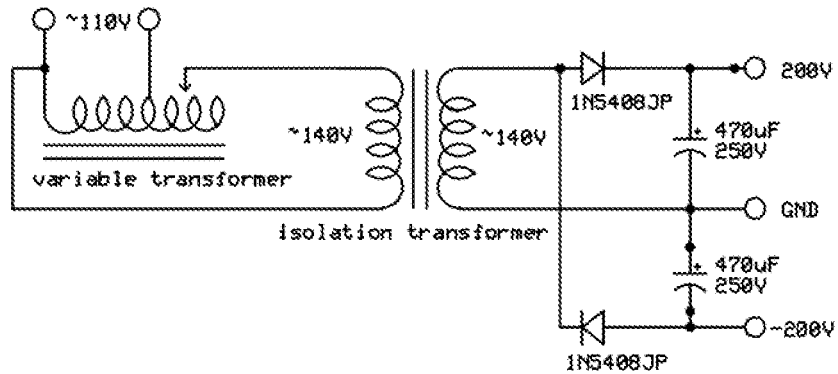
FIG. 12f shows a schematic view of the power supply used in Examples 2 and 3.
Figure 12G:
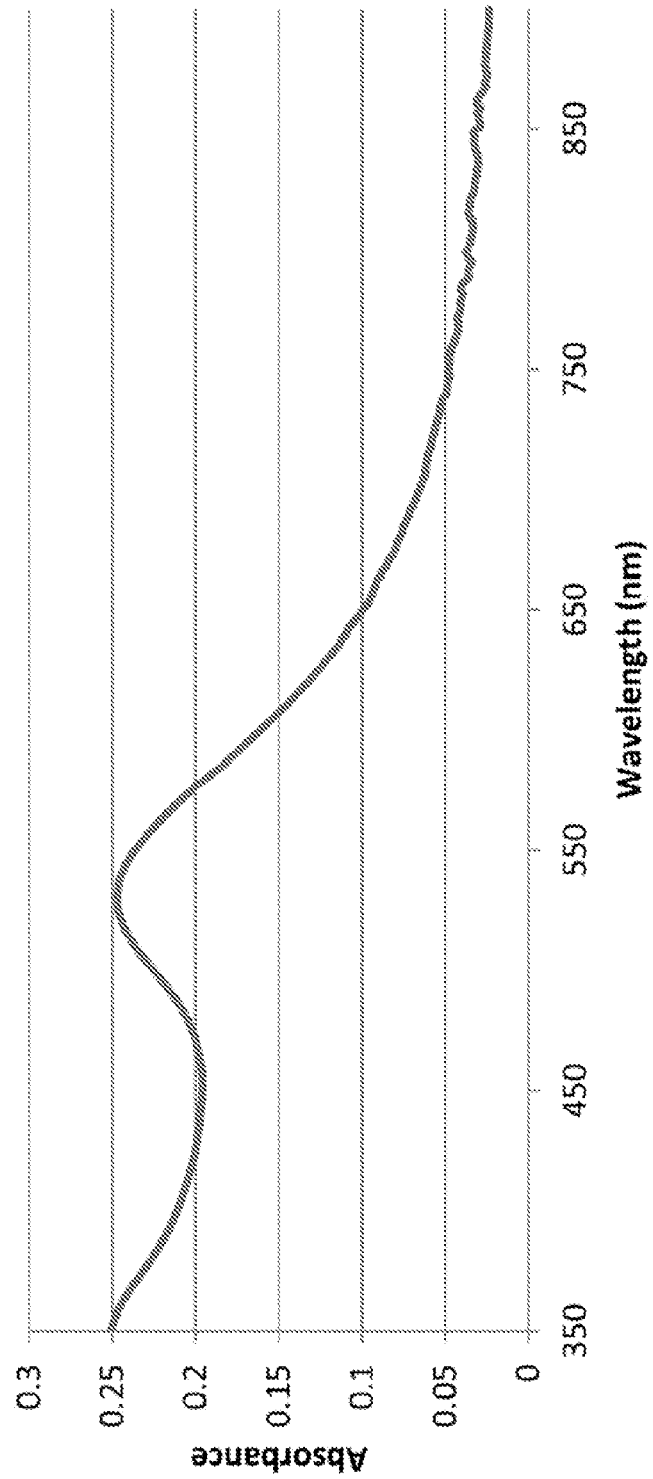
FIG. 12g shows the UV-Vis spectral pattern of the Au—Pt bi-metallic suspensions made according to Example 6.

A second and different transformer was electrically connected to the electrodes 5a/5b shown in FIG. 12d. This transformer was a hy AC power source having a voltage range of about 0-300V, a frequency range of about 47-400 Hz and a maximum power rating of about 1 kVA. The applied voltage was about 300 volts with a frequency of about 60 hertz for approximately a 30-minute operating time. The diameter of the gold wire electrodes was about 0.5 mm. The length of the gold wire was about 159 mm.

Subsequently, the separately prepared Pt and Au water-based materials Pt formulation and Au formulation prepared above were mixed together in the presence of a hydrogen peroxide catalyst (H$_2$O$_2$, Alfa Aesar Cat#L14000) and then studied. Specifically, about 300 mL of Pt formulation 062810 and about 700 mL of Au formulation 061610 were combined and approximately 2504 of H$_2$O$_2$ 0.8 v/v % was added. The measured hydrodynamic radius of the combined formulations was about 35 nm as measured by ViscoTek. The resulting suspension contained about 8.0 ppm of Au and about 1.8 ppm of Pt as measured by the atomic absorption spectroscopy techniques discussed elsewhere herein.

Figure 23A:
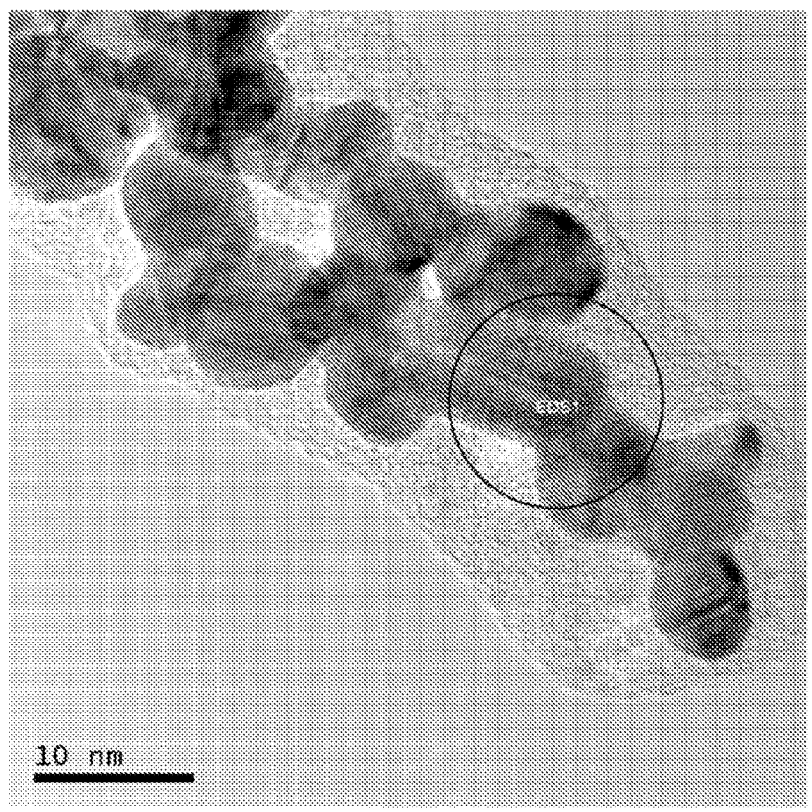
FIGS. 23a and 23b show representative TEM photomicrographs of dried constituents made according to Example 9.
Figure 23B:
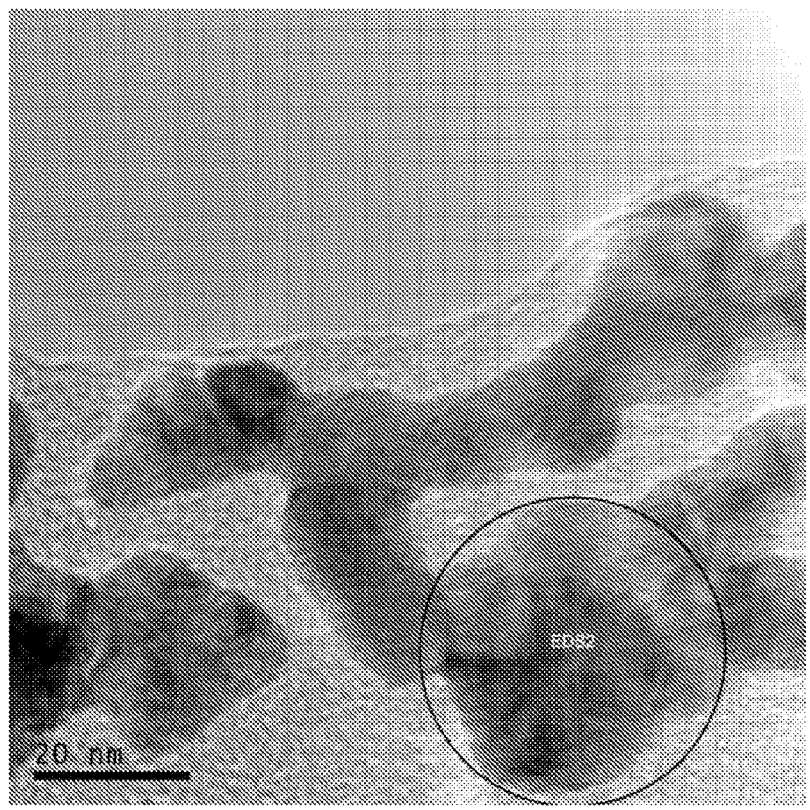

A comparison of this suspension to a previously discussed bi-metallic nanoparticle suspension was then performed. Specifically, high resolution analysis and energy dispersive x-ray analysis indicated that the resultant colloids or suspensions had little to no platinum physically present between the formed gold nanocrystals, as shown in representative FIGS. 23a-23b and in representative EDS FIGS. 24a-24b.

Figure 21A:
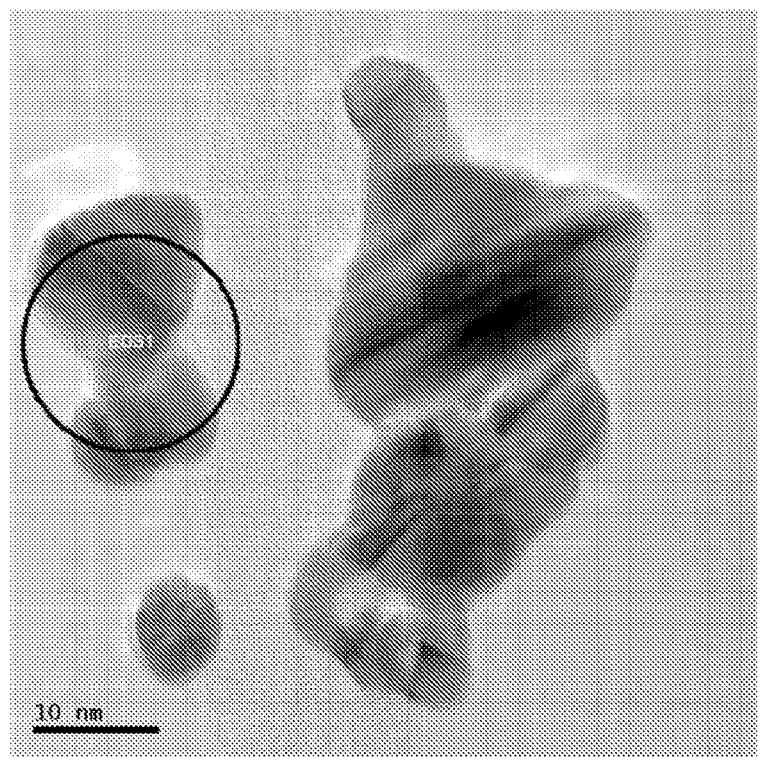
FIGS. 21a and 21b show representative TEM photomicrographs of dried constituents made according to Example 9.
Figure 21B:
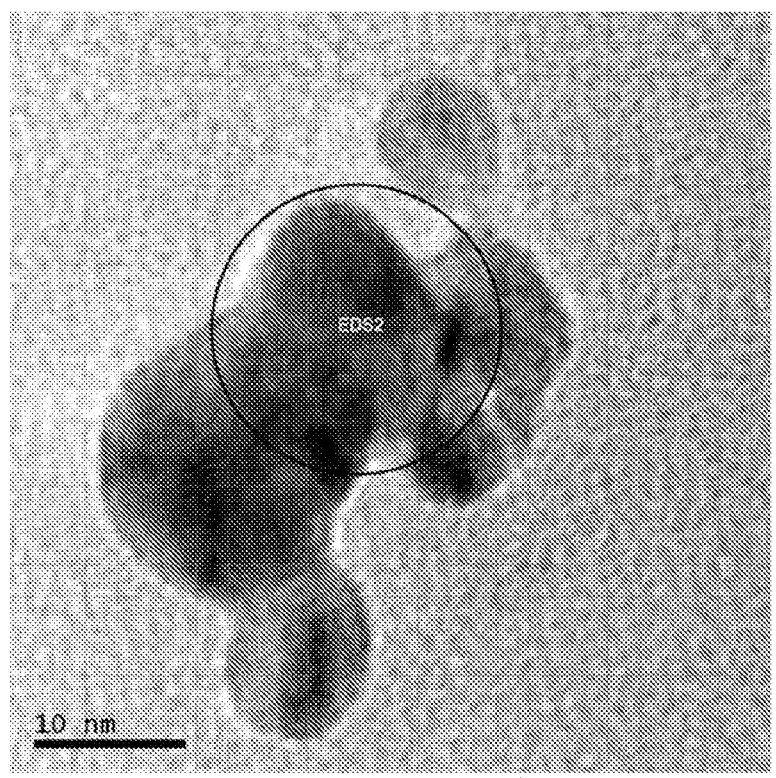

In contrast, sample 111710-9, made substantially identically to sample 112210-1 as described in Example 6, had identifiable platinum present on the formed bi-metallic nanocrystals. The measured hydrodynamic radius of the bi-metallic nanocrystals was about 14.7 nm as measured by ViscoTek. The suspension contained about 16.1 ppm of Au and about 2.1 ppm of Pt as measured by the atomic absorption spectroscopy techniques discussed elsewhere herein. Representative FIGS. 21a-21b illustrate the structures formed when prepared as described above. It is evident through energy dispersive analysis that platinum is present at detectable concentrations, as indicated by representative FIGS. 22a-22b.

High Resolution Transmission Electron Microscopy and EDS

TEM samples were prepared by utilizing a lacey Formvar/carbon-coated copper grid having a mesh size of 200. Approximately 1-3 µL of each inventive nanocrystal suspension, colloid and/or solution was placed onto each grid and was allowed to air dry at room temperature for about 20-30 minutes, or until the droplet evaporated. Upon complete evaporation, the grids were placed onto a holder plate until TEM analysis was performed.

A Philips CM300 FEG High Resolution Transmission Electron Microscope, equipped with an Oxford thin window light element detector and Emispec ES vision 4 processor, was used to interrogate all prepared samples. The instrument was run at an accelerating voltage of about 297 kV. After alignment of the electron beam, the prepared samples were examined at various magnifications up to and including 800,000×. Images were collected via the integrated CCD camera mounted at the back of the Gatan Image Filter (GIF) which is linked directly to a PC equipped with Digital Micrograph Software and Emispec ES Vision 4.0 software. Images were collected at a beam spot size of 2 corresponding to a beam width setting selected on the instrument and energy dispersive x-ray spectra were collected at a spot size of between 3-5, which allowed for the maximum amount of electrons to be collected. To increase the signal to noise ratio further, the Philips double-tilt holder was rotated 10 degrees towards the detector. Finally, the beam was condensed down to the area of interest and then the detector valve was opened and subsequent collection began.

TABLE 14

| Component 1 - Pt solution | | | |
|---|---|---|---|
| Pretreatment - Au GZA | | | |
| Run ID | Volume (mL) | NaHCO$_3$ (grams) | time (hrs) |
| 062810 | 3785 | 4.0 | 0.5 |
| Pt ion treatment (Pt wires, 99.99%) | | | | | |
| Volume (mL) | Voltage (V) | Frequency (Hz) | Time (hrs) | Length of Wire (in/cm) | Wire Diameter (mm) |
| 800 | 130 | 60 | 0.5 | 2.01/5.1 | 1 |
| Component 2 - Gold Solution | | | |
| Pretreatment - Au GZA | | | |
| Run ID | Volume (mL) | NaHCO$_3$ (grams) | time (hrs) |
| 061610 | 800 | 1.0 | 0.5 |
| Au Nanoparticle treatment (Au wires, 99.99%) | | | | | |
| Volume (mL) | Voltage (V) | Frequency (Hz) | Time (hrs) | Length of Wire (in/cm) | Wire Diameter (mm) |
| 800 | 300 | 60 | 0.5 | 6.25/15.88 | 0.5 |
| Mixture | | | | |
| Run ID | Comp. 1 Vol. (Pt) (mL) | Comp. 2 (Au) Vol. (mL) | H$_2$O$_2$ Concentration (v/v %) | H$_2$O$_2$ Vol (μl) |
| MT-55-04 | 300 | 700 | 0.800 | 250 |

Example 10

Manufacturing an Au—Pt Bi-Metallic Nanocrystalline Suspension by a Trough Process Using Potassium Hydroxide as a Processing Enhancer (PGT001)

In general, this Example utilized certain embodiments of the invention associated with the apparatuses generally shown in FIGS. 9, 10d and 11b. Electrical device 501AC, illustrated in FIG. 13, was used as the power supply for this example, while function generator 501FG was sometimes used to drive 501AC. This transformer was an AC power source (Chroma 61604) having an AC voltage range of 0-300V, a frequency range of 15-1000 Hz and a maximum power rating of 2 kVA. The precise electrical connections are described elsewhere herein. Control devices 20, as illustrated in FIGS. 8c and 8j were connected to the electrodes 1/5 and 5/5, respectively. However, due to the relatively short run times in each "Run ID," there was no need to actuate the control devices 20. Thus, the ends 9' of the electrodes 5a and 5b were juxtaposed with the bottom of the trough member 30b'.

The amount of potassium hydroxide (Fisher Scientific, Cat# P250-500) processing enhancer used in Run ID "PB-53" was about 0.604 grams/gallon (i.e., about 0.16 mg/mL.). The feed electrodes were platinum wires (1 mm/0.040"dia.), 99.99%, obtained from Hi-Rel Alloys LTD (Ontario, Canada.)

The applied voltage for each plasma 4 made by electrode 1 was about 750 volts. This voltage was achieved by a transformer 60 (i.e., the Balanced Mid-Point Referenced Design) discussed elsewhere herein.

The AC power source 501AC utilized a Chroma 61604 programmable unit. In particular, sine wave AC frequencies at 80 Hz were utilized to make suspensions of Pt ions and/or Pt colloids, in accordance with the teachings herein. The applied voltage was 215 volts with an applied current between about 4.0 amps and about 5.0 amps.

The resulting Pt-water-based material was then allowed to cool to approximately 50 degrees Celsius. At that point the Pt-water-based material was fed into another separate and different trough unit as described below.

In general, this additional trough which utilized certain embodiments of the invention associated with the apparatuses generally shown in FIGS. 9, 10c and 11a. Electrical device 501AC, illustrated in FIG. 13 was used as the power supply for examples contained herein, while function generator 501FG was sometimes used to drive 501AC. This transformer was an AC power source (Chroma 61604) having an AC voltage range of 0-300V, a frequency range of 15-1000 Hz and a maximum power rating of 2 kVA. Electrical connectivity discussions can be found elsewhere herein. Control devices 20, illustrated in FIGS. 8c and 8j were connected to the electrodes 1/5 and 5/5, respectively, and electrodes 5/5 were actuated at a rate of about 1" per 8 hours. The eight electrode sets 1/5 and 5/5 were all connected to control devices 20 and 20i which automatically adjusted the height of, for example, each electrode 5/5 in each electrode set 5/5; had 2 female receiver tubes o5a/o5a'-o5g/o5g' which were connected to a bottom portion of the trough member 30b' such that the electrodes in each electrode set 5/5 could be removably inserted into each female receiver tube o5 when, and if, desired.

In particular, a sine wave AC frequency at 60 Hz was utilized to form the bi-metallic nanocrystalline suspension in accordance with the teachings herein. The platinum-water based material "PB-53," as discussed above, was fed as a raw material via pump 40 into plasma trough section 30a' as illustrated in FIG. 10c. The AC power source 501AC utilized a Chroma 61604 programmable AC source. The applied voltage was about 260 volts for approximately two minutes followed by about 220 volts for the duration of the run. The applied current varied between about 4 amps and about 5 amps.

Transmission electron microscopy (TEM) was used to examine the bi-metallic nanocrystals made according to this Example. In particular, TEM sample preparation was identical to the methods described earlier in the High Resolution TEM & EDS Section. The TEM micrographs show that the formed bi-metallic nanocrystals exist in some instances in a chain-like form of gold nanocrystals with platinum interconnects as evident in FIGS. 25a and 25b dried from suspension GPB-0001, made according to this Example.

The total amount of platinum species and gold species contained within this bi-metallic nanocrystalline suspension was about 1.6 ppm and 7.7 ppm, respectively, as measured by the atomic absorption spectroscopy techniques discussed elsewhere herein.

Table 15 summarizes key processing parameters used in conjunction with FIGS. 9 and 10*b*. Table 15 also discloses: 1) resultant "ppm" (i.e., atomic platinum and gold concentrations.)

TABLE 15

| | | Run ID: | |
|---|---|---|---|
| | | PB-53 | GPB-001/ PGT-001 |
| Feed: PE/Concentration (mg/ml) | | KOH/0.00156 | PB-53 |
| Input Temp ° C. at 32 | | 23 | 45 |
| Output Temp ° C. at 32 | | 71 | 79 |
| Flow Rate: | In (ml/min) | 215 | 230 |
| | Out (ml/min) | 180 | 200 |
| Volts: | Set #1 | 750 | 750 |
| | Set #'s 2-8 | 215 | 260: 0-2 min/220 |
| | Set #'s 2-8 frequency, Hz | 80 | 60 |
| | Wire Diameter (mm) | 1.0 | 1.0 |
| | Contact "$W_L$" (in/mm) | 1/25 | 1/25 |
| | Electrode Separation "y" (in/mm) | .25/6.4 | .25/6.4 |
| | Electrode Config. FIG. | 8b | 8b |
| | Produced Pt/Au PPM | 1.6/NA | 1.6/7.7 |
| Dimensions | Plasma 4 FIGS. | 9 | 9 |
| | Process FIGS. | 10a, 10d | 10c, 11a |
| | M (in/mm) | 1.5/38 | 1.5/38 |
| | LT (in/mm) | 36/914 | 36/914 |
| | d (in/mm) | 1/25 | 1/25 |
| | S (in/mm) | 1.5/38 | 1.5/38 |
| | Electrode Curr. (A) | 0.63 | 0.69 |
| | Total Curr. Draw (A) | 4.40 | 4.40 |
| | "c-c" (mm) | 76 | 76 |
| Set 1 | electrode # | 1a | 1a |
| | "x" (in/mm) | 0.25/6.4 | 0.25/64 |
| | electrode # | 5a | 5a |
| | "c-c" (mm) | 102 | 102 |
| Set 2 | electrode # | 5b | 5b |
| | "x" (in/mm) | n/a | n/a |
| | electrode # | 5b' | 5b' |
| | "c-c" (mm) | 76 | 76 |
| Set 3 | electrode # | 5c | 5c |
| | electrode # | 5c' | 5c' |
| | "c-c" (mm) | 76 | 76 |
| Set 4 | electrode # | 5d | 5d |
| | electrode # | 5d' | 5d' |
| | "c-c" (mm) | 127 | 127 |
| Set 5 | electrode # | 5e | 5e |
| | electrode # | 5e' | 5e' |
| | "c-c" (mm) | 127 | 127 |
| Set 6 | electrode # | 5f | 5f |
| | electrode # | 5f' | 5f' |
| | "c-c" (mm) | 152 | 152 |
| Set 7 | electrode # | 5g | 5g |
| | electrode # | 5g' | 5g' |
| | "c-c" (mm) | 178 | 178 |
| Set 8 | electrode # | 5h | 5h |
| | electrode # | 5h' | 5h' |
| | "c-c" (mm) | 76 | 76 |

Example 11

Manufacturing an Au—Pt Bi-Metallic Nanocrystalline Suspension by a Batch Process Using KOH as a Process Enhancer (PGB002)

This Example utilized a batch process according to the present invention. FIG. 12*a* shows the apparatus used to condition the liquid 3. Once conditioned, the liquid 3' was processed in the apparatus shown in FIG. 12*c* or 12*d*, for platinum ions/particles and bi-metallic nanocrystals, respectively. The overall process created a bi-metallic nanocrystal suspension, as described below and summarized in Table 16.

Initially, platinum ions and/or particles were prepared by the following process. Approximately 0.580 grams/gallon (i.e., about 0.153 mg/mL) of processing enhancer potassium hydroxide (i.e., KOH) was added to 1 gallon of de-ionized water. The amount of time that the water 3 with processing enhancer was exposed to the plasma 4 was about 30 minutes, prior to subsequent processing in the apparatus shown in FIG. 24*c*.

The applied voltage for the plasma 4 made by the electrode 1 was about 750 volts. This voltage was achieved by a transformer 60 (i.e., the Balanced Mid-Point Referenced Design) discussed elsewhere herein. Note that in Table 16 (and elsewhere herein) the reference to "GZA" is synonymous with creation of plasma 4.

A second and different transformer was electrically connected to the electrodes 5*a*/5*b* shown in FIG. 12*c*. This transformer was an hy AC power source having a voltage range of 0-300V, a frequency range of 47-400 Hz and a maximum power rating of 1 kVA. The applied voltage was about 100 volts with a frequency of 60 hertz for about 3 hours of operation. The diameter of the platinum wire electrodes was about 1 mm.

Subsequently, the platinum species and water material prepared above was further processed as described below. The platinum species and water material was then processed via the apparatus in FIG. 12*d* with gold electrodes (99.99%, 0.5 mm) for about 3 hours, with an hy AC power source having an applied voltage of about 180 volts and about 47 hertz. The average radius of the bi-metallic nanocrystals produced was about 14.6 nm as measured by ViscoTek. The suspension contained about 7.3 ppm of Au and about 1.2 ppm of Pt, as measured by the atomic absorption spectroscopy techniques discussed elsewhere herein.

FIGS. 26*a* and 26*b* show representative TEM Photomicrographs and energy-dispersive x-ray spectra of the formed bi-metallic nanocrystals, respectively, dried from suspension ID# PGB002, made according to this Example 11.

TABLE 16

| Component 1 | | | |
|---|---|---|---|
| Pretreatment - GZA | | | |
| Run ID | Volume (mL) | KOH (grams) | time (hrs) |
| Pt011011 | 3785 | 0.580 | 0.5 |
| Pt ion treatment (Pt wires, 99.99%) | | | | | |
| Volume (mL) | Voltage (V) | Frequency (Hz) | Time (hrs) | Length of Wire (in/cm) | Wire Diameter (mm) |
| 3785 | 100 | 60 | 3 | 2.01/5.1 | 1 |
| Component 2 | | | |
| N/A | | | |
| Run ID | Volume (mL) | NaHCO$_3$ (grams) | time (hrs) |
| N/A | N/A | N/A | N/A |
| Composite Mix | | | |
| Mixture of Component 1 & 2 | | | |
| Run ID | Comp. 1 Vol. (mL) | Comp. 2 Vol. (mL) | Volume (mL) |
| Pt011011 | 3785 | 0 | 3785 |
| Gold Nanoparticle Treatment (Au wires, 99.99%) | | | | | |
| Voltage (V) | Frequency (Hz) | Time (hrs) | Current (A) | Length of Wire (in/cm) | Wire Diameter (mm) |
| 180 | 47 | 3.0 | N/A | 6.25/15.88 | 0.5 |

Example 12

Manufacturing Platinum-Based Nanocrystals/Nanocrystal Suspensions Utilizing a Continuous Trough Process (PB56001)

In general, this Example utilized certain embodiments of the invention associated with the apparatuses generally shown in FIGS. 9, 10d and 11b. Electrical device 501AC, illustrated in FIG. 13, was used as the power supply for this Example, while function generator 501FG was sometimes used to drive 501AC. This transformer was an AC power source (Chroma 61604) having an AC voltage range of 0-300V, a frequency range of 15-1000 Hz and a maximum power rating of 2 kVA. Electrical connectivity discussions can be found in the detailed description of the preferred embodiments. Control devices 20, illustrated in FIGS. 8c and 8j, were connected to the electrodes 1/5 and 5/5, respectively. However, due to the short run times in each "Run ID," there was no need to actuate the control devices 20. Accordingly, in reference to FIGS. 3c and 9c, the ends 9' of the electrodes 5a and 5b were juxtaposed with the bottom of the trough member 30b'. This example utilized about 3.5 g/gallon (i.e., about 0.925 mg/mL) of NaHCO$_3$ as a processing enhancer and a flow rate of about 150 ml/min.

In particular, sine wave AC frequencies at 5 Hz were utilized to make Pt species in water in accordance with the teachings herein. The function generator 501FG provided sine waves at frequencies less than 15 Hz to power supply 501AC, Chroma 61604 programmable AC source, which subsequently amplified the input signal to about 150V. The applied current varied between about 5.0 amps to about 6.5 amps.

The amount of platinum species produced in the water was about 15.9 ppm, as measured by the atomic absorption spectroscopy techniques discussed elsewhere herein.

Table 17 summarizes key processing parameters used in conjunction with FIGS. 9 and 10d. Table 17 also discloses resultant "ppm" (i.e., atomic platinum nanocrystal concentrations.)

TABLE 17

| | | Run ID: PB56001 |
|---|---|---|
| Flow Rate: | In (ml/min) | 150 |
| | Out (ml/min) | 140 |
| Volts: | Set # 1 | 750 |
| | Set #'s 2-8 | 150 |
| | Set #'s 2-8 frequency, Hz | 5 |
| | PE: NaHCO3 (mg/ml) | 0.92 |
| | Wire Diameter (mm) | 1.0 |
| | Contact "W$_L$" (in/mm) | 1/25 |
| | Electrode Separation "y" (in/mm) | .25/6.4 |
| | Electrode Config. Figure | 8b |
| | Produced Pt PPM | 15.9 |
| | Output Temp ° C. at 32 | 79 |
| Dimensions | Plasma 4 Figs. | 9 |
| | Process Figures | 10a, 10d |
| | M (in/mm) | 1.5/38 |
| | LT (in/mm) | 36/914 |
| | d (in/mm) | 1/25 |
| | S (in/mm) | 1.5/38 |
| | Electrode Curr. (A) | 0.92 |
| | Total Curr. Draw (A) | 5.75 |
| | "c-c" (mm) | 76 |
| Set 1 | electrode # | 1a |
| | "x" (in/mm) | 0.25/6.4 |
| | electrode # | 5a |
| | "c-c" (mm) | 102 |

TABLE 17-continued

| | | Run ID: PB56001 |
|---|---|---|
| Set 2 | electrode # | 5b |
| | "x" (in/mm) | n/a |
| | electrode # | 5b' |
| | "c-c" (mm) | 76 |
| Set 3 | electrode # | 5c |
| | electrode # | 5c' |
| | "c-c" (mm) | 76 |
| Set 4 | electrode # | 5d |
| | electrode # | 5d' |
| | "c-c" (mm) | 127 |
| Set 5 | electrode # | 5e |
| | electrode # | 5e' |
| | "c-c" (mm) | 127 |
| Set 6 | electrode # | 5f |
| | electrode # | 5f' |
| | "c-c" (mm) | 152 |
| Set 7 | electrode # | 5g |
| | electrode # | 5g' |
| | "c-c" (mm) | 178 |
| Set 8 | electrode # | 5h |
| | electrode # | 5h' |
| | "c-c" (mm) | 76 |

Example 13

Manufacturing Platinum-Based Nanocrystals/Nanocrystal Suspensions Utilizing a Continuous Trough Process Setup (PB57001)

In general, this Example utilized certain embodiments of the invention associated with the apparatuses generally shown in FIGS. 9, 10d and 11b. Electrical device 501AC, illustrated in FIG. 13, was used as the power supply for this Example, while function generator 501FG was sometimes used to drive 501AC. This transformer was an AC power source (Chroma 61604) having an AC voltage range of 0-300V, a frequency range of 15-1000 Hz and a maximum power rating of 2 kVA. Electrical connectivity discussions can be found in the detailed description of the preferred embodiments. Control devices 20, illustrated in FIGS. 8c and 8j were connected to the electrodes 1/5 and 5/5, respectively. However, due to the short run times in each "Run ID," there was no need to actuate the control devices 20. Accordingly, the ends 9' of the electrodes 5a and 5b were juxtaposed with the bottom of the trough member 30b'. This example utilized about 2.5 g/gallon (i.e, about 0.661 mg/mL) of NaHCO$_3$ as a processing enhancer and a flow rate of about 220 ml/min.

In particular, sine wave AC frequencies at 5 Hz were utilized to make Pt species in water in accordance with the teachings herein. The function generator 501FG provided sine waves at frequencies less than 15 Hz to power supply 501AC, Chroma 61604 programmable AC source, which subsequently amplified the input signal to about 175V. The applied current varied between about 4.0 amps to about 6.5 amps.

The amount of platinum species produced in the water suspensions was about 7.8 ppm, as measured by the atomic absorption spectroscopy techniques discussed elsewhere herein.

Table 18 summarizes key processing parameters used in conjunction with FIGS. 9 and 10d. Table 18 also discloses resultant "ppm" (i.e., atomic platinum nanocrystal concentrations.)

TABLE 18

| | | Run ID: PB57001 |
|---|---|---|
| Flow Rate: | In (ml/min) | 220 |
| | Out (ml/min) | 200 |
| Volts: | Set # 1 | 750 |
| | Set #'s 2-8 | 175 |
| | Set #'s 2-8 frequency, Hz | 5 |
| PE: NaHCO3 (mg/ml) | | 0.66 |
| Wire Diameter (mm) | | 1.0 |
| Contact "$W_L$" (in/mm) | | 1/25 |
| Electrode Separation "y" (in/mm) | | .25/6.4 |
| Electrode Config. Figure | | 8b |
| Produced Pt PPM | | 7.8 |
| Output Temp ° C. at 32 Dimensions | Plasma 4 Figs. | 61 9 |
| | Process Figures | 10a, 10d |
| | M (in/mm) | 1.5/38 |
| | LT (in/mm) | 36/914 |
| | d (in/mm) | 1/25 |
| | S (in/mm) | 1.5/38 |
| Electrode Curr. (A) | | 0.61 |
| Total Curr. Draw (A) | | 4.58 |
| | "c-c" (mm) | 76 |
| Set 1 | electrode # | 1a |
| | "x" (in/mm) | 0.25/6.4 |
| | electrode # | 5a |
| | "c-c" (mm) | 102 |
| Set 2 | electrode # | 5b |
| | "x" (in/mm) | n/a |
| | electrode # | 5b' |
| | "c-c" (mm) | 76 |
| Set 3 | electrode # | 5c |
| | electrode # | 5c' |
| | "c-c" (mm) | 76 |
| Set 4 | electrode # | 5d |
| | electrode # | 5d' |
| | "c-c" (mm) | 127 |
| Set 5 | electrode # | 5e |
| | electrode # | 5e' |
| | "c-c" (mm) | 127 |
| Set 6 | electrode # | 5f |
| | electrode # | 5f' |
| | "c-c" (mm) | 152 |
| Set 7 | electrode # | 5g |
| | electrode # | 5g' |
| | "c-c" (mm) | 178 |
| Set 8 | electrode # | 5h |
| | electrode # | 5h' |
| | "c-c" (mm) | 76 |

Example 14

Manufacturing an Au—Pt Bi-Metallic Nanocrystal Suspension by Using a Continuous Trough Process Using Potassium Hydroxide and Sodium Bicarbonate as the Processing Enhancer (GPB-032)

In general, this Example utilized certain embodiments of the invention associated with the apparatuses generally shown in FIGS. 9, 10c and 11a. Electrical device 501AC, illustrated in FIG. 13, was used as the power supply for the examples contained herein, while function generator 501FG was sometimes used to drive 501AC. This transformer was an AC power source (Chroma 61604) having an AC voltage range of 0-300V, a frequency range of 15-1000 Hz and a maximum power rating of 2 kVA. Electrical connectivity discussions can be found in the detailed description of the preferred embodiments section. Control devices 20, illustrated in FIGS. 8c and 8j, were connected to the electrodes 1/5 and 5/5, respectively, and electrodes 5/5 were actuated at a rate of about 1" per 8 hours. The eight electrode sets 1/5 and 5/5 were all connected to control devices 20 and 20i which automatically adjusted the height of, for example, each electrode or 5/5 in each electrode set 5/5; had 2 female receiver tubes o5a/o5a'-o5g/o5g' which were connected to a bottom portion of the trough member 30b' such that the electrodes in each electrode set 5/5 could be removably inserted into each female receiver tube o5 when, and if, desired.

The amount of potassium hydroxide (Fisher Scientific, Cat# P250-500) processing enhancer used in Run ID "PB-106-2" was about 0.450 grams/gallon (i.e., about 0.119 mg/mL). In addition, the amount of sodium bicarbonate (Fisher Scientific, Cat# S631-3) used in Run ID "PB-106-2" was about 0.850 grams/gallon (i.e., about 0.22 mg/mL). The feed electrodes were platinum wires (1 mm/0.040" dia.), 99.99%, obtained from Hi-Rel Alloys LTD (Ontario, Canada.)

The applied voltage for each plasma 4 made by electrode 1 was about 750 volts. This voltage was achieved by a transformer 60 (i.e., the Balanced Mid-Point Referenced Design) discussed elsewhere herein.

The AC power source 501AC utilized a Chroma 61604 programmable unit. In particular, sine wave AC frequencies at 80 Hz were utilized to make at least one platinum species in water in accordance with the teachings herein. The applied voltage was about 215 volts with an applied current between about 4.0 amps and about 7.0 amps.

The resulting platinum species in water material was then allowed to cool overnight to approximately 23 degrees Celsius. At that point the Pt-water-based material was fed into a second separate and different trough unit as described below.

In general, this second trough utilized certain embodiments of the invention associated with the apparatuses generally shown in FIGS. 9, 10c and 11a. Electrical device 501AC, illustrated in FIG. 13, was used as the power supply for examples contained herein, while function generator 501FG was sometimes used to drive 501AC. This transformer was an AC power source (Chroma 61604) having an AC voltage range of 0-300V, a frequency range of 15-1000 Hz and a maximum power rating of 2 kVA. Electrical connectivity discussions can be found in the detailed description of the preferred embodiments section. Control devices 20, illustrated in FIGS. 8c and 8j, were connected to the electrodes 1/5 and 5/5, respectively, and electrodes 5/5 were actuated at a rate of about 1" per 8 hours. The eight electrode sets 1/5 and 5/5 were all connected to control devices 20 and 20i which automatically adjusted the height of, for example, each electrode 5/5 in each electrode set 5/5 had 2 female receiver tubes o5a/o5a'-o5g/o5g' which were connected to a bottom portion of the trough member 30b' such that the electrodes in each electrode set 5/5 could be removably inserted into each female receiver tube o5 when, and if, desired.

In particular, a sine wave AC frequency at 60 Hz was utilized to make a gold nanocrystal suspension or colloid or ion, in accordance with the teachings herein. The platinum-water based material "PB-106-2," as discussed above, was fed via pump 40 into plasma trough section 30a' as illustrated in FIG. 10c. The AC power source 501AC utilized a Chroma 61604 programmable AC source. The applied voltage was about 260 volts for approximately two minutes followed by about 220 volts for the duration of the run. The applied current varied between about 4 amps and about 7 amps.

The total amount of platinum and gold contained within the bi-metallic nanocrystal suspension this material was about 3.0 ppm and 9.2 ppm, respectively, as measured by the atomic absorption spectroscopy techniques discussed elsewhere herein.

Table 19 summarizes key processing parameters used in conjunction with FIGS. 9 and 10*b*. Table 19 also discloses: 1) resultant "ppm" (i.e., atomic platinum and gold concentrations.)

TABLE 19

|  |  | Run ID | |
| --- | --- | --- | --- |
|  |  | PB-106-2 | GPB-032 |
| Process | NaHCOO$_3$ (mg/mL) | 0.225 | PB-106-2 |
| Enhancer | KOH (mg/mL) | 0.119 |  |
|  | Input Temp ° C. at 32 | 24 | 24 |
|  | Output Temp ° C. at 32 | 86 | 84 |
| Flow Rate | In (ml/min) | 190 | 200 |
|  | Out (ml/min) | 175 | 180 |
| Volts: | Set # 1 | 750 | 750 |
|  | Set #'s 2-8 | 215 | 260: 0-2 min/220 |
|  | Set #'s 2-8 frequency, Hz | 80 | 60 |
|  | Wire Diameter (mm) | 1.0 | 1.0 |
|  | Contact "W$_L$" (in/mm) | 1/25 | 1/25 |
|  | Electrode Separation "y" (in/mm) | .25/6.4 | .25/6.4 |
|  | Electrode Config. Figure | 8b | 8b |
|  | Produced Au/Pt PPM | NA/3.0 | 9.2/3.0 |
|  | Hydrodynamic Radius (nm) | N/A | 15.39 |
|  | Zeta Potential (mV) | N/A | −53.0 |
| Dimensions | Plasma 4 Figs. | 9 | 9 |
|  | Process Figures | 10c, 11a | 10c, 11a |
|  | M (in/mm) | 1.5/38 | 1.5/38 |
|  | LT (in/mm) | 36/914 | 36/914 |
|  | d (in/mm) | 1/25 | 1/25 |
|  | S (in/mm) | 1.5/38 | 1.5/38 |
|  | Total Curr. Draw (A) | 6.34 | 6.53 |
|  | "c-c" (mm) | 76 | 76 |
| Set 1 | electrode # | 1a | 1a |
|  | "x" (in/mm) | 0.25/6.4 | 0.25/6.4 |
|  | electrode # | 5a | 5a |
|  | "c-c" (mm) | 102 | 102 |
| Set 2 | Electrode Pair # | 5b & 5b' | 5b & 5b' |
|  | "c-c" (mm) | 76 | 76 |
| Set 3 | Electrode Pair # | 5c & 5c' | 5c & 5c' |
|  | "c-c" (mm) | 76 | 76 |
| Set 4 | Electrode Pair # | 5d & 5d' | 5d & 5d' |
|  | "c-c"(mm) | 127 | 127 |
| Set 5 | Electrode Pair # | 5e & 5e' | 5e & 5e' |
|  | "c-c" (mm) | 127 | 127 |
| Set 6 | Electrode Pair # | 5f & 5f' | 5f & 5f' |
|  | "c-c" (mm) | 152 | 152 |
| Set 7 | Electrode Pair # | 5g & 5g' | 5g & 5g' |
|  | "c-c" (mm) | 178 | 178 |
| Set 8 | Electrode Pair # | 5h & 5h' | 5h & 5h' |
|  | "c-c" (mm) | 76 | 76 |

Figure 27:
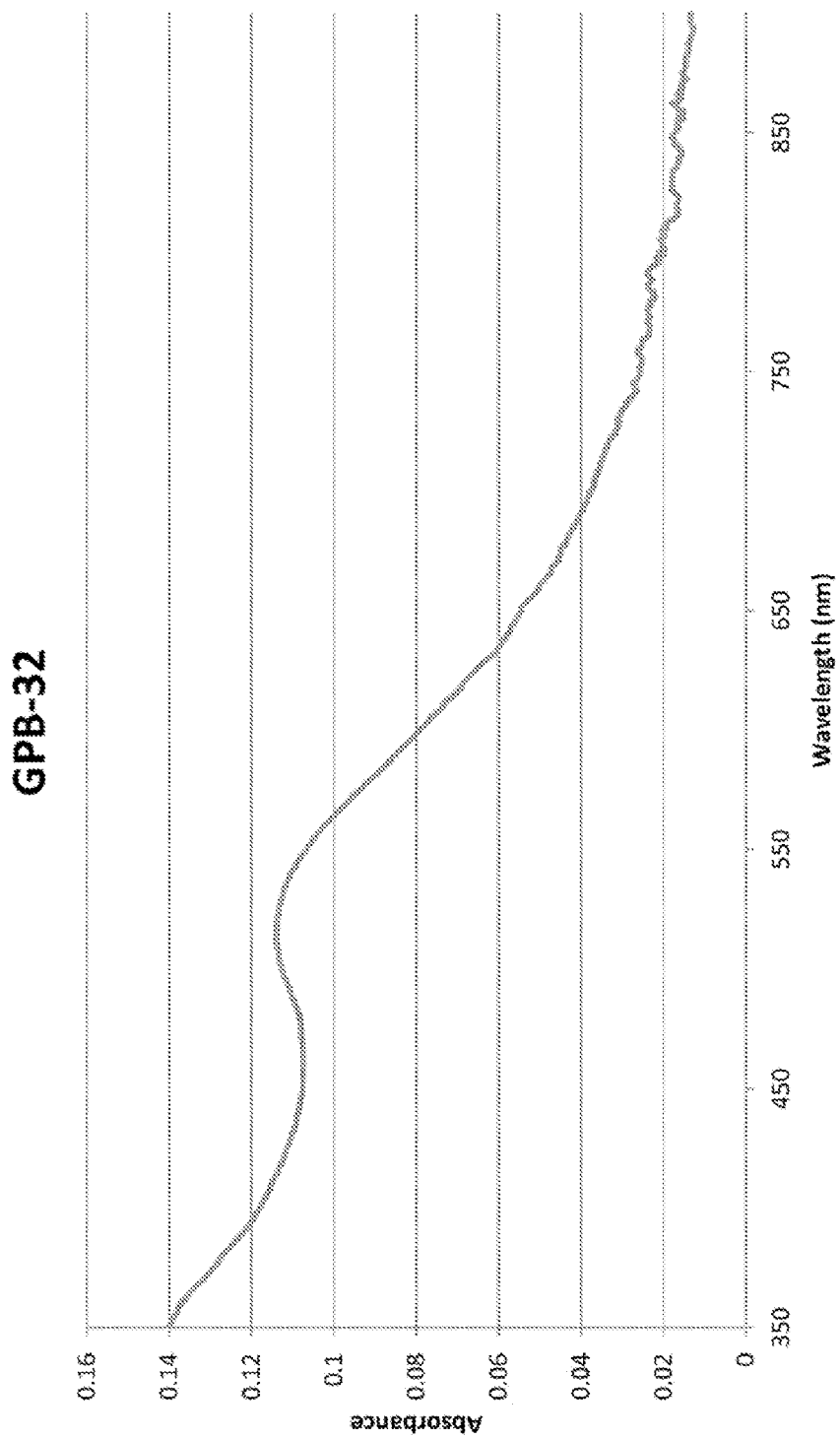
FIG. 27 shows a UV-Vis spectrograph of GPB-032.

In this Example, a Zeta-Sizer "Nano-ZS" produced by Malvern Instruments was utilized to determine zeta potential (the specifics of which are described earlier herein). For each measurement a 1 ml sample was filled into clear disposable zeta cell DTS1060C. Dispersion Technology Software, version 5.10 was used to run the Zeta-Sizer and to calculate the zeta potential. The following settings were used: dispersant—water, temperature—25° C., viscosity—0.8872 cP, refraction index—1.330, dielectric constant—78.5, approximation model—Smoluchowski. Three replications of 60 runs per individual replicate were performed for each sample. Energy absorption spectra was obtained for this sample (GPB-032) using Uv-Vis spectroscopy methods as outlined elsewhere herein. FIG. 27 contains the UV-Vis data collected for this sample (GPB-032), specifically displaying the 350-900 nm range.

Example 15

Manufacturing an Au—Pt Bi-Metallic Nanocrystal Suspension by Using a Continuous Trough Process Using Sodium Bicarbonate as a Processing Enhancer (GPB-010)

In general, this example utilized certain embodiments of the invention associated with the apparatuses generally shown in FIGS. 9, 10*c* and 11*a*. Electrical device 501AC, illustrated in FIG. 13, was used as the power supply for examples contained herein, while function generator 501FG was sometimes used to drive 501AC. This transformer was an AC power source (Chroma 61604) having an AC voltage range of 0-300V, a frequency range of 15-1000 Hz and a maximum power rating of 2 kVA. Electrical connectivity discussions can be found in the detailed description of the preferred embodiments section. Control devices 20, illustrated in FIGS. 8*c* and 8*j*, were connected to the electrodes 1/5 and 5/5, respectively, and electrodes 5/5 were actuated at a rate of about 1" per 8 hours. The eight electrode sets 1/5 and 5/5 were all connected to control devices 20 and 20*i* which automatically adjusted the height of, for example, each electrode 5/5 in each electrode set 5/5 had 2 female receiver tubes o5*a*/o5*a*'-o5*g*/o5*g*' which were connected to a bottom portion of the trough member 30*b*' such that the electrodes in each electrode set 5/5 could be removably inserted into each female receiver tube o5 when, and if, desired.

The amount of sodium bicarbonate (Fisher Scientific, Cat# S631-3) used in Run ID "PB-74" was about 2.5 grams/gallon (i.e., about 0.66 g/L). The feed electrodes were platinum wires (1 mm/0.040" dia.), 99.99%, obtained from Hi-Rel Alloys LTD (Ontario, Canada.)

The applied voltage for each plasma 4 made by electrode 1 was about 750 volts. This voltage was achieved by a transformer 60 (i.e., the Balanced Mid-Point Referenced Design) discussed elsewhere herein.

The AC power source 501AC utilized a Chroma 61604 programmable unit. In particular, sine wave AC frequencies at 80 Hz were utilized to make at least one platinum species in water, in accordance with the teachings herein. The applied voltage was 175 volts with an applied current between about 4.0 amps and about 7.0 amps.

The resulting platinum species in water material was then allowed to cool overnight to approximately 23 degrees Celsius. At that point the Pt-water-based material was fed into a second, separate and different trough unit as described below.

In general, this second trough utilized certain embodiments of the invention associated with the apparatuses generally shown in FIGS. 9, 10*c* and 11*a*. Electrical device 501AC, illustrated in FIG. 13, was used as the power supply for examples contained herein, while function generator 501FG was sometimes used to drive 501AC. This transformer was an AC power source (Chroma 61604) having an AC voltage range of 0-300V, a frequency range of 15-1000 Hz and a maximum power rating of 2 kVA. Electrical connectivity discussions can be found in the detailed description of the preferred embodiments section. Control devices 20, illustrated in FIGS. 8*c* and 8*j*, were connected to the electrodes 1/5 and 5/5, respectively, and electrodes 5/5 were actuated at a rate of about 1" per 8 hours. The eight electrode sets 1/5 and 5/5 were all connected to control devices 20 and 20*i* which automatically adjusted the height of, for example, each electrode 5/5 in each electrode set 5/5 had 2 female receiver tubes o5*a*/o5*a*'-o5*g*/o5*g*' which were connected to a bottom portion of the trough member 30*b*' such that the electrodes in each electrode set 5/5 could be removably inserted into each female receiver tube o5 when, and if, desired.

In particular, a sine wave AC frequency at 60 Hz was utilized to make a gold nanocrystal suspension or colloid or ion, in accordance with the teachings herein. The platinum-water based material "PB-74," as discussed above, was fed via pump 40 into plasma trough section 30a' as illustrated in FIG. 10b. The AC power source 501AC utilized a Chroma 61604 programmable AC source. The applied voltage was initially set to 200 volts but was set to 165 volts due to the initial current reading falling out of the normal range, typically between 2.5 A-3.5 A. The applied current varied between about 4 amps and about 7 amps.

The total amount of atomic platinum and gold contained within the bi-metallic nanocrystal suspension was about 1.7 ppm and 7.8 ppm, respectively, as measured by the atomic absorption spectroscopy techniques discussed elsewhere herein. It should be noted that this particular Au—Pt bi-metallic nanocrystal suspension was not stable as it settled over a period of time no later than four months after production. Accordingly, under certain sets of processing conditions, sodium bicarbonate by itself, without the addition of KOH or other suitable processing enhancers does not promote the development of highly stable Au—Pt bi-metallic nanocrystal suspensions. However, these suspensions could be suitable for some purposes.

Table 20 summarizes key processing parameters used in conjunction with FIGS. 9 and 10b. Table 20 also discloses: 1) resultant "ppm" (i.e., atomic platinum and gold concentrations.) and 2) "Hydrodynamic Radius" (nm).

TABLE 20

| | | Run ID | |
|---|---|---|---|
| | | PB-74 | GPB-010 |
| Process Enhancer | NaHCOO₃ (mg/mL) | 0.661 | PB-74 |
| | Input Temp ° C. at 32 | 24 | 24 |
| | Output Temp ° C. at 32 | 70 | 64 |
| Flow Rate | In (ml/min) | 190 | 200 |
| Volts: | Set # 1 | 750 | 750 |
| | Set #'s 2-8 | 175 | 165 |
| | Set #'s 2-8 frequency, Hz | 80 | 60 |
| | Wire Diameter (mm) | 1.0 | 1.0 |
| | Contact "W$_L$" (in/mm) | 1/25 | 1/25 |
| | Electrode Separation "y" (in/mm) | .25/6.4 | .25/6.4 |
| | Electrode Config. Figure | 8b | 8b |
| | Produced Au/Pt PPM | NA/1.7 | 7.8/1.7 |
| | Hydrodynamic Radius (nm) | N/A | 115 |
| Dimensions | Plasma 4 Figs. | 9 | 9 |
| | Process Figures | 10a, 10d | 10c, 11a |
| | M (in/mm) | 1.5/38 | 1.5/38 |
| | LT (in/mm) | 36/914 | 36/914 |
| | d (in/mm) | 1/25 | 1/25 |
| | S (in/mm) | 1.5/38 | 1.5/38 |
| | Total Curr. Draw (A) | 5.16 | 4.67 |
| | "c-c" (mm) | 76 | 76 |
| Set 1 | electrode # | 1a | 1a |
| | "x" (in/mm) | 0.25/6.4 | 0.25/6.4 |
| | electrode # | 5a | 5a |
| | "c-c" (mm) | 102 | 102 |
| Set 2 | Electrode Pair # | 5b & 5b' | 5b & 5b' |
| | "c-c" (mm) | 76 | 76 |
| Set 3 | Electrode Pair # | 5c & 5c' | 5c & 5c' |
| | "c-c" (mm) | 76 | 76 |
| Set 4 | Electrode Pair # | 5d & 5d' | 5d & 5d' |
| | "c-c" (mm) | 127 | 127 |
| Set 5 | Electrode Pair # | 5e & 5e' | 5e & 5e' |
| | "c-c" (mm) | 127 | 127 |
| Set 6 | Electrode Pair # | 5f & 5f' | 5f & 5f' |
| | "c-c" (mm) | 152 | 152 |

TABLE 20-continued

| | | Run ID | |
|---|---|---|---|
| | | PB-74 | GPB-010 |
| Set 7 | Electrode Pair # | 5g & 5g' | 5g & 5g' |
| | "c-c" (mm) | 178 | 178 |
| Set 8 | Electrode Pair # | 5h & 5h' | 5h & 5h' |
| | "c-c" (mm) | 76 | 76 |

Example 16

Manufacturing a Variety of Au—Pt Bi-Metallic Nanocrystal Suspensions by Using a Continuous Trough Process at Various Applied Frequencies (GPB-017, GPB-018, GPB-019, GPB-020, GPB-021, GPB-023, PGT024, PGT025, PGT026)

In general, this Example utilized certain embodiments of the invention associated with the apparatuses generally shown in FIGS. 9, 10c and 11a. Electrical device 501AC, illustrated in FIG. 13, was used as the power supply for examples contained herein, while function generator 501FG was sometimes used to drive 501AC. This transformer was an AC power source (Chroma 61604) having an AC voltage range of 0-300V, a frequency range of 15-1000 Hz and a maximum power rating of 2 kVA. Electrical connectivity discussions can be found in the detailed description of the preferred embodiments section. Control devices 20, illustrated in FIGS. 8c and 8j, were connected to the electrodes 1/5 and 5/5, respectively, and electrodes 5/5 were actuated at a rate of about 1" per 8 hours. The eight electrode sets 1/5 and 5/5 were all connected to control devices 20 and 20i which automatically adjusted the height of, for example, each electrode 5/5 in each electrode set 5/5 had 2 female receiver tubes o5a/o5a'-o5g/o5g' which were connected to a bottom portion of the trough member 30b' such that the electrodes in each electrode set 5/5 could be removably inserted into each female receiver tube o5 when, and if, desired.

The amount of potassium hydroxide (Fisher Scientific, Cat# P250-500) processing enhancer used in Run IDs "PB-83, 85, 87, and 88" was about 0.450 grams/gallon (i.e., about 0.12 mg/mL.). In addition, the amount of sodium bicarbonate (Fisher Scientific, Cat# S631-3) used in Run IDs "PB-83, 85, 87, and 88" was about 0.850 grams/gallon (i.e., about 0.22 mg/mL). The feed electrodes were platinum wires (1 mm/0.040" dia.), 99.99%, obtained from Hi-Rel Alloys LTD (Ontario, Canada.)

The applied voltage for each plasma 4 made by electrode 1 was about 750 volts. This voltage was achieved by a transformer 60 (i.e., the Balanced Mid-Point Referenced Design) discussed elsewhere herein.

The AC power source 501AC utilized a Chroma 61604 programmable unit. In particular, sine wave AC frequencies at 80 Hz were utilized to at least one platinum species in water in accordance with the teachings herein. The applied voltage was about 215 volts with an applied current between about 4.0 amps and about 7.0 amps.

The resulting platinum species in water material was then allowed to cool overnight to approximately 23 degrees Celsius. At that point the Pt-water-based material was fed into a second, separate and different trough unit as described below.

In general, this second trough utilized certain embodiments of the invention associated with the apparatuses generally shown in FIGS. 9, 10c and 11a. Electrical device 501AC, illustrated in FIG. 13, was used as the power supply for examples contained herein, while function generator 501FG was sometimes used to drive 501AC. This transformer was an AC power source (Chroma 61604) having an AC voltage range of 0-300V, a frequency range of 15-1000 Hz and a maximum power rating of 2 kVA. Electrical connectivity discussions can be found in the detailed description of the preferred embodiments section. Control devices 20, illustrated in FIGS. 8c and 8j, were connected to the electrodes 1/5 and 5/5, respectively, and electrodes 5/5 were actuated at a rate of about 1" per 8 hours. The eight electrode sets 1/5 and 5/5 were all connected to control devices 20 and 20i which automatically adjusted the height of, for example, each electrode 5/5 in each electrode set 5/5 had 2 female receiver tubes o5a/o5a'-o5g/o5g' which were connected to a bottom portion of the trough member 30b' such that the electrodes in each electrode set 5/5 could be removably inserted into each female receiver tube o5 when, and if, desired.

In particular, a sine wave AC frequency at 5 Hz-200 Hz was utilized to make gold nanocrystal suspensions or colloids or ions, in accordance with the teachings herein. The platinum-water based material "PB-83, 85, 87, and 88," as discussed above, was fed via pump 40 into plasma trough section 30a' as illustrated in FIG. 10b. The AC power source 501AC utilized a Chroma 61604 programmable AC source. The applied voltage was about 260 volts for approximately two minutes followed by about 220 volts for the duration of the run. The applied current varied between about 4 amps and about 7 amps.

The total amount of atomic platinum and gold contained within the bi-metallic nanocrystal suspension are outlined in Tables 21a, 21b and 21c. Table 21a outlines the platinum run conditions used to form the platinum species in water and Tables 21b and 21c outline the run conditions used to form the Au—Pt bi-metallic nanocrystal suspensions.

Table 21a summarizes key processing parameters used in conjunction with FIGS. 9 and 10c. Tables 21a, 21b and 21c also disclose: 1) Resultant "ppm" (i.e., atomic platinum and gold concentrations), 2) Hydrodynamic radius, and 3) Zeta Potential.

Energy absorption spectra was obtained for these samples (PGT024, PGT025, PGT026) using Uv-Vis spectroscopy methods as outlined elsewhere herein. FIG. 28a contains the UV-Vis data collected for these samples (PGT024, PGT025, PGT026), specifically displaying the 350-900 nm range.

Energy absorption spectra was obtained for these samples (GPB-017, GPB-018, GPB-019, GPB-020, GPB-023) using Uv-Vis spectroscopy methods as outlined elsewhere herein. FIG. 28a contains the UV-Vis data collected for these samples (GPB-017, GPB-018, GPB-019, GPB-020, GPB-023), specifically displaying the 350-900 nm range.

Figure 28C:
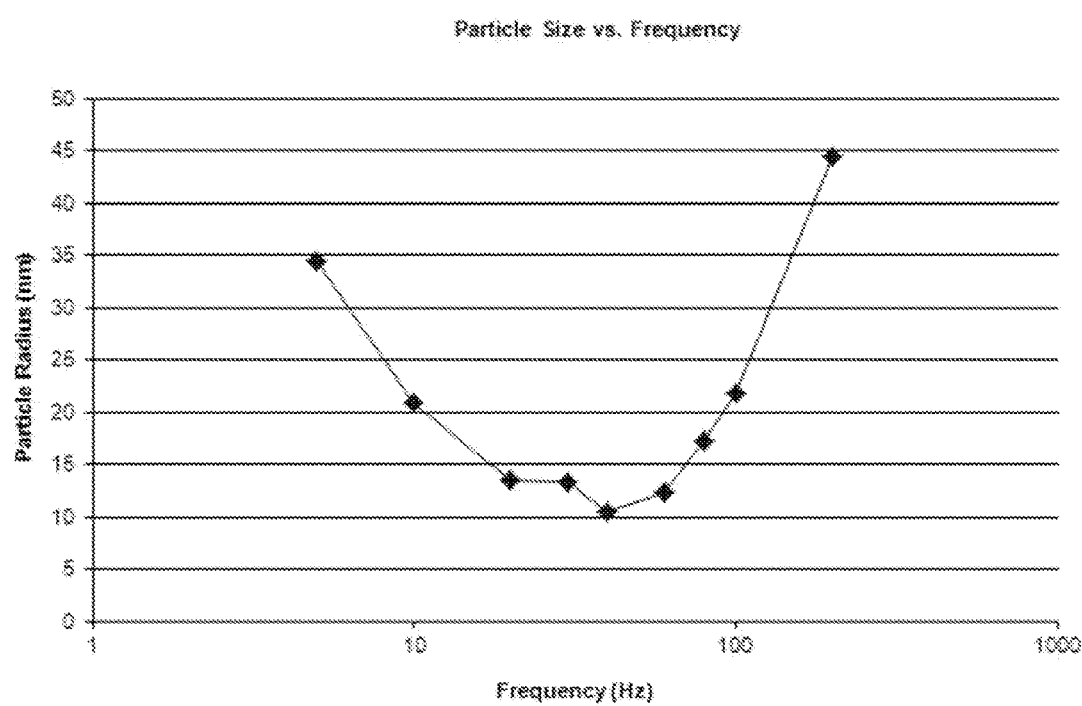
FIG. 28c shows a graph of particle radius versus frequency for bi-metallic nanoparticles made according to Example 16.

A variety of Au—Pt bi-metallic nanocrystal suspensions were prepared at frequencies, as described in this Example, between the range of about 5 Hz-200 Hz. A representative comparison of particle size versus frequency is illustrated in FIG. 28c.

TABLE 21a

| | | Run ID | | | |
|---|---|---|---|---|---|
| | | PB-83 | PB-85 | PB-87 | PB-88 |
| Process Enhancer | $NaHCO_3$ (mg/mL) | 0.225 | 0.225 | 0.225 | 0.225 |
| | KOH (mg/mL) | 0.119 | 0.119 | 0.119 | 0.119 |
| | Input Temp ° C. at 32 | 23 | 25 | 25 | 24 |
| | Output Temp ° C. at 32 | 74 | 80 | 81 | 76 |
| Flow Rate | In (ml/min) | 220 | 220 | 220 | 220 |
| Volts: | Set # 1 | 750 | 750 | 750 | 750 |
| | Set #'s 2-8 | 215 | 215 | 215 | 215 |
| | Set #'s 2-8 frequency, Hz | 80 | 80 | 80 | 80 |
| | Wire Diameter (mm) | 1.0 | 1.0 | 1.0 | 1.0 |
| | Contact "$W_L$" (in/mm) | 1/25 | 1/25 | 1/25 | 1/25 |
| | Electrode Separation "y" (in/mm) | .25/6.4 | .25/6.4 | .25/6.4 | .25/6.4 |
| | Electrode Config. Figure | 8b | 8b | 8b | 8b |
| | Produced Pt PPM | 1.9 | 2.2 | 2.3 | 2.1 |
| Dimensions | Plasma 4 Figs. | 9 | 9 | 9 | 9 |
| | Process Figures | 10a, 10d | 10a, 10d | 10a, 10d | 10a, 10d |
| | M (in/mm) | 1.5/38 | 1.5/38 | 1.5/38 | 1.5/38 |
| | LT (in/mm) | 36/914 | 36/914 | 36/914 | 36/914 |
| | d (in/mm) | 1/25 | 1/25 | 1/25 | 1/25 |
| | S (in/mm) | 1.5/38 | 1.5/38 | 1.5/38 | 1.5/38 |
| | Total Curr. Draw (A) | 5.12 | 5.52 | 5.87 | 5.45 |
| | "c-c" (mm) | 76 | 76 | 76 | 76 |
| Set 1 | electrode # | 1a | 1a | 1a | 1a |
| | "x" (in/mm) | 0.25/6.4 | 0.25/6.4 | 0.25/6.4 | 0.25/6.4 |
| | electrode # | 5a | 5a | 5a | 5a |
| | "c-c" (mm) | 102 | 102 | 102 | 102 |
| Set 2 | Electrode Pair # | 5b & 5b' | 5b & 5b' | 5b & 5b' | 5b & 5b' |
| | "c-c" (mm) | 76 | 76 | 76 | 76 |
| Set 3 | Electrode Pair # | 5c & 5c' | 5c & 5c' | 5c & 5c' | 5c & 5c' |
| | "c-c" (mm) | 76 | 76 | 76 | 76 |
| Set 4 | Electrode Pair # | 5d & 5d' | 5d & 5d' | 5d & 5d' | 5d & 5d' |
| | "c-c" (mm) | 127 | 127 | 127 | 127 |
| Set 5 | Electrode Pair # | 5e & 5e' | 5e & 5e' | 5e & 5e' | 5e & 5e' |
| | "c-c" (mm) | 127 | 127 | 127 | 127 |
| Set 6 | Electrode Pair # | 5f & 5f' | 5f & 5f' | 5f & 5f' | 5f & 5f' |
| | "c-c" (mm) | 152 | 152 | 152 | 152 |
| Set 7 | Electrode Pair # | 5g & 5g' | 5g & 5g' | 5g & 5g' | 5g & 5g' |
| | "c-c" (mm) | 178 | 178 | 178 | 178 |
| Set 8 | Electrode Pair # | 5h & 5h' | 5h & 5h' | 5h & 5h' | 5h & 5h' |
| | "c-c" (mm) | 76 | 76 | 76 | 76 |

TABLE 21b

| Run ID | | GPB-017 | GPB-018 | GPB-019 | GPB-020 | GPB-021 |
|---|---|---|---|---|---|---|
| Process Enhancer | NaHCOO₃ (mg/mL) | PB-83 | PB-83 | PB-83 | PB-85 | PB-85 |
| | KOH (mg/mL) | | | | | |
| Input Temp ° C. at 32 | | 25 | 25 | 25 | 27 | 27 |
| Output Temp ° C. at 32 | | 79 | 78 | 78 | 81 | 83 |
| Flow Rate | In (ml/min) | 230 | 230 | 230 | 230 | 230 |
| Volts: | Set # 1 | 750 | 750 | 750 | 750 | 750 |
| | Set #'s 2-8 | 220 | 220 | 220 | 260 V: 0-2 min/220 | 220 |
| | Set #'s 2-8 frequency, Hz | 20 | 40 | 80 | 5 | 10 |
| Wire Diameter (mm) | | 1.0 | 1.0 | 1.0 | 1.0 | 1.0 |
| Contact "$W_L$" (in/mm) | | 1/25 | 1/25 | 1/25 | 1/25 | 1/25 |
| Electrode Separation "y" (in/mm) | | .25/6.4 | .25/6.4 | .25/6.4 | .25/6.4 | .25/6.4 |
| Electrode Config. Figure | | 8b | 8b | 8b | 8b | 8b |
| Produced Au/Pt PPM | | 3.1/2.0 | 5.8/2.0 | 10.5/2.0 | 1.1/2.3 | 1.7/2.3 |
| Hydrodynamic Radius (nm) | | 18.96 | 16.59 | 20.58 | 24.96 | 51 |
| Zeta Potential (mV) | | −39.0 | −38.0 | −42.0 | −45.0 | −38.0 |
| Dimensions | Plasma 4 Figs. | 9 | 9 | 9 | 9 | 9 |
| | Process Figures | 10c, 11a | 10c, 11a | 10c, 11a | 10c, 11a | 10c, 11a |
| | M (in/mm) | 1.5/38 | 1.5/38 | 1.5/38 | 1.5/38 | 1.5/38 |
| | LT (in/mm) | 36/914 | 36/914 | 36/914 | 36/914 | 36/914 |
| | d (in/mm) | 1/25 | 1/25 | 1/25 | 1/25 | 1/25 |
| | S (in/mm) | 1.5/38 | 1.5/38 | 1.5/38 | 1.5/38 | 1.5/38 |
| Total Curr. Draw (A) | | 5.84 | 5.82 | 5.81 | 5.66 | 5.82 |
| "c-c" (mm) | | 76 | 76 | 76 | 76 | 76 |
| Set 1 | electrode # | 1a | 1a | 1a | 1a | 1a |
| | "x" (in/mm) | 0.25/6.4 | 0.25/6.4 | 0.25/6.4 | 0.25/6.4 | 0.25/6.4 |
| | electrode # | 5a | 5a | 5a | 5a | 5a |
| "c-c" (mm) | | 102 | 102 | 102 | 102 | 102 |
| Set 2 | Electrode Pair # | 5b & 5b' | 5b & 5b' | 5b & 5b' | 5b & 5b' | 5b & 5b' |
| "c-c" (mm) | | 76 | 76 | 76 | 76 | 76 |
| Set 3 | Electrode Pair # | 5c & 5c' | 5c & 5c' | 5c & 5c' | 5c & 5c' | 5c & 5c' |
| "c-c" (mm) | | 76 | 76 | 76 | 76 | 76 |
| Set 4 | Electrode Pair # | 5d & 5d' | 5d & 5d' | 5d & 5d' | 5d & 5d' | 5d & 5d' |
| "c-c" (mm) | | 127 | 127 | 127 | 127 | 127 |
| Set 5 | Electrode Pair # | 5e & 5e' | 5e & 5e' | 5e & 5e' | 5e & 5e' | 5e & 5e' |
| "c-c" (mm) | | 127 | 127 | 127 | 127 | 127 |
| Set 6 | Electrode Pair # | 5f & 5f' | 5f & 5f' | 5f & 5f' | 5f & 5f' | 5f & 5f' |
| "c-c" (mm) | | 152 | 152 | 152 | 152 | 152 |
| Set 7 | Electrode Pair # | 5g & 5g' | 5g & 5g' | 5g & 5g' | 5g & 5g' | 5g & 5g' |
| "c-c" (mm) | | 178 | 178 | 178 | 178 | 178 |
| Set 8 | Electrode Pair # | 5h & 5h' | 5h & 5h' | 5h & 5h' | 5h & 5h' | 5h & 5h' |
| "c-c" (mm) | | 76 | 76 | 76 | 76 | 76 |

TABLE 21C

| | | Run ID | | | |
|---|---|---|---|---|---|
| | | GPB-023 | PGT024 | PGT025 | PGT026 |
| Process Enhancer | NaHCOO₃ (mg/mL) | PB-85 | PB-87 | PB-83 | PB-85 |
| | KOH (mg/mL) | | | | |
| Input Temp ° C. at 32 | | 27 | 27 | 25 | 25 |
| Output Temp ° C. at 32 | | 83 | 83 | 84 | 83 |
| Flow Rate | In (ml/min) | 230 | 230 | 230 | 230 |
| Volts: | Set # 1 | 750 | 750 | 750 | 750 |
| | Set #'s 2-8 | 220 | 260 V: 0-2 min/220 | 260 V: 0-2 min/220 | 220 |
| | Set #'s 2-8 frequency, Hz | 200 | 60 | 30 | 100 |
| Wire Diameter (mm) | | 1.0 | 1.0 | 1.0 | 1.0 |
| Contact "$W_L$" (in/mm) | | 1/25 | 1/25 | 1/25 | 1/25 |
| Electrode Separation "y" (in/mm) | | .25/6.4 | .25/6.4 | .25/6.4 | .25/6.4 |
| Electrode Config. Figure | | 8b | 8b | 8b | 8b |
| Produced Au/Pt PPM | | 12.3/2.3 | 8.5/2.7 | 4.8/2.6 | 12.2/2.5 |
| Hydrodynamic Radius (nm) | | 41.31 | 19.17 | 17.43 | 28.84 |
| Zeta Potential (mV) | | −44.0 | −40.0 | −56.0 | −50.0 |
| Dimensions | Plasma 4 Figures | 9 | 9 | 9 | 9 |
| | Process Figures | 10c, 11a | 10c, 11a | 10c, 11a | 10c, 11a |
| | M (in/mm) | 1.5/38 | 1.5/38 | 1.5/38 | 1.5/38 |
| | LT (in/mm) | 36/914 | 36/914 | 36/914 | 36/914 |
| | d (in/mm) | 1/25 | 1/25 | 1/25 | 1/25 |
| | S (in/mm) | 1.5/38 | 1.5/38 | 1.5/38 | 1.5/38 |
| Total Curr. Draw (A) | | 6.04 | 5.81 | 5.86 | 5.82 |
| "c-c" (mm) | | 76 | 76 | 76 | 76 |

TABLE 21C-continued

| | | Run ID | | | |
|---|---|---|---|---|---|
| | | GPB-023 | PGT024 | PGT025 | PGT026 |
| Set 1 | electrode # | 1a | 1a | 1a | 1a |
| | "x" (in/mm) | 0.25/6.4 | 0.25/6.4 | 0.25/6.4 | 0.25/6.4 |
| | electrode # | 5a | 5a | 5a | 5a |
| | "c-c" (mm) | 102 | 102 | 102 | 102 |
| Set 2 | Electrode Pair # | 5b & 5b' | 5b & 5b' | 5b & 5b' | 5b & 5b' |
| | "c-c" (mm) | 76 | 76 | 76 | 76 |
| Set 3 | Electrode Pair # | 5c & 5c' | 5c & 5c' | 5c & 5c' | 5c & 5c' |
| | "c-c" (mm) | 76 | 76 | 76 | 76 |
| Set 4 | Electrode Pair # | 5d & 5d' | 5d & 5d' | 5d & 5d' | 5d & 5d' |
| | "c-c" (mm) | 127 | 127 | 127 | 127 |
| Set 5 | Electrode Pair # | 5e & 5e' | 5e & 5e' | 5e & 5e' | 5e & 5e' |
| | "c-c" (mm) | 127 | 127 | 127 | 127 |
| Set 6 | Electrode Pair # | 5f & 5f' | 5f & 5f' | 5f & 5f' | 5f & 5f' |
| | "c-c" (mm) | 152 | 152 | 152 | 152 |
| Set 7 | Electrode Pair # | 5g & 5g' | 5g & 5g' | 5g & 5g' | 5g & 5g' |
| | "c-c" (mm) | 178 | 178 | 178 | 178 |
| Set 8 | Electrode Pair # | 5h & 5h' | 5h & 5h' | 5h & 5h' | 5h & 5h' |
| | "c-c" (mm) | 76 | 76 | 76 | 76 |

Example 17

Analysis of the Surface of Manufactured Au—Pt Bi-Metallic Nanocrystal Suspensions by High Resolution Transmission Electron Microscopy/Scanning Transmission Electron Microscopy and X-Ray Photoelectron Spectroscopy (GPB-040)

In general, this Example utilized certain embodiments of the invention associated with the apparatuses generally shown in FIGS. 9, 10c and 11a to make Au—Pt bi-metallic nanocrystal suspensions. Electrical device 501AC, illustrated in FIG. 13, was used as the power supply for examples contained herein, while function generator 501FG was sometimes used to drive 501AC. This transformer was an AC power source (Chroma 61604) having an AC voltage range of 0-300V, a frequency range of 15-1000 Hz and a maximum power rating of 2 kVA. Electrical connectivity discussions can be found in the detailed description of the preferred embodiments section. Control devices 20, illustrated in FIGS. 18c and 18j, were connected to the electrodes 1/5 and 5/5, respectively, and electrodes 5/5 were actuated at a rate of about 1" per 8 hours. The eight electrode sets 1/5 and 5/5 were all connected to control devices 20 and 20i which automatically adjusted the height of, for example, each electrode 5/5 in each electrode set 5/5 had 2 female receiver tubes o5a/o5a'-o5g/o5g' which were connected to a bottom portion of the trough member 30b' such that the electrodes in each electrode set 5/5 could be removably inserted into each female receiver tube o5 when, and if, desired.

The amount of potassium hydroxide (Fisher Scientific, Cat# P250-500) processing enhancer used in Run ID "PB-118" was about 0.450 grams/gallon (i.e., about 0.12 mg/mL.). In addition, the amount of sodium bicarbonate (Fisher Scientific, Cat # S631-3) used in Run ID "PB-118" was about 0.850 grams/gallon (i.e., about 0.22 mg/mL). The feed electrodes were platinum wires (1 mm/0.040" dia.), 99.99%, obtained from Hi-Rel Alloys LTD (Ontario, Canada.)

The applied voltage for each plasma 4 made by electrode 1 was about 750 volts. This voltage was achieved by a transformer 60 (i.e., the Balanced Mid-Point Referenced Design) discussed elsewhere herein.

The AC power source 501AC utilized a Chroma 61604 programmable unit. In particular, sine wave AC frequencies at 80 Hz were utilized to make at least one platinum species in water, in accordance with the teachings herein. The applied voltage was about 215 volts with an applied current between about 4.0 amps and about 7.0 amps.

The resulting platinum species in water material was then allowed to cool overnight to approximately 23 degrees Celsius. At that point the Pt-water-based material was fed into a second, separate and different trough unit as described below.

In general, this second trough utilized certain embodiments of the invention associated with the apparatuses generally shown in FIGS. 9, 10c and 11a. Electrical device 501AC, illustrated in FIG. 13, was used as the power supply for examples contained herein, while function generator 501FG was sometimes used to drive 501AC. This transformer was an AC power source (Chroma 61604) having an AC voltage range of 0-300V, a frequency range of 15-1000 Hz and a maximum power rating of 2 kVA. Electrical connectivity discussions can be found in the detailed description of the preferred embodiments section. Control devices 20, illustrated in FIGS. 8c and 8j, were connected to the electrodes 1/5 and 5/5, respectively, and electrodes 5/5 were actuated at a rate of about 1" per 8 hours. The eight electrode sets 1/5 and 5/5 were all connected to control devices 20 and 20i which automatically adjusted the height of, for example, each electrode 5/5 in each electrode set 5/5 had 2 female receiver tubes o5a/o5a'-o5g/o5g' which were connected to a bottom portion of the trough member 30b' such that the electrodes in each electrode set 5/5 could be removably inserted into each female receiver tube o5 when, and if, desired.

In particular, a sine wave AC frequency at 60 Hz was utilized to make a gold nanocrystal suspension or colloid or ion, in accordance with the teachings herein. The platinum-water based material "PB-118," as discussed above, was fed via pump 40 into plasma trough section 30a' as illustrated in FIG. 10c. The AC power source 501AC utilized a Chroma 61604 programmable AC source. The applied voltage was about 260 volts for approximately two minutes followed by about 220 volts for the duration of the run. The applied current varied between about 4 amps and about 7 amps.

The total amount of atomic platinum and gold contained within the bi-metallic nanocrystalline suspension was about 3.2 ppm and 9.3 ppm, respectively, as measured by the atomic absorption spectroscopy techniques discussed elsewhere herein.

Table 23 summarizes key processing parameters used in conjunction with FIGS. 9 and 11a. Table 23 also discloses: 1) resultant "ppm" (i.e., atomic platinum and gold concentrations.), 2) "Hydrodynamic Radius" and 3) "Zeta Potential."

Figure 29A:
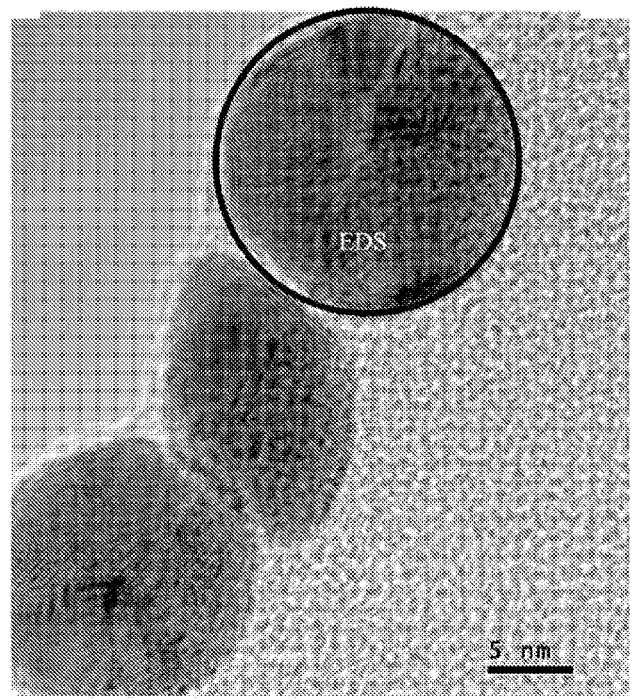
FIG. 29a shows a representative TEM photomicrograph of the dried constituents made according to Example 17.
Figure 29B:
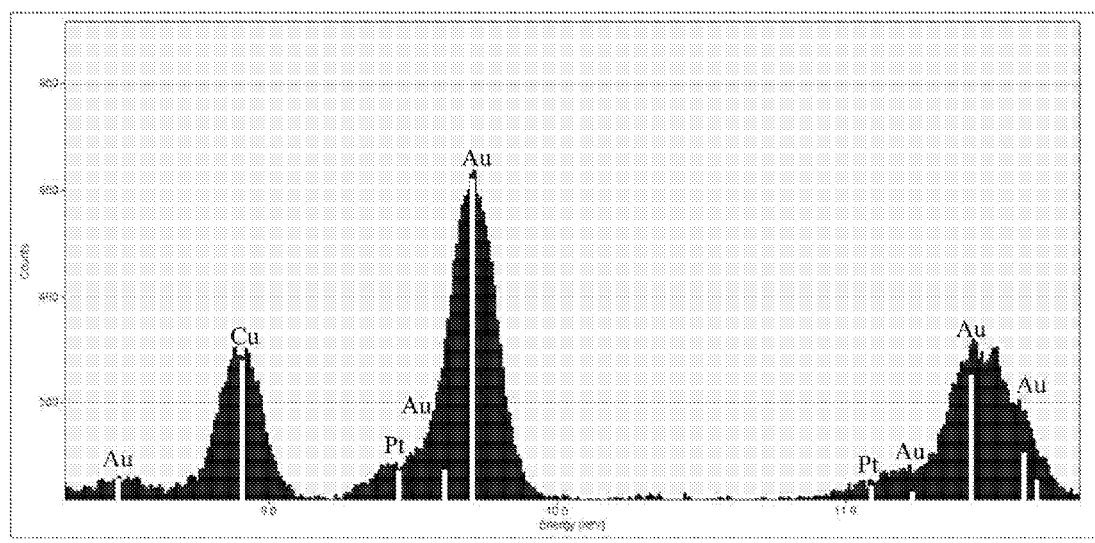
Figure 29C:
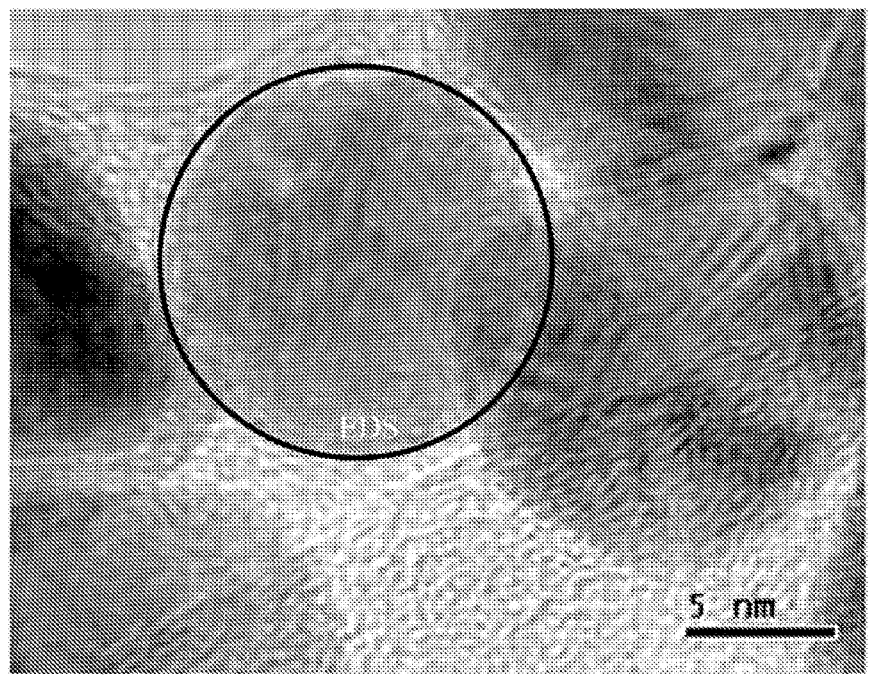
FIG. 29c shows a representative TEM photomicrograph of the dried constituents made according to Example 17.
Figure 29D:
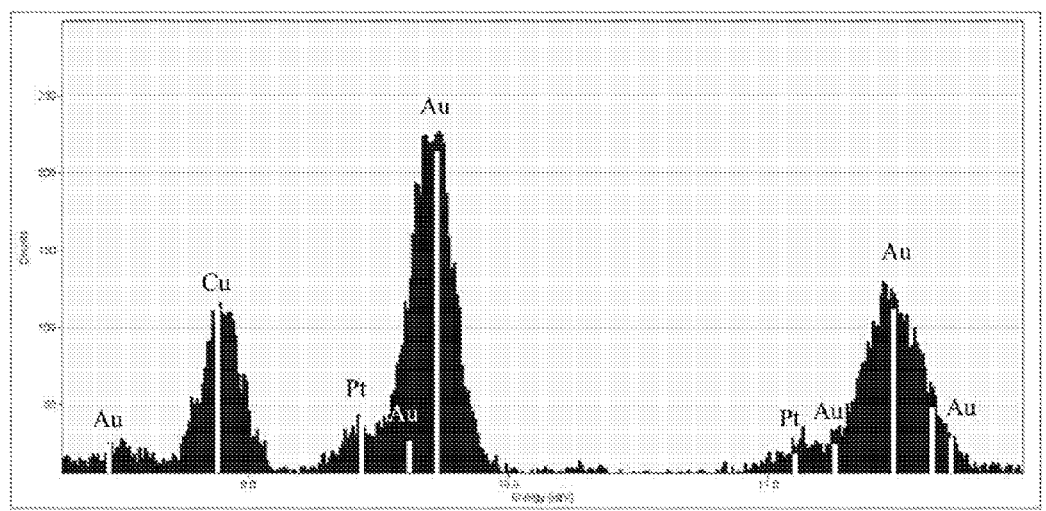
FIG. 29d is a representative EDS spectra corresponding to FIG. 29c.
Figure 29E:
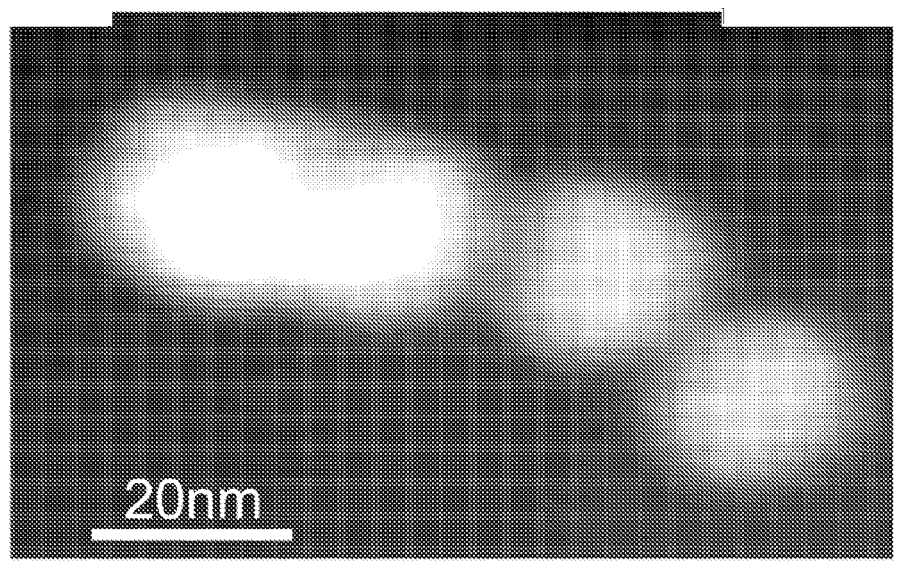
FIGS. 29e, 29f and 29g are Scanning Transmission Electron Microscopy images of nanocrystals in a GPB-040 suspension.
Figure 29F:
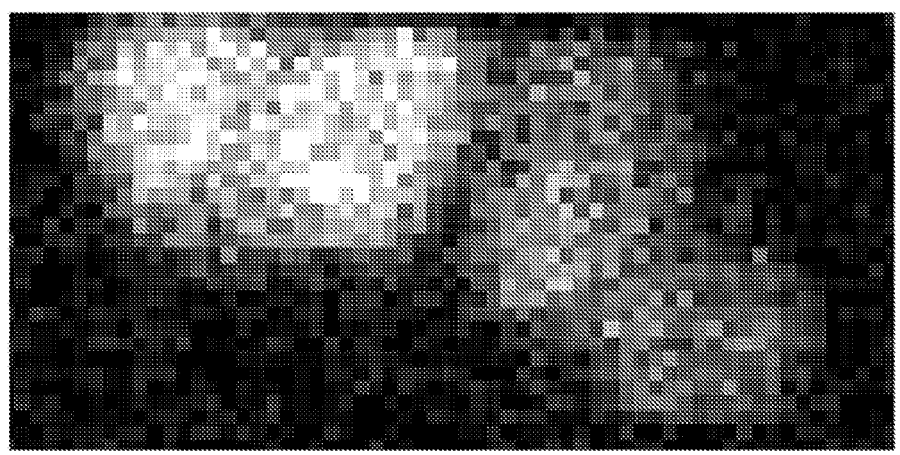
Figure 29G:
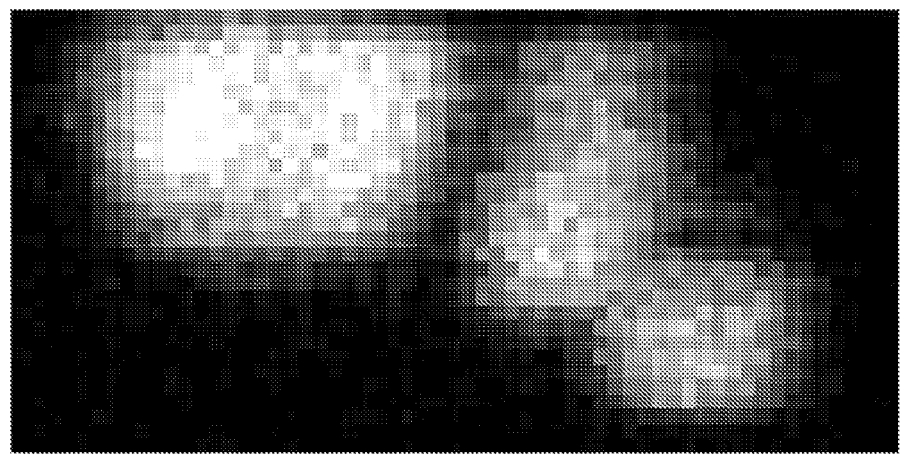

High-resolution transmission electron microscopy (HR-TEM) was performed using a Philips CM300 FEG High Resolution Transmission Electron Microscope described elsewhere herein. Scanning transmission electron microscopy (STEM) was also performed on the CM300 in STEM mode. Calibration was performed prior to analysis via an internal calibration procedure within the instrument computer. FIGS. 29a and 29c are representative TEM micrographs. FIGS. 29b and 29d are representative EDS spectra of dried nanocrystals in FIGS. 29a and 29c. FIGS. 29e, 29f and 29g are STEM mappings of dried Au—Pt bi-metallic nanocrystals dried from the nanocrystal suspensions.

Figure 30:
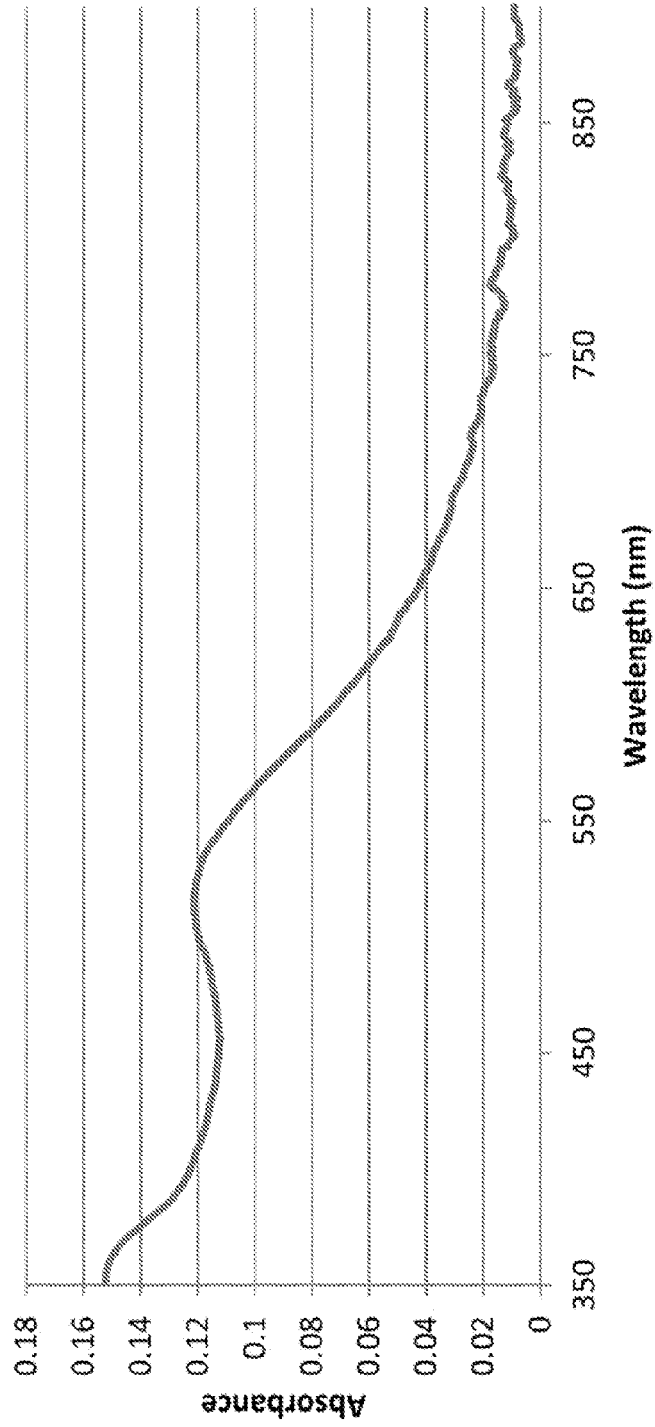
FIG. 30 is a UV-Vis spectrograph of GPP-040 made according to Example 17.

Energy absorption spectra were obtained for this sample (GPB-040) using Uv-Vis spectroscopy methods as outlined elsewhere herein. FIG. 30 contains the UV-Vis data collected for this sample (GPB-040), specifically displaying the 350-900 nm range.

GPB-040 concentrated samples were prepared via Tangential Flow Filtration (TFF), as described herein where the diafiltration buffer was substituted with de-ionized water to remove the process enhancer from the solution. GPB-040 was concentrated 20 fold by volume three times, each time reconstituting with de-ionized water. Subsequently, TFF concentrated GPB-040 was then centrifuged at 11,000 rpm for 10 minutes resulting in the presence of a Au—Pt bi-metallic pellet at the bottom of a 1.5 mL centrifuge tube. Approximately 24 tubes were used to collect a final sample of about 1.5 mL with a concentration that is about 400 times greater than the starting solution. This solution was then deposited onto the sample stub as discussed below.

Tangential Flow Filtration (TFF)

Figure 31C:
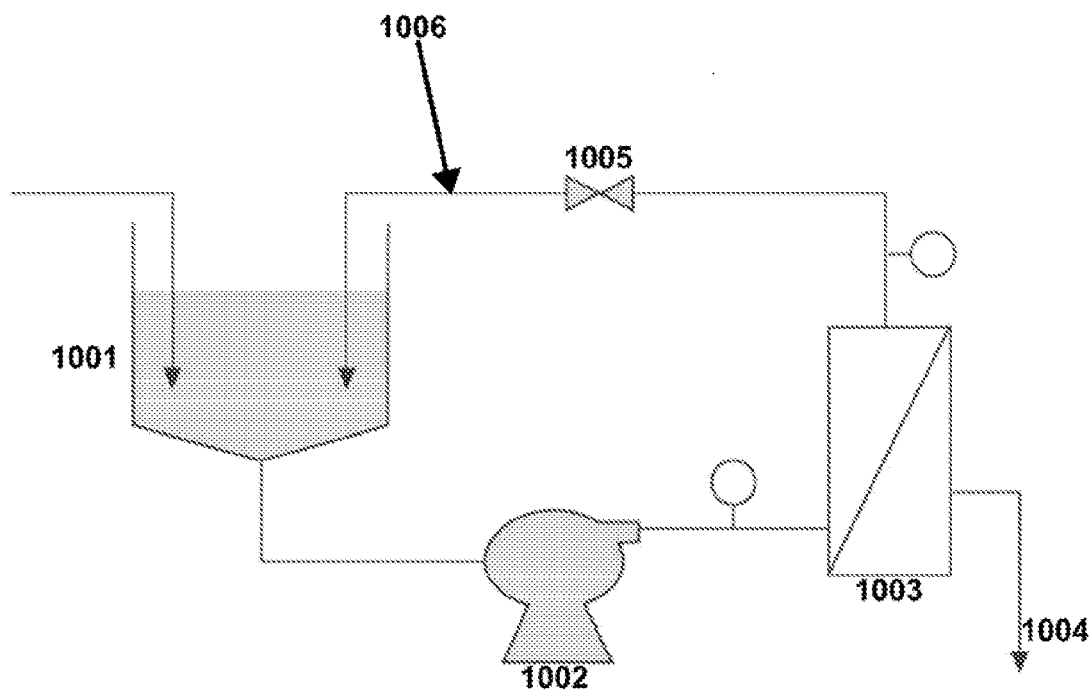
FIG. 31c is a schematic representation of a TFF apparatus.

In order to concentrate the bi-metallic nanocrystals in GPB-040, a tangential flow filtration (TFF) process was utilized. In the process filtration is a pressure driven separation process that uses membranes to separate nanocrystals in the suspension based on their size and/or charge differences. In TFF, the fluid is pumped tangentially along the surface of the membrane. A schematic of a simple TFF system is shown in FIG. 31c.

A feed tank 1001 provides fluid to a feed pump 1002 and into a filtration module 1003. The filtrate stream 1004 is discarded. Retentate is diverted through the retentate valve 1005 and returned as 1006 into the feed tank 1001. During each pass of the fluid over the surface of the membrane in the filtration module 1003, the applied pressure forces a portion of the fluid through the membrane and into the filtrate stream, 1004. Any particulates and macromolecules that are too large to pass through the membrane pores are retained on the upper stream and swept along by the tangential flow into the retentate, 1006. The retentate, having a higher concentration of colloidal particles, is returned back to the feed tank, 1001. If there is no diafiltration buffer added to the feed tank, then the colloid volume in the feed tank, 1001, is reduced by the amount of filtrate removed and the suspension becomes concentrated.

In this example, Millipore Pellicon XL cassettes were used with 5 kDa and 10 kDa MWCO cellulose membranes. The retentate pressure was set to 40 PSI by a retentate valve, 1005. 10 kDa membrane allows approximately 4 times higher filtrate flow rate related to a 5 kDa membrane under the same transmembrane pressure, which is expected for a larger pore size. At the same time, pores of 10 kDa membrane are small enough to retain all formed bi-metallic nanocrystals in the retentate in GPB-040.

X-Ray Photoelectron Spectroscopy:

Surface chemical analysis of bi-metallic gold-platinum nanocrystals was performed by X-ray photoelectron spectroscopy (XPS.) The spectra were collected using a Physical Electronics (PHI) Model 5400 photoelectron spectrometer equipped with a Mg K-alpha source operating at 300 W beam power with an accelerating voltage of 15 kV. Ejected photoelectrons were detected by a hemispherical analyzer that provided both high sensitivity and resolution. The operating pressure in the sampling chamber was below $5 \times 10^{-8}$ Torr during analysis.

Spectra were collected within two ranges, (i.e., a low resolution survey scan and a higher resolution multiplex scan in specific regions of interest). Survey scans were taken between binding energies of 0-1200 eV while higher resolution scans were taken between 80-100 eV and 65-85 eV. Elemental gold exhibits a multiplet ($4f_{5/2}$ & $4f_{7/2}$) at 87.6 eV and 83.9 eV, respectively, and information such as oxide composition and concentration can be determined from the expanded region at 80-100 eV. Platinum exhibits a multiplet ($4f_{5/2}$ & $4f_{7/2}$) at 74.5 eV and 71.2 eV, respectively, and information such as concentration and oxide content can be determined from the expanded region at 65-85 eV.

Sputter cleaning and depth profiling were carried out with a Sputter Ion Gun, (PHI, Model 04-303). The incident ion gun was operated at an accelerating voltage of 4.0 keV, and sample currents were maintained at about 25 mA across the sample area. The pressure in the main chamber was maintained at about $5 \times 10^{-8}$ Torr. The corresponding raster size is $4 \times 4$ mm with a pressure of 25 mPa. Sputtering was done at intervals of 5, 10, 20, 30, 40, 50, 70, 90, 120, 180, & 240 minutes.

Figure 29H:
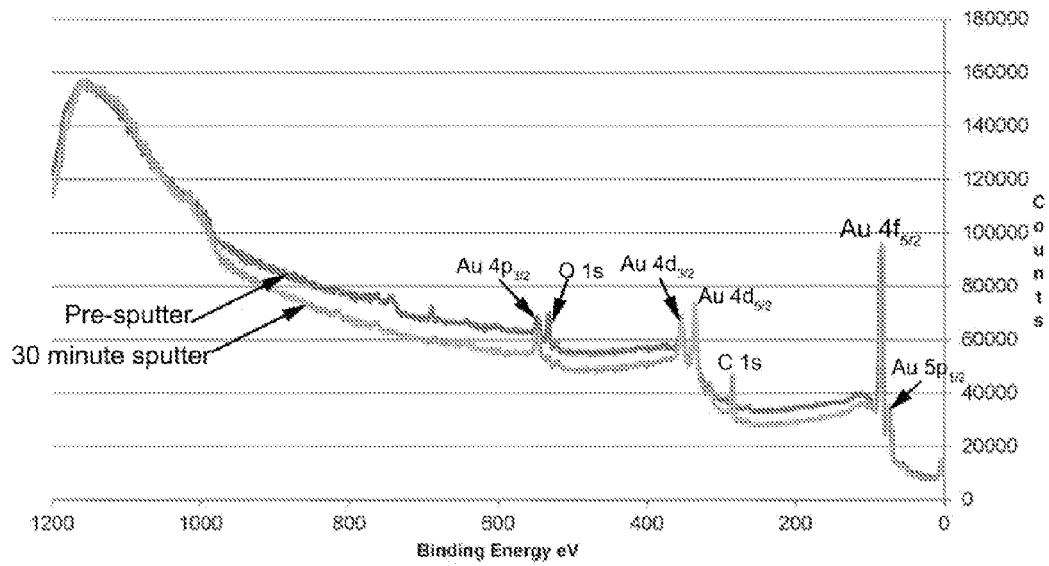
FIGS. 29h and 29i are representative XPS spectra corresponding to Example 17.
Figure 29I:
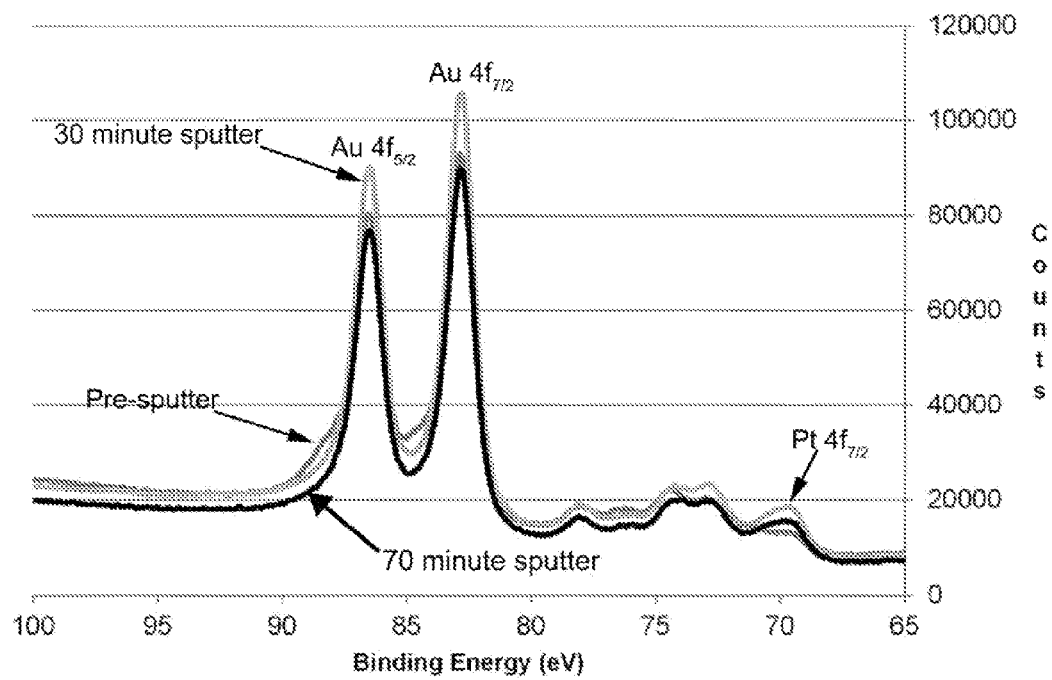

FIGS. 29h-29i are spectra collected from GPB-040, a gold-platinum bi-metallic nanocrystal suspension. The spectra were prepared by placing 100-200 uL of sample onto the sample stub and subsequently pulling a vacuum to dry the material onto the carbon tape. The chamber was then opened and another 100-200 uL was deposited. This process was repeated eleven times to produce a thin film of material on the carbon tape.

The initial survey scan, FIG. 29h, is useful in determining surface contaminants and elemental composition of the nanocrystals. Clearly labeled are peaks indicative of carbon, oxygen, platinum, and gold. The small carbon peak at 285 eV is from incomplete sample coverage of the carbon tape while the oxygen peak at 531 eV is likely a result of trapped oxygen due to the sample preparation technique; however in a layer of adsorbed oxygen may have become trapped in between drop depositions. Peaks at 690 eV and 750 eV can be attributed to fluorine sample chamber contamination and oxygen, respectively. In both instances the peaks disappeared after a 30 minute sputter.

Higher resolution multiplex scans, FIG. 29i, between 60 eV-100 eV provide additional information on the gold and platinum composition of the nanocrystals. The Au $4f_{5/2}$ peak at 88 eV contains a small shoulder that can be attributed to sample charging. After a 30 minute sputter, the flow of positive argon ions neutralized the sample and the shoulder disappeared. In addition, the Pt $4f_{7/2}$ peak rises after the 30 minute sputter at about 71 eV.

As shown clearly in FIGS. 29a-g, Au—Pt bi-metallic nanocrystal solutions are heterogeneous in structure with respect to atomic platinum and atomic gold. As indicated by specific areas of interest in FIGS. 29a and 29c, energy dispersive spectra (EDS) were collected by condensing the electron beam of the TEM onto individual nanocrystals. Resultant EDS data is displayed in FIGS. 29b and 29d. In both cases, a platinum peak at about 9.4 keV and a gold peak at about 9.7 keV are present. FIGS. 29e-g are Scanning Transmission Electron Microscopy (STEM) images of bi-metallic nanocrystals from suspension GPB-040. FIG. 29e is a STEM image of at least four Au—Pt bi-metallic nanocrystals dried on a copper grid. FIGS. 29f and g are platinum and gold EDS mappings, respectively, of the nanocrystals imaged in FIG. 29e. It is clear from FIGS. 29f and 29g that both platinum and gold exist heterogeneously throughout the examined nanocrystals. In addition, FIGS. 29h and 29i provide further evidence that the nanocrystal surfaces are both free from organic contamination and do not exhibit a core-shell behavior. The relative intensities of the Au $4f_{7/2}$ and Pt $4f_{7/2}$ do not change as a function of sputtering time. One would expect the relative intensities of Pt to decrease if the nanocrystals were core-shell in nature. By combining both HRTEM, EDS, and XPS data, it is clear that the nanocrystals prepared by the methods disclosed in this Example are Au—Pt bi-metallic alloys.

TABLE 23

|  |  | Run ID | |
| --- | --- | --- | --- |
|  |  | PB-118 | GPB-040 |
| Process | NaHCO₃ (mg/mL) | 0.225 | PB 120 |
| Enhancer | KOH (mg/mL) | 0.119 |  |
|  | Input Temp ° C. at 32 | 24 | 24 |
|  | Output Temp ° C. at 32 | 88 | 86 |
| Flow Rate | In (ml/min) | 190 | 200 |
| Volts: | Set # 1 | 750 | 750 |
|  | Set #'s 2-8 | 215 | 260: 0-2 min/220 |
|  | Set #'s 2-8 frequency, Hz | 80 | 60 |
|  | Wire Diameter (mm) | 1.0 | 1.0 |
|  | Contact "$W_L$" (in/mm) | 1/25 | 1/25 |
|  | Electrode Separation "y" (in/mm) | .25/6.4 | .25/6.4 |
|  | Electrode Config. Figure | 8b | 8b |
|  | Produced Pt PPM | 3.2 | N/A |
|  | Produced Au PPM | N/A | 9.3 |
|  | Hydrodynamic Radius (nm) | N/A | 14.16 |
|  | Zeta Potential (mV) | N/A | −47.0 |
| Dimensions | Plasma 4 Figures | 9 | 9 |
|  | Process Figures | 10c, 11a | 10c, 11a |
|  | M (in/mm) | 1.5/38 | 1.5/38 |
|  | LT (in/mm) | 36/914 | 36/914 |
|  | d (in/mm) | 1/25 | 1/25 |
|  | S (in/mm) | 1.5/38 | 1.5/38 |
|  | Total Curr. Draw (A) | 6.25 | 6.04 |
|  | "c-c" (mm) | 76 | 76 |
| Set 1 | electrode # | 1a | 1a |
|  | "x" (in/mm) | 0.25/6.4 | 0.25/6.4 |
|  | electrode # | 5a | 5a |
|  | "c-c" (mm) | 102 | 102 |
| Set 2 | Electrode Pair # | 5b & 5b' | 5b & 5b' |
|  | "c-c" (mm) | 76 | 76 |
| Set 3 | Electrode Pair # | 5c & 5c' | 5c & 5c' |
|  | "c-c" (mm) | 76 | 76 |
| Set 4 | Electrode Pair # | 5d & 5d' | 5d & 5d' |
|  | "c-c" (mm) | 127 | 127 |
| Set 5 | Electrode Pair # | 5e & 5e' | 5e & 5e' |
|  | "c-c" (mm) | 127 | 127 |
| Set 6 | Electrode Pair # | 5f & 5f' | 5f & 5f' |
|  | "c-c" (mm) | 152 | 152 |
| Set 7 | Electrode Pair # | 5g & 5g' | 5g & 5g' |
|  | "c-c" (mm) | 178 | 178 |
| Set 8 | Electrode Pair # | 5h & 5h' | 5h & 5h' |
|  | "c-c" (mm) | 76 | 76 |

Example 18

Concentrating Gold and Gold/Platinum Bi-Metallic Suspensions with a Dialysis Technique A dialysis bag technique permits the gradual concentration of colloids made according to the teachings herein. Colloidal suspensions were placed inside of a dialysis bag and the bag itself was immersed into an aqueous solution of a PEG-based polymer, which creates a negative osmotic pressure. The negative osmotic pressure resulted in the extraction of water from the colloid maintained within (i.e., inside) the dialysis bag.

Specifically, FIG. 31a shows a dialysis bag 2000, containing a representative colloid suspensions 3000. A suitable plastic container 5000 (made of HDPE plastic) and a PEG-based polymer material 1000 therein.

The dialysis membrane, which forms the dialysis bag 2000, is characterized by molecular weight cut off (MWCO)—an approximate achieved threshold size above which larger-sized species will be retained inside of the membrane. Dialysis concentration was achieved by using a cellulose membrane having a 3.5 kDa MWCO for the dialysis bag 2000 and the polymer solution 1000 was made from a PEG-8000 polymer. Under these conditions, water molecules and small ions could pass through the dialysis membrane of the bag 2000, but colloidal nanoparticles larger than the 3.5 kDa MWCO would be retained inside the dialysis bag. However, PEG-8000 molecules cannot pass through (i.e., due to their size) the membrane and remained outside of the dialysis bag 2000.

FIG. 31b shows that the dialysis bag 2000 shrank in volume (over time) relative to its size in FIG. 31a. The dialysis bag 2000 should not be allowed to collapse as liquid is removed from the bag. In this regard, nanocrystals that may remain on the inner surface of the bag should not be over-stressed so as to prevent their possible aggregation.

Each dialysis bag 2000 was filled with approximately 400 to 500 mL of nanocrystal suspension 3000, and maintained in the PEG-8000 solution 1000 until the bag volume was reduced approximately 10 times in size and volume. Further suspension concentration, if required, occurred by combining 10× concentrated colloids from several bags into one bag and repeating the same set of concentration steps again. Dialysis bags 2000 can safely be used about 10 times without achieving any noticeable membrane fouling.

The starting PEG-8000 concentration 1000 in the polymer solution outside the dialysis bag 2000 was about 250 g/L and was naturally lowered in concentration due to water being drawn out from the colloid 3000 through the dialysis bags 2000 (i.e., due to the created osmotic pressure). Higher polymer concentrations and gentle stirring can increase the rate of water removal from the colloid 3000.

This dialysis process concentrated the gold colloids with no visible staining of the dialysis bags 2000. The concentration of remaining gold nanocrystals in suspension 4000 was estimated by volume reduction and also measured by ICP-MS techniques (discussed in detail later herein). The remaining gold in the suspension 4000 was similar to the gold concentration measured directly by ICP-MS techniques. However, in the case of the bi-metallic gold/platinum nanocrystal suspension, part of the platinum produced in the first electrochemical step was ionic, and some amount of this ionic form of platinum removal after the second electrochemical processing steps and passed through the dialysis bag 2000 during concentration. This effect resulted in a lower concentration factor for atomic platinum relative to atomic gold (all of the atomic gold was apparently in metallic form). In addition, the Au—Pt bi-metallic nanocrystal suspension slightly stained the membrane of the dialysis bag 2000 to a yellowish-green uniform color.

The dialysis bag technique was used to achieve a series of concentration ranges of two different colloidal suspensions that were used in a subsequent in-vitro cellular culture experiment. Specifically, Table 24 sets forth 9 different concentrations of metals in a formed gold suspension (NE10214) and in an Au/Pt bi-metallic suspension (GPB-032) the formations of which are described earlier herein. Concentration values were measured by inductively coupled plasma-mass spectrometry (ICP-MS) as described immediately below.

Inductively Coupled Plasma-Mass Spectometry (ICP-MS)

The ICP-MS values were obtained from an Agilent 7700x
I) Principle

The technique of inductively coupled plasma spectroscopy-mass spectrometry requires a liquid sample to be introduced into a sample chamber via a nebulizer, thus removing the larger droplets, and introducing a fine aerosol spray into the torch chamber carried via a supply of inert Argon gas. The torch temperature ranges between 8000K-10000K. The aerosol is instantly desolvated and ionized within the plasma and extracted into the first vacuum stage via the sampling cone and then subsequently passes through a second orifice, the skimmer cone. The ions are then collimated by the lens system and then focused by the ion optics.

The ion lenses allow the ICP-MS to achieve high signal sensitivity by preventing photons and neutral species from reaching the detector by mounting the quadrupole and detector off axis from the entering ion beam. The cell gas, Helium, is introduced into the ORS which is an octopole ion guide positioned between the ion lens assembly and the quadrupole. Interferences such as polyatomic species are removed via kinetic energy discrimination. The ions that pass through then proceed into the quadrupole mass analyzer which consists of four long metal rods. RF and DC voltages are applied at the rods and it is the variation in voltages that allow the rods to filter ions of specific mass-to-charge ratios.

The ions are then measured by the pulse analog detector. When an ion enters the electron multiplier, it strikes a dynode and creates an abundance of free electrons which then strike the next dynode, resulting in the creation of additional electrons. The amount of ions from a specific element correlates to the amount of electrons generated, thus resulting in more or less counts, or CPS.

II) Sample Preparation

Samples were prepared by diluting 500₄ of sample in 4.5 mL of 5% $HNO_3$/2% HCl for 30 minutes at 70° C. Samples were prepared in triplicate. Subsequently, samples were transferred to a polypropylene test tube which was then placed in a rack in the Cetac autosampler.

III) Instrument Setup

The Agilent ICP-MS 7700x plasma was turned on and a start up procedure was initialized. The plasma was allowed to warm up for 26 minutes prior to running the initial optimization. After successful completion of the optimization steps, the instrument was then ready for analysis. A quick manual tune was performed and the signal of low, mid, and high masses (59, 89, & 205) were checked to ensure that the instrument was within our internal specifications. Afterwards, the internal standard line tubing was switched from a 5% $HNO_3$ blank to an internal standard solution containing In 115.

IV) Analysis Procedure

Calibration samples and independent continuous concentration verification (ICCV) standards were prepared from external stock solutions prepared by SPEX CertiPrep. Multi-Element 3 calibration standards containing gold were serially diluted from 10 ppm to 1000 ppb, 100 ppb, 10 ppb, and 1 ppb, respectively. A blank solution of the diluent, 5% $HNO_3$/2% HCl, was used as the 0 ppb standard. The ICCV sample was placed in a sample vial and placed on a rack with the calibration standards.

Prior to sample analysis, a calibration curve was created by measuring 0 ppb, 1 ppb, 10 ppb, 100 ppb, & 1000 ppb. Samples of interest were then measured with a 90 second 5% $HNO_3$ rinse step in between sample uptake. After every 6 samples, the ICCV was run to ensure that the calibration curve was within 10% of the actual values.

V) Data Analysis

Data was exported from the Mass-hunter Data analysis software to excel to be formatted and checked. Replicates were averaged together to obtain a mean concentration, standard deviation and relative standard deviation.

TABLE 24

| | NE10214 Au | | | GPB-032 Au/Pt | |
|---|---|---|---|---|---|
| ID: | [Au], ppm | volume, mL | ID: | Au + Pt ppm | volume, mL |
| 1-1 | 981 | 10 | 2-1 | 982 | 3.2 |
| 1-2 | 800 | 10 | 2-2 | 800 | 3.5 |
| 1-3 | 600 | 10 | 2-3 | 600 | 4 |
| 1-4 | 400 | 10 | 2-4 | 400 | 4 |
| 1-5 | 200 | 10 | 2-5 | 385 | 5.2 |
| 1-6 | 80 | 10 | 2-6 | 180 | 4.5 |
| 1-7 | 40 | 10 | 2-7 | 40 | 4 |
| 1-8 | 20 | 10 | 2-8 | 20 | 4 |
| 1-9 | 8 | 10 | 2-9 | 8 | 4 |
| 1-10 | blank control | 10 | 2-10 | blank control | 4 |

Example 19

In Vitro Cancer Cell Line Efficacy Comparison Between Concentrated Au Suspension (NE10214) and Concentrated Au/Pt Bi-Metallic Suspension (GPB-032)

A cell line panel was assembled with 30 different human tumor types selected from the ATCC and DSMZ (all DSMZ cell lines are marked with "**") culture banks and included typical bladder, breast, cervix, CNS, colon, H&N, lung, ovary, prostate, stomach, thyroid, uterus and vulva cancers. The 30 specific cell lines and tumor types are set forth in Table 25.

TABLE 25

| CAT # | Cell Line | Morphology | Cancer Type | Organ |
|---|---|---|---|---|
| ACC 414 | 647-V | Epithelial | Bladder | Bladder** |
| ACC 279 | BHT-101 | Epithelial | Endocrine | Thyroid** |
| HTB-20 | BT474 | Epithelial | Breast | Breast |
| CRL-2273 | CHP-212 | Neuroblast | CNS | CNS |
| CRL-2062 | DMS53 | Small cell | Lung | SCLC |
| ACC 231 | EFM-19 | Epithelioid | Breast | Breast** |
| ACC 317 | KPL-1 | N/A | Breast | Breast** |
| ACC 403 | MT-3 | Epithelial | Breast | Breast** |
| HTB-178 | NC1-H596 | Epithelial | Lung | Lung |

TABLE 25-continued

| CAT # | Cell Line | Morphology | Cancer Type | Organ |
|---|---|---|---|---|
| HTB-3 | SCaBER | Epithelial | Bladder | Bladder |
| HTB-58 | SKMES1 | Squamous Cell | Lung | Lung |
| HTB-13 | SW1783 | Fibroblast | CNS | CNS |
| ACC 291 | U-138MG | Fibroblastoid | CNS | Glioblastoma** |
| CRL-2505 | 22Rv1 | Epithelial | Prostate | Prostate |
| ACC 143 | BPH1 | Epithelioid | Prostate | Prostate** |
| HTB-54 | Calu1 | Squamous Cell | Lung | Lung |
| HTB-75 | CaOV3 | Epithelial | Female GU | Ovary |
| CCL-138 | Detroit 562 | Epithelial | Head & Neck | H&N |
| CRL-7920 | DoTc2 4510 | Epithelial | Female GU | Cervix |
| HTB-81 | DU145 | Epithelial | Prostate | Prostate |
| HTB-135 | HS 746T | Epithelial | Colon/GI | Stomach |
| HTB-32 | HT-3 | Epithelial | Female GU | Cervix |
| CCL-253 | NCI-H508 | Epithelial | Colon/GI | Colon |
| CRL-1671 | RL95-2 | Epithelial | Female GU | Uterus |
| CRL-1628 | SCC-25 | Epithelial | Head & Neck | H&N |
| HTB-77 | SKOV3 | Epithelial | Female GU | Ovary |
| CCL-238 | SW1417 | Epithelial | Colon/GI | Colon |
| CCL-235 | SW837 | Epithelial | Colon/GI | Colon |
| HTB-117 | SW 954 | Epithelial | Female GU | Vulva |
| HTB-118 | SW 962 | Mixed | Female GU | Vulva |

Experimental Procedure:

Cells were grown in RPMI1640, 10% FBS, 2 mM L-alanyl-L-Glutamine, 1 mM Na Pyruvate in a humidified atmosphere of 5% $CO_2$ at 37° C. Cells were seeded into 384-well plates and incubated in a humidified atmosphere of 5% $CO_2$ at 37° C. Compounds NE10214 and GPB-032 were added 24 hours post cell seeding. At the same time, a time zero untreated cell plate was generated.

After a 72 hour incubation period, cells were fixed and stained with fluorescently labeled antibodies and nuclear dye to allow visualization of nuclei, apoptotic cells and mitotic cells. Apoptotic cells were detected using an anti-active caspase-3 antibody. Mitotic cells were detected using an anti phospho-histone-3 antibody.

The concentrated Au suspension (NE10214, also "Compound 1") and the concentrated bi-metallic suspension AuPt (GPB-032, also "Compound 2") were diluted as shown in Table 26 below and assayed over 9 concentrations from the highest test concentration to the lowest test concentration. When the two test compounds were added to the growth medium they became diluted by the growth media. The actual atomic concentrations of the metallic components (i.e., Au in NE10214; and Au+Pt in GPB-032) in the growth media are shown in Table 26 as "In Vitro Conc microM".

Automated fluorescence microscopy was carried out using a GE Healthcare IN Cell Analyzer 1000, and images were collected with a 4× objective.

TABLE 26

Initial and In Vitro Concentrations

| Compound 1 (NE10214) | | | Compound 2 (GPB-032) | | |
|---|---|---|---|---|---|
| sample ID | initial conc., ppm | In Vitro Conc microM | sample ID | initial conc., ppm | In Vitro Conc microM |
| 1-1 | 981 | 701 | 2-1 | 982 | 701 |
| 1-2 | 800 | 571 | 2-2 | 800 | 571 |
| 1-3 | 600 | 429 | 2-3 | 600 | 429 |
| 1-4 | 400 | 286 | 2-4 | 400 | 286 |
| 1-5 | 200 | 143 | 2-5 | 385 | 275 |
| 1-6 | 80 | 57 | 2-6 | 180 | 129 |
| 1-7 | 40 | 29 | 2-7 | 40 | 29 |
| 1-8 | 20 | 14 | 2-8 | 20 | 14 |
| 1-9 | 8 | 5.7 | 2-9 | 8 | 5.7 |
| 1-10 | vehicle | vehicle | 2-10 | vehicle | vehicle |

Data Analysis

Twelve bit tiff images were acquired using the InCell Analyzer 1000 3.2 and analyzed with Developer Toolbox 1.6 software. $EC_{50}$ and $IC_{50}$ values were calculated using nonlinear regression to fit data to a sigmoidal 4 point, 4 parameter One-Site dose response model, where: y (fit)=A+[(B−A)/(1+ ((C/x)^D))]. Curve-fitting, $EC_{50}/IC_{50}$ calculations and report generation are performed using a custom data reduction engine MathIQ based software (AIM).

TABLE 27

Summary table for vehicle background

| Plate # | Cell line | Relative cell count (POC) | | | Apoptosis (fold induction) | | | Mitosis (fold induction) | | | Doublings |
|---|---|---|---|---|---|---|---|---|---|---|---|
| | | Mean | StdDev | CV | Mean | StdDev | CV | Mean | StdDev | CV | |
| 4 | HS 746T | 100.00 | 3.40 | 0.03 | 1.00 | 0.21 | 0.21 | 1.00 | 0.28 | 0.28 | 2.17 |
| 4 | NCI-H596 | 100.00 | 4.07 | 0.04 | 1.00 | 0.30 | 0.30 | 0.98 | 0.61 | 0.62 | 2.08 |
| 4 | NCI-H508 | 100.00 | 3.20 | 0.03 | 1.00 | 0.26 | 0.26 | 1.00 | 0.15 | 0.15 | 2.92 |
| 4 | HT-3 | 100.00 | 2.68 | 0.03 | 0.99 | 0.28 | 0.28 | 0.99 | 0.17 | 0.17 | 2.50 |
| 4 | KPL-1 | 100.00 | 8.31 | 0.08 | 1.01 | 0.59 | 0.59 | 1.01 | 0.18 | 0.18 | 2.40 |
| 4 | EFM-19 | 100.00 | 6.45 | 0.06 | 1.00 | 0.26 | 0.26 | 1.00 | 0.15 | 0.15 | 1.10 |
| 4 | DU145 | 100.00 | 3.35 | 0.03 | 1.00 | 0.44 | 0.44 | 1.00 | 0.10 | 0.10 | 3.07 |
| 4 | SKMES1 | 100.00 | 3.81 | 0.04 | 1.00 | 0.45 | 0.45 | 1.00 | 0.12 | 0.12 | 3.46 |
| 4 | SKOV3 | 100.00 | 3.14 | 0.03 | 1.00 | 0.24 | 0.24 | 1.00 | 0.16 | 0.16 | 1.47 |
| 4 | SW837 | 100.00 | 6.10 | 0.06 | 1.01 | 0.25 | 0.25 | 1.00 | 0.15 | 0.15 | 2.26 |
| 4 | SCaBER | 100.00 | 3.07 | 0.03 | 1.00 | 0.38 | 0.38 | 1.00 | 0.17 | 0.17 | 3.29 |
| 4 | U-138MG | 100.00 | 2.89 | 0.03 | 1.00 | 0.45 | 0.45 | 0.99 | 0.24 | 0.25 | 2.63 |
| 4 | MT-3 | 100.00 | 6.96 | 0.07 | 1.00 | 0.29 | 0.29 | 1.00 | 0.12 | 0.12 | 3.16 |
| 4 | RL95-2 | 100.00 | 4.68 | 0.05 | 1.00 | 0.30 | 0.30 | 1.00 | 0.13 | 0.13 | 1.76 |
| 4 | SCC-25 | 100.00 | 5.11 | 0.05 | 1.01 | 0.36 | 0.36 | 1.00 | 0.14 | 0.14 | 3.08 |
| 4 | SW962 | 100.00 | 5.43 | 0.05 | 1.01 | 0.32 | 0.32 | 1.00 | 0.29 | 0.29 | 1.99 |
| 4 | SW954 | 100.00 | 6.77 | 0.07 | 1.00 | 0.26 | 0.26 | 1.00 | 0.15 | 0.15 | 2.37 |
| 4 | 647-V | 100.00 | 5.46 | 0.05 | 1.00 | 0.30 | 0.30 | 1.00 | 0.12 | 0.12 | 4.05 |
| 4 | BHT-101 | 100.00 | 6.02 | 0.06 | 0.99 | 0.32 | 0.32 | 1.00 | 0.13 | 0.13 | 3.89 |

TABLE 27-continued

Summary table for vehicle background

| Plate # | Cell line | Relative cell count (POC) | | | Apoptosis (fold induction) | | | Mitosis (fold induction) | | | Doublings |
|---|---|---|---|---|---|---|---|---|---|---|---|
| | | Mean | StdDev | CV | Mean | StdDev | CV | Mean | StdDev | CV | |
| 4 | BPH1 | 100.00 | 4.60 | 0.05 | 1.00 | 0.28 | 0.28 | 1.00 | 0.13 | 0.13 | 3.73 |
| 4 | SW1783 | 100.00 | 4.26 | 0.04 | 1.00 | 0.30 | 0.30 | 1.00 | 0.26 | 0.26 | 1.55 |
| 4 | SW1417 | 100.00 | 2.70 | 0.03 | 1.00 | 0.23 | 0.23 | 1.00 | 0.13 | 0.13 | 1.92 |
| 4 | 22Rv1 | 100.00 | 6.12 | 0.06 | 1.00 | 0.27 | 0.26 | 1.00 | 0.11 | 0.11 | 2.40 |
| 4 | DoTc2 4510 | 100.00 | 7.65 | 0.08 | 1.01 | 0.28 | 0.28 | 1.00 | 0.12 | 0.12 | 2.21 |
| 4 | DMS53 | 100.00 | 2.22 | 0.02 | 1.00 | 0.38 | 0.38 | 1.00 | 0.12 | 0.12 | 1.81 |
| 4 | CaOV3 | 100.00 | 3.09 | 0.03 | 1.00 | 0.19 | 0.19 | 1.00 | 0.12 | 0.12 | 1.94 |
| 4 | Detroit 562 | 100.00 | 9.02 | 0.09 | 1.01 | 0.22 | 0.22 | 1.01 | 0.15 | 0.15 | 3.13 |
| 4 | BT474 | 100.00 | 1.41 | 0.01 | 1.00 | 0.34 | 0.34 | 1.00 | 0.23 | 0.23 | 1.36 |
| 4 | Calu1 | 100.00 | 2.60 | 0.03 | 1.00 | 0.55 | 0.55 | 1.00 | 0.15 | 0.15 | 2.41 |
| 4 | CHP-212 | 100.00 | 3.05 | 0.03 | 1.00 | 0.26 | 0.26 | 1.00 | 0.18 | 0.18 | 2.55 |

TABLE 28

Performance Summary for Compounds 1 (NE10214) and 2 (GPB-032)

| Plate # | Compound | Cell line | Relative cell count EC50 (ppm) | Relative cell count IC50 (ppm) | Apoptosis 5X Fold Induction (ppm) | Max Apoptosis Fold Induction | G2/M cell cycle block (ppm) | G1/S cell cycle block (ppm) | Max G2/M cell cycle block |
|---|---|---|---|---|---|---|---|---|---|
| 4 | 1 | SW1417 | >9.81E+02 | >9.81E+02 | N/A | 1.20 | N/A | N/A | 0.96 |
| 4 | 1 | SW1783* | 6.37E+02* | 6.37E+02* | N/A | 0.82 | N/A | 6.65E+01* | 0.80 |
| 4 | 1 | 22Rv1 | >9.81E+02 | >9.81E+02 | N/A | 1.33 | N/A | N/A | 0.95 |
| 4 | 1 | 647-V | >9.81E+02 | >9.81E+02 | N/A | 2.10 | N/A | N/A | 0.91 |
| 4 | 1 | SW954* | 2.44E+02* | 2.94E+02* | N/A | 0.97 | N/A | 7.63E+01* | 1.05 |
| 4 | 1 | SW962 | 8.00E+02 | 8.00E+02 | N/A | 0.65 | N/A | N/A | 1.40 |
| 4 | 1 | BHT-101* | 7.52E+02* | 7.52E+02* | N/A | 2.75 | N/A | 7.67E+02* | 0.98 |
| 4 | 1 | BPH1 | >9.81E+02 | >9.81E+02 | N/A | 1.65 | N/A | N/A | 0.95 |
| 4 | 1 | BT474 | >9.81E+02 | >9.81E+02 | N/A | 2.48 | N/A | N/A | 0.97 |
| 4 | 1 | Calu1* | 5.27E+02* | 5.27E+02* | N/A | 2.53 | N/A | 1.05E+02* | 0.83 |
| 4 | 1 | CHP-212* | 4.37E+02* | 4.37E+02* | N/A | 1.02 | N/A | N/A | 1.02 |
| 4 | 1 | CaOV3 | >9.81E+02 | >9.81E+02 | N/A | 1.35 | N/A | N/A | 1.45 |
| 4 | 1 | DoTc2 4510 | >9.81E+02 | >9.81E+02 | N/A | 1.42 | N/A | N/A | 0.88 |
| 4 | 1 | DMS53 | >9.81E+02 | >9.81E+02 | N/A | 2.02 | N/A | N/A | 0.86 |
| 4 | 1 | Detroit 562* | 2.30E+02* | 8.65E+02 | N/A | 1.33 | N/A | 6.96E+02* | 1.00 |
| 4 | 1 | DU145 | 8.88E+02 | 8.88E+02 | N/A | 2.86 | N/A | N/A | 0.92 |
| 4 | 1 | EFM-19* | 1.71E+02* | 1.71E+02* | N/A | 1.90 | N/A | 5.56E+02* | 1.22 |
| 4 | 1 | SKMES1* | 6.60E+02* | 6.60E+02* | N/A | 1.63 | N/A | N/A | 0.97 |
| 4 | 1 | NCI-H508 | >9.81E+02 | >9.81E+02 | N/A | 1.06 | N/A | 9.21E+02 | 1.01 |
| 4 | 1 | NCI-H596 | >9.81E+02 | >9.81E+02 | N/A | 1.08 | N/A | N/A | 1.81 |
| 4 | 1 | HS 746T* | 5.02E+02* | 5.02E+02* | N/A | 0.88 | N/A | 1.23E+02* | 1.08 |
| 4 | 1 | HT-3 | >9.81E+02 | >9.81E+02 | N/A | 0.80 | N/A | N/A | 1.01 |
| 4 | 1 | KPL-1 | 9.02E+02 | 9.02E+02 | N/A | 3.54 | N/A | 8.09E+02 | 1.31 |
| 4 | 1 | MT-3 | >9.81E+02 | >9.81E+02 | N/A | 0.83 | N/A | N/A | 1.03 |
| 4 | 1 | RL95-2 | >9.81E+02 | >9.81E+02 | N/A | 1.48 | N/A | N/A | 0.96 |
| 4 | 1 | SCC-25* | 4.60E+02* | 4.60E+02* | N/A | 1.52 | N/A | 9.39E+01* | 0.84 |
| 4 | 1 | SCaBER* | 6.20E+01* | >9.81E+02 | N/A | 1.12 | N/A | N/A | 0.85 |
| 4 | 1 | SKOV3* | >9.81E+02 | >9.81E+02 | N/A | 0.83 | N/A | 2.66E+02* | 1.20 |
| 4 | 1 | SW837 | >9.81E+02 | >9.81E+02 | N/A | 1.01 | N/A | 8.14E+02 | 0.80 |
| 4 | 1 | U-138MG* | 6.35E+02* | >9.81E+02 | N/A | 0.99 | N/A | 7.97E+01* | 0.75 |
| 4 | 2 | SW1417 | 9.54E+02 | 9.54E+02 | N/A | 1.39 | N/A | N/A | 0.95 |
| 4 | 2 | SW1783 | >9.82E+02 | >9.82E+02 | N/A | 1.06 | N/A | 5.91E+02* | 0.92 |
| 4 | 2 | 22Rv1* | 4.75E+02* | 4.75E+02* | 6.08E+02* | 4.77* | N/A | 5.58E+02* | 0.89 |
| 4 | 2 | 647-V | >9.82E+02 | >9.82E+02 | N/A | 4.89 | N/A | N/A | 0.90 |
| 4 | 2 | SW954* | 5.22E+02* | 5.22E+02* | N/A | 1.15 | N/A | N/A | 0.87 |
| 4 | 2 | SW962* | 5.25E+02* | 5.25E+02* | 5.98E+02* | 5.39* | 5.81E+02* | N/A | 4.09* |
| 4 | 2 | BHT-101* | 5.83E+02* | 5.83E+02* | 8.67E+02* | 7.34* | N/A | N/A | 1.00 |
| 4 | 2 | BPH1* | 5.80E+02* | 5.80E+02* | N/A | 2.85 | N/A | 8.28E+02 | 0.92 |
| 4 | 2 | BT474* | 7.28E+02* | 7.28E+02* | 5.91E+02* | 6.70* | N/A | N/A | 1.01 |
| 4 | 2 | Calu1* | 4.36E+02* | 4.36E+02* | N/A | 3.40 | N/A | N/A | 0.87 |
| 4 | 2 | CHP-212* | 5.11E+02* | 5.11E+02* | N/A | 1.60 | N/A | 6.77E+02* | 0.88 |
| 4 | 2 | CaOV3* | 5.64E+02* | 5.74E+02* | 9.67E+02* | 5.21* | 5.90E+02* | N/A | 3.64* |
| 4 | 2 | DoTc2 4510* | 4.54E+02* | 4.54E+02* | 5.89E+02* | 5.59* | N/A | N/A | 0.95 |
| 4 | 2 | DMS53 | >9.82E+02 | >9.82E+02 | N/A | 2.86 | N/A | N/A | 0.86 |
| 4 | 2 | Detroit 562* | 5.32E+02* | 5.63E+02* | N/A | 2.71 | N/A | 5.50E+02* | 0.97 |
| 4 | 2 | DU145* | 4.57E+02* | 4.60E+02* | 4.82E+02* | 35.16* | N/A | N/A | 1.07 |
| 4 | 2 | EFM-19* | 1.10E+02* | 1.10E+02* | N/A | 3.83 | N/A | 5.60E+02* | 7.50* |
| 4 | 2 | SKMES1* | 6.86E+02* | 6.86E+02* | N/A | 1.68 | N/A | 8.77E+02* | 0.97 |
| 4 | 2 | NCI-H508* | 8.79E+02* | 8.79E+02* | N/A | 1.56 | N/A | 7.84E+02* | 0.99 |
| 4 | 2 | NCI-H596 | >9.82E+02 | >9.82E+02 | N/A | 1.50 | N/A | N/A | 1.90 |
| 4 | 2 | HS 746T* | 4.25E+02* | >9.82E+02 | N/A | 0.96 | N/A | N/A | 1.02 |

TABLE 28-continued

Performance Summary for Compounds 1 (NE10214) and 2 (GPB-032)

| Plate # | Compound | Cell line | Relative cell count EC50 (ppm) | Relative cell count IC50 (ppm) | Apoptosis 5X Fold Induction (ppm) | Max Apoptosis Fold Induction | G2/M cell cycle block (ppm) | G1/S cell cycle block (ppm) | Max G2/M cell cycle block |
|---|---|---|---|---|---|---|---|---|---|
| 4 | 2 | HT-3* | 5.71E+02* | 5.71E+02* | N/A | 2.49 | N/A | 4.58E+02* | 1.11 |
| 4 | 2 | KPL-1* | 9.00E+02 | 9.00E+02 | 3.51E+02* | 14.20* | N/A | 9.21E+02* | 1.30 |
| 4 | 2 | MT-3 | 9.35E+02 | 9.35E+02 | N/A | 2.63 | N/A | N/A | 1.07 |
| 4 | 2 | RL95-2* | 4.99E+02* | 5.01E+02* | N/A | 2.96 | 5.28E+02* | N/A | 6.80* |
| 4 | 2 | SCC-25* | 4.89E+02* | 4.89E+02* | N/A | 1.28 | N/A | N/A | 1.01 |
| 4 | 2 | SCaBER* | 7.40E+02* | 7.40E+02* | N/A | 1.29 | N/A | 6.52E+02* | 0.91 |
| 4 | 2 | SKOV3 | >9.82E+02 | >9.82E+02 | N/A | 2.28 | N/A | N/A | 0.94 |
| 4 | 2 | SW837* | 5.69E+02* | 5.69E+02* | N/A | 1.00 | 7.43E+02* | N/A | 2.22* |
| 4 | 2 | U-138MG* | >9.82E+02 | >9.82E+02 | N/A | 1.11 | N/A | 5.29E+02* | 0.88 |

An "*" in column 3 "Cell Line" indicates significant anti-cancer activity in that tumor cell line.
An "*" in columns 4 and 5 "Relative Cell Count" indicates significant cell count reduction and anti-cancer activity.
An "*" in columns 6 and 7 "Apoptosis" indicates significant anti-cancer activity.
An "*" in columns 8, 9 or 10 "Cell Cycle" indicated significant mitotic anti-cancer activity.

Data Interpretation

The multiplexed cytotoxicity assay used a cell image based analysis technique where cells were fixed and stained with fluorescently labeled antibodies and nuclear dye as mentioned above.

Cell proliferation was measured by the signal intensity of the incorporated nuclear dye. The cell proliferation assay output is referred to as the relative cell count. To determine the cell proliferation end point, the cell proliferation data output was transformed to percent of control (POC) using the following formula:

POC=relative cell count(compound wells)/relative cell count(vehicle wells)×100

Relative cell count $IC_{50}$ is the test compound concentration at 50% of maximal possible response. A relative cell count $EC_{50}$ is the test compound concentration at the curve inflection point or half the effective response (parameter C of the fitted curve solution). $GI_{50}$ is the concentration needed to reduce the observed growth by half. This is the concentration that inhibits the growth midway between untreated cells and the number of cells seeded in the well (Time zero value).

Time zero non-treated plate is used to determine number of doublings in 72 hour assay period: Number of doublings in 72 hours=LN[Cell number(72 hrs end point)*Cell number (time zero)]/LN(2)

The output of each biomarker is fold increase over vehicle background normalized to the relative cell count in each well.

The activated caspase-3 marker labels cells from early to late stage apoptosis. The output is shown as a fold increase of apoptotic cells over vehicle background normalized to the relative cell count in each well. Concentrations of test compound that cause a 5-fold induction in the caspase-3 signal indicates significant apoptosis induction. Wells with concentrations higher than the relative cell count $IC_{95}$ are eliminated from the caspase3 induction analysis.

The phospho-histone-3 marker labels mitotic cells. The output is shown as a fold induction of mitotic cells over vehicle background normalized to the relative cell count in each well. When the fold induction of mitotic cell signal over background is ~1, there is "no effect" on the cell cycle. Two or more fold increase in phospho-histone-3 signal over vehicle background indicates significant test compound induction of mitotic block.

Two or more fold decrease in the phospho-histone-3 signal may indicate G1/S block only when cytotoxicity levels are below the measured relative cell count $IC_{95}$. When 2 or more fold decrease in the phospho-histone-3 signal are observed at concentrations higher than the relative cell count $IC_{95}$, the decrease in mitotic cell counts are most likely due to a more general cytotoxicity effect rather than a true G1/S phase block. Wells with concentrations higher than the relative cell count $IC_{95}$ are eliminated from the phospho-histone-3 analysis.

Criteria for Positive Responses
Cell proliferation measured by relative cell counts
Apoptosis:
>5-fold increase in activated caspase-3 signal indicates an apoptotic response
Mitosis:
>2-fold increase in phospho-histone-3 indicates mitotic block
<2-fold decrease in phospho-histone-3 indicates G1/S block Because the compounds are at relatively low concentration levels in vitro, most concentrations provided were too low to obtain IC50 results. As concentration levels increase, activity becomes clearly apparent with both compounds in many of the tumor cell lines tested. Table 28 entitled, "Performance Summary for Compounds 1 (NE10214) and 2 (GPB-032)" above highlights in Column 3 ("Cell Line") a "*" for each tumor cell line where significant anti-cancer activity was demonstrated for each compound/cell line combination.

Results

The data summarized in Table 28 clearly demonstrate significant anti-cancer activity in response to treatment with the concentrated Au suspension (NE10214) in 13 of 30 tumor cell lines tested, and in 23 of the 30 tumor cell lines treated with the concentrated Au—Pt bi-metallic suspension (GPB-032).

Equally important, the concentrated Au suspension and the concentrated Au—Pt bi-metallic suspension show distinctly different patterns of the presence of anti-cancer activity, and distinctly different patterns of the type of anti-cancer activity, across the thirty different tumor cell lines.

Figures 32A, 32B:
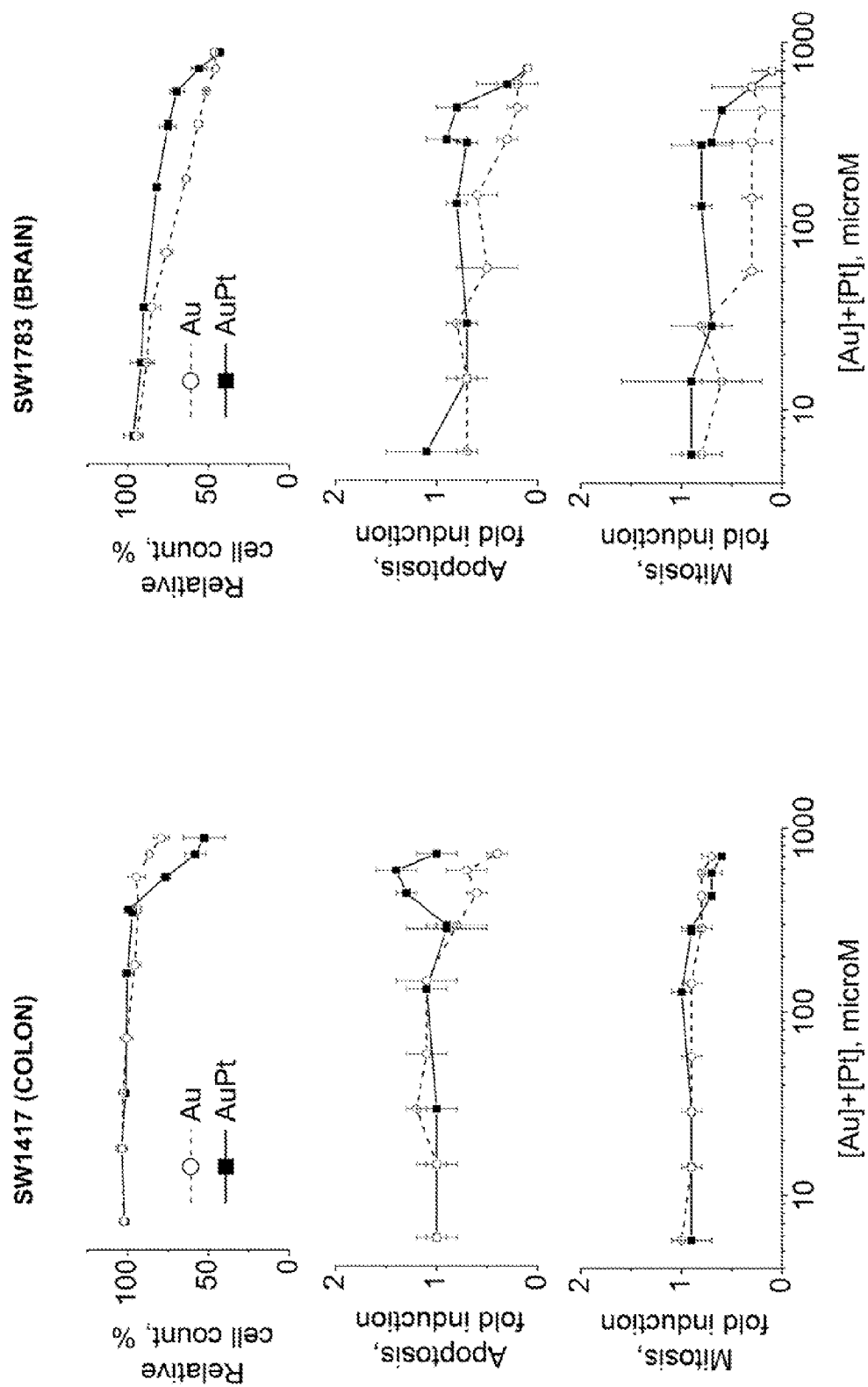
FIGS. 32a-32ad are graphical depictions of anti-cancer activity of two suspensions (NE10214 and a bi-metallic nanocrystal suspension, GPB-032).
Figures 32C, 32D:
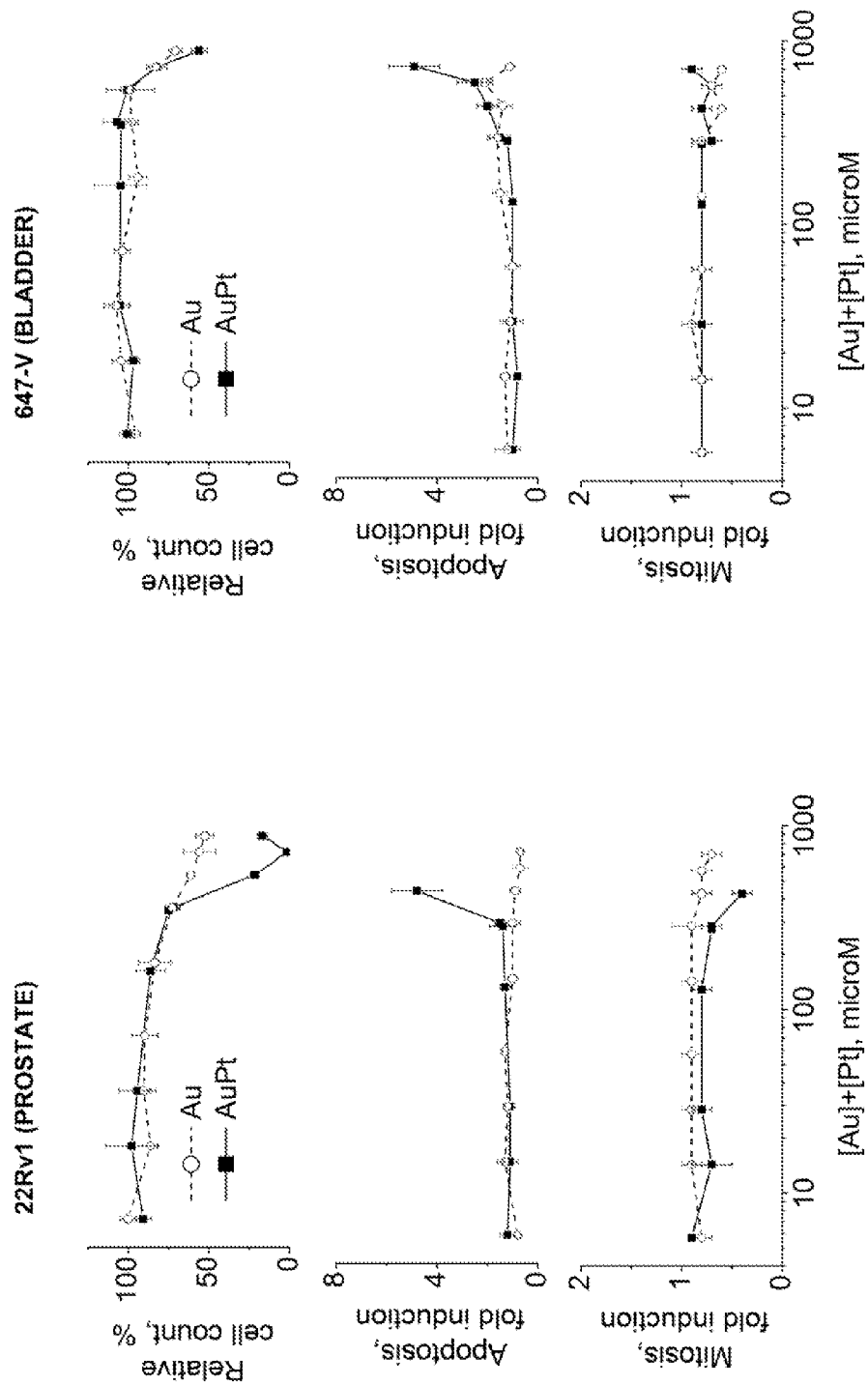
Figure 32F:
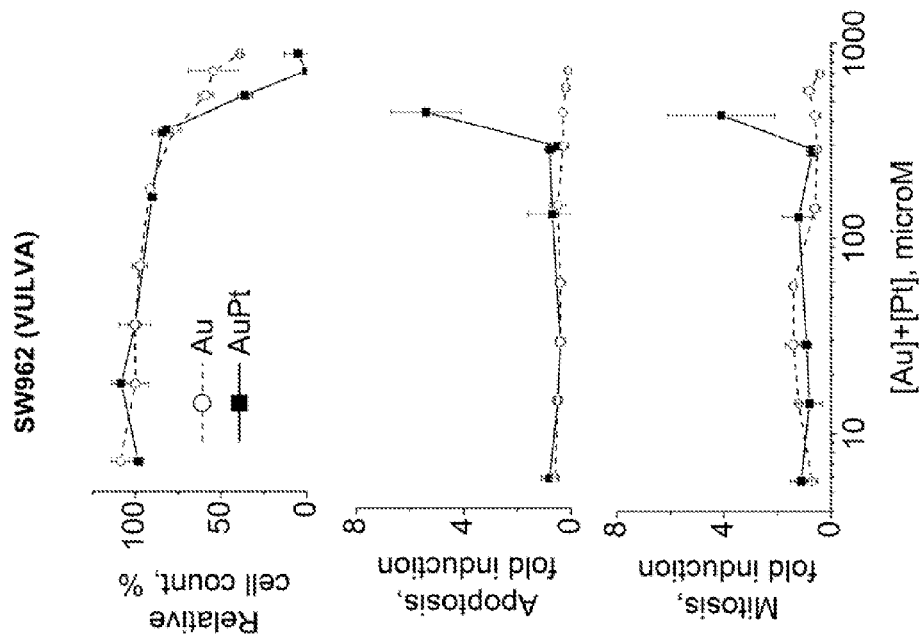
Figure 32E:
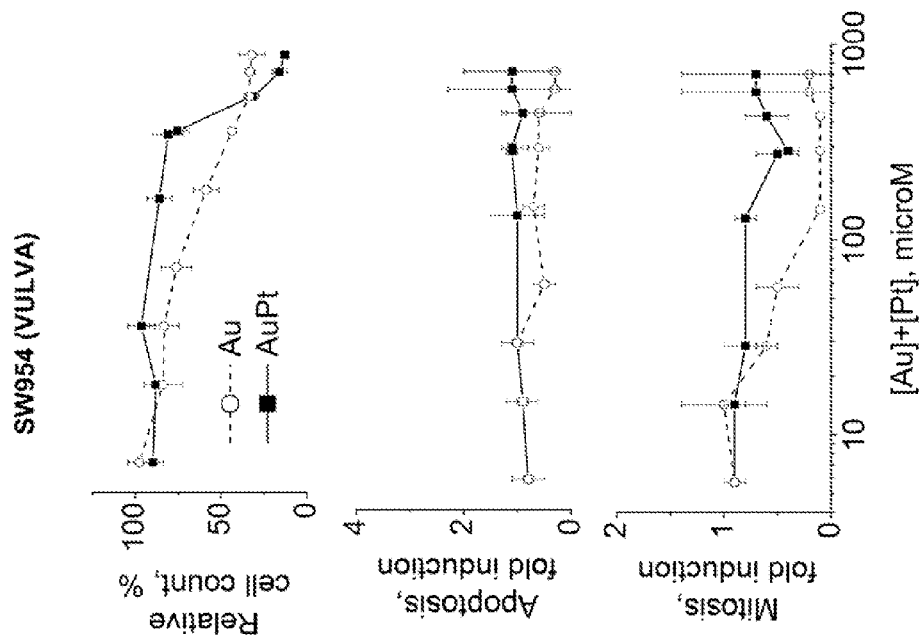
Figures 32G, 32H:
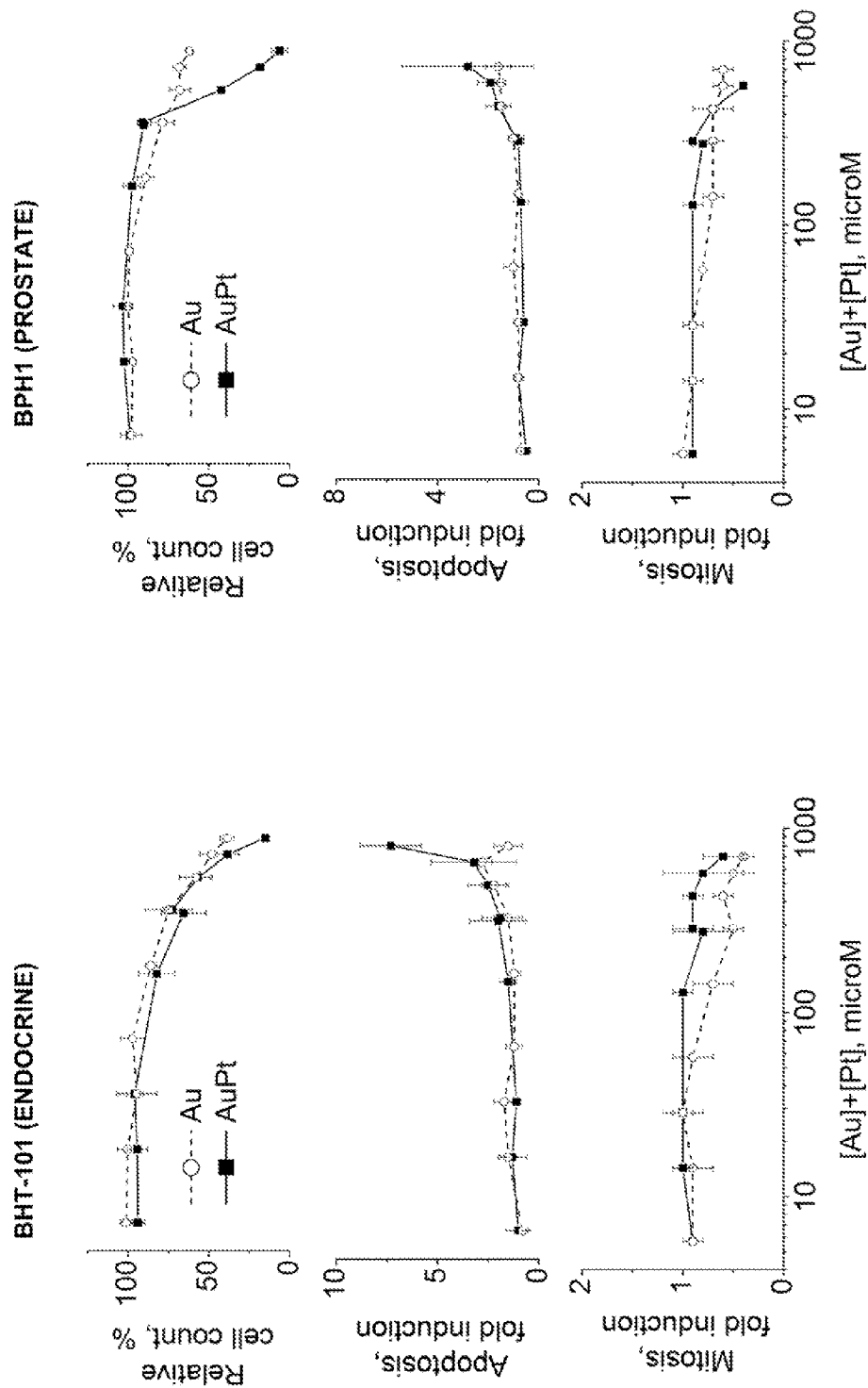
Figure 32J:
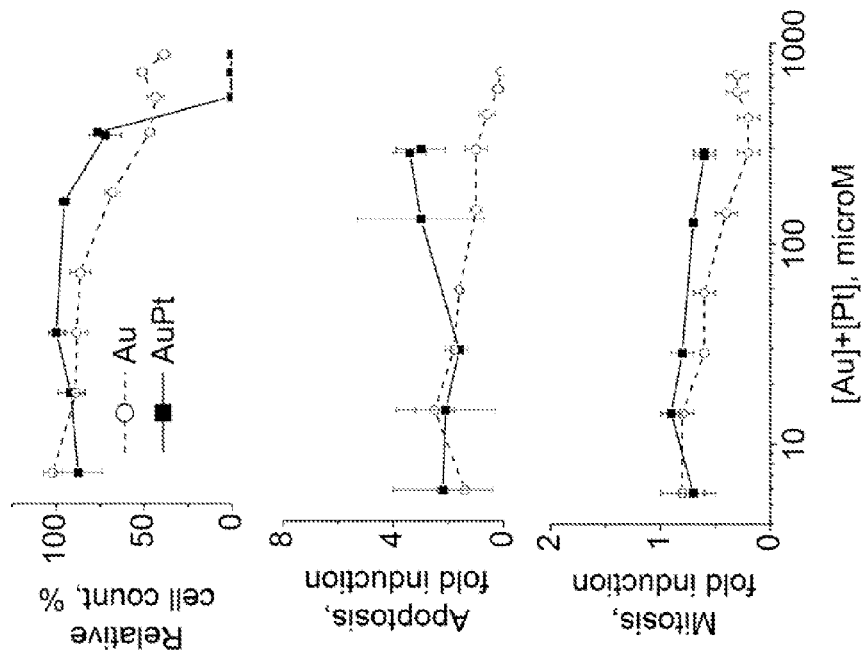
Figure 32I:
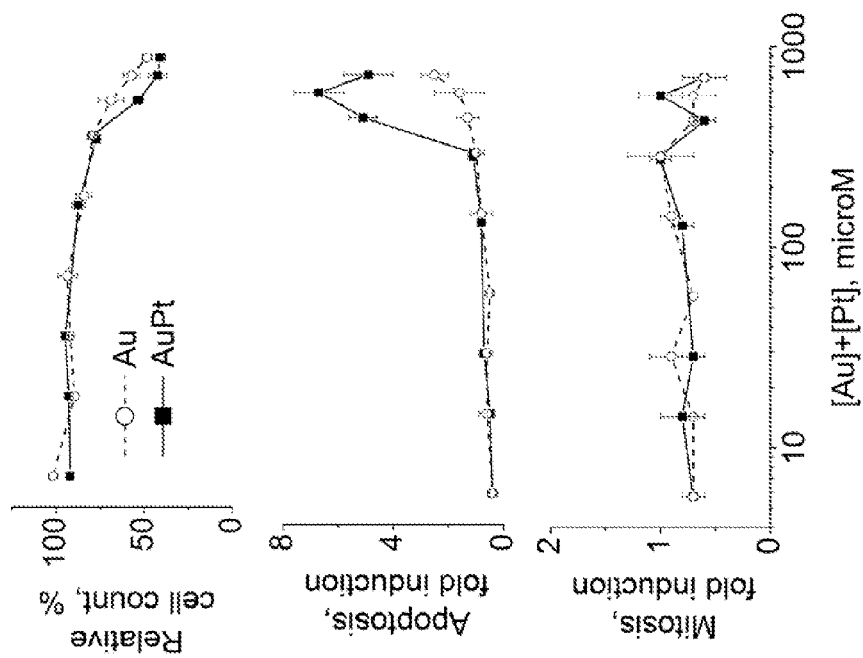
Figures 32J, 32K:
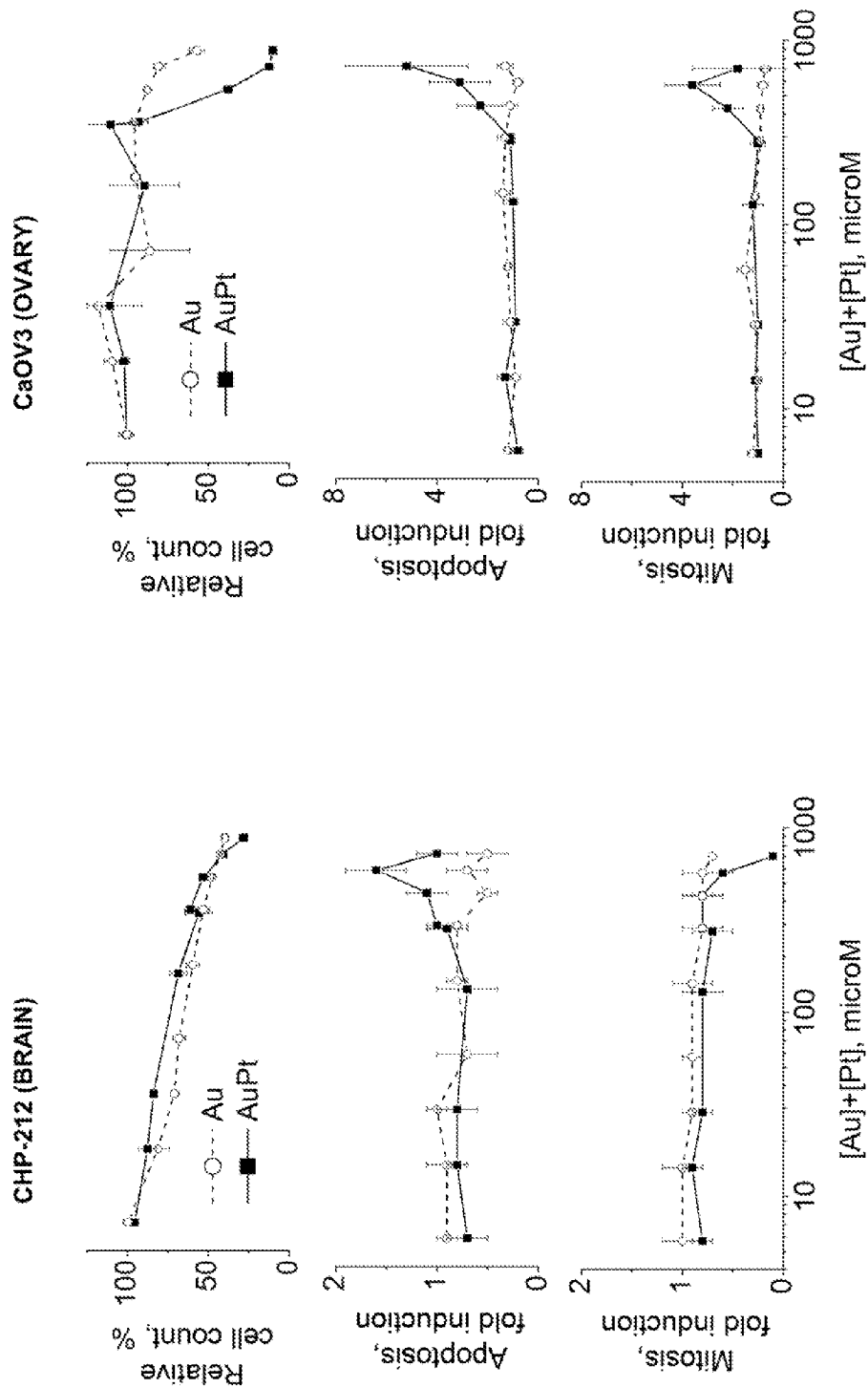
Figure 32M:
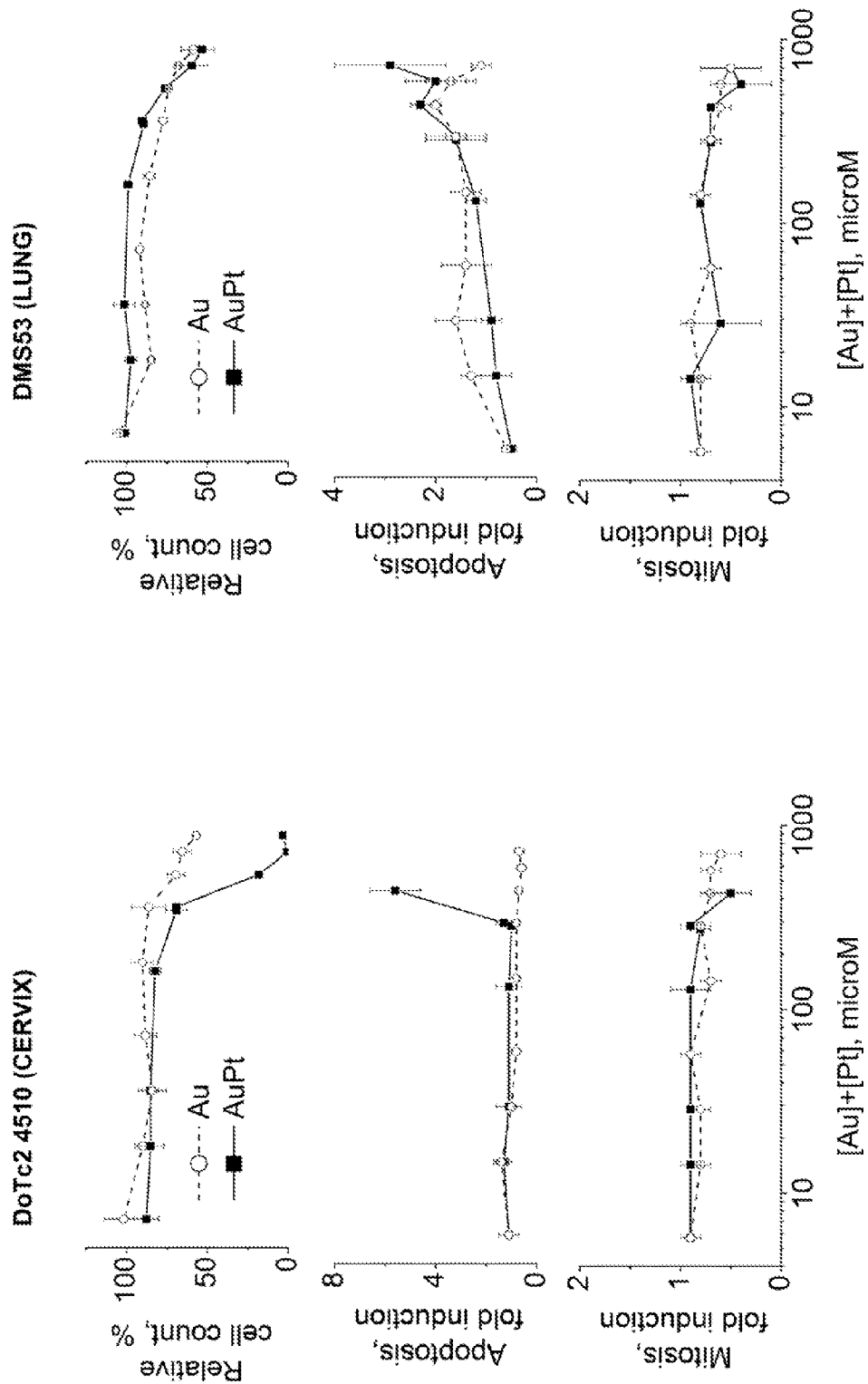
Figures 32O, 32P:
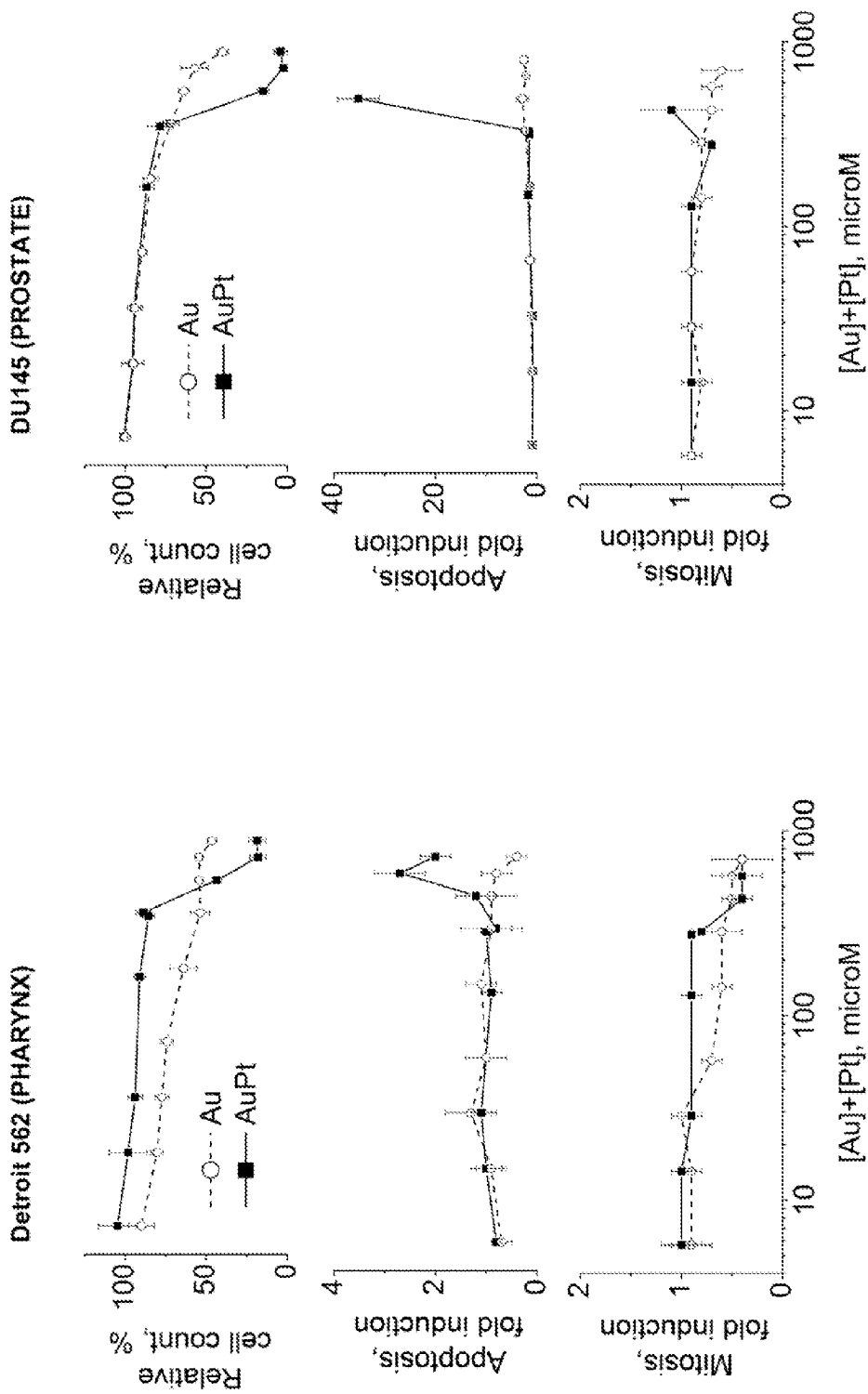
Figures 32Q, 32R:
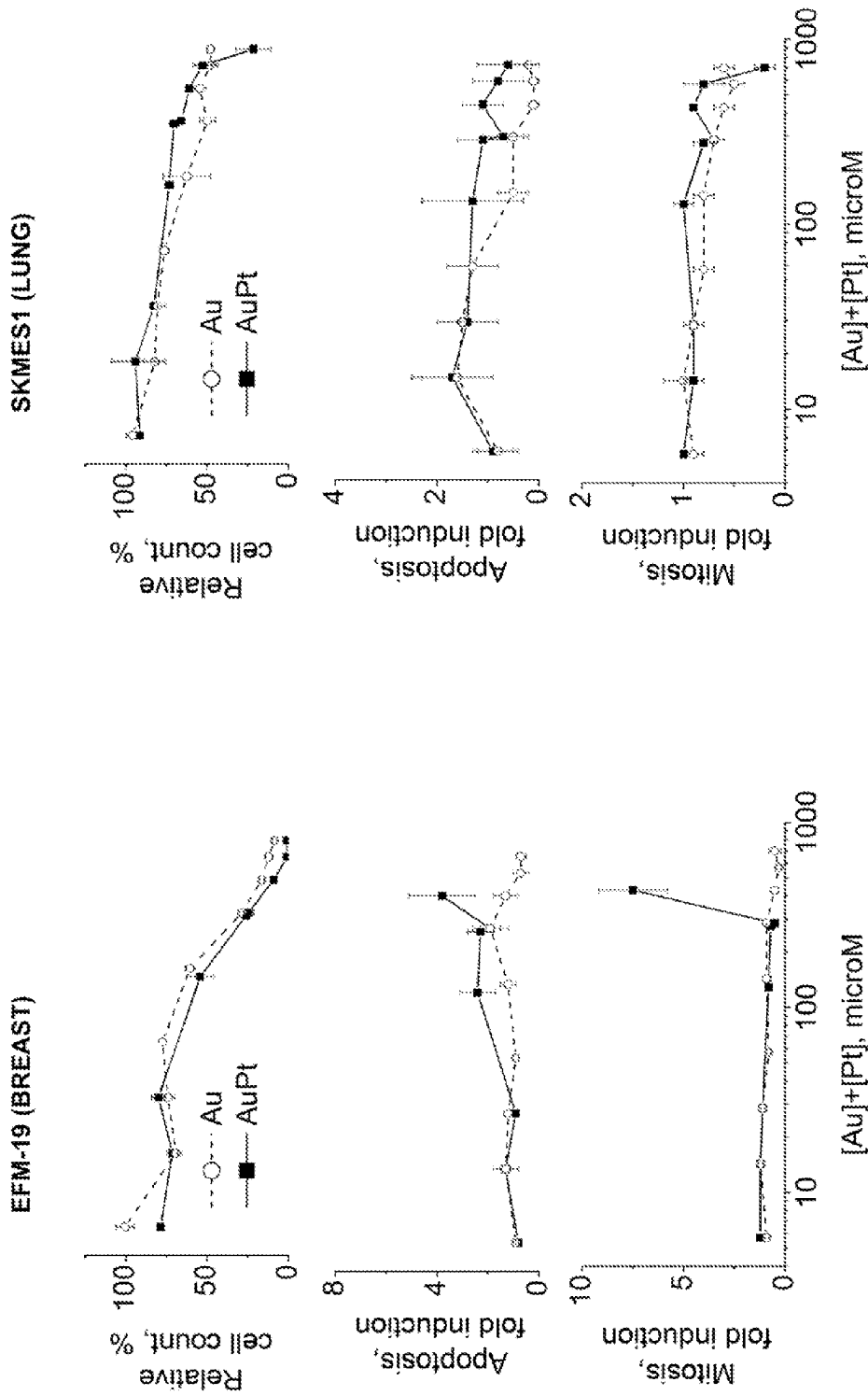
Figure 32T:
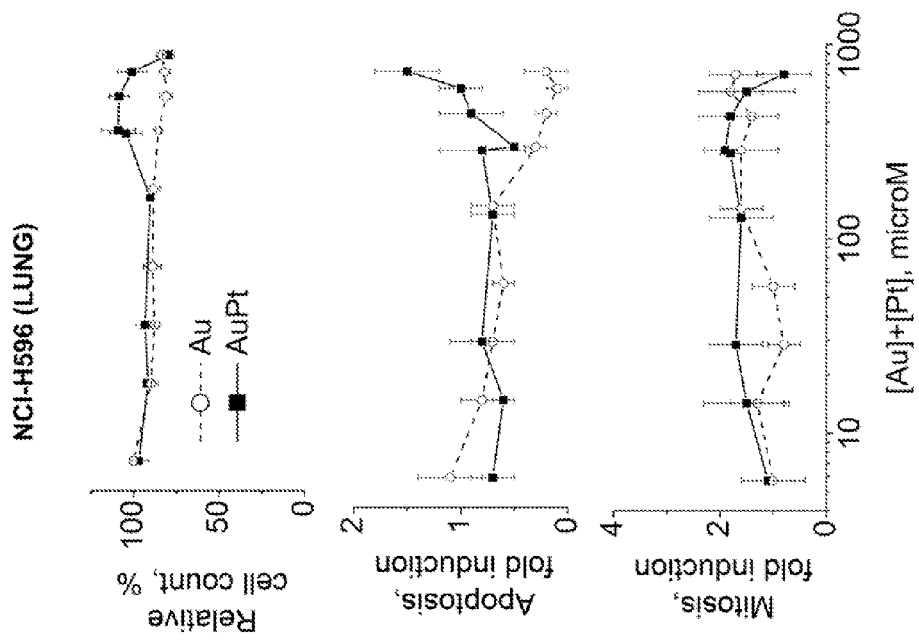
Figure 32S:
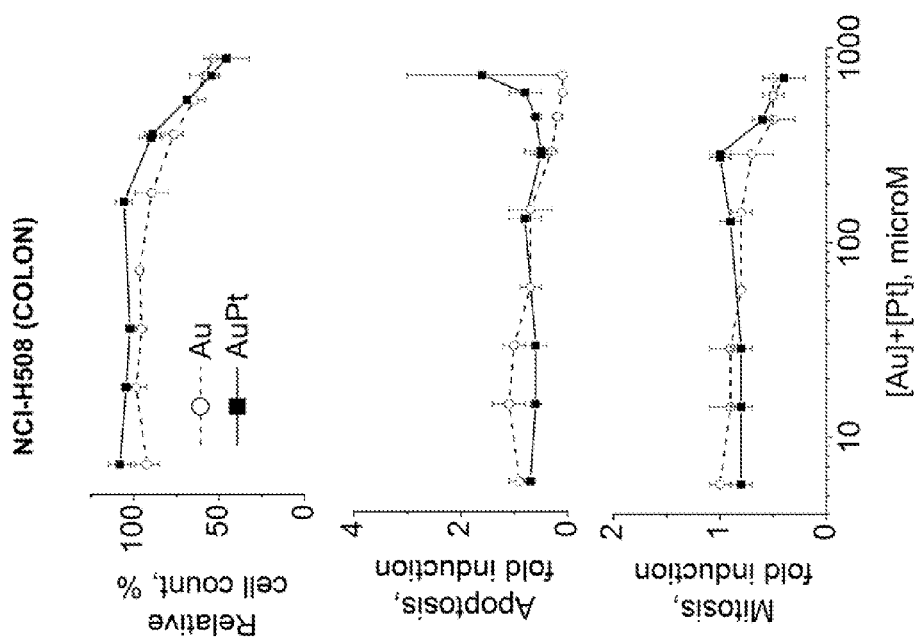
Figure 32V:
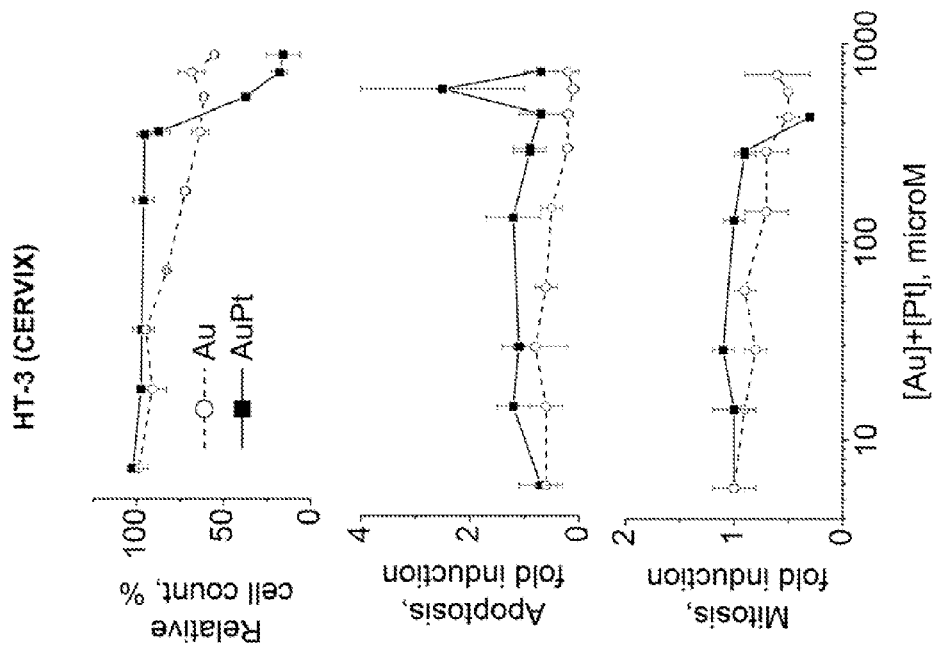
Figure 32U:
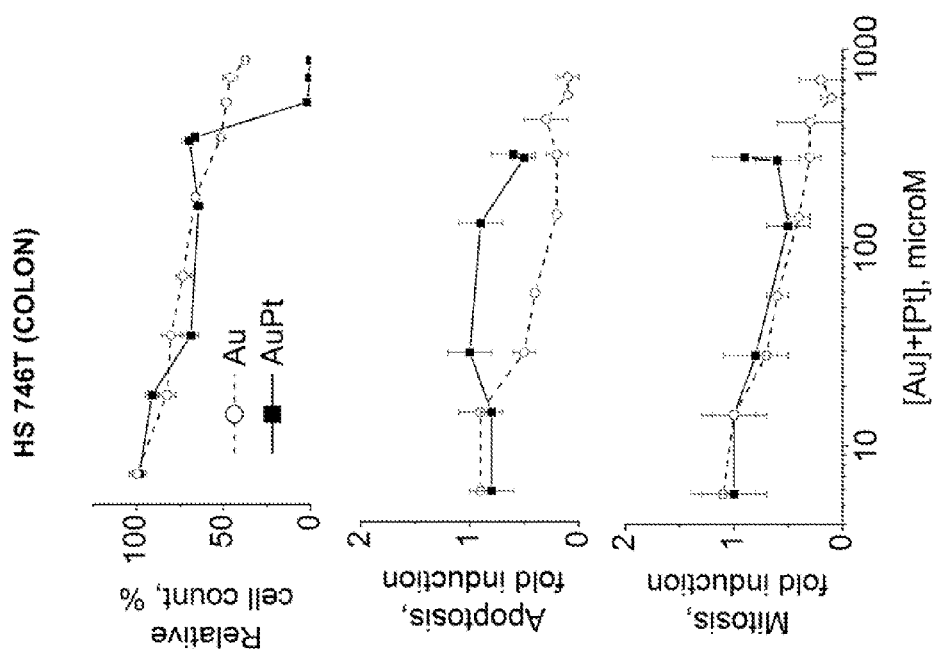
Figures 32W, 32X:
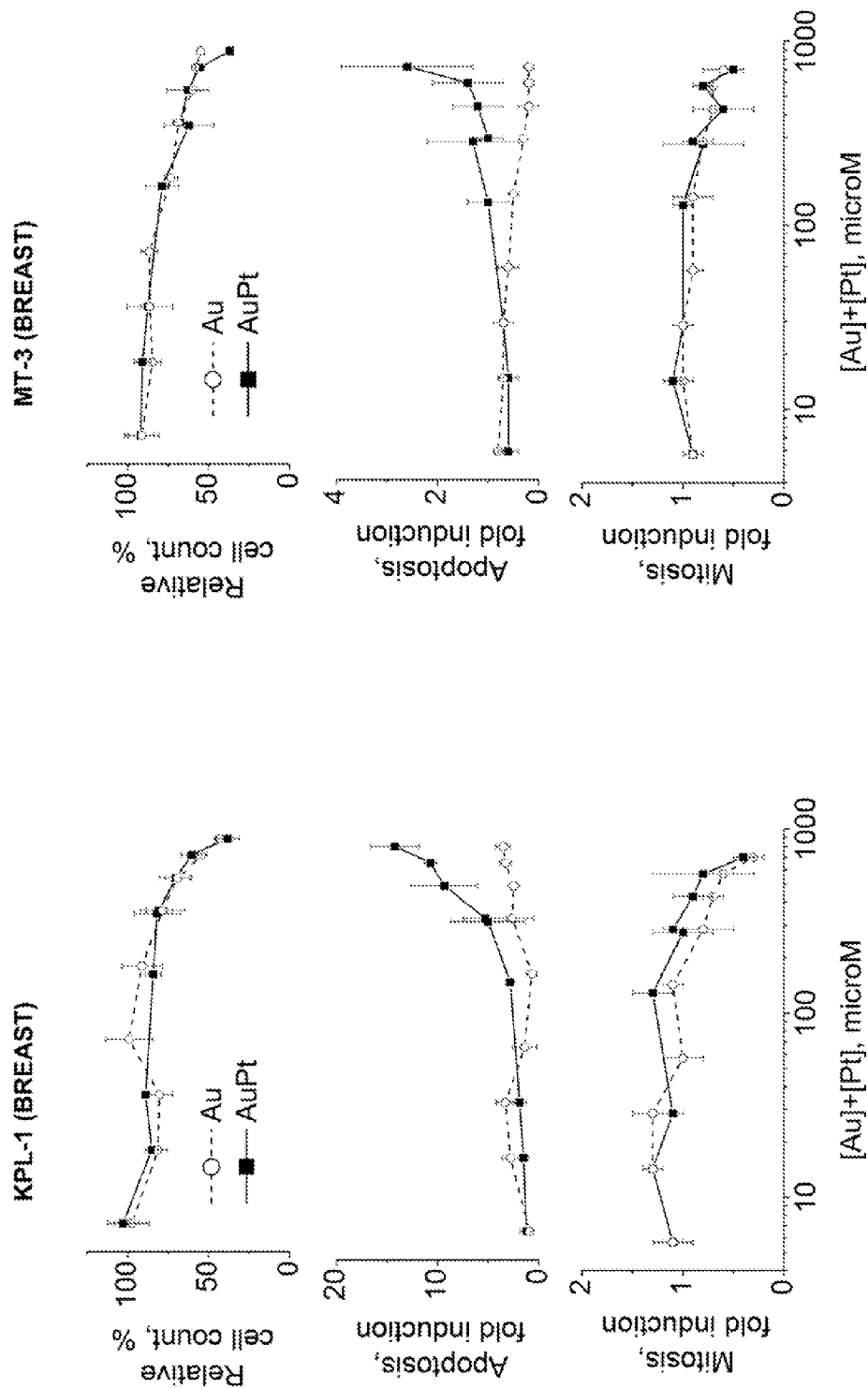
Figures 32Y, 32Z:
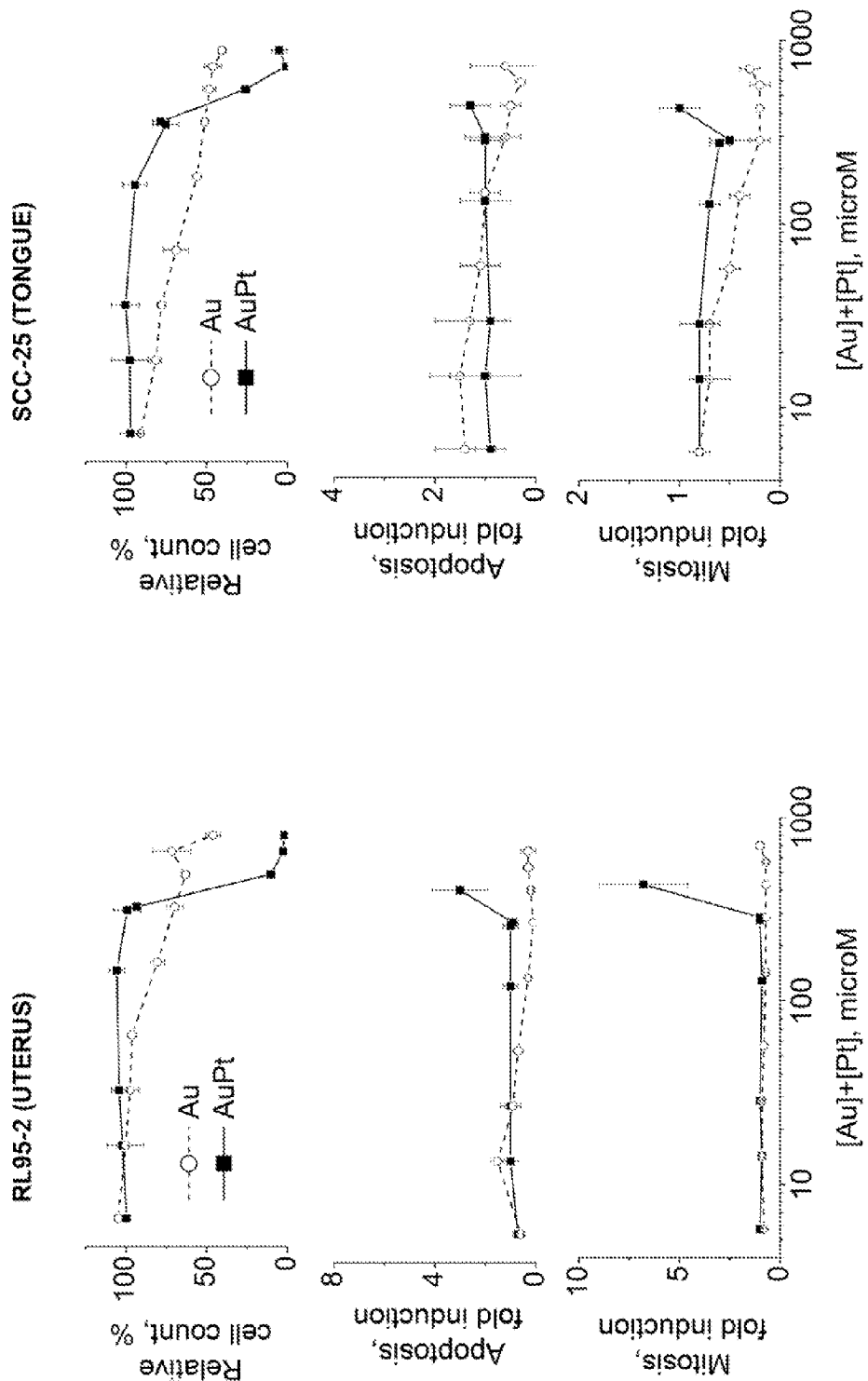
Figure 32A:
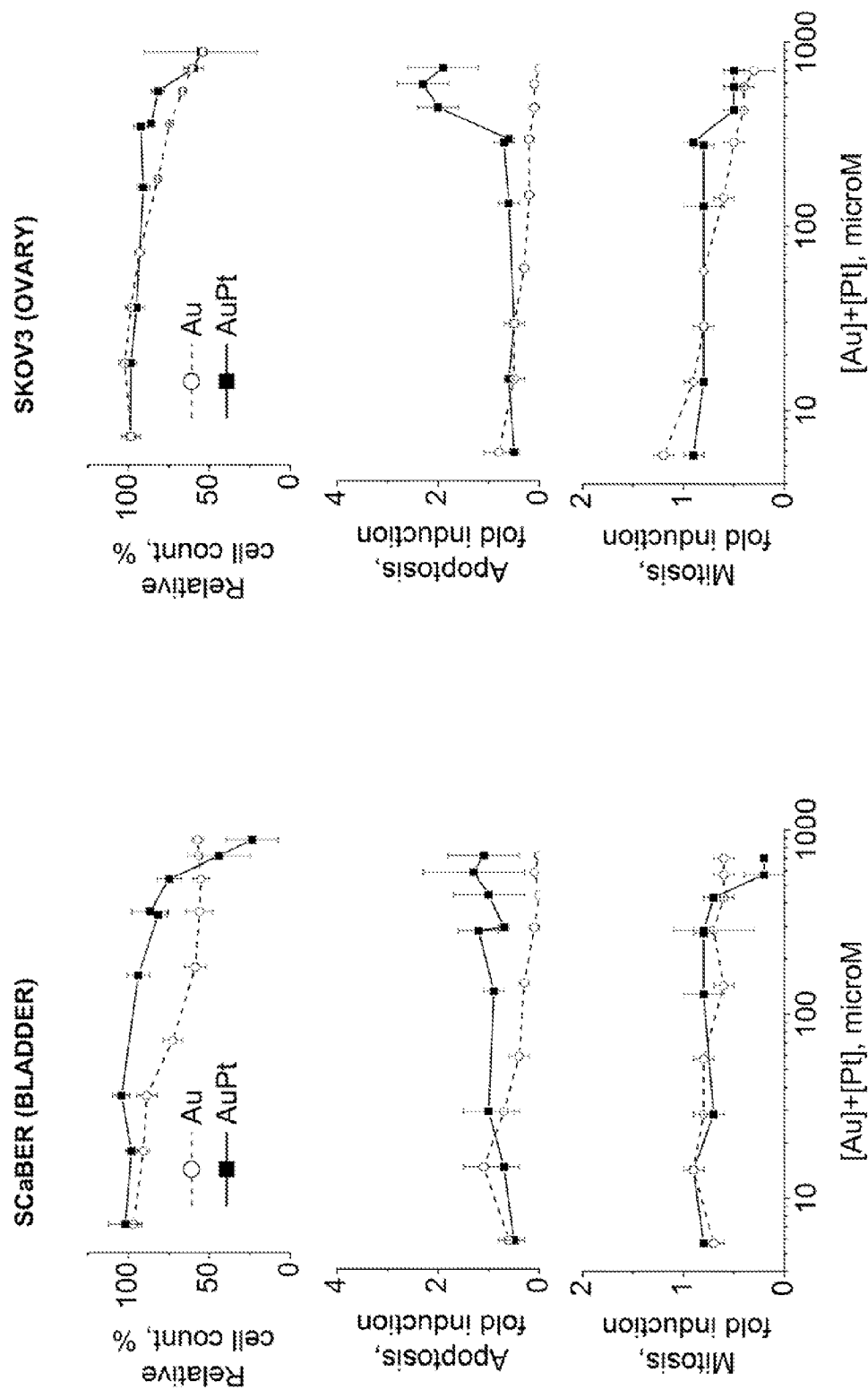
Figure 32A:
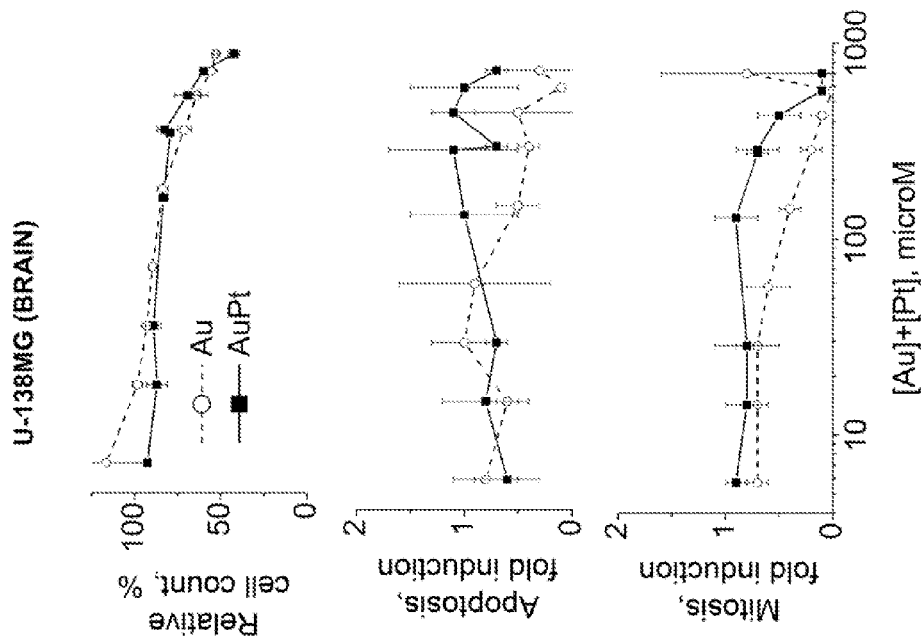
Figure 32A:
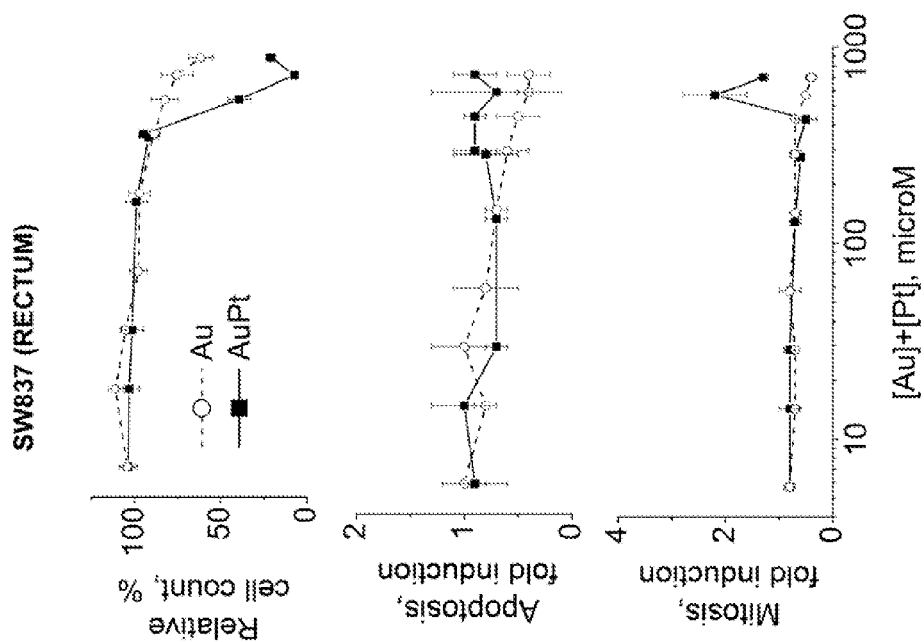

Reference is now made to FIGS. 32a-32ad. These figures show graphically the difference in performance of compound 1 and compound 2 against each of the 30 cell lines tested. Specifically, comparisons are set forth for each of "Relative Cell Count %", "Apoptosis (fold induction)" and "Mitosis (fold induction)". The data show that there is a significant elevation in apoptosis induction in eight different tumor cell lines treated with the concentrated Au—Pt bi-metallic suspension (GPB-032), but this kind of activity is not shown in any of the tumor cell lines treated with the concentrated Au compound (NE10214).

Significant Elevation of Apoptosis Induction is clearly present in the eight tumor cell lines set forth below treated with the concentrated Au—Pt bi-metallic suspension, but in none with the concentrated Au suspension:

| | |
|---|---|
| 22Rv1 | Prostate |
| SW962 | Vulva |
| BHT 101 | Endocrine |
| BT474 | Breast |
| CaOV-3 | Ovary |
| DoTc2 4510 | Cervix |
| Du 145 | Prostate |
| KPL-1 | Breast. |

Secondly, there is significant induction of Mitosis block in the five different tumor cell lines treated with the concentrated Au—Pt bi-metallic suspension (GPB-032), but this kind of activity is not shown in any of the cell lines when treated with the concentrated Au suspension (NE10214).

Significant Induction of Mitotic Block is present in five types of tumor cell lines set forth below treated with the concentrated Au—Pt bi-metallic suspension, but in none treated with the concentrated Au suspension:

| | |
|---|---|
| SW837 | Rectum |
| RL95-2 | Uterus |
| EFM-19 | Breast |
| SW962 | Vulva |
| CAOV3 | Ovary |

Third, the concentrated Au—Pt bi-metallic suspension shows significant anti-cancer activity in twelve tumor cell lines where the concentrated Au compound showed no activity at all, and the concentrated Au suspension is effective in two additional tumor cell lines where the concentrated AuPt bi-metallic suspension shows no activity at all,—so in fourteen of thirty tumor cell lines, there is no shown overlap in the presence of any kind of anti-cancer activity.

Furthermore, in the twenty-five of thirty cell lines where either the concentrated Au suspension or the concentrated Au—Pt bi-metallic suspension, or both, showed anti-cancer activity, in only four (4/30=13%) do both compounds have the same pattern or type of anti-cancer activity. In twenty-three of twenty-seven cases, the pattern of activity is distinctly different.

In summary,
1) Significant Level of Anti-Cancer Activity: either the concentrated Au suspension, or the concentrated AuPt bi-metallic suspension, or both compounds, had significant anti-cancer activity against twenty-five of the thirty (25/30=83%) tumor cell lines tested;
2) Distinctly Different Patterns of Anti-Cancer Activity: the pattern of anti-cancer activity of the two compounds (Au and AuPt) was distinctly different in twenty-one of the twenty-five tumor cell lines where there was activity 21/25→84% had distinctly different patterns of activity as between the concentrated Au suspension and the concentrated Au—Pt bi-metallic suspension.

Example 20a

Xenograft Cancer Study in Mice—HCT116 Oral Administration

Summary

This Example demonstrates the efficacy of several orally administered inventive compositions in a mouse xenograft cancer model. Female Balb/C, immunologically deficient recipient mice (6-8 weeks old) had tumors implanted therein. The Balb/C donor mice were used to grow HCT116 tumors, which tumors were excised therefrom and subsequently sectioned into small fragments about 2 mm$^3$ in size. The Balb/C recipient mice were given brief general anesthesia and then one HCT116 2 mm$^3$ tumor fragment from the donor mice was implanted into each of the left and right flank of the recipient mice using a trocar needle. Once the tumors in the recipient mice had reached a measurable size of about 4×4 mm, as measured by calipers placed against each mouse skin, the recipient mice were randomly placed into treatment groups, 3 per group and the oral treatment was started. Treatment was given exclusively via the drinking bottle shared between 3 mice in each group. Tumor size was assessed five times per week using a pair of calipers and mouse weight was also obtained by a scale, such measuring occurring until the mouse died (or was removed from the study) or the study was terminated at day 24. The results of the Example are summarized in FIGS. 33a-33b.

Certain comparative nanocrystal suspensions and ionic solutions were prepared to compare to the bi-metallic Au—Pt nanocrystal suspensions.

Briefly, GB-218 was prepared similarly to Example 1 resulting in a gold concentration of 7.6 ppm as measured by AAS. Additionally said solution was determined to have a hydrodynamic radius of 15.1 nm as measured by the Viscotek. GB-219 was prepared similarly in regards to Example 1 wherein potassium hydroxide was replaced as the process enhancer for sodium bicarbonate at a concentration of 0.63 g/gallon (i.e., about 0.17 mg/mL). GB-219 had a gold concentration of 8.7 ppm as measured by AAS. Additionally said solution was determined to have a hydrodynamic radius of 18.3 nm as measured by the Viscotek.

In addition, PB-39 was prepared similarly to Example 13 PB57001 example, resulting in a suspension of nanocyrystal platinum particles having a Pt concentration of 7.4 ppm. PB-22-C4 was prepared similarly to Example 13, wherein the applied frequency of 501AC was set to 80 Hz instead of 5 Hz to produce a solution comprising predominantly of Pt ionic species with a small amount of Pt nanocrystalline species. The concentration of sodium bicarbonate was 2.5 g/gallon (i.e., about 0.66 mg/mL). PB-22-C4 was then subsequently concentrated using an electrical hot plate to produce a Pt concentration of about 8.3 ppm.

Methodology

Animals

Species: Mice

Strain: Balb/C immunodeficient mice

Source: Harlan

Gender and number: Female, 24

Age: About 6-8 weeks old at the start of the study.

Identification: Each mouse was given a unique identity number.

Animal husbandry: On receipt, all animals were examined for external signs of ill-health and all unhealthy animals were excluded from further evaluation. Animals were housed in groups of three under specific pathogen free (spf) conditions, in a thermostatically monitored room (22±4° C.) in an animal unit. Animals were equilibrated under standard animal house conditions for at least 72 hours prior to use. The health status of the animals was monitored throughout this period and the suitability of each animal for experimental use was assessed prior to study start.

Housing Animals were housed in groups of 3 per cage in a controlled room, to ensure correct temperature, humidity and 12 hour light/dark cycle for the duration of the study.

Diet: Irradiated pellet diet and water was available ad libitum throughout the holding, acclimatisation and post-dose periods.

Compound and Reagents

HCT 116 cell line (ATCC CCL-247).

Phosphate buffered saline ("PBS").

Test compounds: platinum nanocrystal suspension, gold nanocrystal suspension and Au—Pt bi-metallic suspension.

Positive control compound: cisplatin.

Negative control compound: drinking water.

Treatment Groups and Dosages

Negative Control Group 1: Days 0-24, given normal drinking water.

Positive Control Group 2: Days 0-24, given normal drinking water; and given a daily cisplatin dose of 8 mg/kg by intraperitoneal injection ("IP").

Treatment Group 3-6: Days 0-24, given test compounds as their drinking water.

Protocol A: Preparation and Growth of Donor Tumors a.) Preparation of Tumor Cells 1. Cells were grown in complete medium and all contaminants were excluded.
2. When the cells were approximately 70-80% confluent, then approximately 3-4 hours before harvesting, the old cell growth medium was replaced with fresh cell growth medium to remove any dead and/or detached cells.
3. The cell growth medium was once again removed and the cells were washed with PBS. A small amount (e.g., 10 ml) of trypsin-EDTA was then added. The cells were then dispersed in complete cell growth medium in a ratio of between 10/1 and 5/1. The dispersed cells and medium were thereafter immediately centrifuged at about 1500 rpm for about 5 minutes and were further washed twice with PBS and the cells were stored on ice.
4. The cells were then placed on a glass slide in the traditional manner and were counted using a hemocytometer.
5. Trypan-blue stain was then added to identify and subsequently exclude dead cells. Specifically, the cells were mixed in an approximate 1:1 ratio using trypan-blue solution. The trypan-blue was diluted to about 0.8 mM in PBS. The trypan-blue was stored at room temperature. Because all living or viable cells exclude trypan-blue, dead cells are stained blue by the dye. Accordingly, all cells stained blue were removed. Cells were suspended so that about 300 μL contained about $3 \times 10^6$ tumor growth cells. This concentration of cells was required for successful tumor growth at each injection site.

b.) Injection and Growth of Tumor Cells

1. Simultaneous with preparation of tumor growth cells, Balb/C mice had previously arrived and their health was checked.
2. All animals were allowed to acclimate for at least 72 hours.
3. All mice were about 6-8 weeks old at time of inoculation. The inoculation area was cleaned and sterilized with ethanol prior to inoculation.
4. A 1 cc syringe was filled with the cancer cells by drawing the cell mixture into the syringe without the needle. A 26 gauge needle was subsequently added to the syringe.
5. The cells were then injected subcutaneously into one lower flank of each mouse and allowed to grow until they formed a tumor which reached an average volume of about 50-60 $mm^3$.
6. The mice were then anesthetized and the tumors were harvested by using a scalpel and appropriately stored prior to being injected into the recipient mice.

Protocol B: Insertion of Tumors from Donor Mice into Recipient Mice

1. Additional Balb/C recipient mice had previously arrived. Upon arrival of the recipient mice, the health of all mice was checked; and after passing the health test, each was numbered with a unique ear tag.
2. The recipient mice were allowed to acclimate for at least 72 hours.
3. HCT116 tumors produced in Protocol A above were removed from the donor mice by scalpel and cut into small fragments, approximately 2 $mm^3$ in size. The 2 $mm^3$ tumors were implanted using a 3 mm diameter trocar syringe into the right and the left flanks of each mouse (i.e., 1 tumor per flank). The tumors were permitted to grow in the recipient mice until they reached a size of about 100-200 $mm^3$ before treatment started at day 0. Treatments continued for 24 days or until the mouse was removed from the study and euthanized or the mouse died.
4. The tumor sizes and weights of the animals were determined daily until the end of the study at day 24.

Figure 33A:
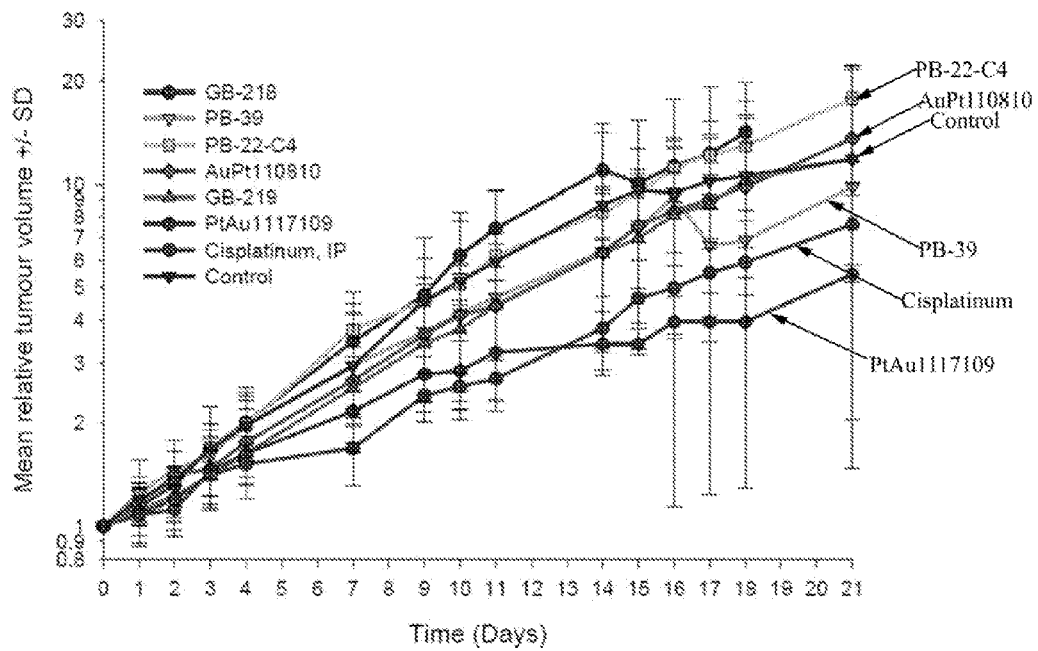
Figure 33B:
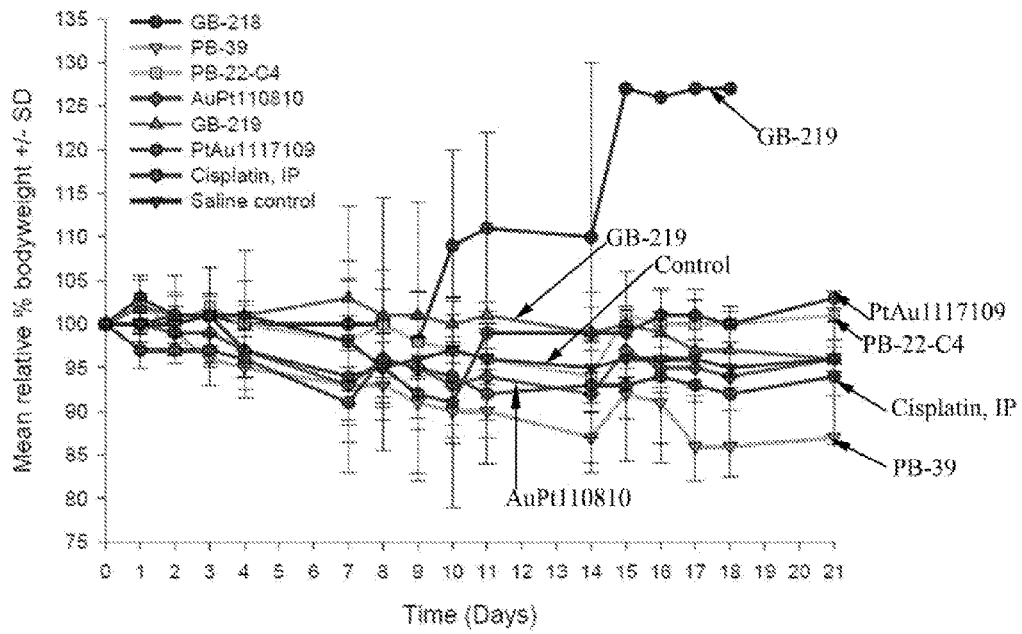

FIGS. 33a and 33b show graphically the results of the oral test. FIG. 33a shows clear difference in measured tumor volume, as a function of time, between the different compounds. The smaller the tumor, the better. Further, FIG. 33b shows differences in mean mouse weight, as a function of time, between the different compounds. The greater the weight, the better.

Table 29 summarizes the number and the point in time during the study that the mice were removed from the study. Reasons for mice leaving the study were primarily death and large tumor size, resulting in euthanasia. The Sample ID's relate to compounds manufactured according to procedures discussed earlier herein.

TABLE 29

Oral Treatment

| Sample ID | No. of Mice Removed | No. of Days into Study |
|---|---|---|
| GB-218 | 1 | 9 |
|  | 1 | 14 |
|  | 1 | 18 |
| PB-39 | 2 | 16 |
|  | 1 | 24 |
| PB-22-C4 | 1 | 16 |
|  | 2 | 23 |
| AuPt110810 | 1 | 23 |
|  | 2 | 24 |
| GB-219 | 1 | 18 |
|  | 2 | 24 |
| PtAu-111710-9 | 1 | 7 |
|  | 1 | 10 |
|  | 1 | 24 |
| Cisplatin | 3 | 24 |
| Controls | 1 | 15 |
|  | 1 | 22 |
|  | 1 | 24 |

Example 20b

Xenograft Cancer Study in Mice—HCT 116 Intratumoral Administration

Summary

This Example demonstrates the efficacy of several intratumorally ("IT") administered inventive metallic nanocrystal suspensions in a mouse xenograft cancer model. Female Balb/C, immunologically deficient recipient mice (6-8 weeks old) had tumors implanted therein. The Balb/C donor mice were used to grow HCT116 tumors, which tumors were excised therefrom and subsequently sectioned into small fragments about 2 $mm^3$ in size. The Balb/C recipient mice were given brief general anesthesia and then one HCT 116 2 mm³ tumor fragment from the donor mice was implanted into each of the left and right flank of the recipient mice using a trocar needle. Once the tumors in the recipient mice had reached a measurable size of about 7×7 mm, as measured by calipers placed against each mouse skin, the recipient mice were randomly placed into treatment groups, 3 per group and the "IT" treatment was started. Treatment was given exclusively by needle injection into the tumor twice a day. Tumor size was assessed five times per week using a pair of calipers and mouse weight was also obtained by a scale, such measuring occurring until the mouse died (or was removed from the study) or the study was terminated at day 30. The results of the Example are summarized in FIG. 34a-34b.

Certain comparative nanocrystal suspensions and ionic solutions were prepared to compare to the bi-metallic Au—Pt nanocrystal suspensions.

Briefly, GB-218 was prepared similarly to Example 1 resulting in a gold concentration of 7.6 ppm as measured by AAS. Additionally said solution was determined to have a hydrodynamic radius of 15.1 nm as measured by the Viscotek. GB-219 was prepared similarly in regards to Example 1 wherein potassium hydroxide was replaced as the process enhancer for sodium bicarbonate at a concentration of 0.63 g/gallon (i.e., about 0.17 mg/mL). GB-219 had a gold concentration of 8.7 ppm as measured by AAS. Additionally said solution was determined to have a hydrodynamic radius of 18.3 nm as measured by the Viscotek.

In addition, PB-39 was prepared similarly to Example 13 PB57001 example, resulting in a suspension of nanocyrystal platinum particles having a Pt concentration of 7.4 ppm. PB-22-C4 was prepared similarly to Example 13, wherein the applied frequency of 501AC was set to 80 Hz instead of 5 Hz to produce a solution comprising predominantly of Pt ionic species with a small amount of Pt nanocrystalline species. The concentration of sodium bicarbonate was 2.5 g/gallon (i.e., about 0.66 mg/mL). PB-22-C4 was then subsequently concentrated using an electrical hot plate to produce a Pt concentration of about 8.3 ppm.

Methodology

Animals

Species: Mice

Strain: Balb/C immunodeficient mice

Source: Harlan

Gender and number: Female, 24

Age: About 6-8 weeks old at the start of the study.

Identification: Each mouse was given a unique identity number.

Animal husbandry: On receipt, all animals were examined for external signs of ill-health and all unhealthy animals were excluded from further evaluation. Animals were housed in groups of three under specific pathogen free (spf) conditions, in a thermostatically monitored room (22±4° C.) in an animal unit. Animals were equilibrated under standard animal house conditions for at least 72 hours prior to use. The health status of the animals was monitored throughout this period and the suitability of each animal for experimental use was assessed prior to study start.

Housing Animals were housed in groups of 3 per cage in a controlled room, to ensure correct temperature, humidity and 12 hour light/dark cycle for the duration of the study.

Diet: Irradiated pellet diet and water was available ad libitum throughout the holding, acclimatization and post-dose periods.

Compound and Reagents

HCT 116 cell line (ATCC CCL-247).

Phosphate buffered saline ("PBS").

Test compounds: platinum nanocrystal suspension, gold nanocrystal suspension and Au—Pt bi-metallic suspension.

Positive control compound: cisplatin.

Negative control compound: drinking water.

Treatment Groups and Dosages

Negative Control Group 1: Days 0-30, saline injection twice a day, with a total of 100 µl in each tumor divided between 2-3 injection points; (given normal drinking water to drink).

Positive Control Group 2: Days 0-30, cisplatin injection 8 mg/kg given once a day into the peritoneum (IP) (given normal drinking water to drink).

Treatment Group 3-6: Days 0-30, nanocrystal formulation injection twice a day, with a total of 100 µl in each tumor divided between 2-3 injection points; (given normal drinking water to drink).

Protocol A: Preparation and Growth of Donor Tumors a.) Preparation of Tumor Cells 1. Cells were grown in complete medium and all contaminants were excluded.
2. When the cells were approximately 70-80% confluent, then approximately 3-4 hours before harvesting, the old cell growth medium was replaced with fresh cell growth medium to remove any dead and/or detached cells.
3. The cell growth medium was once again removed and the cells were washed with PBS. A small amount (e.g., 10 ml) of trypsin-EDTA was then added. The cells were then dispersed in complete cell growth medium in a ratio of between 10/1 and 5/1. The dispersed cells and medium were thereafter immediately centrifuged at about 1500 rpm for about 5 minutes and were further washed twice with PBS and the cells were stored on ice.
4. The cells were then placed on a glass slide in the traditional manner and were counted using a hemocytometer.
5. Trypan-blue stain was then added to identify and subsequently exclude dead cells. Specifically, the cells were mixed in an approximate 1:1 ratio using trypan-blue solution. The trypan-blue was diluted to about 0.8 mM in PBS. The trypan-blue was stored at room temperature. Because all living or viable cells exclude trypan-blue, dead cells are stained blue by the dye. Accordingly, all cells stained blue were removed. Cells were suspended so that about 300 µL contained about 3×10⁶ tumor growth cells. This concentration of cells was required for successful tumor growth at each injection site.

b.) Injection and Growth of Tumor Cells

1. Simultaneous with preparation of tumor growth cells, Balb/C mice had previously arrived and their health was checked.
2. All animals were allowed to acclimate for at least 72 hours.
3. All mice were about 6-8 weeks old at time of inoculation. The inoculation area was cleaned and sterilized with ethanol prior to inoculation.
4. A 1 cc syringe was filled with the cancer cells by drawing the cell mixture into the syringe without the needle. A 26 gauge needle was subsequently added to the syringe.
5. The cells were then injected subcutaneously into one lower flank of each mouse and allowed to grow until they formed a tumor which reached an average volume of about 50-60 mm³.
6. The mice were then anesthetized and the tumors were harvested by using a scalpel and appropriately stored prior to being injected into the recipient mice.

Protocol B: Insertion of Tumors from Donor Mice into Recipient Mice

5. Additional Blab/C recipient mice had previously arrived. Upon arrival of the recipient mice, the health of all mice was checked; and after passing the health test, each was numbered with a unique ear tag.
6. The mice were allowed to acclimate for at least 72 hours.
7. HCT116 tumors produced in Protocol A above were removed from the donor mice by scalpel and cut into small fragments, approximately 2 mm³ in size. The 2 mm³ tumors were implanted using a 3 mm diameter trocar syringe into the right and the left flanks of each mouse (i.e., 1 tumor per flank). The tumors were permitted to grow in the recipient mice until they reached a size of about 7×7 mm before treatment started at day 0. Treatments continued for 30 days or until the mouse was removed from the study and euthanized or the mouse died.
8. The tumor sizes and weights of the animals were determined daily until the end of the study at day 24.

Protocol C: Intertumoral Injection into Recipient Mice

1. Each tumor in each recipient mouse was injected twice daily (about 12 hours apart) with about 100 µl of either negative control, positive control or test compound. The needle used for injection was either a 25 Ga or 26 Ga needle. Depending on the tumor size, there were either 2 or 3 injection points for each tumor.

Figure 34A:
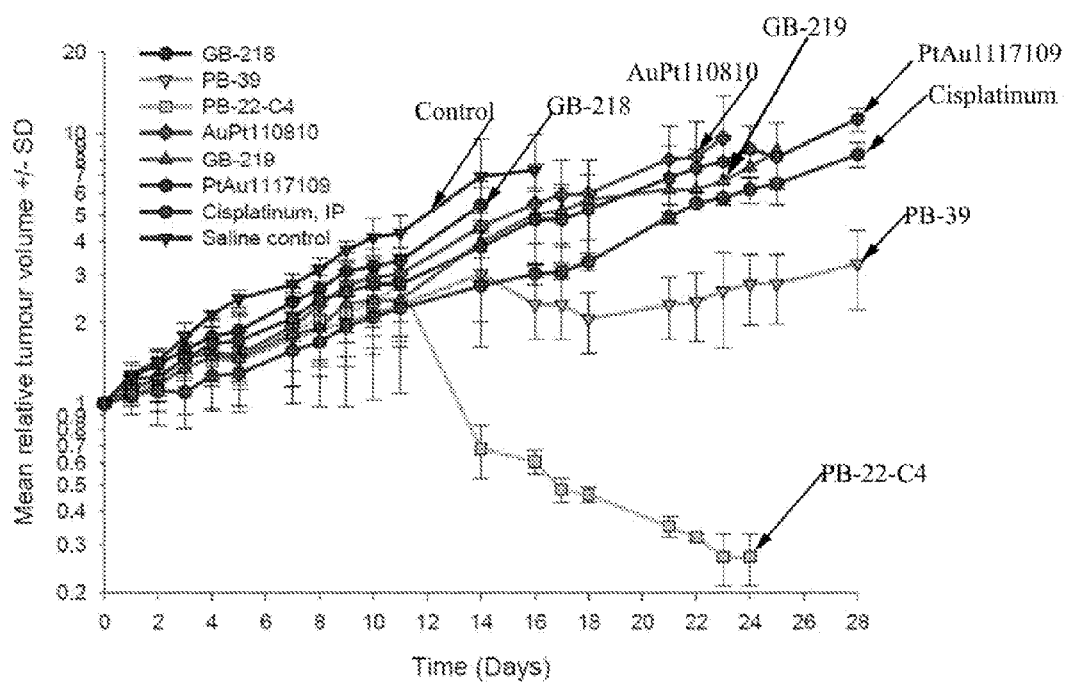
FIGS. 34a and 34b show the results of the cancer xenograft tests set forth in Example 20b.
Figure 34B:
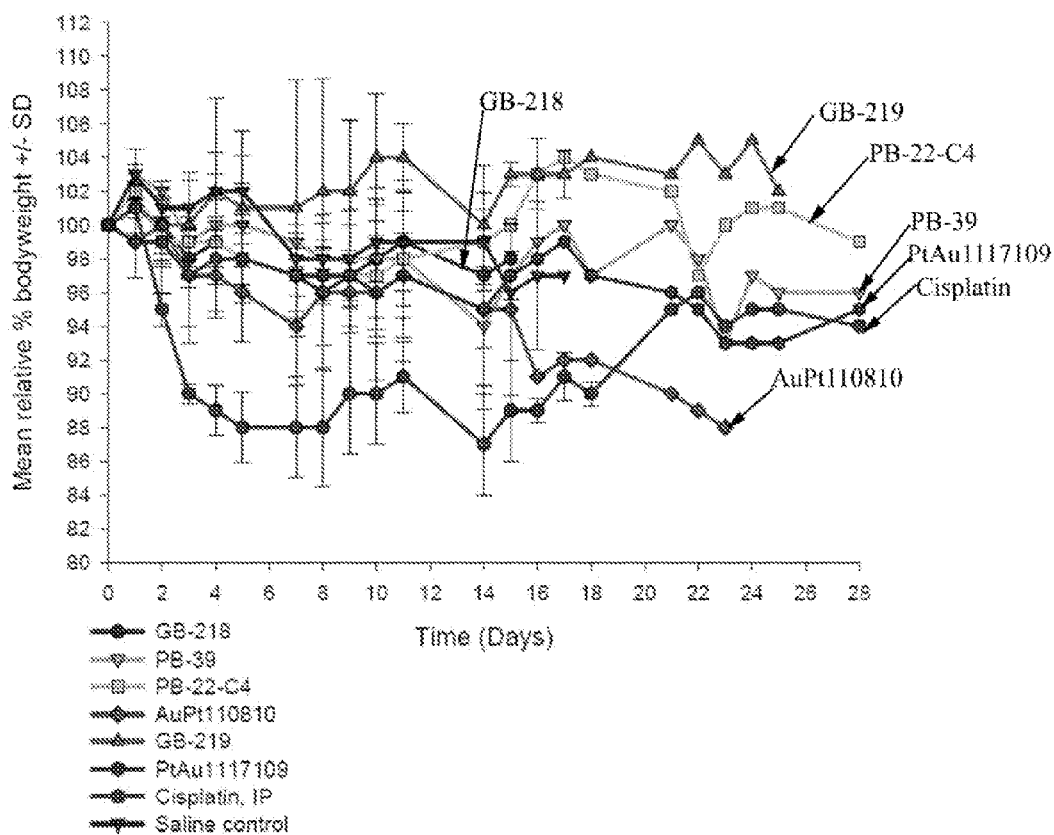

FIGS. 34a and 34b shows graphically the results of the IT test. FIG. 34a shows clear difference in measured tumor volume, as a function of time, between the different compounds. The smaller the tumor, the better. Further, FIG. 34b shows differences in mean mouse weight, as a function of time, between the different compounds. The greater the weight, the better.

Table 30 summarizes the number and the point in time during the study that the mice were removed from the study. Reasons for mice leaving the study were primarily death and large tumor size, resulting in euthanasia. The Sample ID's relate to compounds manufactured according to procedures discussed earlier herein.

TABLE 30

IT Treatment

| Sample ID | No. of Mice Removed | No. of Days into Study |
|---|---|---|
| GB-218 | 1 | 9 |
|  | 1 | 11 |
|  | 1 | 15 |
| PB-39 | 1 | 7 |
|  | 1 | 15 |
|  | 1 | 28 |
| PB-22-C4 | 2 | 11 |
|  | 1 | 30 |
| AuPt110810 | 2 | 15 |
|  | 1 | 23 |
| GB-219 | 1 | 14 |
|  | 1 | 17 |
|  | 1 | 25 |
| PtAu-111710-9 | 2 | 14 |
|  | 1 | 30 |
| Cisplatin | 1 | 15 |
|  | 1 | 18 |
|  | 1 | 30 |
| Controls | 1 | 15 |
|  | 1 | 16 |

Example 20c

Xenograft Cancer Study in Mice—HCT116 Oral Administration

Summary

This Example demonstrates the relative efficacy of four orally administered inventive metallic nanocrystal suspensions in a mouse xenograft cancer model. Female Balb/C, immunologically deficient recipient mice (6-8 weeks old) had tumors implanted therein. The Balb/C donor mice were used to grow HCT116 tumors, which tumors were excised therefrom and subsequently sectioned into small fragments about 2 mm³ in size. The Balb/C recipient mice were given brief general anesthesia and then one HCT116 2 mm³ tumor fragment from the donor mice was implanted into each of the left and right flank of the recipient mice using a trocar needle. Once the tumors in the recipient mice had reached a measurable size of about 4×4 mm, as measured by calipers placed against each mouse skin, the recipient mice were randomly placed into treatment groups, 6 per group and the oral treatment was started. 6 mice were in the positive control group ("Cisplatin") and 6 mice were in the negative control group and received only water ("Control"). Treatment was given exclusively via the drinking bottle shared between the mice in each Treatment group. Cisplatin was given by intraperitoneal injection on day 0. Tumor size was assessed five times per week using a pair of calipers and mouse weight was also obtained by a scale, such measuring occurring until the mouse died (or was removed from the study) or the study was terminated as scheduled. The results of the Example are summarized in FIGS. 35a-35b.

Methodology

Animals

Species: Mice

Strain: Balb/C immunodeficient mice

Source: Harlan

Gender and number: Female, 36

Age: About 6-8 weeks old at the start of the study.

Identification: Each mouse was given a unique identity number.

Animal husbandry: On receipt, all animals were examined for external signs of ill-health and all unhealthy animals were excluded from further evaluation. Animals were housed in groups of three under specific pathogen free (spf) conditions, in a thermostatically monitored room (22±4° C.) in an animal unit. Animals were equilibrated under standard animal house conditions for at least 72 hours prior to use. The health status of the animals was monitored throughout this period and the suitability of each animal for experimental use was assessed prior to study start.

Housing Animals were housed in groups of 3 per cage in a controlled room, to ensure correct temperature, humidity and 12 hour light/dark cycle for the duration of the study.

Diet: Irradiated pellet diet and water was available ad libitum throughout the holding, acclimatisation and post-dose periods.

Compound and Reagents

HCT 116 cell line (ATCC CCL-247).

Phosphate buffered saline ("PBS").

Test compounds: platinum nanocrystal suspension, gold nanocrystal suspension and Au—Pt bi-metallic suspension.

Positive control compound: cisplatin.
Negative control compound: drinking water.
Treatment Groups and Dosages
Negative Control Group 1: Days 0-24, given normal drinking water.
Positive Control Group 2: Days 0-24, given normal drinking water; and given a one-time cisplatin dose of 8 mg/kg by intraperitoneal injection ("IP") on day 0.
Treatment Group 3-6: Days 0-24, given test compounds as their drinking water.
Protocol A: Preparation and Growth of Donor Tumors
  a.) Preparation of Tumor Cells
1. Cells were grown in complete medium and all contaminants were excluded.
2. When the cells were approximately 70-80% confluent, then approximately 3-4 hours before harvesting, the old cell growth medium was replaced with fresh cell growth medium to remove any dead and/or detached cells.
3. The cell growth medium was once again removed and the cells were washed with PBS. A small amount (e.g., 10 ml) of trypsin-EDTA was then added. The cells were then dispersed in complete cell growth medium in a ratio of between 10/1 and 5/1. The dispersed cells and medium were thereafter immediately centrifuged at about 1500 rpm for about 5 minutes and were further washed twice with PBS and the cells were stored on ice.
4. The cells were then placed on a glass slide in the traditional manner and were counted using a hemocytometer.
5. Trypan-blue stain was then added to identify and subsequently exclude dead cells. Specifically, the cells were mixed in an approximate 1:1 ratio using trypan-blue solution. The trypan-blue was diluted to about 0.8 mM in PBS. The trypan-blue was stored at room temperature. Because all living or viable cells exclude trypan-blue, dead cells are stained blue by the dye. Accordingly, all cells stained blue were removed. Cells were suspended so that about 3000 μL contained about $3 \times 10^6$ tumor growth cells. This concentration of cells was required for successful tumor growth at each injection site.
  b.) Injection and Growth of Tumor Cells
1. Simultaneous with preparation of tumor growth cells, Balb/C mice had previously arrived and their health was checked.
2. All animals were allowed to acclimate for at least 72 hours.
3. All mice were about 6-8 weeks old at time of inoculation. The inoculation area was cleaned and sterilized with ethanol prior to inoculation.
4. A 1 cc syringe was filled with the cancer cells by drawing the cell mixture into the syringe without the needle. A 26 gauge needle was subsequently added to the syringe.
5. The cells were then injected subcutaneously into one lower flank of each mouse and allowed to grow until they formed a tumor which reached an average volume of about 50-60 $mm^3$.
6. The mice were then anesthetized and the tumors were harvested by using a scalpel and appropriately stored prior to being injected into the recipient mice.
Protocol B: Insertion of Tumors from Donor Mice into Recipient Mice
9. Additional Balb/C recipient mice had previously arrived. Upon arrival of the recipient mice, the health of all mice was checked; and after passing the health test, each was numbered with a unique ear tag.
10. The recipient mice were allowed to acclimate for at least 72 hours.
11. HCT116 tumors produced in Protocol A above were removed from the donor mice by scalpel and cut into small fragments, approximately 2 $mm^3$ in size. The 2 $mm^3$ tumors were implanted using a 3 mm diameter trocar syringe into the right and the left flanks of each mouse (i.e., 1 tumor per flank). The tumors were permitted to grow in the recipient mice until they reached a size of about 100-200 $mm^3$ before treatment started at day 0. Treatments continued for 24 days or until the mouse was removed from the study and euthanized or the mouse died.
12. The tumor sizes and weights of the animals were determined daily until the end of the study at day 24.

Figure 35A:
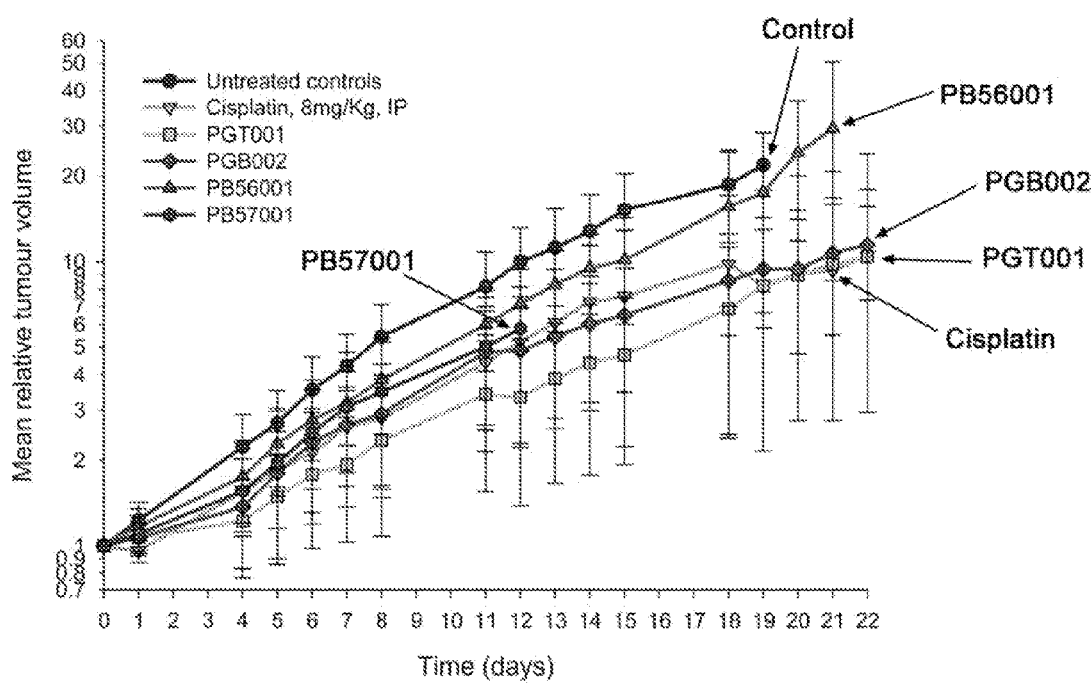
FIGS. 35a and 35b show the results of the cancer xenograft tests set forth in Example 20c.
Figure 35B:
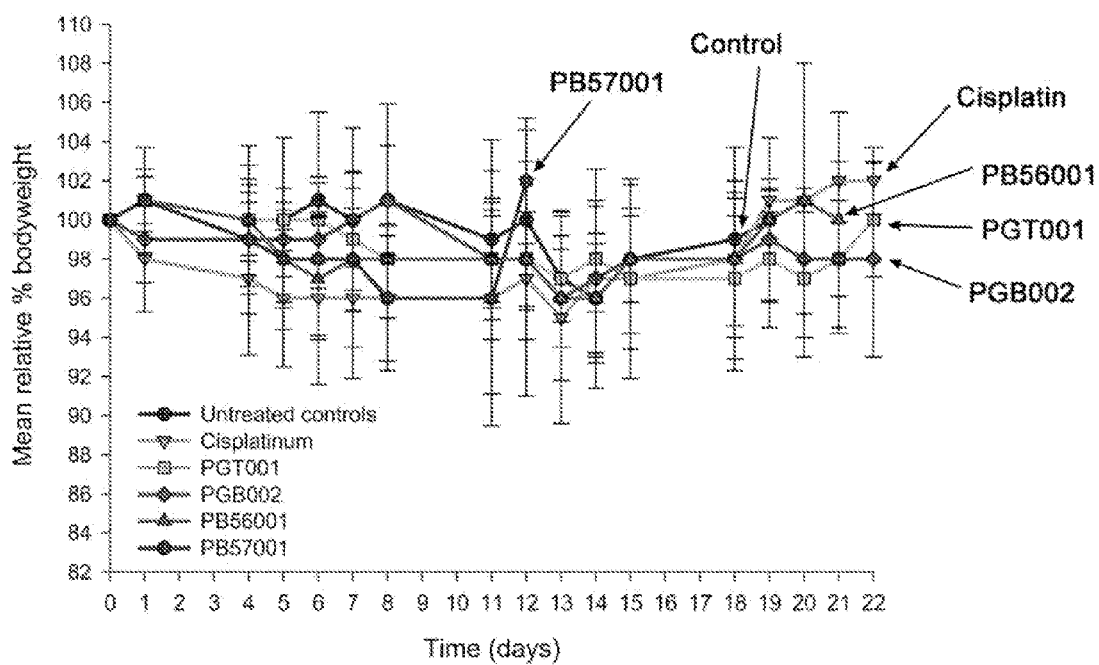

FIGS. 35a and 35b show graphically the results of the oral test. FIG. 35a shows clear difference in measured tumor volume, as a function of time, between the different compounds. The smaller the tumor, the better. Further, FIG. 35b shows differences in mean mouse weight, as a function of time, between the different compounds. The greater the weight, the better.

Table 31 summarizes the number and the point in time during the study that the mice were removed from the study. Reasons for mice leaving the study were primarily death and large tumor size, resulting in euthanasia. The Sample ID's relate to compounds manufactured according to procedures discussed earlier herein.

TABLE 31

Oral Treatment

| Sample ID | No. of Mice Removed | No. of Days into Study |
|---|---|---|
| PGT001 | 1 | 11 |
| PGB002 | 1 | 14 |
|  | 1 | 18 |
|  | 1 | 19 |
|  | 1 | 22 |
| PB56001 | 1 | 14 |
|  | 1 | 15 |
|  | 1 | 18 |
|  | 1 | 19 |
|  | 1 | 20 |
|  | 1 | 21 |
| PB57001 | 4 | 11 |
| Cisplatin | 1 | 11 |
|  | 1 | 13 |
|  | 1 | 14 |
|  | 2 | 18 |
|  | 1 | 22 |
| Control | 4 | 12 |
|  | 1 | 15 |
|  | 1 | 18 |
|  | 1 | 19 |

Table 32 provides a comparison of the doubling time (RTV2) for each group in the study. In addition, table 32 also lists the growth delay in days, maximum percent weight loss and statistical significance of the data.

TABLE 32

| Group Number | Mean Time to RTV2 (days) | Median Time to RTV2 (days) | Growth Delay (days) | Significance | Maximum % Weight Loss |
|---|---|---|---|---|---|
| 1 | 3.9 | 3.6 | — | — | 1 (d4) |
| 2 | 6.7 | 5.2 | 1.6 | $p < 0.05$ | 4 (d5) |
| 3 | 8.3 | 7.6 | 4.0 | $p < 0.01$ | 2 (d8) |
| 4 | 5.7 | 5.6 | 2.0 | $p < 0.05$ | 2 (d11) |
| 5 | 5.0 | 4.4 | 0.8 | $p > 0.05$ ns | 3 (d6) |
| 6 | 5.9 | 5.5 | 1.9 | $p > 0.05$ ns | 4 (d8) |

Example 20d

Xenograft Cancer Study in Mice—HCT116 Oral Administration

Summary

This Example demonstrates the relative efficacy of three orally administered inventive metallic nanocrystal suspensions in a mouse xenograft cancer model relative to Cisplatin. Female Balb/C, immunologically deficient recipient mice (6-8 weeks old) had tumors implanted therein. The Balb/C donor mice were used to grow HCT116 tumors, which tumors were excised therefrom and subsequently sectioned into small fragments about 2 mm$^3$ in size. The Balb/C recipient mice were given brief general anesthesia and then one HCT116 2 mm$^3$ tumor fragment from the donor mice was implanted into each of the left and right flank of the recipient mice using a trocar needle. Once the tumors in the recipient mice had reached a measurable size of about 4×4 mm, as measured by calipers placed against each mouse skin, the recipient mice were randomly placed into treatment groups, 8 per group and the oral treatment was started. 8 mice were in the positive control group ("Cisplatin") and 8 mice were in the negative control group and received only water ("Control"). Treatment was given exclusively via the drinking bottle shared between the mice in each Treatment group. Cisplatin was given by intraperitoneal injection on day 0. Tumor size was assessed five times per week using a pair of calipers and mouse weight was also obtained by a scale, such measuring occurring until the mouse died (or was removed from the study) or the study was terminated as scheduled. The results of the Example are summarized in FIGS. 36a-36b.

Methodology

Animals

Species: Mice

Strain: Balb/C immunodeficient mice

Source: Harlan

Gender and number: Female, 36

Age: About 6-8 weeks old at the start of the study.

Identification: Each mouse was given a unique identity number.

Animal husbandry: On receipt, all animals were examined for external signs of ill-health and all unhealthy animals were excluded from further evaluation. Animals were housed in groups of three under specific pathogen free (spf) conditions, in a thermostatically monitored room (22±4° C.) in an animal unit. Animals were equilibrated under standard animal house conditions for at least 72 hours prior to use. The health status of the animals was monitored throughout this period and the suitability of each animal for experimental use was assessed prior to study start.

Housing Animals were housed in groups of 3 per cage in a controlled room, to ensure correct temperature, humidity and 12 hour light/dark cycle for the duration of the study.

Diet: Irradiated pellet diet and water was available ad libitum throughout the holding, acclimatisation and post-dose periods.

Compound and Reagents

HCT 116 cell line (ATCC CCL-247).

Phosphate buffered saline ("PBS").

Test compounds: Au—Pt bi-metallic nanocrystal suspensions.

Positive control compound: cisplatin.

Negative control compound: drinking water.

Treatment Groups and Dosages

Negative Control Group 1: Days 0-21, given normal drinking water.

Positive Control Group 2: Days 0-21, given normal drinking water; and given a one-time cisplatin dose of 8 mg/kg by intraperitoneal injection ("IP") on day 0.

Treatment Group 3-5: Days 0-21, given test compounds as their drinking water.

Protocol A: Preparation and Growth of Donor Tumors a.) Preparation of Tumor Cells 1. Cells were grown in complete medium and all contaminants were excluded.
2. When the cells were approximately 70-80% confluent, then approximately 3-4 hours before harvesting, the old cell growth medium was replaced with fresh cell growth medium to remove any dead and/or detached cells.
3. The cell growth medium was once again removed and the cells were washed with PBS. A small amount (e.g., 10 ml) of trypsin-EDTA was then added. The cells were then dispersed in complete cell growth medium in a ratio of between 10/1 and 5/1. The dispersed cells and medium were thereafter immediately centrifuged at about 1500 rpm for about 5 minutes and were further washed twice with PBS and the cells were stored on ice.
4. The cells were then placed on a glass slide in the traditional manner and were counted using a hemocytometer.
5. Trypan-blue stain was then added to identify and subsequently exclude dead cells. Specifically, the cells were mixed in an approximate 1:1 ratio using trypan-blue solution. The trypan-blue was diluted to about 0.8 mM in PBS. The trypan-blue was stored at room temperature. Because all living or viable cells exclude trypan-blue, dead cells are stained blue by the dye. Accordingly, all cells stained blue were removed. Cells were suspended so that about 300 µL contained about 3×10$^6$ tumor growth cells. This concentration of cells was required for successful tumor growth at each injection site.

b.) Injection and Growth of Tumor Cells

1. Simultaneous with preparation of tumor growth cells, Balb/C mice had previously arrived and their health was checked.
2. All animals were allowed to acclimate for at least 72 hours.
3. All mice were about 6-8 weeks old at time of inoculation. The inoculation area was cleaned and sterilized with ethanol prior to inoculation.
4. A 1 cc syringe was filled with the cancer cells by drawing the cell mixture into the syringe without the needle. A 26 gauge needle was subsequently added to the syringe.
5. The cells were then injected subcutaneously into one lower flank of each mouse and allowed to grow until they formed a tumor which reached an average volume of about 50-60 mm$^3$.
6. The mice were then anesthetized and the tumors were harvested by using a scalpel and appropriately stored prior to being injected into the recipient mice.

Protocol B: Insertion of Tumors from Donor Mice into Recipient Mice

13. Additional Balb/C recipient mice had previously arrived. Upon arrival of the recipient mice, the health of all mice was checked; and after passing the health test, each was numbered with a unique ear tag.
14. The recipient mice were allowed to acclimate for at least 72 hours.
15. HCT116 tumors produced in Protocol A above were removed from the donor mice by scalpel and cut into small fragments, approximately 2 mm$^3$ in size. The 2 mm$^3$ tumors were implanted using a 3 mm diameter trocar syringe into the right and the left flanks of each mouse (i.e., 1 tumor per flank). The tumors were permitted to grow in the recipient mice until they reached a size of about 100-

200 mm$^3$ before treatment started at day 0. Treatments continued for 21 days or until the mouse was removed from the study and euthanized or the mouse died.

16. The tumor sizes and weights of the animals were determined daily until the end of the study at day 21.

Figure 36A:
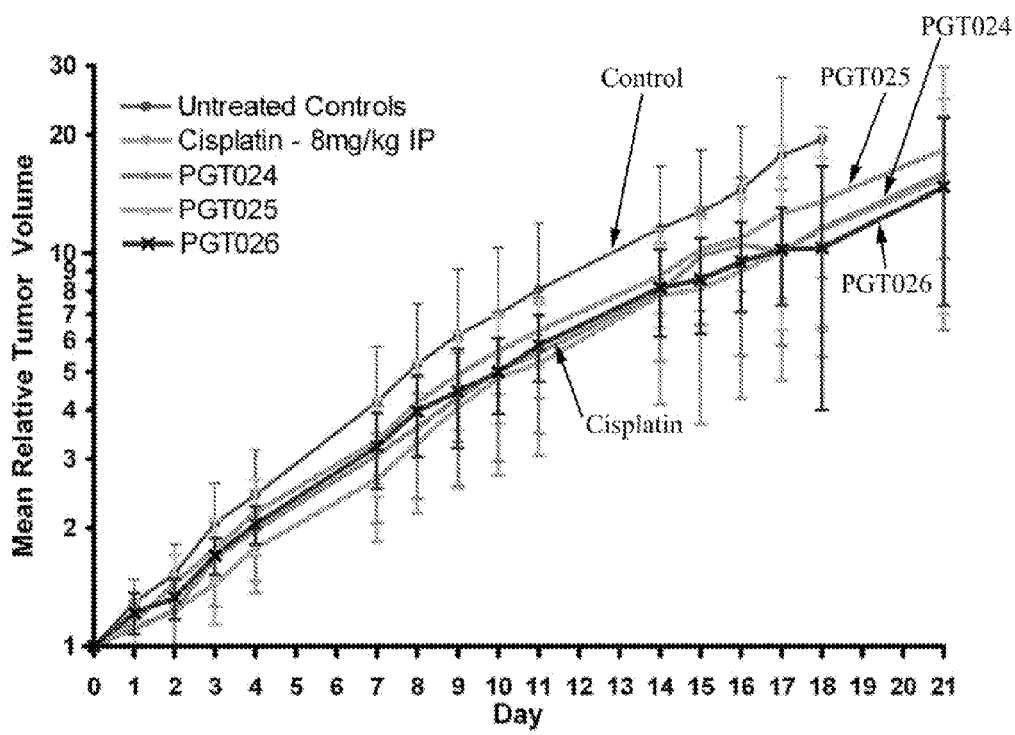
FIGS. 36a and 36b show the results of the cancer xenograft tests set forth in Example 20d.
Figure 36B:
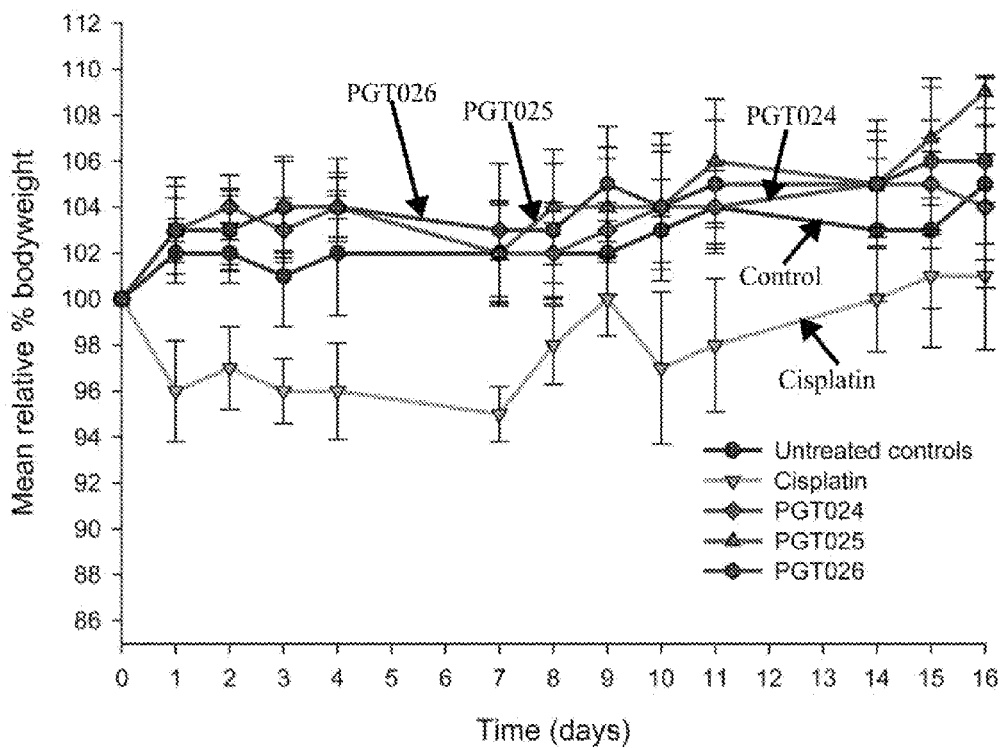

FIGS. 36a and 36b show graphically the results of the oral test. FIG. 36a shows clear difference in measured tumor volume, as a function of time, between the different compounds. The smaller the tumor, the better. Further, FIG. 36b shows differences in mean mouse weight, as a function of time, between the different compounds. The greater the weight, the better.

Table 33 summarizes the number and the point in time during the study that the mice were removed from the study. Reasons for mice leaving the study were primarily death and large tumor size, resulting in euthanasia. The Sample IDs relate to compounds manufactured according to procedures discussed earlier herein.

TABLE 33

Oral Treatment

| Group Number | Sample ID | No. of Mice Removed | No. of Days into Study |
|---|---|---|---|
| 3 | PGT024 | 1 | 15 |
|   |   | 3 | 16 |
|   |   | 1 | 17 |
|   |   | 1 | 21 |
| 4 | PGT025 | 1 | 4 |
|   |   | 1 | 14 |
|   |   | 2 | 15 |
|   |   | 2 | 16 |
| 5 | PGT026 | 1 | 11 |
|   |   | 1 | 14 |
|   |   | 1 | 15 |
|   |   | 2 | 21 |
| 2 | Cisplatin | 1 | 9 |
|   |   | 1 | 15 |
| 1 | Control | 1 | 15 |
|   |   | 4 | 16 |

Table 34 provides a comparison of the doubling time (RTV2) for each group in the study. In addition, table 34 also lists the growth delay in days, maximum percent weight loss and statistical significance of the data.

TABLE 34

| Group Number | Mean Time to RTV2 (days) | Median Time to RTV2 (days) | Growth Delay (days) | Significance | Maximum % Weight Loss |
|---|---|---|---|---|---|
| 1 | 3.3 | 3.5 | — | — | 0 |
| 2 | 5.2 | 5.2 | 1.7 | p < 0.05 | 5 (d7) |
| 3 | 4.6 | 3.8 | 0.3 | p < 0.05 ns | 0 |
| 4 | 3.8 | 3.6 | 0.1 | p < 0.05 ns | 0 |
| 5 | 4.0 | 3.7 | 0.2 | p > 0.05 ns | 0 |

Example 20e

Xenograft Cancer Study in Mice—H460 Oral Administration

Summary

This Example demonstrates the relative efficacy of three orally administered inventive Au—Pt bi-metallic nanoparticle suspensions in a mouse xenograft cancer model relative to Cisplatin. Female Balb/C, immunologically deficient recipient mice (6-8 weeks old) had tumors implanted therein. The Balb/C donor mice were used to grow H460 tumors, which tumors were excised therefrom and subsequently sectioned into small fragments about 2 mm$^3$ in size. The Balb/C recipient mice were given brief general anesthesia and then one H4602 mm$^3$ tumor fragment from the donor mice was implanted into each of the left and right flank of the recipient mice using a trocar needle. Once the tumors in the recipient mice had reached a measurable size of about 4×4 mm, as measured by calipers placed against each mouse skin, the recipient mice were randomly placed into treatment groups, 8 per group and the oral treatment was started. 8 mice were in the positive control group ("Cisplatin") and 8 mice were in the negative control group and received only water ("Control"). Treatment was given exclusively via the drinking bottle shared between the mice in each Treatment group. Cisplatin was given by intraperitoneal injection on day 0. Tumor size was assessed five times per week using a pair of calipers and mouse weight was also obtained by a scale, such measuring occurring until the mouse died (or was removed from the study) or the study was terminated as scheduled. The results of the Example are summarized in FIGS. 37a-37b.

Methodology

Animals

Species: Mice

Strain: Balb/C immunodeficient mice

Source: Harlan

Gender and number: Female, 36

Age: About 6-8 weeks old at the start of the study.

Identification: Each mouse was given a unique identity number.

Animal husbandry: On receipt, all animals were examined for external signs of ill-health and all unhealthy animals were excluded from further evaluation. Animals were housed in groups of three under specific pathogen free (spf) conditions, in a thermostatically monitored room (22±4° C.) in an animal unit. Animals were equilibrated under standard animal house conditions for at least 72 hours prior to use. The health status of the animals was monitored throughout this period and the suitability of each animal for experimental use was assessed prior to study start.

Housing Animals were housed in groups of 3 per cage in a controlled room, to ensure correct temperature, humidity and 12 hour light/dark cycle for the duration of the study.

Diet: Irradiated pellet diet and water was available ad libitum throughout the holding, acclimatisation and post-dose periods.

Compound and Reagents

H460 cell line (ATCC HTB-177).

Phosphate buffered saline ("PBS").

Test compounds: Au—Pt bi-metallic nanocrystal suspensions.

Positive control compound: cisplatin.

Negative control compound: drinking water.

Treatment Groups and Dosages

Negative Control Group 1: Days 0-21, given normal drinking water.

Positive Control Group 2: Days 0-21, given normal drinking water; and given a one-time cisplatin dose of 8 mg/kg by intraperitoneal injection ("IP") on day 0.

Treatment Group 3-5: Days 0-21, given test compounds as their drinking water.

Protocol A: Preparation and Growth of Donor Tumors a.) Preparation of Tumor Cells 1. Cells were grown in complete medium and all contaminants were excluded.

2. When the cells were approximately 70-80% confluent, then approximately 3-4 hours before harvesting, the old cell growth medium was replaced with fresh cell growth medium to remove any dead and/or detached cells.
3. The cell growth medium was once again removed and the cells were washed with PBS. A small amount (e.g., 10 ml) of trypsin-EDTA was then added. The cells were then dispersed in complete cell growth medium in a ratio of between 10/1 and 5/1. The dispersed cells and medium were thereafter immediately centrifuged at about 1500 rpm for about 5 minutes and were further washed twice with PBS and the cells were stored on ice.
4. The cells were then placed on a glass slide in the traditional manner and were counted using a hemocytometer.
5. Trypan-blue stain was then added to identify and subsequently exclude dead cells. Specifically, the cells were mixed in an approximate 1:1 ratio using trypan-blue solution. The trypan-blue was diluted to about 0.8 mM in PBS. The trypan-blue was stored at room temperature. Because all living or viable cells exclude trypan-blue, dead cells are stained blue by the dye. Accordingly, all cells stained blue were removed. Cells were suspended so that about 300 μL contained about $3 \times 10^6$ tumor growth cells. This concentration of cells was required for successful tumor growth at each injection site.

b.) Injection and Growth of Tumor Cells
1. Simultaneous with preparation of tumor growth cells, Balb/C mice had previously arrived and their health was checked.
2. All animals were allowed to acclimate for at least 72 hours.
3. All mice were about 6-8 weeks old at time of inoculation. The inoculation area was cleaned and sterilized with ethanol prior to inoculation.
4. A 1 cc syringe was filled with the cancer cells by drawing the cell mixture into the syringe without the needle. A 26 gauge needle was subsequently added to the syringe.
5. The cells were then injected subcutaneously into one lower flank of each mouse and allowed to grow until they formed a tumor which reached an average volume of about 50-60 $mm^3$.
6. The mice were then anesthetized and the tumors were harvested by using a scalpel and appropriately stored prior to being injected into the recipient mice.

Protocol B: Insertion of Tumors from Donor Mice into Recipient Mice

17. Additional Balb/C recipient mice had previously arrived. Upon arrival of the recipient mice, the health of all mice was checked; and after passing the health test, each was numbered with a unique ear tag.
18. The recipient mice were allowed to acclimate for at least 72 hours.
19. H460 tumors produced in Protocol A above were removed from the donor mice by scalpel and cut into small fragments, approximately 2 $mm^3$ in size. The 2 $mm^3$ tumors were implanted using a 3 mm diameter trocar syringe into the right and the left flanks of each mouse (i.e., 1 tumor per flank). The tumors were permitted to grow in the recipient mice until they reached a size of about 100-200 $mm^3$ before treatment started at day 0. Treatments continued for 24 days or until the mouse was removed from the study and euthanized or the mouse died.
20. The tumor sizes and weights of the animals were determined daily until the end of the study at day 21.

Figure 37A:
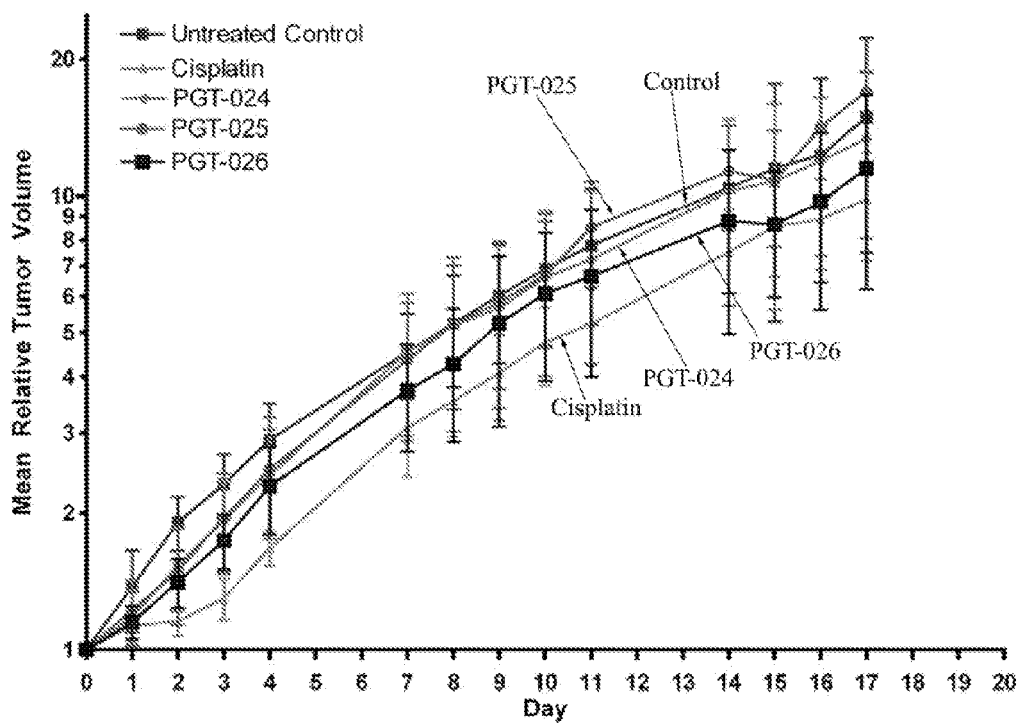
FIGS. 37a and 37b show the results of the cancer xenograft tests set forth in Example 20e.
Figure 37B:
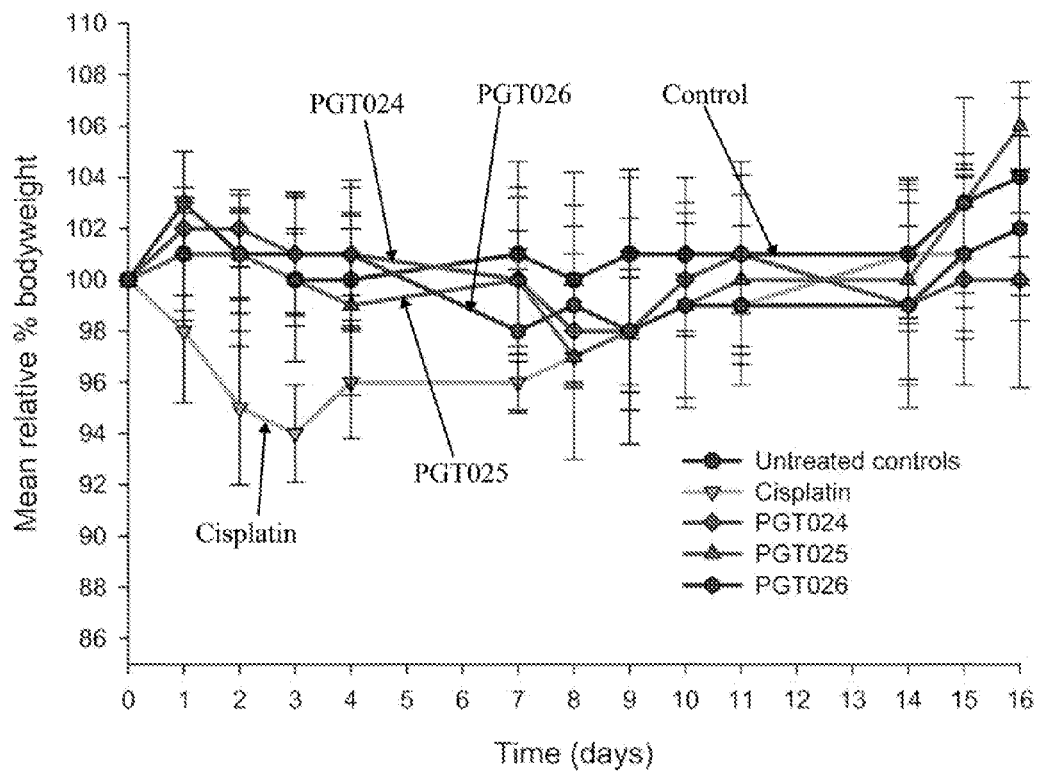

FIGS. 37a and 37b show graphically the results of the oral test. FIG. 37a shows clear difference in measured tumor volume, as a function of time, between the different compounds. The smaller the tumor, the better. Further, FIG. 37b shows differences in mean mouse weight, as a function of time, between the different compounds. The greater the weight, the better.

Table 35 summarizes the number and the point in time during the study that the mice were removed from the study. Reasons for mice leaving the study were primarily death and large tumor size, resulting in euthanasia. The Sample ID's relate to compounds manufactured according to procedures discussed earlier herein.

TABLE 35

Oral Treatment

| Group Number | Sample ID | No. of Mice Removed | No. of Days into Study |
| --- | --- | --- | --- |
| 3 | PGT024 | 1 | 14 |
|   |   | 2 | 15 |
|   |   | 1 | 16 |
|   |   | 1 | 18 |
| 4 | PGT025 | 1 | 3 |
|   |   | 1 | 11 |
|   |   | 2 | 14 |
|   |   | 2 | 15 |
| 5 | PGT026 | 2 | 11 |
|   |   | 1 | 14 |
|   |   | 1 | 18 |
| 2 | Cisplatin | 1 | 8 |
|   |   | 1 | 14 |
|   |   | 1 | 18 |
| 1 | Control | 1 | 14 |
|   |   | 4 | 15 |
|   |   | 3 | 18 |

Table 36 provides a comparison of the doubling time (RTV2) for each group in the study. In addition, table 34 also lists the growth delay in days, maximum percent weight loss and statistical significance of the data.

TABLE 36

| Group Number | Mean Time to RTV2 (days) | Median Time to RTV2 (days) | Growth Delay (days) | Significance | Maximum % Weight Loss |
| --- | --- | --- | --- | --- | --- |
| 1 | 2.3 | 2.5 | — | — | 0 |
| 2 | 5.0 | 5.0 | 2.5 | p < 0.01 | 6 (d3) |
| 3 | 3.5 | 3.4 | 0.9 | P < 0.05 | 0 |
| 4 | 3.5 | 3.0 | 0.5 | p > 0.05 ns | 0 |
| 5 | 3.7 | 3.6 | 1.1 | P < 0.01 | 0 |

Example 20f

Xenograft Cancer Study in Mice—HCT116 Oral Administration

Summary

This Example demonstrates the relative efficacy of one orally administered inventive Au—Pt bi-metallic nanocrystalline suspension in a mouse xenograft cancer model. Female Balb/C, immunologically deficient recipient mice (6-8 weeks old) had tumors implanted therein. The Balb/C donor mice were used to grow HCT116 tumors, which tumors were excised therefrom and subsequently sectioned into small fragments about 2 $mm^3$ in size. The Balb/C recipient mice were given brief general anesthesia and then one HCT116 2 $mm^3$ tumor fragment from the donor mice was implanted into each of the left and right flank of the recipient mice using a trocar needle. Once the tumors in the recipient mice had reached a measurable size of about 4×4 mm, as measured by calipers placed against each mouse skin, the recipient mice were randomly placed into treatment groups, 8 per group and the oral treatment was started. 8 mice were in the positive control group ("Cisplatin") and 8 mice were in the negative control group and received only water ("Control"). Treatment was given exclusively via the drinking bottle shared between the mice in each Treatment group. Cisplatin was given by intraperitoneal injection on day 0. Tumor size was assessed five times per week using a pair of calipers and mouse weight was also obtained by a scale, such measuring occurring until the mouse died (or was removed from the study) or the study was terminated as scheduled. The results of the Example are summarized in FIGS. 38a-38b

Methodology

Animals

Species: Mice

Strain: Balb/C immunodeficient mice

Source: Harlan

Gender and number: Female, 36

Age: About 6-8 weeks old at the start of the study.

Identification: Each mouse was given a unique identity number.

Animal husbandry: On receipt, all animals were examined for external signs of ill-health and all unhealthy animals were excluded from further evaluation. Animals were housed in groups of three under specific pathogen free (spf) conditions, in a thermostatically monitored room (22±4° C.) in an animal unit. Animals were equilibrated under standard animal house conditions for at least 72 hours prior to use. The health status of the animals was monitored throughout this period and the suitability of each animal for experimental use was assessed prior to study start.

Housing Animals were housed in groups of 3 per cage in a controlled room, to ensure correct temperature, humidity and 12 hour light/dark cycle for the duration of the study.

Diet: Irradiated pellet diet and water was available ad libitum throughout the holding, acclimatisation and post-dose periods.

Compound and Reagents

HCT 116 cell line (ATCC CCL-247).

Phosphate buffered saline ("PBS").

Test compounds: gold nanocrystal suspension NE-28-10X (NE-28 produced equivalent to NE10214 in Example 1) Concentrated 10×.

Positive control compound: cisplatin.

Negative control compound: drinking water.

Treatment Groups and Dosages

Negative Control Group 1: Days 0-21, given normal drinking water.

Positive Control Group 2: Days 0-21, given normal drinking water; and given a one-time cisplatin dose of 8 mg/kg by intraperitoneal injection ("IP") on day 0.

Treatment Group 3: Days 0-21, given test compounds as their drinking water.

Protocol A: Preparation and Growth of Donor Tumors a.) Preparation of Tumor Cells 1. Cells were grown in complete medium and all contaminants were excluded.
2. When the cells were approximately 70-80% confluent, then approximately 3-4 hours before harvesting, the old cell growth medium was replaced with fresh cell growth medium to remove any dead and/or detached cells.
3. The cell growth medium was once again removed and the cells were washed with PBS. A small amount (e.g., 10 ml) of trypsin-EDTA was then added. The cells were then dispersed in complete cell growth medium in a ratio of between 10/1 and 5/1. The dispersed cells and medium were thereafter immediately centrifuged at about 1500 rpm for about 5 minutes and were further washed twice with PBS and the cells were stored on ice.
4. The cells were then placed on a glass slide in the traditional manner and were counted using a hemocytometer.
5. Trypan-blue stain was then added to identify and subsequently exclude dead cells. Specifically, the cells were mixed in an approximate 1:1 ratio using trypan-blue solution. The trypan-blue was diluted to about 0.8 mM in PBS. The trypan-blue was stored at room temperature. Because all living or viable cells exclude trypan-blue, dead cells are stained blue by the dye. Accordingly, all cells stained blue were removed. Cells were suspended so that about 3000 μL contained about 3×10$^6$ tumor growth cells. This concentration of cells was required for successful tumor growth at each injection site.

b.) Injection and Growth of Tumor Cells

1. Simultaneous with preparation of tumor growth cells, Balb/C mice had previously arrived and their health was checked.
2. All animals were allowed to acclimate for at least 72 hours.
3. All mice were about 6-8 weeks old at time of inoculation. The inoculation area was cleaned and sterilized with ethanol prior to inoculation.
4. A 1 cc syringe was filled with the cancer cells by drawing the cell mixture into the syringe without the needle. A 26 gauge needle was subsequently added to the syringe.
5. The cells were then injected subcutaneously into one lower flank of each mouse and allowed to grow until they formed a tumor which reached an average volume of about 50-60 mm$^3$.
6. The mice were then anesthetized and the tumors were harvested by using a scalpel and appropriately stored prior to being injected into the recipient mice.

Protocol B: Insertion of Tumors from Donor Mice into Recipient Mice

21. Additional Balb/C recipient mice had previously arrived. Upon arrival of the recipient mice, the health of all mice was checked; and after passing the health test, each was numbered with a unique ear tag.
22. The recipient mice were allowed to acclimate for at least 72 hours.
23. HCT116 tumors produced in Protocol A above were removed from the donor mice by scalpel and cut into small fragments, approximately 2 mm$^3$ in size. The 2 mm$^3$ tumors were implanted using a 3 mm diameter trocar syringe into the right and the left flanks of each mouse (i.e., 1 tumor per flank). The tumors were permitted to grow in the recipient mice until they reached a size of about 100-200 mm$^3$ before treatment started at day 0. Treatments continued for 21 days or until the mouse was removed from the study and euthanized or the mouse died.
24. The tumor sizes and weights of the animals were determined daily until the end of the study at day 21.

Figure 38A:
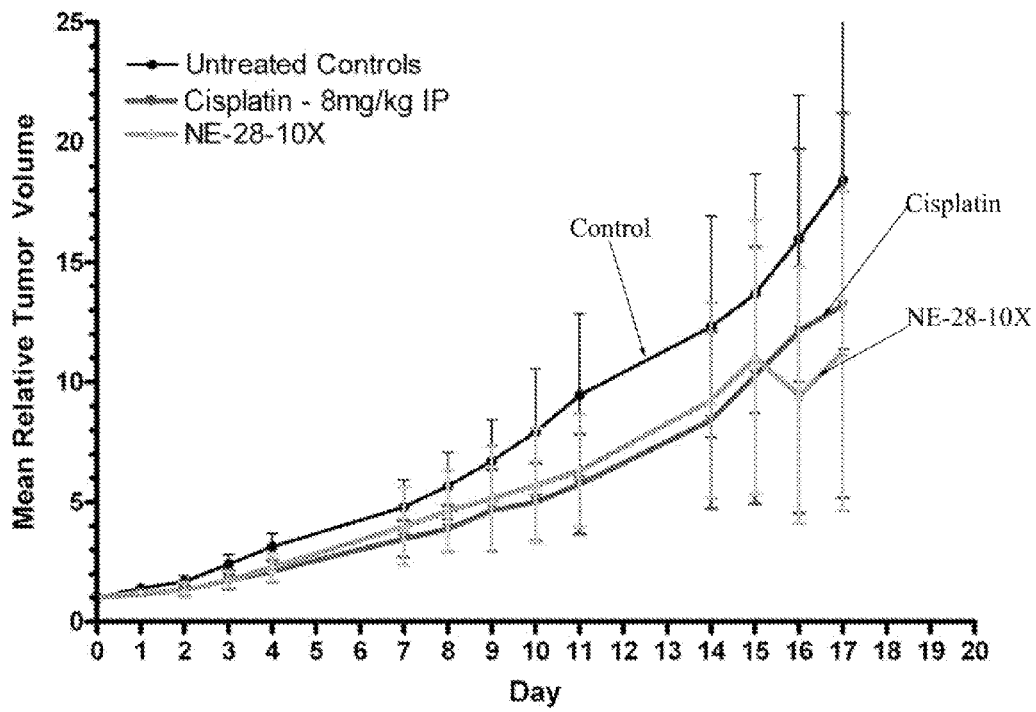
FIGS. 38a and 38b show the results of the cancer xenograft tests set forth in Example 20f.
Figure 38B:
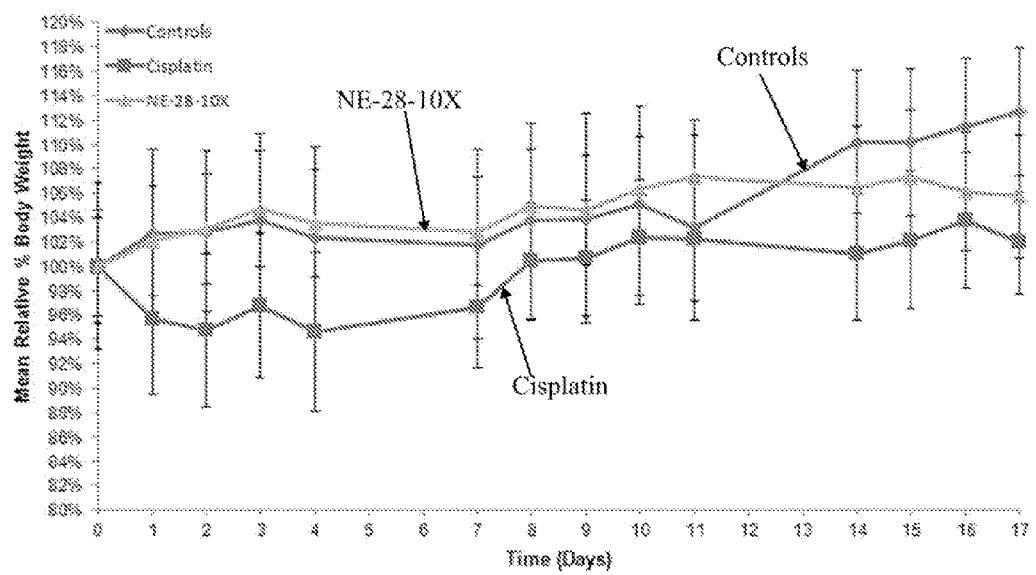

FIGS. 38a and 38b show graphically the results of the oral test. FIG. 38a shows clear difference in measured tumor volume, as a function of time, between the different compounds. The smaller the tumor, the better. Further, FIG. 38b shows differences in mean mouse weight, as a function of time, between the different compounds. The greater the weight, the better.

Table 37 summarizes the number and the point in time during the study that the mice were removed from the study. Reasons for mice leaving the study were primarily death and large tumor size, resulting in euthanasia. The Sample ID's relate to compounds manufactured according to procedures discussed earlier herein.

TABLE 37

Oral Treatment

| Group Number | Sample ID | No. of Mice Removed | No. of Days into Study |
|---|---|---|---|
| 3 | NE-28-10X | 1 | 11 |
|   |   | 2 | 14 |
|   |   | 1 | 15 |
| 2 | Cisplatin | 1 | 8 |
|   |   | 1 | 11 |
|   |   | 1 | 14 |
|   |   | 1 | 16 |
| 1 | Control | 1 | 7 |
|   |   | 2 | 11 |

Table 38 provides a comparison of the doubling time (RTV2) for each group in the study. In addition, Table 38 also lists the growth delay in days, maximum percent weight loss and statistical significance of the data.

TABLE 38

| Group Number | Mean Time to RTV2 (days) | Median Time to RTV2 (days) | Growth Delay (days) | Significance | Maximum % Weight Loss |
|---|---|---|---|---|---|
| 1 | 2.5 | 2.6 | — | — | 0 |
| 2 | 3.9 | 3.5 | 0.9 | $p < 0.05$ | 5 (d2) |
| 3 | 4.0 | 3.7 | 1.1 | $p < 0.05$ | 0 |

Example 21

In Vivo Study of the Effects of Au—Pt Bi-Metallic Nanocrystalline Formulation GPB-15-1, GPB-15-2 and GPB-030-01 on Mouse Behavior and Quality of Life Summary This in vivo experiment was designed to determine the effects of bi-metallic Au—Pt nanocrystalline suspensions GPB-15-1, GPB-15-2 and GPB-030-1 on the behavior and quality of life in Swiss Webster mice. Specifically, female mice were given GPB-15-1 ad libitum at the start of the study (17 Jun. 2011) for 47 days. GPB-15-2 was given ad libitum for 56 days starting on 2 Aug. 2011. GPB-030-01 has been given ad libitum starting on 26 Sep. 2011 and is currently being administered. The three different bi-metallic nanocrystalline suspensions were made essentially the same way and equivalent to PGT25 herein. The female Swiss Websters have been actively drinking GPB-030-01 for 147 days as of Feb. 20, 2012. GPB-030-01 started on Sep. 26, 2011.

Animals

Species: Mice
Strain: Swiss Webster ND4
Source: Harlan
Gender and number: Female, 13
Age: About 6-8 weeks old at the start of the study.
Identification: Each mouse was given a unique identity color.
Animal husbandry: On receipt, all animals were examined for external signs of ill-health and all unhealthy animals were excluded from further evaluation. Animals were housed in groups of 6 and 7 under normal drinking conditions, in a thermostatically monitored room (22±4° C.) in an animal unit. The health status of the animals was monitored throughout this period and the suitability of each animal for experimental use was assessed prior to study start.

Housing Animals were housed in groups of 6 and 7 per cage in a controlled room, to ensure correct temperature, humidity and 12 hour light/dark cycle for the duration of the study on weekends. An 8 hour light and 16 hour dark during the week, Monday-Friday.

Diet: Rodent Diet 5002 and Bottled water (such as deer park) or gold/platinum nanocrystalline suspensions are available ad libitum throughout the experimental period of the study. Only bottled water and Rodent Diet 5002 were present during the acclimatization period.

Reagents

Test gold/platinum bi-metallic nanocrystalline suspensions GPB-15-1, GPB-15-2 and GPB-030-01 (equivalent to PGT24).

Vehicle: Water.

Treatment Groups and Dosages

Control "Cage 1", Treatment "Cage 2". The numbers of animals in each group are respectively 6 and 7.

Cage 1 (control): Day 0 Normal drinking water, given normal Rodent Diet 5002 from day 0-month 8 and present.

Cage 2 (treatment): Day 0 gold/platinum bi-metallic nanocrystalline suspension GPB-15-1 (average 4.0 ml 1 d; gold ppm: 8.6. platinum ppm: 2.3) as drinking water from day 0-day 47. GPB-15-2 (average 3.9 ml 1 d; gold ppm: 8.6: platinum ppm: 2.3) as drinking water from day 48-day 101. GPB-030-01 (average 4.3 ml 1 d; gold ppm: 8.6, platinum ppm: 2.5) as drinking water from day 102 through 39 weeks. The mice were given normal Rodent Diet 5002 from day 0 through 39 weeks.

Protocol

On arrival of animals, the health of all animals was checked and after passing the health test, each was colored with a unique tail marking The animals were allowed to acclimate for at least 1 week.

13 animals were purchased and separated into two ten gallon glass tanks Seven animals were placed in a treatment group and 6 animals were placed in a control group.

Gold/platinum bi-metallic nanocrystalline suspension were prepared so as to achieve a suspension with a concentration of about 8.6 ppm Au and 2.3 ppm Pt for GPB-15-1, 8.6 ppm Au and 2.3 ppm Pt for GPB-15-2 and 8.6 ppm Au and 2.5 ppm Pt in GPB-030-01.

Treatments were given daily, i.e. new suspensions were replaced every 24 hours until 11 Oct. 2011, after this date suspensions were changed every 48 hours. Samples were tested for particle size to see if there was any growth. After collecting data during the 24 hr suspension change period and no significant growth effects present, suspensions were then changed every 48 hours.

All suspensions were are administered in a glass bottle to eliminate the potential effects of plastic bottle.

Animals were housed in a 10 gallon glass tank with a metal mesh cover. A corn cob bedding material (Bed O' Cobs manufactured by the Andersons) was provided as a floor material, one nestlet (purchased from Ancare) was given per animal per week. Animals had access to a wheel for exercise (8 in diameter Run around wheel manufactured by Super Pet), as well as a housing unit (Pet igloo by Super Pet) and a plastic food dish (Petco plastic dish) for Certified Rodent diet.

Cage cleaning occurred weekly where animals are housed in a plastic shoebox cage with food and drinking solution for no more than two hours.

Each animal was weighed weekly by a calibrated balance. Balance was checked with a certified 50 g weight to insure no drifting has occurred. (Scout pro 200 g balance purchased from Fisher Scientific)

Animal health was monitored daily

Figure 39A:
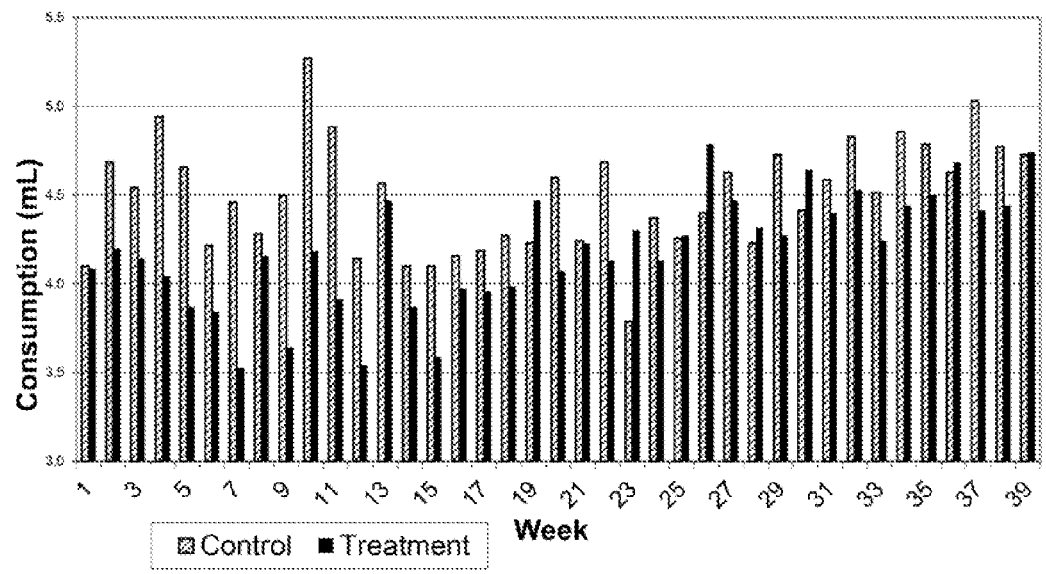
FIGS. 39a and 39b represent the liquid consumption amount and weight gain for the mice set forth in Example 21.
Figure 39B:
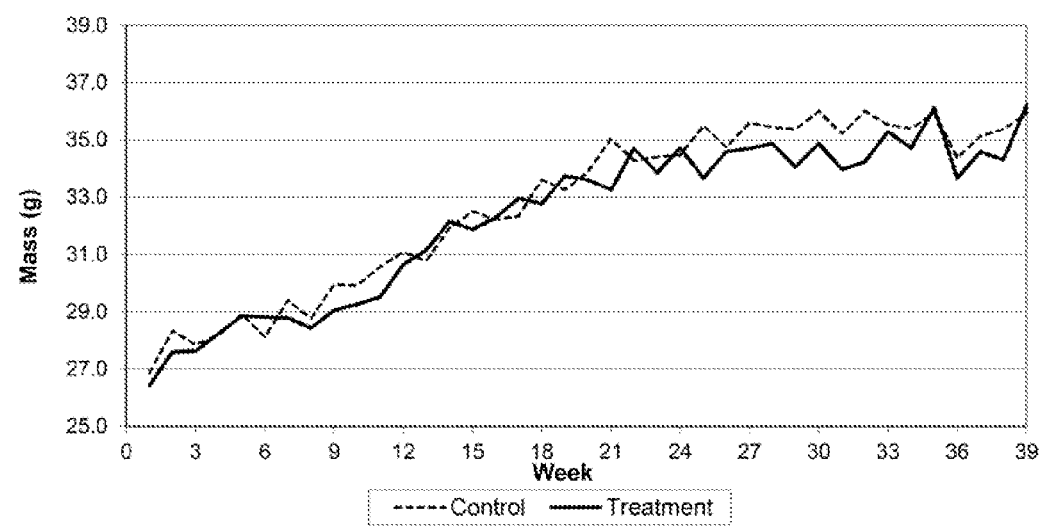

Results
1. All animals have appeared to be in good health and are behaving normally since the study began, 17 Jun. 2011. No animals have been lost, nor removed from the study due to illness.
2. FIG. 39a shows average consumption of bi-metallic Au—Pt nanocrystalline suspensions for Cage 2 ("Treatment") and average consumption of control drinking water in Cage 1 ("Control") over a 39 week period.
FIG. 39b shows the average weight gain of Treatment Group 2 and Control Group 1.
3. No difference in amount of liquid consumed nor any weight gain is apparent.

Example 22

In Vitro Study of the Binding of Au—Pt Bi-Metallic Nanocrystal Suspension GPB-11 to Genomic DNA and to Albumin Summary This in vitro experiment was designed to determine if nanocrystals in Au—Pt bi-metallic suspension GPB-11 could bind with genomic DNA and/or albumin; and if there was preferential binding. GPB-11 was incubated with genomic DNA from a human or a mouse, in the presence or absence of human, mouse or bovine albumin. The DNA or albumin binding to GPB-11 was characterized qualitatively and quantitatively by UV-Visible spectrophotometry.

Albumin is a known stabilizing agent and could provide a biofunctionalized layer for water-dispersed nanoparticles. The binding affinity between gold nanoparticles and DNA has been indicated to affect DNA transcription. Albumin is also known to assist in drug delivery.

Albumin was incubated with GPB-11 in a binding buffer at room temperature for about 1 hour to determine the differential binding of albumin to GPB-11 in the absence or presence of genomic DNA. Similarly, at the same temperature and in the same binding buffer, genomic DNA was incubated with GPB-11 for about 1 hour to measure the binding abilities of DNA to the GPB-11 when co-incubating with or without albumin. After reactions were allowed to occur, the GPB-11 suspension was spun down, washed and placed into an elution buffer for absorbance measurements.

The binding capacities of albumin or DNA to GPB-11 were monitored by 201-UV-VIS spectrometer at A280 or A260 (e.g., $\lambda=280$ or $\lambda=260$). Absorption spectra from samples were acquired by a double beam Czerny-Turner monochromator system and dual silicon photodiodes equipped in 201-UV-VIS. The background of GPB-11, albumin and DNA were subtracted from the reaction tubes.

Further, to visualize interactions between the DNA and GPB-11, a Fast-scan atomic force microscopy (AFM) set-up was utilized. Additionally, a nano-scale-resolution type of scanning, probe microscopy, was used to take a photomicrograph of the interaction.

Concentration of Au—Pt Bi-Metallic Nanocrystal Suspension GPB-11

Equipment and Materials Used for Concentration

| | Supplier | Cat. No. |
|---|---|---|
| Eppendorf centrifuge | Brinkmann Instruments Inc | 5417 C w Rotor |
| Zetasizer | Malvern | Nano-ZS90; Model: Zen3690 |

| | Supplier | Cat. No. |
|---|---|---|
| 1.5 ml Eppendorf Tubes | Fisher Scientific | 05-402-24B |
| Pipet Tips | Fisher Scientific | 02-681-140 |
| Pipetter | Fisher Scientific | 21-377-821 |
| Sodium bicarbonate | Fisher Scientific | 144-55-8 |
| Potassium hydroxide | Fisher Scientific | 1310-58-3 |

Concentration Method
1. GPB-11 (having an atomic concentration of Au, 8.2 ppm; and Pt, 2.5 ppm) was placed into eppendorf tubes, and centrifuged at about 20,000×g for about 10 mins.
2. The pellets were clearly observed on the bottom of these tubes. The top 95% supernatant was discarded and bottom 5% supernatant and pellets were collected. The concentrated suspension was then resuspended in the binding reaction studies.

Rehydration of Concentrated GPB-11

The concentrated GPB-11 suspension was rehydrated in a solution containing 2.7 mM Sodium Hydrogen Carbonate and 2.1 mM Potassium hydroxide with the same amount as the above-described supernatant. Zeta potentials of rehydared GPB-11 and original GPB-11 solutions were measured using a Zetasizer as discussed elsewhere herein, and the results were −50.3 mV and −51.7 mV respectively. The very similar Zeta potential values suggested that rehydration of concentrated GPB-11 in the binding reaction studies should have the same effect as adding an original concentration of GPB-11.

Binding Assays of Albumin or Genomic DNA with Co-Nanocrystalline GPB-11

Equipment and Materials Used for Binding Assays

| | Supplier | Cat. No. |
|---|---|---|
| 201-UV-VIS (Uvcalc-bio) | Thermo Spectronic | 001201 |
| pH/Conductivity Meter | Fisher Scientific | Accumet AR 20; ID: I928 |
| Vertex Mixer | Fisher Scientific | 02215365 |
| Bovine serum albumin | Sigma Aldrich | A9418 |
| Mouse serum albumin | Sigma Aldrich | A3139 |
| Human serum albumin | MP Biomedicals, LLC | 191349 |
| Human genomic DNA (female) | Promega | G1521 |
| Isopropyl alcohol | Sigma Aldrich | W292907 |
| Ethanol | Sigma Aldrich | 459836 |
| Wizard Genomic DNA Purification Kit | Promega | A1120 |
| Tris base | Fisher Scientific | 77-86-1 |
| Potassium chloride (KCl) | Fisher Scientific | 7447-40-7 |
| Magnesium chloride (MgCl2) | Sigma Aldrich | M4880 |
| IGEPAL ® CA-630 | Sigma Aldrich | 18896 |
| Hydrochloric acid | Fisher Scientific | 7647-01-0 |
| Sodium hydroxide (NaOH) | Fisher Scientific | 1310-73-2 |
| Ethylenediaminetetraacetic acid (EDTA) | Acros Organics | 60-00-4 |

Isolation of Genomic DNA from Mouse Spleen and Human Whole Blood

Isolation of Genomic DNA from Mouse Spleen
  10 mg of thawed normal mouse spleen was added to 600 ul of chilled Nuclei Lysis Solution and incubated at 65° C. for 20 minutes.
  3 ul of RNase Solution was put into tissue nuclei lysate, mixed and incubated at 37° C. for 25 minutes. After incubation the lysates was cooled down to room temperature.

200 ul of Protein Precipitation was mixed with tissue lysate, vertexed and chilled on ice for 5 minutes.

The above mixture was centrifuged at 16000×g for 4 minutes.

After centrifugation the supernatant was transferred to a fresh tube containing 600 ul of room temperature isopropanol and mixed gently by inversion.

The above reactive mixture was centrifuged at 16000×g for 1 minute.

The supernatant was removed and the pellet was resuspended in 600 ul of room temperature 70% ethanol and centrifuged at 16000×g for 1 minute.

The ethanol was aspirated and DNA pellet was air dried for 15 minutes.

The dried DNA pellet was rehydrated in 100 ul of DNA Rehydration Solution for overnight at 4° C.

Isolation of Genomic DNA from Human Whole Blood 3 ml of normal human male whole blood was combined with 9 ml of Cell Lysis Solution, mixed by inversion and incubated for 10 minutes at room temperature.

The above mixed solution was centrifuged at 2000×g for 10 minutes. The supernatant was discarded and the pellet was vertexed.

3 ml of Nuclei Lysis Solution was added onto the above pellet and mixed by inversion.

1 ml of Protein Precipitation Solution was added into the above nuclei lysate and vortexed for 20 seconds following by centrifuging at 2000×g for 10 minutes.

After centrifugation the supernatant was transferred to a fresh tube containing 3 ml of room temperature isopropanol and mixed gently.

The above reactive mixture was centrifuged at 2000×g for 1 minute.

The supernatant was removed and the pellet was washed in 3 ml of room temperature 70% ethanol and centrifuged at 2000×g for 1 minute.

The ethanol was aspirated and DNA pellet was air dried for 15 minutes.

The dried DNA pellet was rehydrated in 250 ul of DNA Rehydration Solution for overnight at 4° C.

Preparation of Binding Buffer

The binding buffer was prepared with 20 mM Tris, 100 mM KCl, 3 mM MgCl2 and 0.1% IGEPAL. The pH was adjusted to about 7.5 by pH/Conductivity Meter with Hydrochloric acid and NaOH.

Preparation of DNA Elution Buffer

To make 10×50T1E (50 mM Tris-HCL/1 mM EDTA), 6.05 gram Tris base and 0.37 gram EDTA were mixed in 100 ml distilled water to dissolve. The pH of the solution was regulated to be about 8 by monitoring with a pH/Conductivity Meter and adjusting with Hydrochloric acid and NaOH. Before eluting DNA from the nanoparticles, the 10×50T1E solution was diluted 10 times with distilled water.

Design for Binding Assays

TABLE 29

| Combinations | | Groups | | | | | | | |
|---|---|---|---|---|---|---|---|---|---|
| | | 1 | 2 | 3 | 4 | 5 | 6 | 7 | 8 |
| Albumin | 0.4 mg/ml | − | + | − | + | − | + | − | + |
| DNA | 15 ug/ml | − | − | − | − | + | + | + | + |
| GPB11 | 22 ug/ml | − | − | + | + | − | − | + | + |
| Binding buffer | | + | + | + | + | + | + | + | + |

Protocol of Binding Assays

25. The binding reaction was carried out by the incubation of GPB-11, albumin and DNA with binding buffer for about 1 hour at room temperature in eight combinations as shown in Table 29. During incubating the samples were vertexed every 5 minutes.

26. After incubation, the reaction solution was spun down at 20000×g for about 10 minutes at room temperature.

27. The pellets were washed once and resuspended in 400 ul DNA elution buffer.

28. The absorbance at 280 nm for albumin (i.e., absorption peak) and 260 nm for DNA (i.e., absorption peak) was measured with 201-UV-VIS.

AFM Imaging for DNA Binding

Equipment and Materials Used for Imaging

| | Supplier | Cat. No. |
|---|---|---|
| Dimension FastScan AFM system | Bruker | |
| FastScan A probe | AppNano | Probe model: UHF Series |
| Mica | Bruker | |
| Spin Coater | Instras Scientific | SCK-100 |

AFM Samples Preparation and Analysis

After the binding reaction was permitted to occur, 50 ul of the mixture of human female genomic DNA and GPB-11 in binding buffer was deposited and spin-coated (at least 3000 rpm) onto a fresh mica sheet. The mica-containing sample was rinsed with clean water once, followed by drying in air. Imaging was carried out by FastScan AFM with NanoScope V and Stage Controller. The AFM was operated in tapping mode and FastScan A probe (k~17 N/m) was used. High resolution phase mapping, overlaying topography (3D) and height in cross sections were analyzed by FastScan NanoScope Software. Results are discussed later herein.

Albumin Binding

The absorbance of albumin binding to GPB-11 was measured at 280 nm. Different combinations of albumin and GPB-11 were tested in the presence or absence of genomic DNA. Table 30 shows that very similar results were achieved among different albumin and GPB11 combinations. Representative data are also depicted in FIG. 40a.

TABLE 30

| Combinations | | Experiments | | | | | |
|---|---|---|---|---|---|---|---|
| | | 1 | 2 | 3 | 4 | 5 | 6 |
| Albumin | Bovine | + | − | − | + | − | − |
| | Mouse | − | + | − | − | + | − |
| | Human | − | − | + | − | − | + |
| Genomic DNA | Mouse | − | − | − | + | + | − |
| | Human | − | − | − | − | − | + |
| GPB-11 | | + | + | + | + | + | + |

Figure 40A:
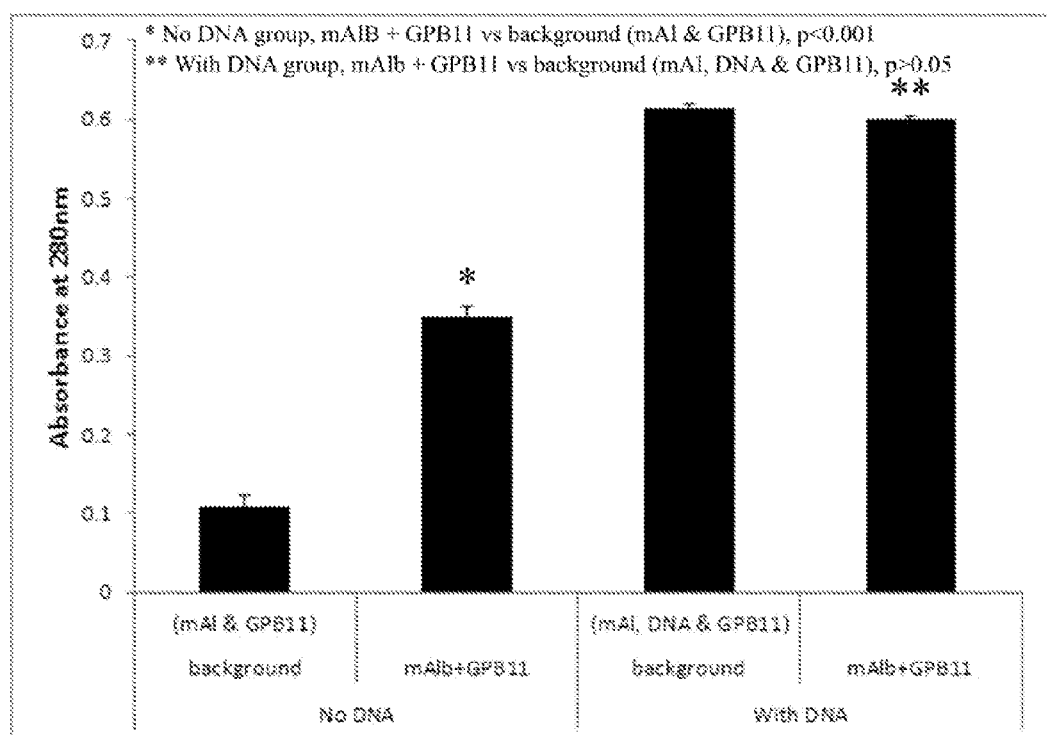
FIGS. 40a and 40b are graphs depicting the amount of absorbance of GPB-11 and various protein binders.

Specifically, FIG. 40a shows graphically the amount of mouse albumin binding in the presence or absence of mouse genomic DNA as a function of the absorbance at 280 nm. In the absence of genomic DNA, albumin significantly bound to the bi-metallic nanocrystals in GPB-11. But when genomic DNA was added in binding assay, no albumin binding to the nanocrystals in GPB-11 was observed. These results indicated that the nanocrystals in GPB-11 can bind with albumin, but preferentially binds to mouse genome DNA. In another words, the Au—Pt bi-metallic nanocrystals in GPB-11 apparently have a soft corona of albumin.

DNA Binding

DNA binding to nanocrystals in GPB-11 was determined by measuring the absorbance at 260 nm. The binding ability of mouse or human genomic DNA to bi-metallic nanocrystals in GPB-11 was measured with different combinations of albumin. Table 31 shows the various combinations or mixtures tested. Highly consistent results were observed between different DNA and nanocrystals in GPB-11 combinations. The representative results are depicted graphically in FIG. 40b.

TABLE 31

| Combinations | | Experiments | | | | |
|---|---|---|---|---|---|---|
| | | 1 | 2 | 3 | 4 | 5 |
| Genomic DNA | Mouse | + | − | + | − | + |
| | Human | − | + | − | + | − |
| Albumin | Bovine | − | − | + | − | − |
| | Mouse | − | − | − | − | + |
| | Human | − | − | − | + | − |
| GPB-11 | | + | + | + | + | + |

Figure 40B:
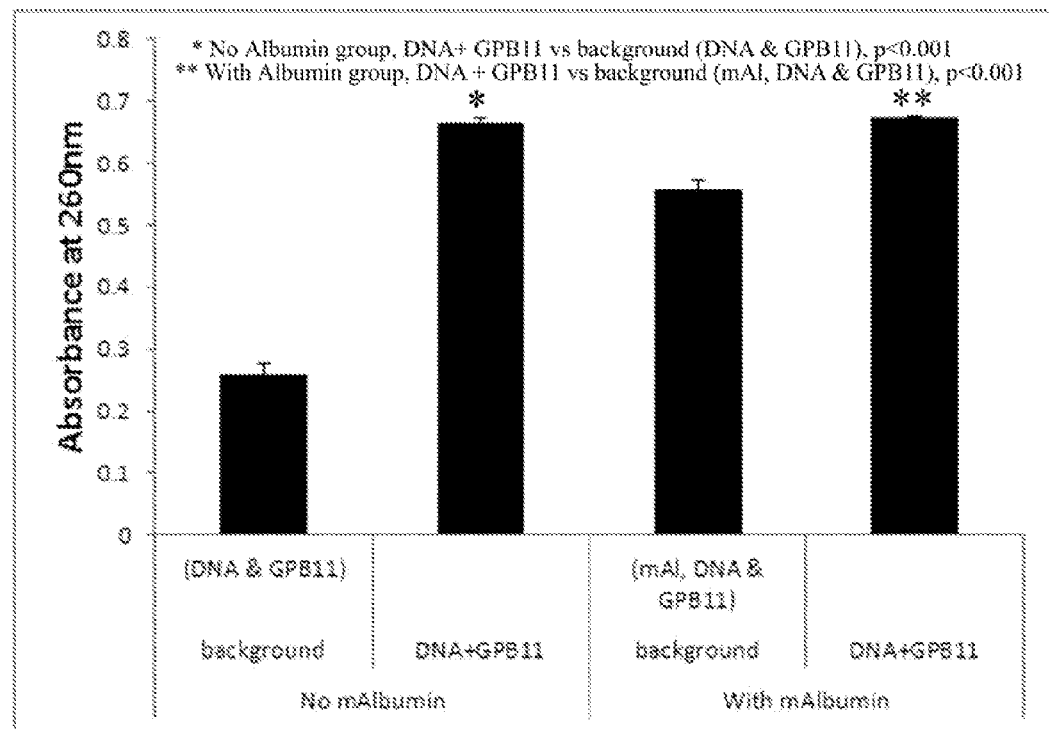

Specifically, FIG. 40b shows graphically the amount of DNA binding in the presence or absence of mouse albumin. FIG. 40b shows that in both, the presence and the absence of albumin, genomic DNA significantly bound to nanocrystals in GPB-11. When albumin was absent, the amount of DNA binding with GPB-11 nanocrystals was dramatic. Even when a large amount of albumin was added in the binding assay, a statistically significant amount of DNA was observed to be bound to the GPB-11 bi-metallic nanocrystals. These results further confirm that bi-metallic nanocrystals in GPB-11 bind to genomic DNA much stronger than albumin. Further, without wishing to be bound by any particular theory or explanation, it is possible that the Au—Pt bi-metallic nanocrystals in GPB-11 may bind to genomic DNA (when in the presence thereof) with covalent bonds. Such bonding could affect DNA function.

Figure 40C:
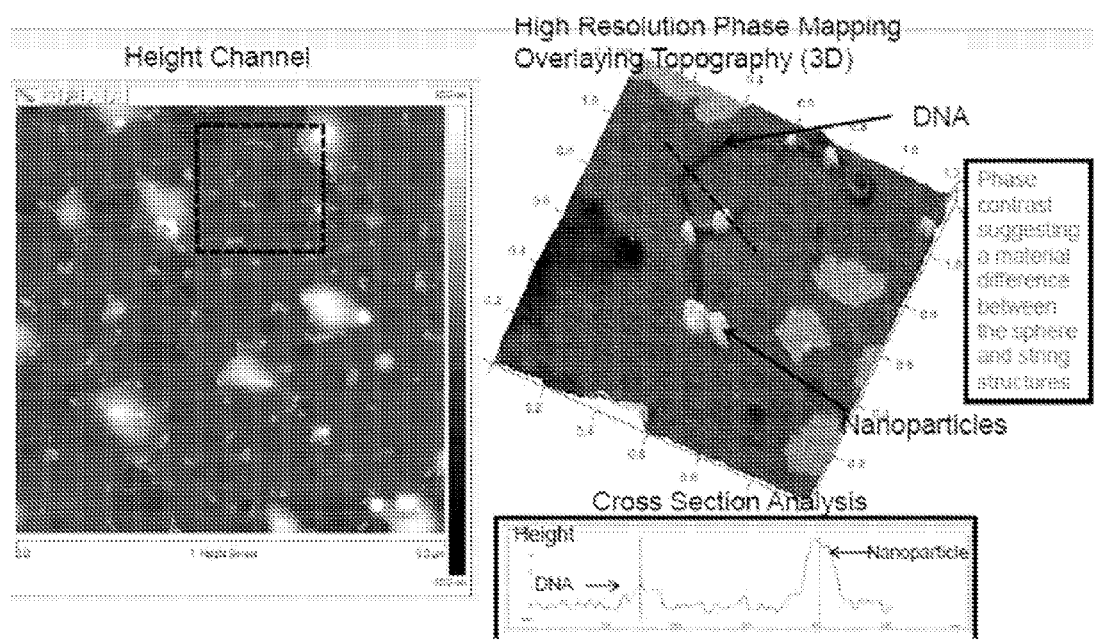
FIG. 40c shows an AFS photomicrograph of DNA binding to nanocrystals of GPB-11.

An attempt was made to image DNA binding to Au—Pt bi-metallic nanocrystals. Specifically, the samples in DNA binding assay were imaged by an AFM. A representative result is shown in FIG. 40c. It is clearly shown that Au—Pt bi-metallic nanocrystals bound to human genomic DNA. Most nanocrystals were observed binding on the end of string DNA molecules. The diameters of the imaged nanoparticles are within the size range of the nanocrystals in GPB-11, thus confirming the binding.

The invention claimed is:

1. A process for forming gold-platinum bi-metallic nanocrystals suspended in water comprising:
providing at least one processing enhancer in said water;
providing at least one first trough member;
creating a flow direction of said water and processing enhancer through said at least one first trough member;
providing at least one platinum-based plasma forming electrode spaced apart from a surface of said water, thereby forming a space between said at least one platinum-based plasma-forming electrode and said surface of said water;
forming at least one plasma in said space between said at least one platinum-based plasma forming electrode and said surface of said water;
providing at least one set of electrodes comprising platinum and contacting said at least one set of electrodes with said water after said water has flowed past said at least one platinum-based plasma forming electrode;
causing said at least one set of electrodes to form at least one platinum species in said water to create a water-platinum species liquid;
providing said water-platinum species liquid to at least one second trough member;
creating a flow direction of said water-platinum species liquid through said at least one second trough member;
providing at least one gold-based, plasma-forming electrode spaced apart from a surface of said water-platinum species liquid, thereby forming a space between said at least one gold-based, plasma-forming electrode and said water-platinum species liquid;
forming at least one plasma in said space between said at least one gold-based, plasma-forming electrode and said water-platinum species liquid;
providing at least one set of electrodes comprising gold contacting said water-platinum species liquid, said at least one set of gold electrodes contacting said water-platinum species liquid after said water-platinum species liquid has flowed past said at least one gold-based, plasma-forming electrode; and
causing said at least one set of gold electrodes to form said gold-platinum bi-metallic nanocrystals.

2. A product manufactured by the method of claim 1.

3. The process of claim 1, wherein at least one electrode from said at least one set of electrodes comprising platinum comprises the shape of a wire.

4. The process of claim 1, wherein said at least one set of electrodes comprising gold comprises the shape of wires.

5. The process of claim 1, wherein said at least one processing enhancer is added to said water before said water is contacted with said at least one set of electrodes comprising platinum.

6. The process of claim 1, wherein said at least one processing enhancer comprises $NaHCO_3$.

7. The process of claim 1, wherein said at least one processing enhancer comprises $Na_2CO$.

8. The process of claim 1, wherein said at least one processing enhancer comprises $K_2CO_3$.

9. The process of claim 1, wherein said at least one processing enhancer is selected from the group consisting of $NaHCO_3$, $Na_2CO_3$, $K_2CO_3$, $KHCO_3$, $NaOH$, $KOH$, $NaBr$, $KBr$, $Na_2PO_4$, $NaCl$, and $CaCl_2$.

10. The process of claim 1, wherein an alternating current power source provides power to each of said electrodes.

11. The process of claim 10, wherein said alternating current power source operates at a frequency range of 5-1000 Hz.

12. The process of claim 10, wherein said alternating current power source operates at a voltage of 20-2000 volts.

13. The process of claim 1, wherein said processing enhancer causes said water to have a pH in the range of 8-11.

14. The process of claim 1, wherein said processing enhancer causes said water to have a pH in the range of 9-12.

15. The process of claim 1, wherein said processing enhancer is provided in an amount of 0.0026-2.1730 mg/ml.

16. The process of claim 1, wherein processing enhancer is provided in an amount of 0.13210-0.5283 mg/ml.

17. A process for forming gold-platinum bi-metallic nanocrystals suspended in water comprising:
first forming electrochemically at least one platinum species in water and at least one lysis product of water, thereby creating a water-platinum species liquid; and
contacting said water-platinum species liquid with at least one set of electrodes comprising gold and causing a second electrochemical reaction to form a bi-metallic gold-platinum nanocrystal suspension.

18. The process of claim 17, wherein at least one platinum electrode is used to form said water-platinum species liquid.

19. The process of claim 17, wherein no chlorides or chlorine-based materials are required in said process to form said gold-platinum bi-metallic nanocrystals.

20. The process of claim 17, wherein said gold-platinum bi-metallic nanocrystals comprise an alloy of gold and platinum.

21. The process of claim 17, wherein at least one processing enhancer selected from the group consisting of $NaHCO_3$, $Na_2CO_3$, $K_2CO_3$, $KHCO_3$, $NaOH$, $KOH$, $NaBr$, $KBr$, $Na_2PO_4$, $NaCl$, and $CaCl_2$ is added to said water prior to forming said at least one platinum species in water.

22. The process of claim 21, wherein said at least one processing enhancer causes said water to have a pH in the range of 8-11.

23. The process of claim 17, wherein a processing enhancer is provided in an amount of 0.0026-2.1730 mg/ml.

24. The process of claim 17, wherein a processing enhancer is provided in an amount of 0.13210-0.5283 mg/ml.

25. A process for forming gold-platinum bi-metallic nanocrystals in water comprising:
providing a container;
at least partially filling said container with water comprising at least one processing enhancer selected from the group of materials consisting of $NaHCO_3$, $Na_2CO_3$, $K_2CO_3$, $KHCO_3$, $NaOH$, $KOH$, $NaBr$, $KBr$, $Na_2PO_4$, $NaCl$, and $CaCl_2$, said water having an upper surface;
providing a first electrode set comprising at least one platinum-based plasma-forming electrode spaced apart from said upper surface of said water and at least one platinum electrode at least partially immersed in said water;
forming at least one plasma between at least a portion of said upper surface of said water and said at least one platinum-based plasma-forming electrode to create at least one platinum species in said water; and
subsequently contacting at least one second electrode set comprising gold with said water after said water has been contacted with said at least one plasma from the platinum-based plasma-forming electrode and causing gold-platinum bi-metallic nanocrystals to be formed and suspended in said water.

26. The process of claim 25, wherein said at least one processing enhancer comprises $NaHCO_3$ present in an amount of about 0.264 g/L to about 0.528 g/L and said at least one set of electrodes comprising gold comprise gold wires.

27. The process of claim 25, wherein said first electrode set and said second electrode set are powered by separate alternating current power sources.

28. The process of claim 25, wherein said at least one plasma is created with an applied voltage of about 750 volts.

29. The process of claim 25, wherein an alternating current power source is provided to said second electrode set comprising gold, said power source providing a voltage of about 250 volts to said second electrode set.

* * * * *